(12) United States Patent
Yuan et al.

(10) Patent No.: US 10,017,507 B2
(45) Date of Patent: Jul. 10, 2018

(54) DIAZA-BENZOFLUORANTHRENE COMPOUNDS

(71) Applicant: HARBIN PHARMACEUTICAL GROUP CO., LTD. GENERAL PHARMACEUTICAL FACTORY, Harbin, Heilongjiang (CN)

(72) Inventors: Shujie Yuan, Heilongjiang (CN); Xinchun Yang, Heilongjiang (CN); Jinlong Zhao, Heilongjiang (CN); Daoxu Zhang, Heilongjiang (CN); Mingda Sun, Heilongjiang (CN); Jiaji Liu, Heilongjiang (CN); Tao Wei, Heilongjiang (CN); Huanan Zhao, Heilongjiang (CN); Yunfu Luo, Shanghai (CN); Chundao Yang, Shanghai (CN)

(73) Assignee: HARBIN PHARMACEUTICAL GROUP CO., LTD. GENERAL PHARMACEUTICAL FACTORY, Harbin (CN)

( * ) Notice: Subject to any disclaimer, the term of this patent is extended or adjusted under 35 U.S.C. 154(b) by 0 days.

(21) Appl. No.: 15/548,776

(22) PCT Filed: Feb. 2, 2016

(86) PCT No.: PCT/CN2016/073143
§ 371 (c)(1),
(2) Date: Aug. 4, 2017

(87) PCT Pub. No.: WO2016/124129
PCT Pub. Date: Aug. 11, 2016

(65) Prior Publication Data
US 2018/0016270 A1  Jan. 18, 2018

(30) Foreign Application Priority Data

Feb. 4, 2015 (CN) .......................... 2015 1 0058257
Jan. 26, 2016 (CN) .......................... 2016 1 0052158

(51) Int. Cl.
*A01N 43/42* (2006.01)
*A61K 31/44* (2006.01)
*C07D 461/00* (2006.01)
*C07D 519/00* (2006.01)

(52) U.S. Cl.
CPC ............ *C07D 461/00* (2013.01); *A61K 31/44* (2013.01); *C07D 519/00* (2013.01)

(58) Field of Classification Search
CPC ........................... A61K 31/439; C07D 461/00
USPC ............................................. 514/281; 546/43
See application file for complete search history.

(56) References Cited

FOREIGN PATENT DOCUMENTS

WO  2013076646 A1  5/2013

OTHER PUBLICATIONS

International Search Report of PCT Patent Application No. PCT/CN2016/073143 dated May 10, 2016.

*Primary Examiner* — Jeffrey H Murray

(57) ABSTRACT

Disclosed are a series of diaza-benzofluoranthrene compounds. The present invention particularly relates to a compound represented by formula (I), pharmaceutically acceptable salts or tautomers thereof.

18 Claims, No Drawings

DIAZA-BENZOFLUORANTHRENE COMPOUNDS

FIELD OF THE INVENTION

The present invention relates to a series of diaza-benzofluoranthrene compounds, particularly relates to a compound of formula (I), pharmaceutically acceptable salts or tautomers thereof.

BACKGROUND OF THE INVENTION

According to the research of the World Health Organization (WHO), cerebral stroke, following ischemic heart disease, has become the second leading cause of death. Meanwhile, cerebral stroke is very likely to lead to deformity and disability, and seriously affects patients and their family's quality of life. Therefore, it is necessary to find a way to improve the stroke patients' health status and restore their body function and ability to work, so that they can live a better life and have a good prognosis. This is also beneficial to reduce the burden of not only individuals but also the whole society.

Vinpocetine, which is represented by the formula B-I, is an indole alkaloid extracted from the lesser periwinkle plant. Vinpocetine is highly fat-soluble and can easily go through the blood brain barrier, so it can exert efficacy with high concentration in the brain tissue. Vinpocetine is developed by Gedeon Richter Co., a Hungarian company, in 1978. It has a history over 30 years in Europe. It is mainly used to improve the symptoms caused by cerebral infarction sequelae, cerebral hemorrhage sequelae, cerebral atherosclerosis and so on. Since vinpocetine came into the market, it has been considered as a routine medicine to treat cardiovascular and cerebrovascular diseases. Recently, it is found that vinpocetine can improve age-related memory impairment and healthy people's mental activity. In addition, it is found that vinpocetine is also helpful in improving tangled mind, attention-deficit disorder, irritability, visual and auditory disorders, emotional fluctuation and so on.

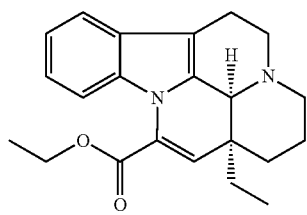

(B-I)

The morbidity and disability of cerebral stroke is very high in China, which has become a heavy burden for Chinese medical system. Vinpocetine is widely used for treating cerebral stroke and other related diseases in China, and is a main treatment means for improving prognosis of cerebral stroke. However, the therapeutic effect of vinpocetine is dubious, and the bioavailability is quite low.

Epilepsy is a chronic recurrent transient brain dysfunction syndrome, and is characterized by the abnormal discharge of neurons in the brain, which leads to a risk of recurrent seizures. Epilepsy is a common nervous system disease. The morbidity is second only to cerebral stroke.

SUMMARY OF THE INVENTION

The aim of the present invention is to provide a compound of formula (I), the pharmaceutically acceptable salts or tautomers thereof, wherein

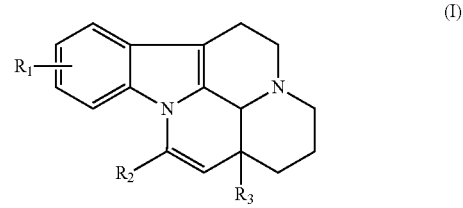

(I)

$R_1$ and $R_3$ are separately and independently selected from H, F, Cl, Br, I, CN, OH, SH, $NH_2$, CHO, or COOH; or $R_1$ and $R_3$ are separately and independently selected from the group, optionally substituted by $R_{01}$, consisting of C(=O)$NH_2$, S(=O)$NH_2$, S(=O)$_2NH_2$, $C_{1-10}$ alkyl, $C_{1-10}$ heteroalkyl, $C_{3-10}$ cyclic hydrocarbyl, $C_{3-10}$ heterocyclic hydrocarbyl, $C_{1-10}$ alkyl substituted by $C_{3-10}$ cyclohydrocarbyl or $C_{3-10}$ heterocyclohydrocarbyl, $C_{1-10}$ heteroalkyl substituted by $C_{3-10}$ cyclohydrocarbyl or $C_{3-10}$ heterocyclohydrocarbyl, $C_{1-10}$ alkenyl, and $C_{1-10}$ heteroalkenyl;

$R_2$ is selected from 5- or 6-membered unsaturated cyclic hydrocarbyl, 5- or 6-membered unsaturated heterocyclic hydrocarbyl,

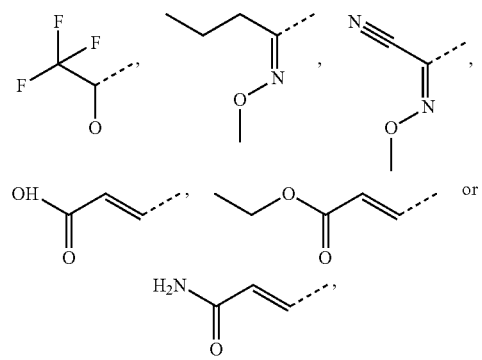

each optionally substituted by $R_{01}$;

$R_{01}$ is selected from F, Cl, Br, I, CN, OH, SH, $NH_2$, CHO, COOH, C(=O)$NH_2$, S(=O)$NH_2$, S(=O)$_2NH_2$ or $R_{02}$;

$R_{02}$ is selected from $C_{1-10}$ alkyl, $C_{1-10}$ heteroalkyl, $C_{3-10}$ cycloalkyl, $C_{3-10}$ heterocyclic alkyl, aminoacyl, or a 5- to 12-membered unsaturated heterocyclic group;

"hetero-" represents a hetero atom or a hetero atom-containing group, which is selected from the group consisting of —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, =O, =S, —C(=O)O—, —C(=O)—, —C(=S)—, —S(=O)—, —S(=O)$_2$— and —N($R_{d8}$)C(=O)N($R_{d9}$)—;

$R_{d3-d9}$ are separately and independently selected from H, $NH_2$, or $R_{02}$;

$R_{02}$ is optionally substituted by $R_{001}$;

$R_{001}$ is selected from F, Cl, Br, I, CN, OH, N(CH$_3$)$_2$, NH(CH$_3$), $NH_2$, CHO, COOH, C(=O)$NH_2$, S(=O)$NH_2$, $S(=O)_2NH_2$, trifluoromethyl, aminomethyl, hydroxymethyl, methyl, methoxy, formyl, methoxycarbonyl, methanesulfonyl, or methylsulfinyl;

the number of $R_{01}$, $R_{001}$, the hetero atom or the hetero atom-containing group are separately and independently selected from 0, 1, 2, 3.

In an embodiment of the present application, $R_1$ and $R_3$ are separately and independently selected from H,

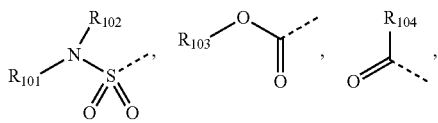

or $R_{05}$; $R_{101-105}$ are separately and independently selected from $C_{1-6}$ alkyl or $C_{1-6}$ heteroalkyl, each optionally substituted by $R_{001}$; or $R_1$ and $R_3$ are separately and independently selected from 5- or 6-membered unsaturated cyclic hydrocarbyl, 5- or 6-membered unsaturated heterocyclic hydrocarbyl,

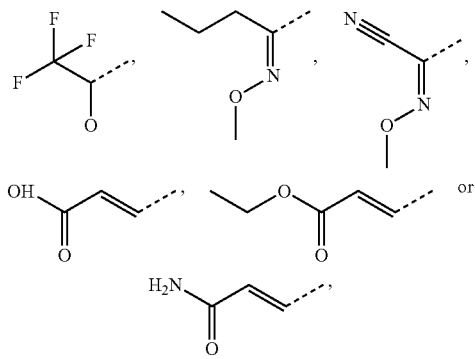

each substituted by 0, 1, 2 or 3 $R_{01}$.

In an embodiment of the present application, $R_{101-105}$ are separately and independently selected from the group consisting of H,

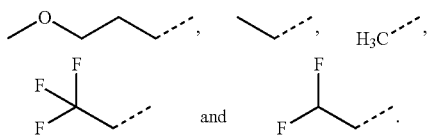

In an embodiment of the present application, $R_1$ and $R_3$ are separately and independently selected from the group consisting of H,

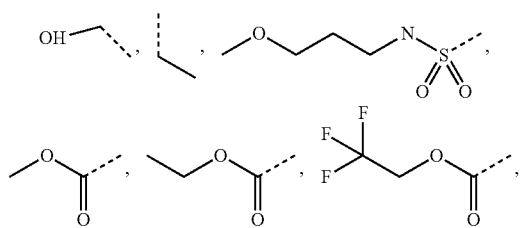

In an embodiment of the present application, $R_2$ is selected from

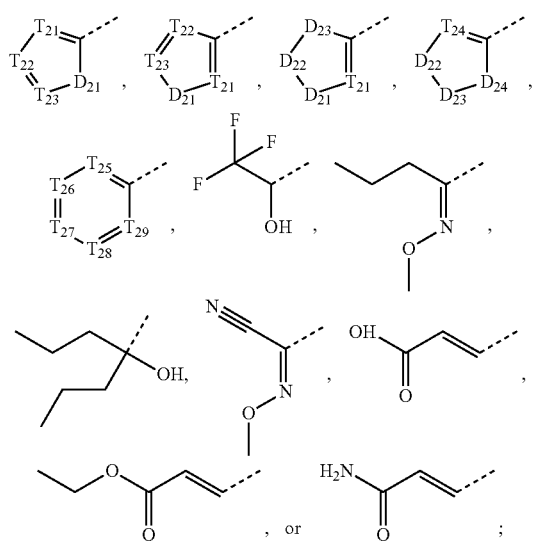

wherein:
from zero to two of $T_{21-23}$ is N, and the rest is $C(R_t)$;
$D_{21}$ is selected from $—C(R_{d1})(R_{d2})—$, $—C(=O)N(R_{d3})—$, $—N(R_{d4})—$, $—C(=NR_{d5})—$, $—S(=O)_2N(R_{d6})—$, $—S(=O)N(R_{d7})—$, $—O—$, $—S—$, $—C(=O)O—$, $—C(=O)—$, $—C(=S)—$, $—S(=O)—$, $—S(=O)_2—$ or $—N(R_{d8})C(=O)N(R_{d9})—$;
$T_{24}$ is selected from N or $C(R_t)$;
$D_{22-24}$ are separately and independently selected from $—C(R_{d1})(R_{d2})—$, $—C(=O)N(R_{d3})—$, $—N(R_{d4})—$, $—C(=NR_{d5})—$, $—S(=O)_2N(R_{d6})—$, $—S(=O)N(R_{d7})—$, $—O—$, $—S—$, $—C(=O)O—$, $—C(=O)—$, $—C(=S)—$, $—S(=O)—$, $—S(=O)_2—$ or $—N(R_{d8})C(=O)N(R_{d9})—$;
from zero to two of $T_{25-29}$ is N, and the rest is $C(R_t)$;
optionally, any two of $R_t$ and $R_{d1-d9}$ are bonded to a common atom or group together to form one or two 3- to 8-membered rings;
$R_t$, $R_{d1}$ and $R_{d2}$ are separately and independently selected from H, F, Cl, Br, I, CN, OH, SH, $NH_2$, CHO, COOH, $C(=O)NH_2$, $S(=O)NH_2$, or $S(=O)_2NH_2$; or $R_t$, $R_{d1}$ and $R_{d2}$ are separately and independently selected from the group, optionally substituted by $R_{01}$, consisting of $C_{1-10}$ alkyl, $C_{1-10}$ alkyl heteroalkyl, $C_{3-10}$ cyclic hydrocarbyl, or $C_{3-10}$ heterocyclic hydrocarbyl, $C_{1-10}$ alkyl substituted by $C_{3-10}$ cyclohydrocarbyl or $C_{3-10}$ heterocyclohydrocarbyl, $C_{1-10}$ heteroalkyl substituted by $C_{3-10}$ cyclohydrocarbyl or $C_{3-10}$ heterocyclohydrocarbyl, $C_{1-10}$ alkenyl, and $C_{1-10}$ heteroalkenyl;

In an embodiment of the present application, $R_2$ is separately and independently selected from

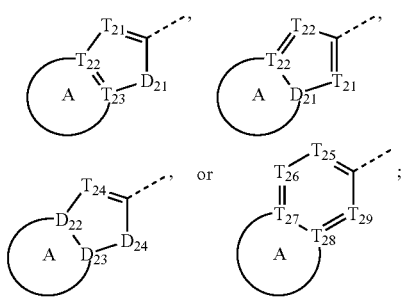

wherein a represents 3- to 8-membered saturated or unsaturated carbocycle or heterocycle, each optionally substituted by 0, 1, 2 or 3 $R_t$.

In an embodiment of the present application, $R_2$ is separately and independently selected from

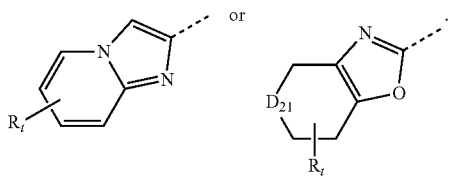

In an embodiment of the present application, $R_t$ and $R_{d1-d9}$ are separately and independently selected from H, $NH_2$, or CN; or $C_{1-6}$ alkyl, $C_{1-6}$ heteroalkyl, $C_{3-6}$ cycloalkyl, $C_{3-6}$ heterocyclic alkyl, a 5- or 6-membered unsaturated heterocyclic group, or aminoacyl, each optionally substituted by $R_{001}$; $R_t$ and $R_{d1-d2}$ are separately and independently selected from F, Cl, Br, or I.

In an embodiment of the present application, $R_t$ and $R_{d1-d9}$ are preferably separately and independently selected from $C_{1-6}$ alkylamino, N,N-di($C_{1-3}$ alkyl) amino, $C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{3-6}$ cycloalkyl, $C_{3-6}$ cycloalkylamino, $C_{3-6}$ heterocyclic alkylamino, $C_{3-6}$ cycloalkoxy, $C_{3-6}$ cycloalkyl acyl, $C_{3-6}$ cyclic alkoxycarbonyl, $C_{3-6}$ cycloalkylsulfonyl, $C_{3-6}$ cycloalkylsulfinyl, aminoacyl, or 5- to 6-membered unsaturated heterocyclyl, each optionally substituted by $R_{001}$.

In an embodiment of the present application, $R_t$ and $R_{d1-d9}$ are separately and more preferably independently selected from 5- to 6-membered aryl or 5- to 6-membered heteroaryl, each optionally substituted by $R_{001}$.

In an embodiment of the present application, $R_t$ and $R_{d1-d9}$ are more preferably separately and independently selected from phenyl, pyridyl or thienyl, each optionally substituted by $R_{001}$.

In an embodiment of the present application, wherein the hetero atom or the hetero atom-containing group is selected from O, N, S, —C(=O)O—, or

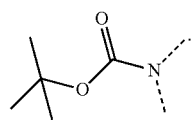

In an embodiment of the present application, $R_t$ and $R_{d1-d9}$ are separately and independently selected from H, F, Cl, Br, I, $NH_2$, $CH_3$, CN,

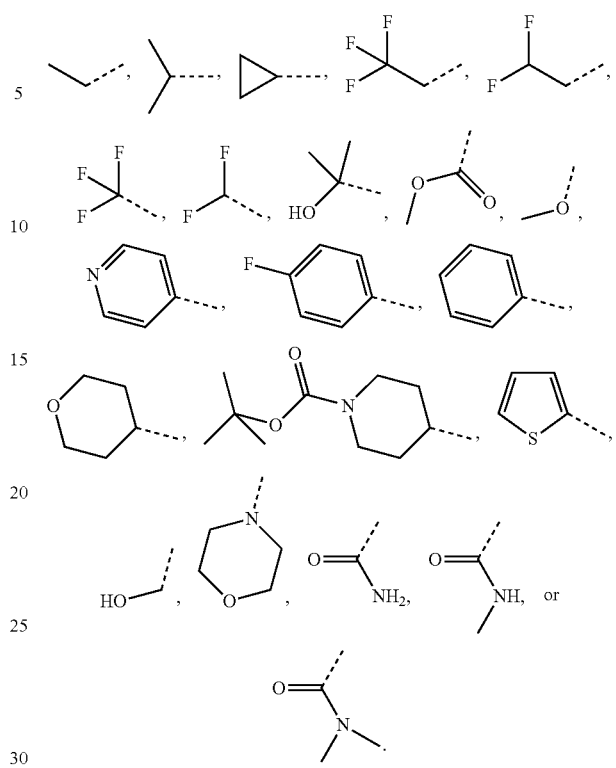

In an embodiment of the present application, $R_{1-3}$ are separately and independently selected from:

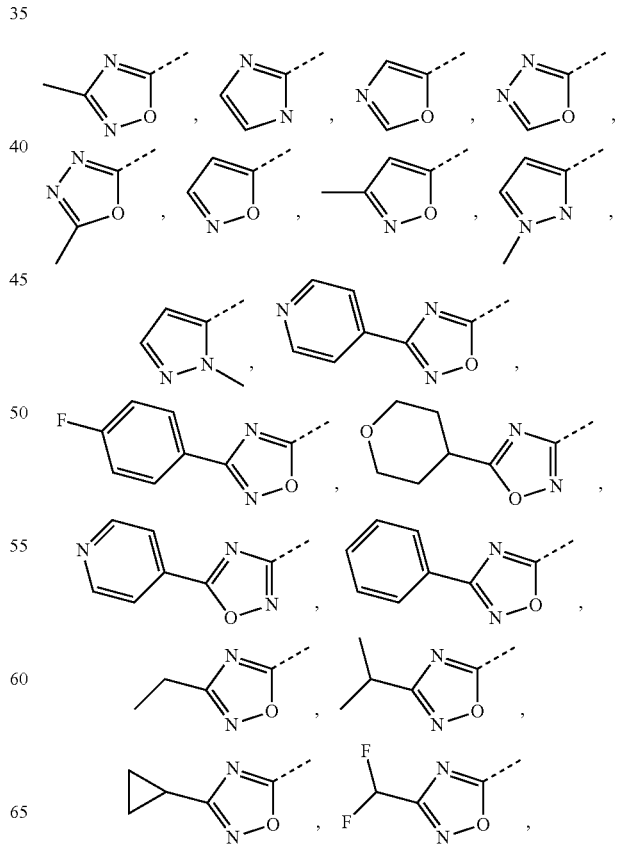

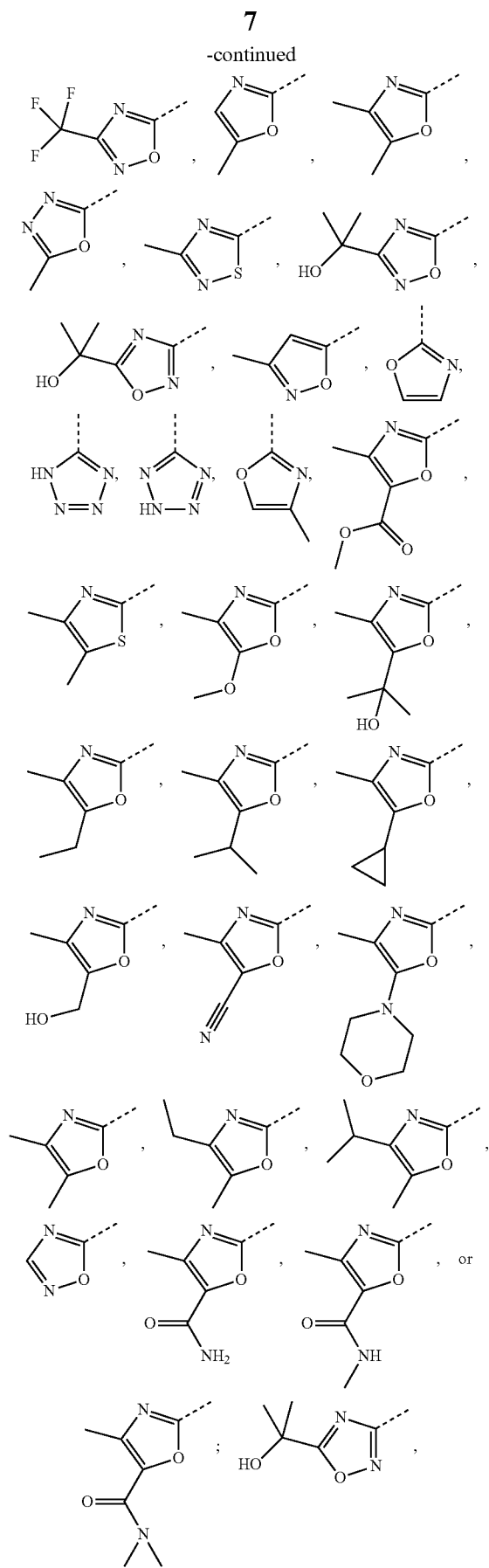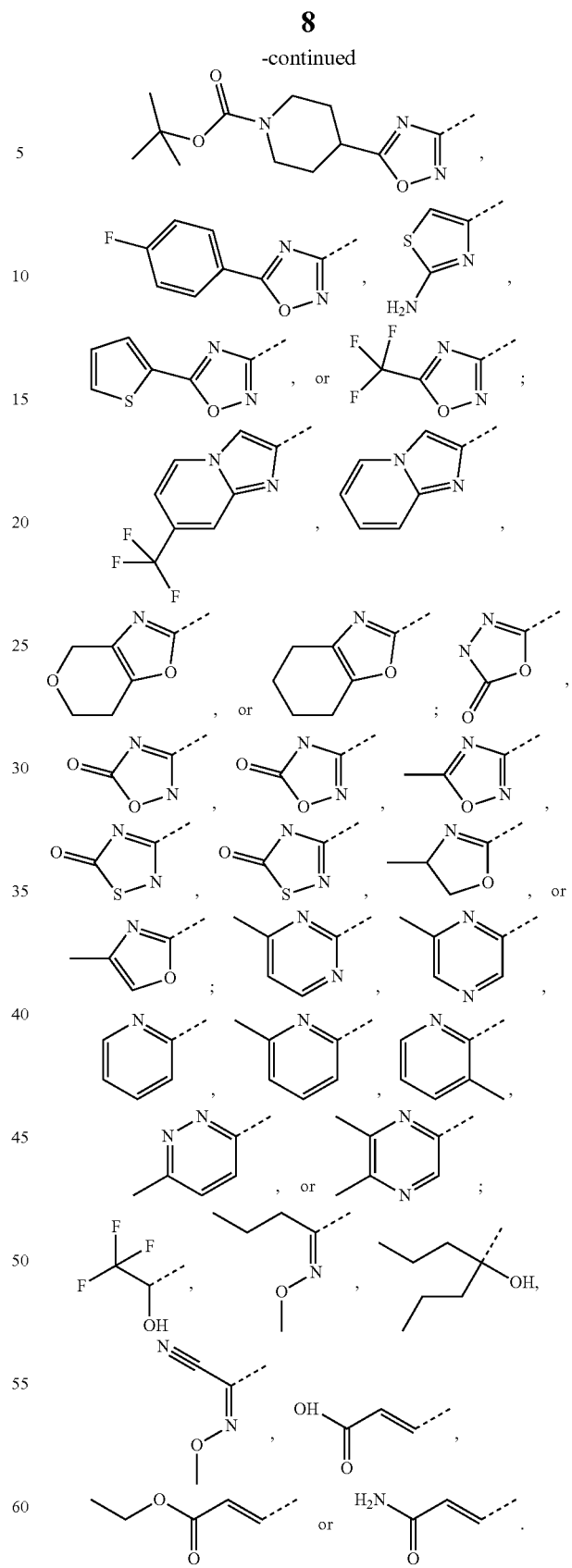
In an embodiment of the present application, the compound and the pharmaceutically acceptable salts and tautomers thereof according to Claim 1 selected from:

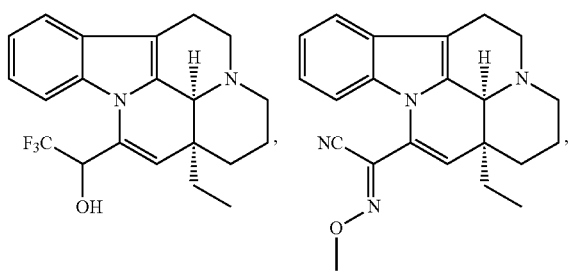
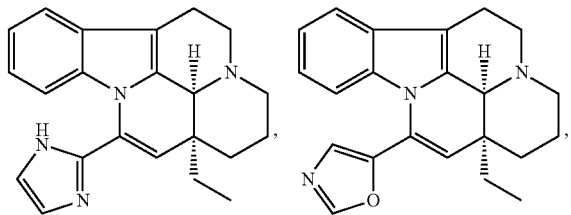
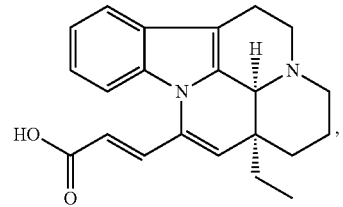
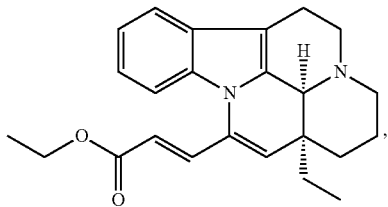
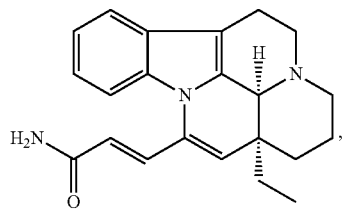
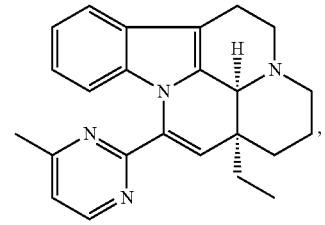
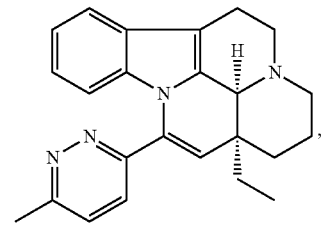
-continued
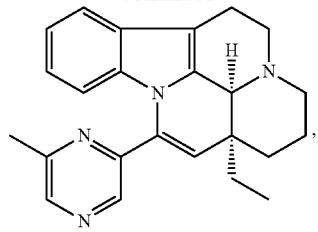
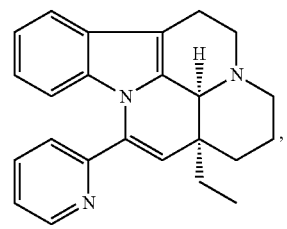
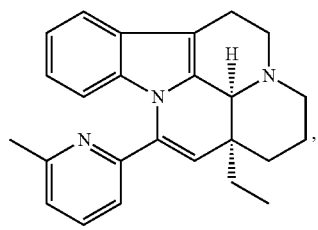
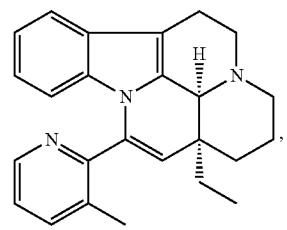
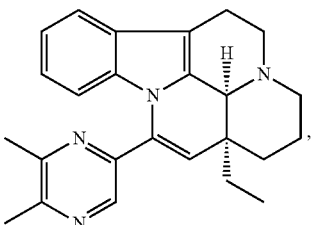
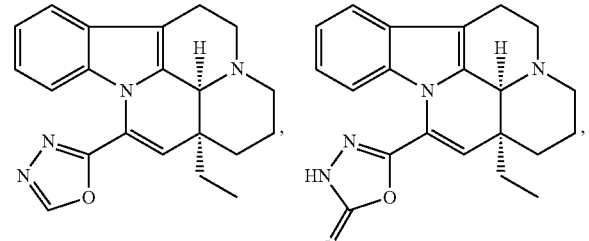
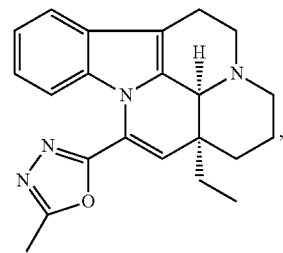

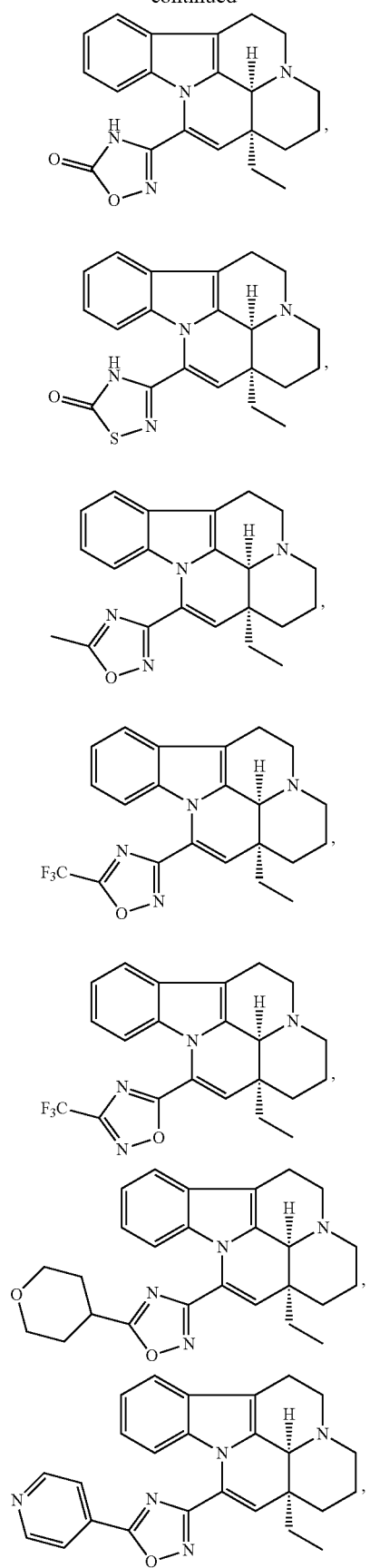

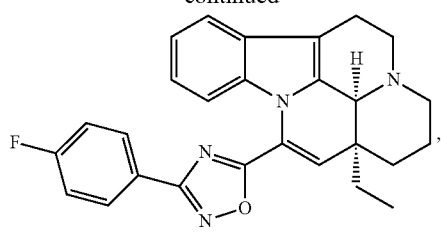
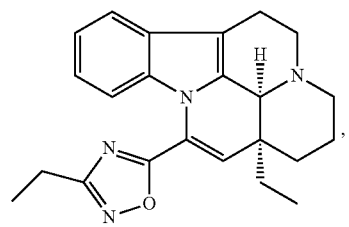
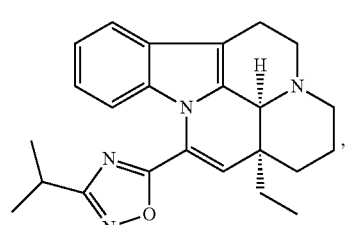
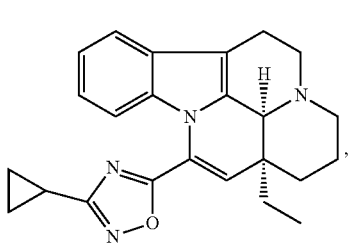
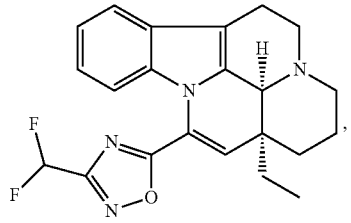
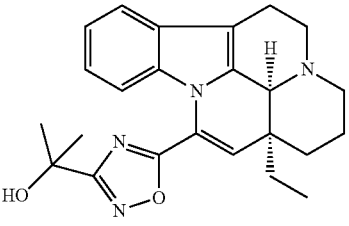
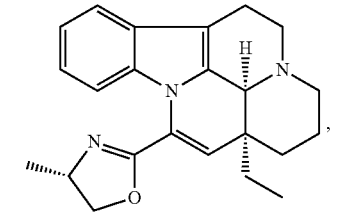
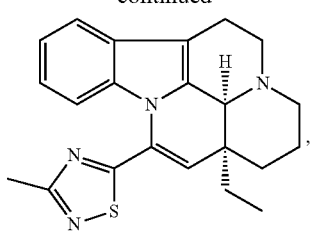
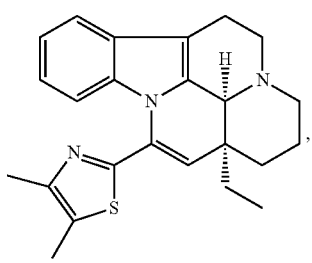
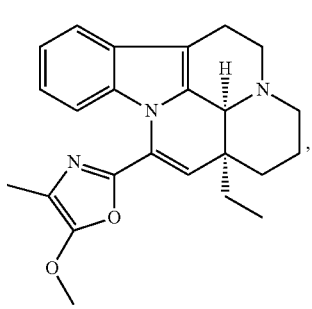
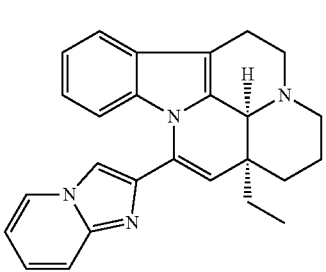
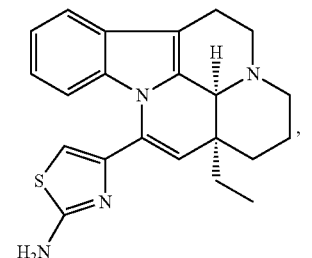
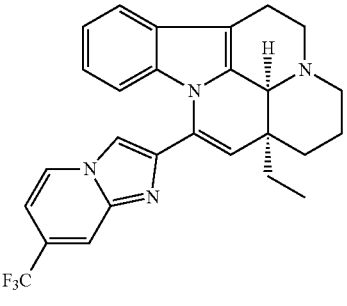

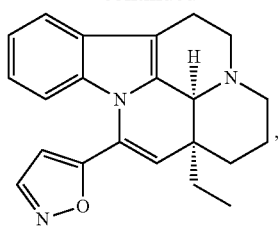
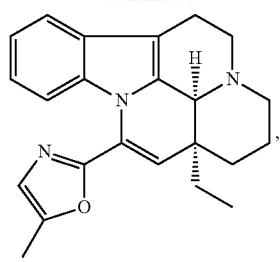
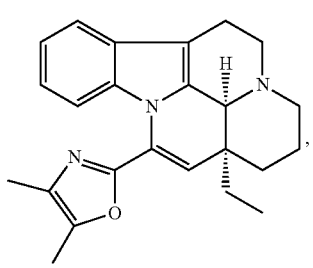
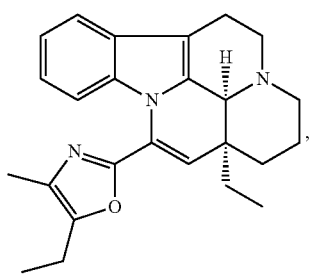
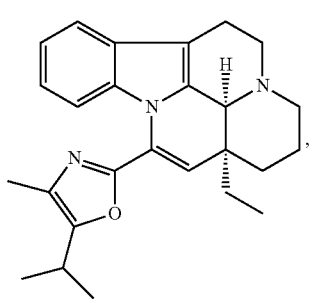
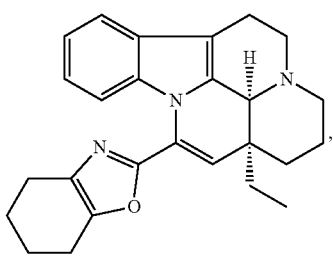
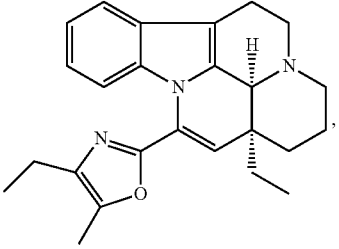

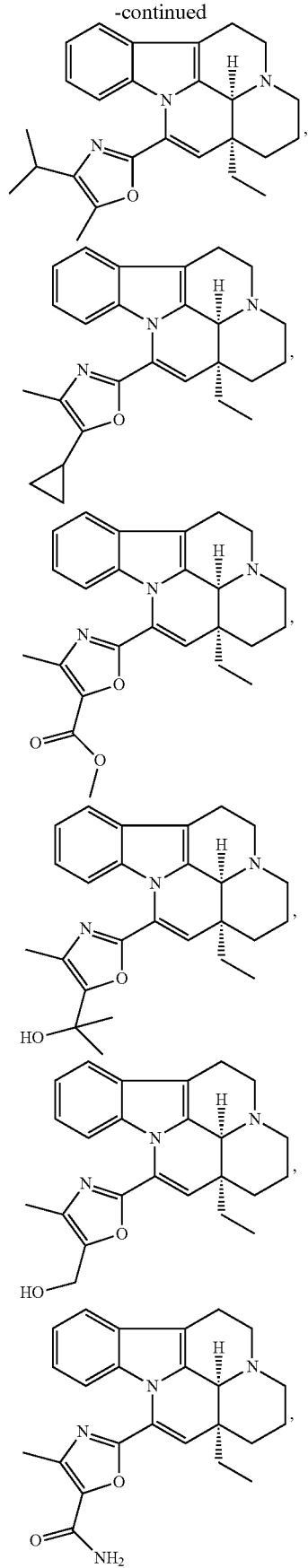
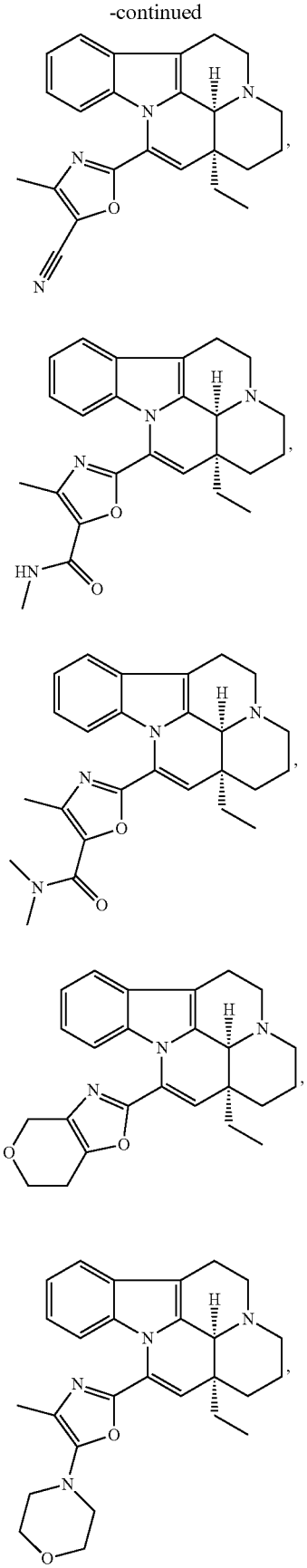

-continued
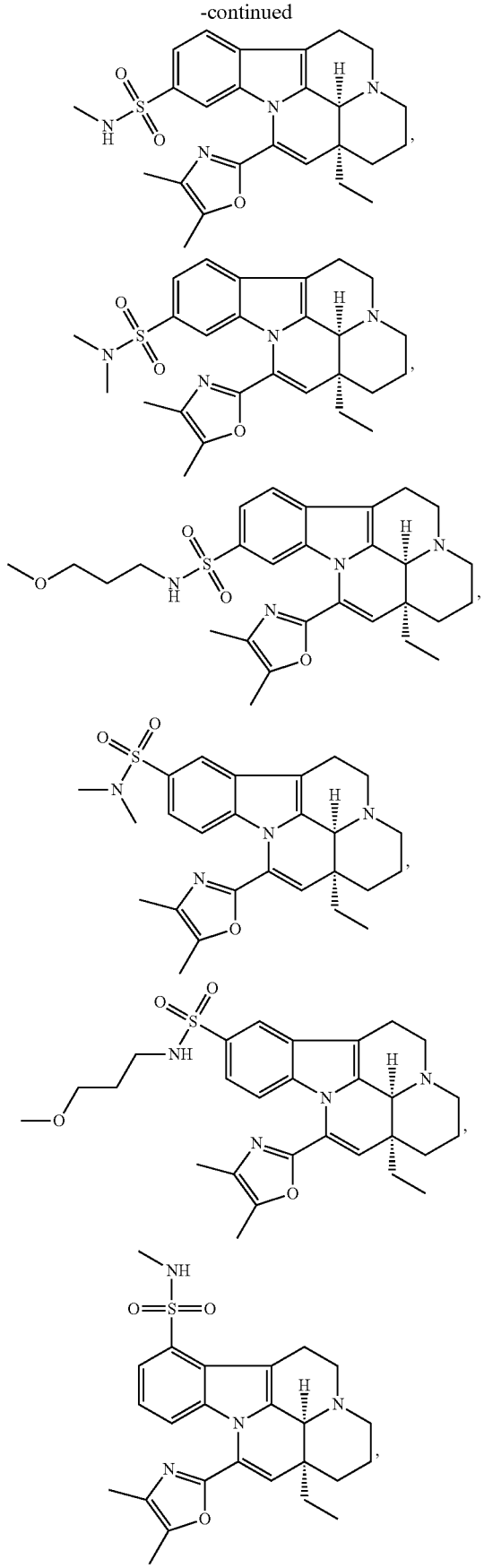
-continued
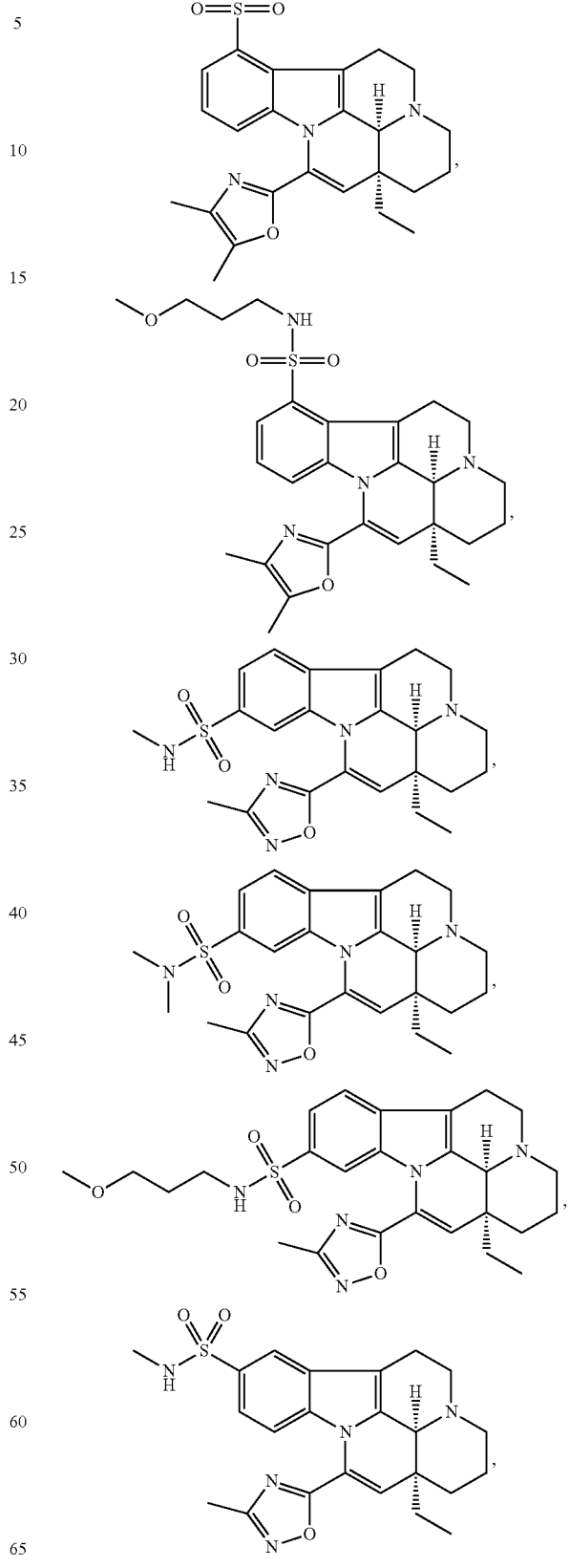

21
-continued

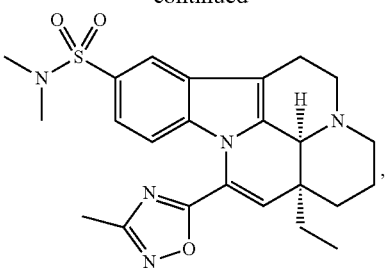

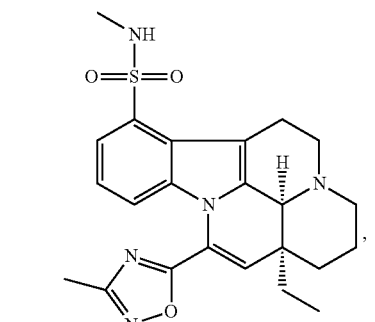

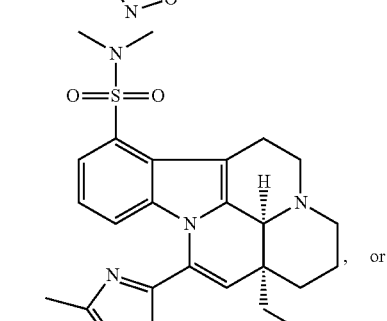

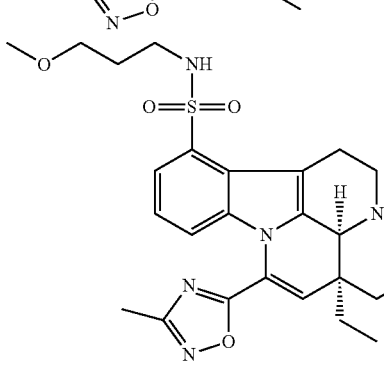

, or

The present application also provides a use of the compound and the pharmaceutically acceptable salts and tautomers thereof in the manufacture of a medicament for treating cerebral apoplexy or epilepsy.

22
Definition

Unless otherwise defined, the terms and phrases used herein have the meaning stated below. If a particular term or phrase is not specifically defined, such term or phrase should not be considered indefinite. Rather, terms are used within their accepted meanings. The trade names used herein are intended to refer to the corresponding products or active ingredients.

$C_{1-10}$ is selected from $C_1$, $C_2$, $C_3$, $C_4$, $C_5$, $C_6$, $C_7$, $C_8$, $C_9$, or $C_{10}$; and $C_{3-10}$ is selected from $C_3$, $C_4$, $C_5$, $C_6$, $C_7$, $C_8$, $C_9$, or $C_{10}$.

$C_{1-10}$ alkyl or heteroalkyl, $C_{3-10}$ cyclic hydrocarbyl or heterocyclic hydrocarbyl, $C_{1-10}$ alkyl or heteroalkyl substituted by $C_{3-10}$ cyclic hydrocarbyl or heterocyclic hydrocarbyl include, but are not limit to the groups as follows:

$C_{1-10}$ alkyl, $C_{1-10}$ alkylamino, N,N-di ($C_{1-10}$ alkyl) amino, $C_{1-10}$ alkoxy, $C_{1-10}$ alkylacyl, $C_{1-10}$ alkoxycarbonyl, $C_{1-10}$ alkyl sulfonyl, $C_{1-10}$ alkyl sulfinyl, $C_{3-10}$ cyclic alkyl, $C_{3-10}$ cyclic alkylamino, $C_{3-10}$ hetero cyclic alkylamino, $C_{3-10}$ cyclic alkoxy, $C_{3-10}$ cyclic alkylacyl, $C_{3-10}$ cyclic alkoxycarbonyl, $C_{3-10}$ cyclic alkyl sulfonyl, $C_{3-10}$ cyclic alkyl sulfinyl;

methyl, ethyl, propyl, isopropyl, —CH$_2$C(CH$_3$)(CH$_3$)(OH), cyclopropyl, cyclobutyl, propyl methene, cyclopropionyl, benzyloxy, trifluoromethyl, aminomethyl, hydroxymethyl, methoxy, formyl, methoxyl carbonyl, methyl sulfonyl, methyl sulfonyl, ethoxy, acetyl, ethyl sulfonyl, ethoxy carbonyl, dimethyl amine, diethyl amine, dimethyl amino carbonyl, diethyl amino carbonyl;

N(CH$_3$)$_2$, NH(CH$_3$), —CH$_2$CF$_3$, —CH2CH$_2$CF$_3$, —CH$_2$CH$_2$F, —CH$_2$CH$_2$S(=O)$_2$CH$_3$, —CH$_2$CH$_2$CN,

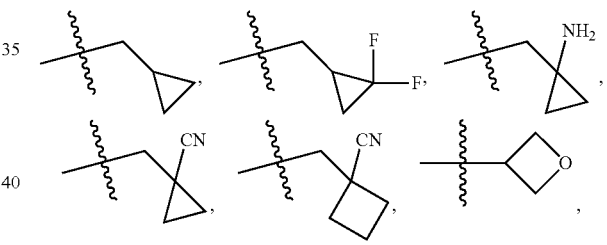

—CH$_2$CH(OH)(CH3)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$,

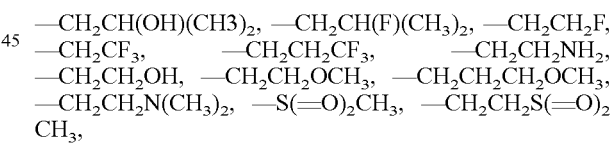

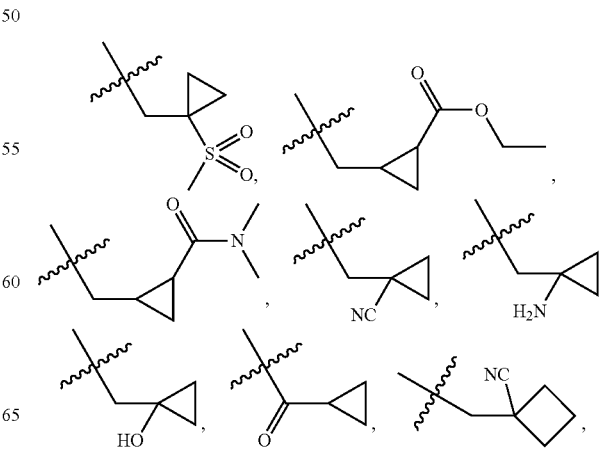

-continued
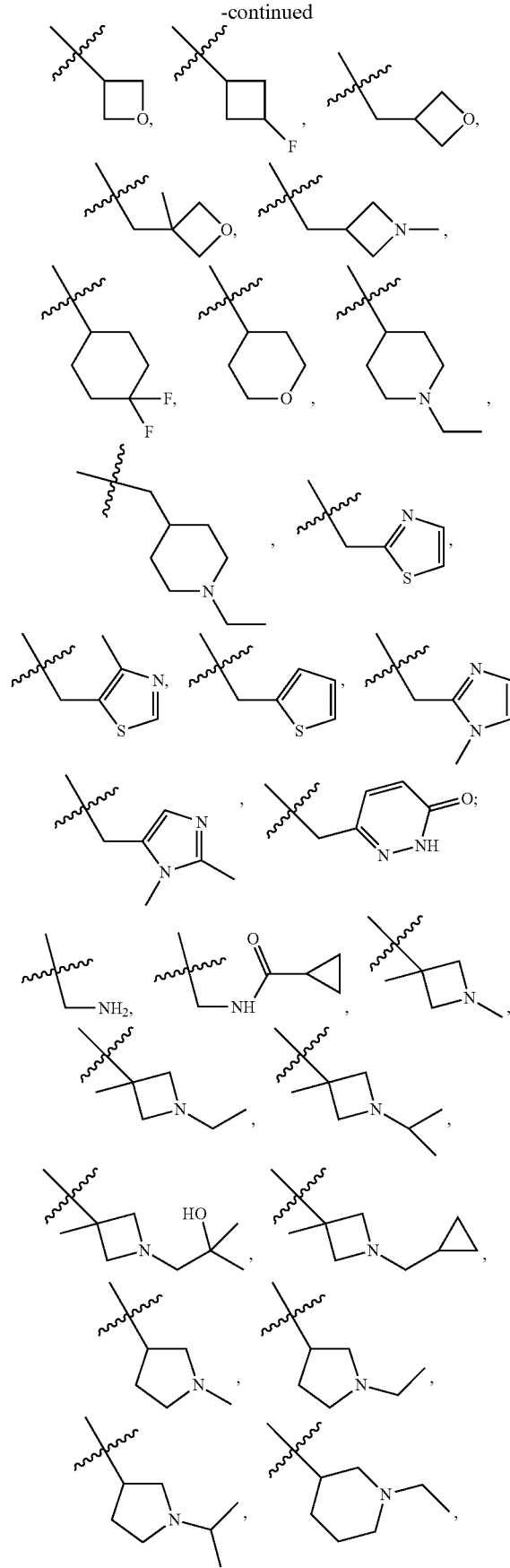
-continued
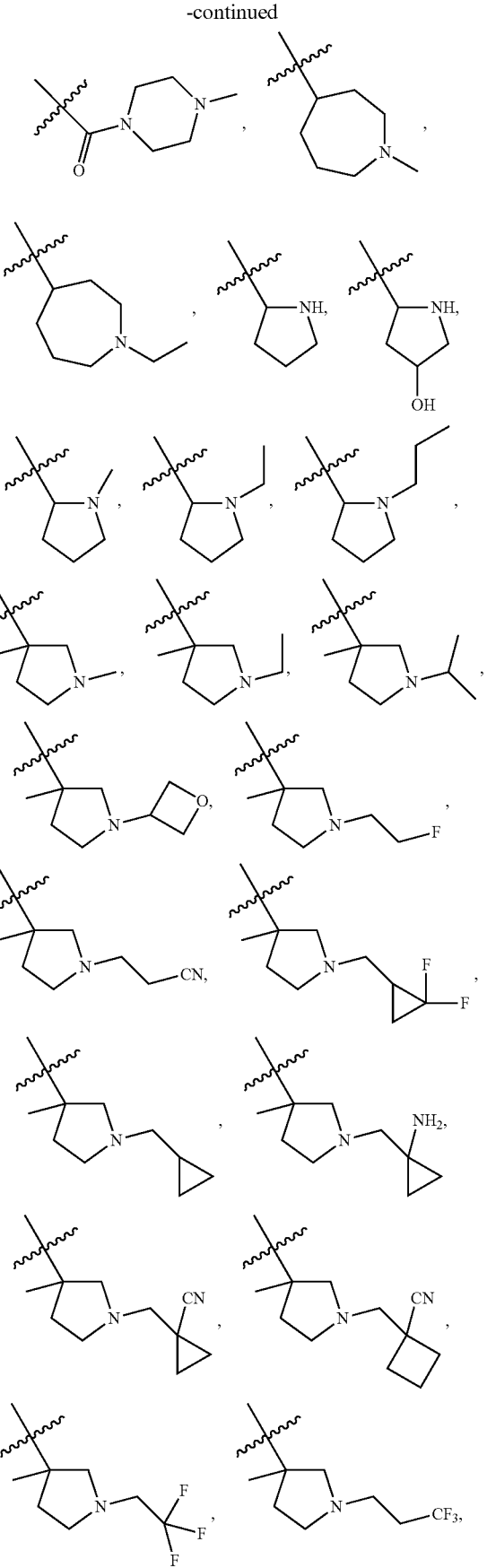

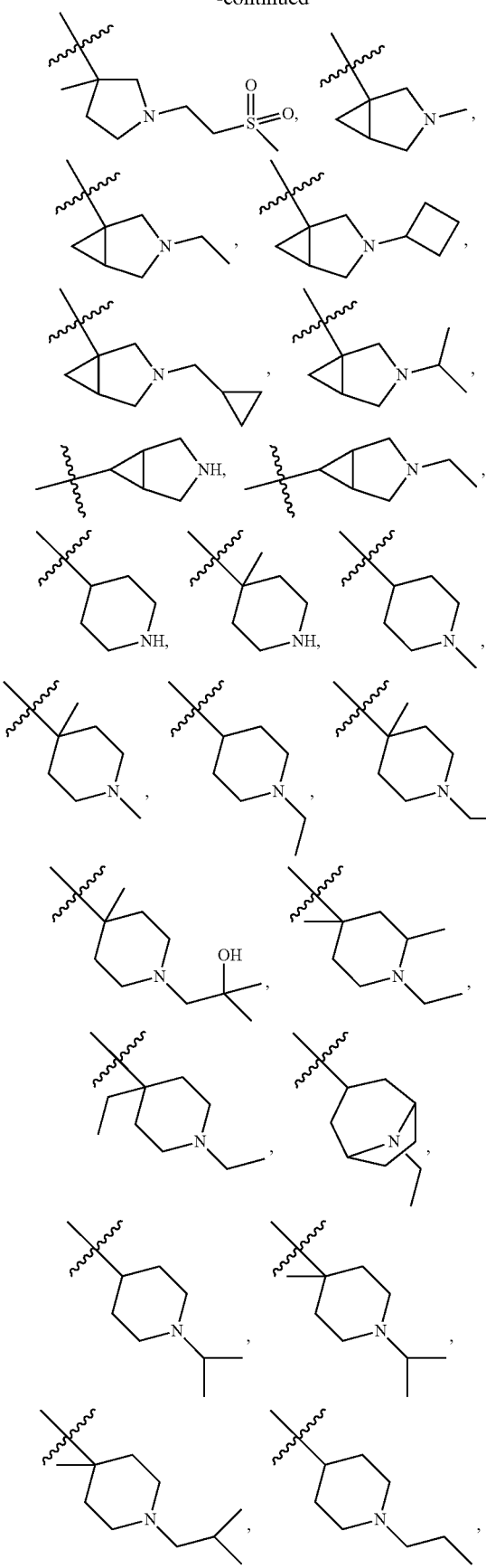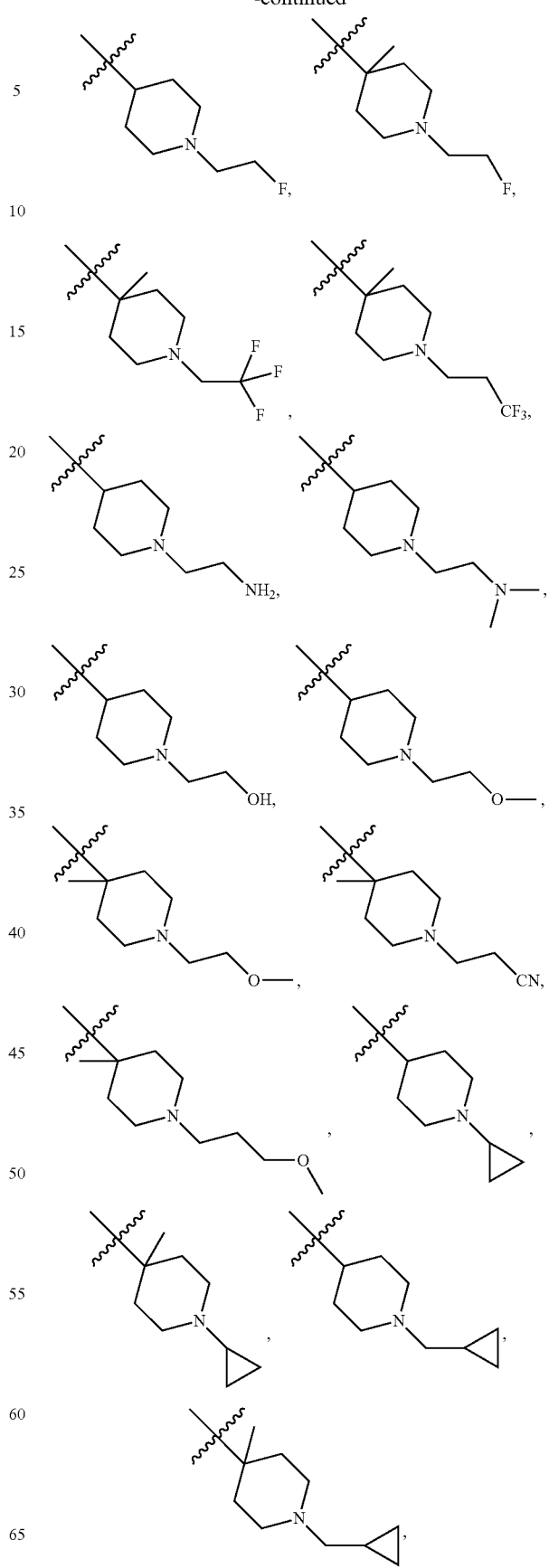

-continued
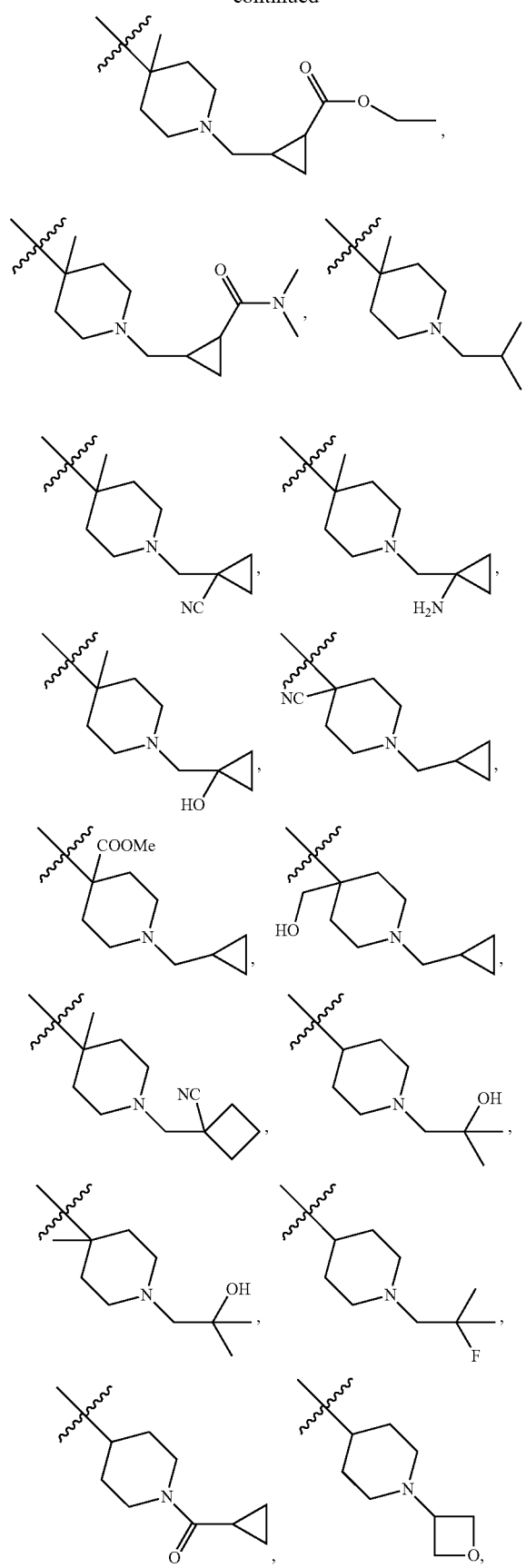
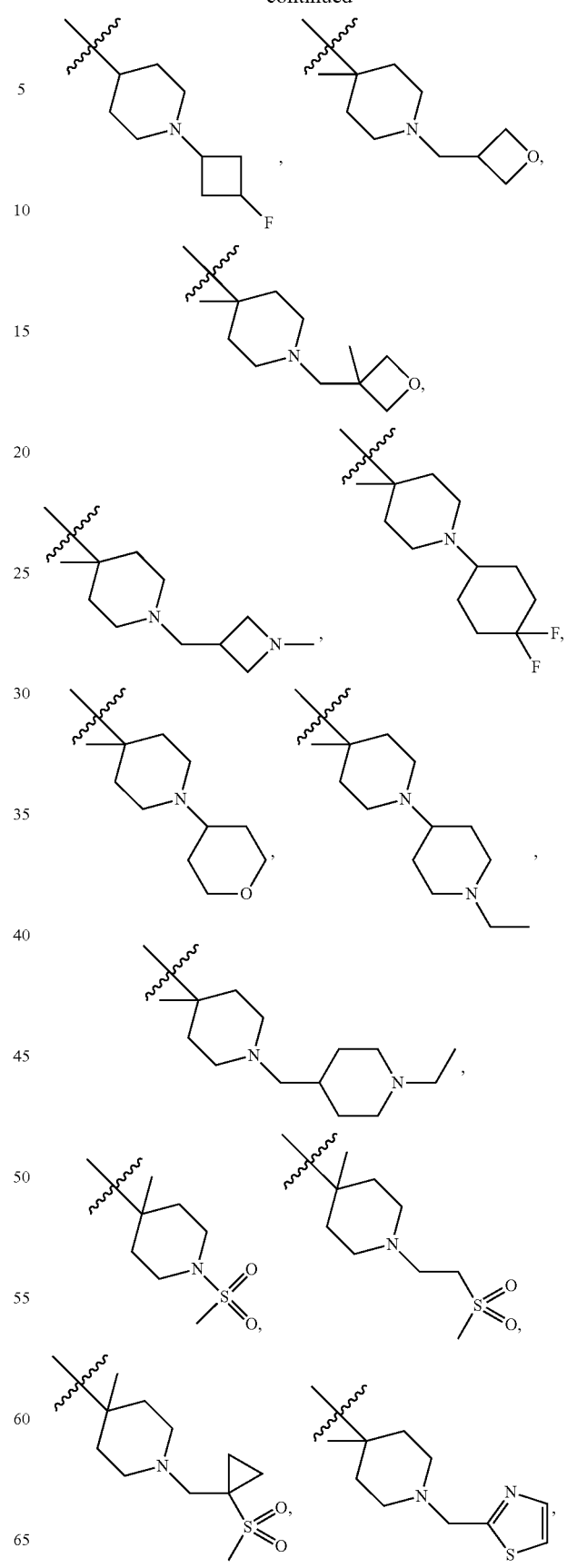

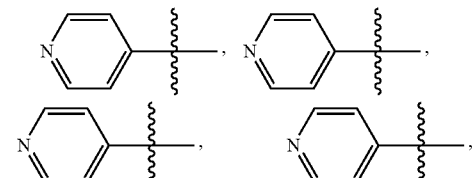
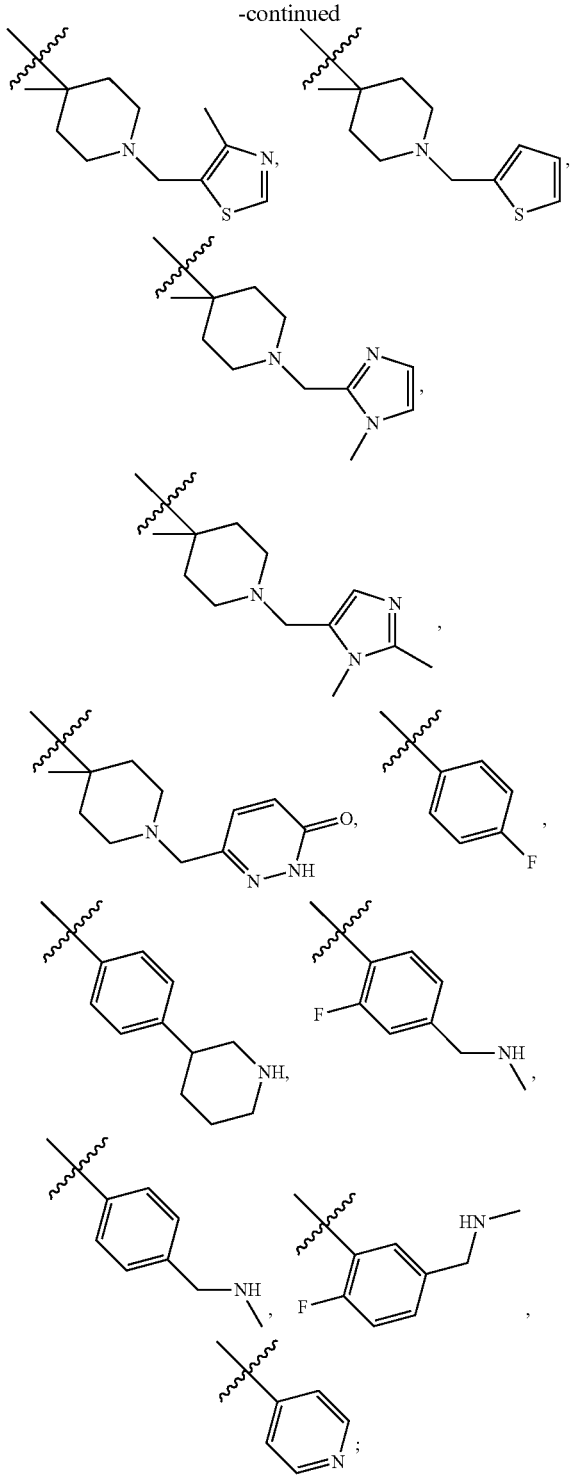

phenyl, thiazolyl, biphenyl, naphthyl, cyclopentyl, furan, 3-pyrrolidine pyrrolidine, 1,3-dioxolan, pyrazolyl, 2-pyrazolinyl, pyrazolidinyl, imidazole, oxazolyl, thiazolyl, 1,2,3-imidazolyl, 1,2,3-triazolyl, 1,2,4-triazolyl, 1,3,4-thiadiazolyl, 4H-pyranyl, pyridyl, piperidinyl, 1,4-dioxane, morpholinyl, pyridazinyl, pyrimidinyl, pyrazinyl, piperazinyl, 1,3,5-trithiane, 1,3,5-triazinyl, benzofuranyl, benzothienyl, indolyl, benzimidazolyl, benzothiazolyl, purinyl, quinolinyl, iso quinolinyl, cinnolinyl or quinoxalinyl;

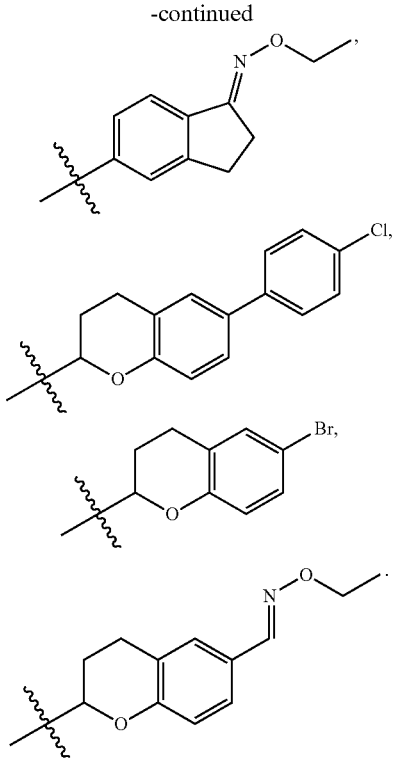

As used herein, the term "pharmaceutically acceptable" refers to those compounds, materials, compositions and/or dosage forms that are within the scope of reliable medical judgment, are suitable for contacting with the tissues of human beings and animals without excessive toxicity, irritation, allergic response or other problems or complications, and are commensurate with a reasonable benefit/risk ratio.

The term "pharmaceutically acceptable salts" refers to salts of the compounds of the present invention, which are prepared with relatively non-toxic acids or bases and compounds having particular substituents of the present invention. When compounds of the present invention contain relatively acidic functional groups, base addition salts can be obtained by contacting the neutral form of such compounds with a sufficient amount of base, either neat or in a suitable inert solvent. Pharmaceutically acceptable base addition salts include sodium, potassium, calcium, ammonium, organic amino or magnesium salt or a similar salt. When compounds of the present invention contain relatively basic functional groups, acid addition salts can be obtained by contacting the neutral form of such compounds with a sufficient amount of acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxy naphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic.

The pharmaceutically acceptable salts of the present invention can be synthesised by conventional chemical methods from parent compounds containing acidic or basic residues. In general, such salts are prepared by reacting the free acid or base forms of these compounds with a stoichiometric amount of a suitable base or acid in water or in an organic solvent or in a mixture of the two. In general, non-aqueous media such as ether, ethyl acetate, ethanol, isopropanol or acetonitrile are preferred.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an in vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention possess asymmetric carbon atoms (optical centers) or double bonds. The racemates, diastereomers, geometric isomers and individual isomers are encompassed within the scope of the invention.

The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included within the scope of the present invention.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (5)-isomers and d and l isomers can be prepared using chiral synthons, chiral catalysts, or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radio labeled with radioactive isotopes, such as for example tritium ($^3H$), iodine-125 ($^{125}I$) or C-14 ($^{14}C$). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not negatively interfere with the effectiveness of the biological activity of the active agent, and that is sufficiently non-toxic to the host. Representative carriers include water, oils, both vegetable and mineral, cream bases, lotion bases, ointment bases and the like. These bases include suspending agents, thickeners, penetration enhancers, and the like. Their formulation is well known to those in the art of topical pharmaceuticals. Additional information concerning carriers can be found in Remington: The Science and Practice of Pharmacy. 21st Ed., Lippincott, Williams & Wilkins (2005) which is incorporated herein by reference.

The term "excipient" generally refers to carriers, diluents and/or mediums required to formulate an effective pharmaceutical composition.

For drugs or pharmacologically active agents, the term "effective amount" or "therapeutically effective amount" refers to a non-toxic but sufficient amount of the drug or formulation to provide the desired effect. For the oral formulations of the present invention, the "effective amount" of an active substance in a composition refers to the amount required to achieve the desired effect when used in combination with another active substance in the composition. The effective amount varies from person to person, depending on the age and general condition of the recipient, as well as on the particular active substance. The appropriate effective amount in every individual case can be determined by the person skilled in the art using conventional testing.

The term "active ingredient", "therapeutic agent", "active substance" or "active agent" refers to a chemical entity, which is effective in treating disorder, disease or illness of a target subject.

The term "substituted" means that any one or more of the hydrogen atoms on a particular atom is substituted by a substituent or substituents, including deuterium and variants of hydrogen, as long as the valence state of the particular atom is normal and the substituted compound is stable. When the substituent is a ketone group (i.e., =O), it means that two hydrogen atoms are substituted. Ketone substitutions do not occur in at aromatic groups. The term "optionally substituted" means that it may or may not be substituted. Unless otherwise specified, the type and number of substituents can be arbitrary under the premise that they are chemically achievable.

When any variable (e.g., R) occurs more than once in the composition or structure of the compound, its definition in each case is independent. Thus, for example, if a group is substituted with 0-2 R, the group may optionally be substituted by up to two R, and in each case the R has an independent option. In addition, the combination of substituents and/or their variants is allowed only if such a combination will produce a stable compound.

When a bond of a substituent could be cross-linked to two atoms on a ring, such substituent may be bonded to any atoms in the ring. Where the listed substituent does not specify through which atom it is connected to the general structure formula including the compound that is not specifically mentioned, the substituent may be bonded through any one of its atoms. The combination of substituents and/or variant thereof is allowed only if such a combination results in a stable compound.

The substituents for an alkyl and heteroalkyl groups (including those groups commonly referred to as alkylene, alkenyl, heteroalkylene, heteroalkenyl, alkynyl, cycloalkyl, heterocycloalkyl, cycloalkenyl and heterocycloalkenyl) are generally referred to as "alkyl substituents". They may be selected from, but not limited to, one or more of the following groups: —R', —OR', =O, =NR', =N—OR', —NR'R", —SR', halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR""—C(NR'R"R'") =NR"", NR""C(NR'R")=NR'", —S(O)R', —S(O)$_2$R', —S(O)$_2$NR'R", NR"SO$_2$R', —CN, —NO$_2$, —N$_3$, —CH(Ph)$_2$ and fluoro(C$_1$-C$_4$)alkyl, the number of the substituent is 0 to (2m'+1), where m' is the total number of carbon atoms in such groups. Preferably, R', R", R'", R"" and R""' are each independently hydrogen, substituted or unsubstituted heteroalkyl, substituted or unsubstituted aryl (e.g., aryl substituted by 1 to 3 halogen(s)), substituted or unsubstituted alkyl, alkoxy, thioalkoxy or aralkyl. When the compound of the present invention includes more than one R groups, for example, each R group is independently selected, and so does when the compounds of the present invention comprise more than one R', R", R'", R"" or R""' group When R' and R" are attached to the same nitrogen atom, they may bind to the nitrogen atom to form a 5-, 6- or 7-membered ring. For example, —NR'R" is intended to include, but are not limited to, 1-pyrrolidinyl and 4-morpholinyl. According to the above discussion on substituents, it will be understood by those skilled in the art that the term "alkyl" is intended to include groups in which carbon atoms are bonded to non-hydrogen groups, such as haloalkyl (e.g., —CF3, —CH2CF3) and acyl (e.g., —C(O)CH3, —C(O)CF3, —C(O)CH2OCH3, etc.).

Similar to the substituents described for alkyl radicals, substituents for aryl and heteroaryl are generically referred to as "aryl group substituents", which are selected from, for example, —R', —OR', —NR'R', —SR', halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR""—C(NR'R"R'")=NR"", NR""C(NR'R")=NR'", —S(O)R', —S(O)$_2$R', —S(O)$_2$NR'R", NR"SO$_2$R', —CN, —NO$_2$, —N$_3$, —CH(Ph)$_2$, Fluoro (C$_1$-C$_4$) alkoxy and fluoro (C$_1$-C$_4$) alkyl in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(0)-(CRR')q-U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula —A—(CH2)r—B—, wherein A and B are independently —CRR'—, —O—, —NR—, —S—, —S(O)—, —S(0)2-, —S(0)2NR'— or a single bond, and r is an integer from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X—(CR"R'")d-, where s and d are independently integers from 0 or 1 or 2 or 3, and X is —O—, —NR'—, —S—, —S(O)—, —S(0)2—, or —S(0)2NR'—. The substituents R, R', R" and R'" are preferably independently selected from hydrogen or substituted or unsubstituted (C1 or C2 or C3 or C4 or C5 or C6)alkyl.

Unless otherwise specified, the terms "halo" and "halogen," by themselves or as part of another substituent, refer to a fluorine, chlorine, bromine, or iodine atom. Additionally, terms such as "haloalkyl" are meant to include monohaloalkyl and polyhaloalkyl. For example, the term "halo (C$_1$-C$_4$) alkyl" is intended to include, but are not limited to, trifluoromethyl, 2,2,2-trifluoroethyl, 4-chlorobutyl and 3-bromopropyl.

Examples of haloalkyl include, but are not limited to trifluoromethyl, trichloromethyl, pentafluoroethyl, and pentachloroethyl. The term "alkoxy" refers to the alkyl as described above having a specific number of carbon atoms attached by an oxygen bridge. C$_{1-6}$ alkoxy includes C$_1$, C$_2$, C$_3$, C$_4$, C$_5$ and C$_6$ alkoxy. Examples of "alkoxy" include, but are not limited to, methoxy, ethoxy, n-propoxy, isopropoxy, n-butoxy, sec-butoxy, tert-butoxy, n-pentyloxy and S-pentyloxy. Cycloalkyl groups include saturated cyclic groups such as cyclopropyl, cyclobutyl or cyclopentyl groups. C$_{3-7}$ cycloalkyl include C$_3$, C$_4$, C$_5$, C$_6$ and C$_7$ cycloalkyl. Alkenyl includes a linear or branched hydrocarbon chain in which one or more carbon-carbon double bonds such as vinyl and propenyl are present at any stable sites on the chain.

The terms "halo" or "halogen" refers to fluorine, chlorine, bromine and iodine.

Unless otherwise specified, the term "hetero" refers to a hetero atom or hetero radical (i.e., a hetero atom-containing group), including the atoms besides carbon (C) and hydrogen (H) and groups containing these heteroatoms, such as oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)2-, and optionally substituted —C(=O)N(H)—, —N(H)—, —C(=NH)—, —S(=O)2N(H)—, or —S(=O)N(H)—.

Unless otherwise specified, the term "ring" refers to substituted or unsubstituted cycloalkyl, heterocycloalkyl, cycloalkenyl, heterocycloalkenyl, cycloalkynyl, heterocycloalkynyl, aryl or heteroaryl. As described herein "ring" includes monocyclic, bicyclic, spiro, fused or bridged ring. The number of atoms on the ring is generally defined by the number of members on the ring, for example, a "5- to 7-membered ring" means that there are 5 to 7 atoms in the encircling arrangement. Unless otherwise specified, the ring optionally comprises from 1 to 3 heteroatoms. Thus, the term "5- to 7-membered ring" includes, for example phenylpyridine and piperidinyl; on the other hand, the term "5- to 7-membered heterocycloalkyl ring" would include pyridyl and piperidinyl, but not phenyl. The term "ring" also includes a ring system comprising at least one ring, wherein each ring is independently within the definitions as described above.

Unless otherwise specified, the term "heterocycle" or "heterocyclyl" refers to a stable monocyclic, bicyclic or tricyclic ring containing a hetero atom or a hetero atom-containing group, which may be saturated, partially unsaturated or unsaturated (e.g., aromatic), and comprises carbon atoms and 1, 2, 3 or 4 hetero atoms independently selected from N, O or S; wherein any of heterocycles as described herein may be fused to a benzene ring to form a bicyclic ring. Optionally, the nitrogen and sulfur heteroatoms may be oxidized (i.e., NO and S(O)p). Nitrogen atom may be substituted or unsubstituted (i.e., N or NR, wherein R is H or other substituents already defined herein). The heterocyclic ring may be attached to its pendant group at any heteroatom or carbon atom which results in a stable structure. If the resulting compound is stable, the heterocyclic rings described herein may be substituted on carbon or on a nitrogen atom. A nitrogen atom in the heterocyclic ring may optionally be quaternized. In a preferred embodiment, when the total number of S and O atoms in the heterocyclic ring exceeds 1, then these heteroatoms are not adjacent to each other. In another preferred embodiment, the total number of S and O atoms in the heterocycle is not more than 1. As used herein, the terms "aromatic heterocyclic group" or "heteroaryl" means a stable 5-, 6-, or 7-membered monocyclic or bicyclic aromatic ring or a 7-, 8-, 9- or 10-membered bicyclic heterocyclyl aromatic ring, Which contains carbon atoms and 1, 2, 3 or 4 heteroatoms independently selected from N, O and S. The nitrogen atom may be substituted or unsubstituted (i.e., N or NR, wherein R is H or other substituent already defined herein). Optionally, the nitrogen and sulfur heteroatoms may be oxidized (i.e., NO and S(O)p). It should be noted that the total number of S and O atoms in the aromatic heterocycle is not more than one. The bridged ring is also within the definition of the heterocycle. A bridged ring is formed when one or more atoms (i.e., C, O, N, or S, which are defined as "bridge atoms" herein) are attached to two non-adjacent carbon atoms or nitrogen atoms. Preferred examples of bridge atom(s) in the rings include, but are not limited to, one carbon atom, two carbon atoms, one nitrogen atom, two nitrogen atoms or one carbon-nitrogen group. It should be noted that a bridge always turns a monocyclic ring into a tricyclic ring. In the bridged ring, the substituent in the ring may also be present on the bridge.

Examples of heterocyclic compounds include, but are not limited to, acridinyl, azocinyl, benzimidazolyl, benzofuranyl, benzimidofuranyl, benzhydrylphenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyl decahydroquinolyl, 2H,6H-1,5,2-dithiazinyl, dihydrofuro [2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, pyran, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, oxindolyl, pyrimidinyl, phenanthridyl, phenanthrolyl, phenazine, phenothiazine, benzoxanthinyl, phenoxazinyl, phthalazinyl, piperazinyl, piperidinyl, piperidone, 4-piperidone, piperonyl, pteridinyl, purinyl, pyranyl, pyrazinyl, pyrazolidinyl, pyrazolinyl, pyrazolyl, pyridazinyl, pyridoxazoles, pyridimidazoles, pyridthiazoles, pyridyl, pyrimidinyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuranyl, tetrahydroisoquinolyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thienanthryl, thiazolyl, isothiazolylthienyl, thienyl, thienoxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthyl. Fused and spiro compounds are also included.

Unless otherwise specified, the term "hydrocarbyl" or hyponym thereof (e.g., alkyl, alkenyl, alkynyl, phenyl, etc.), by itself or as part of another substituent, refers to a linear, branched or cyclic hydrocarbon radical or combination thereof, which may be saturated, mono- or polyunsaturated; may be mono-, di- or polysubstituted; may be monovalent (e.g., methyl), divalent (e.g., methylene) or multivalent (e.g., methenyl); and may include a divalent or multivalent radical having the number of carbon atoms designated (e.g., $C_{1-10}$ means 1 to 10 carbons). Examples of "Hydrocarbyl" includes, but are not limited to, aliphatic and aromatic hydrocarbyl. The aliphatic hydrocarbyl is linear or cyclic, including but not limited to, alkyl, alkenyl and alkynyl. The aromatic hydrocarbyl includes, but is not limited to, 6 to 12-membered aromatic hydrocarbyl such as benzene, naphthalene and the like. In some embodiments, the term "alkyl" means a linear or branched radical or combination thereof, which may be saturated, mono- or polyunsaturated, and may include a divalent and multivalent radical. Examples of saturated hydrocarbon radicals include, but are not limited to, methyl, ethyl, n-propyl, isopropyl, n-butyl, tert-butyl, isobutyl, sec-butyl, isobutyl, cyclohexyl, (cyclohexyl) methyl, cyclopropyl methyl, and homologs or isomers of n-pentyl, n-hexyl, n-heptyl, n-octyl radicals and the like. The unsaturated alkyl has one or more double or triple bonds, examples of unsaturated alkyl include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers thereof.

Unless otherwise specified, the term "heterohydrocarbyl" or hyponym thereof (e.g., heteroalkyl, heteroalkenyl, heteroalkynyl, heteroaryl, etc.), by itself or in combination with another term, refers to a stable linear, branched or cyclic hydrocarbon radical or combination thereof, consisting of the stated number of carbon atoms and at least one heteroatom. In some embodiments, the term "heteroalkyl", by itself or in combination with another term, refers to a stable linear, branched hydrocarbon radical or combination thereof, consisting of the stated number of carbon atoms and at least one heteroatom. In a typical embodiment, the heteroatoms are selected from B, O, N or S, wherein the nitrogen and sulfur atoms may optionally be oxidized and the nitrogen heteroatoms may optionally be quaternized. The heteroatoms B, O, N and S may be placed at any interior positions of the heterohydrocarbyl group, including the position at which the hydrocarbyl is attached to the remainder of the molecule. Examples include but are not limited to —CH2—CH2—O—CH3, —CH2—CH2—NH—CH3, —CH2—CH2—N(CH3)—CH3, —CH2—S—CH2—CH3, —CH2—CH2, —S(O)—CH3, —CH2—CH2—S(O)2—CH3, —CH—CH—O—CH3, —CH2—CH=N—OCH3 and —CH=CH—N(CH3)—CH3. Up to two heteroatoms may be consecutive, such as, for example, —CH2—NH—OCH3.

The terms "alkoxy," "alkylamino" and "alkylthio (or thioalkoxy)" are used in their conventional sense, and refer to those alkyl groups attached to the remainder of the molecule via an oxygen atom, an amino group, or a sulfur atom, respectively.

Unless otherwise specified, the terms "cyclohydrocarbyl", "heterocyclohydrocarbyl" or hyponym thereof (e.g., aryl, heteroaryl, cycloalkyl, heterocycloalkyl, cycloalkenyl, heterocycloalkenyl, cycloalkynyl, heterocycloalkynyl, etc.), by themselves or in combination with other terms, refer to cyclic version of "hydrocarbyl", "heterohydrocarbyl", respectively. Additionally, for heterohydrocarbyl or heterocyclohydrocarbyl (e.g., heteroalkyl, heterocycloalkyl), a heteroatom may occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl and the like. Non-limiting examples of heterocyclyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydrothiophen-2-yl, tetrahydrothiophen-3-yl, 1-piperazinyl and 2-piperazinyl.

Unless otherwise specified, the term "aryl" means a polyunsaturated aromatic hydrocarbon substituent, which may be mono-, di- or polysubstituted, and may be a single ring or multiple rings (preferably, 1 to 3 rings) which are fused together or covalently linked. The term "heteroaryl" refers to an aryl group (or ring) containing from one to four heteroatoms. In an exemplary embodiment, the heteroatoms are selected from B, N, O and S, wherein the nitrogen and sulfur atoms are optionally oxidized and the nitrogen atom is optionally quaternized. A heteroaryl group may be attached to the remainder of the molecule through a heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. The substituents of each of the aryl and heteroaryl ring systems are selected from the acceptable substituents as described below.

For simplicity, the term "aryl", when used in combination with other terms (e.g., aryloxy, arylthio, aralkyl), includes both aryl and heteroaryl rings as defined above. Thus, the term "aralkyl" is intended to include those radicals in which an aryl group is attached to an alkyl group (e.g., benzyl, phenethyl, pyridylmethyl, etc.), including those alkyl groups where a carbon atom (e.g., a methylene group) has been replaced by, for example, an oxygen atom, such as phenoxymethyl, 2-pyridyloxymethyl, 3-(1-naphthyloxy) propyl, and the like.

The term "leaving group" refers to a functional group or an atom that may be substituted by another functional group or atom in a substitution reaction (e.g., nucleophilic substitution). The representative leaving groups include, for example, triflate; chlorine, bromine, iodine; sulfonic ester groups, such as mesylate, tosylate, brosylate, nosylate; acyloxy such as acetoxy, trifluoroacetoxy and the like.

The term "protecting group" includes, but is not limited to, an amino protecting group, a hydroxy protecting group or a thiol protecting group. The term "amino protecting group" refers to a protecting group suitable for preventing side reactions at an amino nitrogen site. Representative alkyl protecting groups include, but are not limited to, formyl; acyl such as alkanoyl (e.g., acetyl, trichloroacetyl or trifluoroacetyl); alkoxycarbonyl such as t-butoxycarbonyl (Boc); arylmethyl such as benzyl (Bn), trityl (Tr), 1,1-bis (meth), and the like; arylmethoxycarbonyl such as benzyloxycarbonyl (Cbz) and 9-fluorenylmethoxycarbonyl (Fmoc); aryl methyl such as benzyl (Bn), trityl (Tr), 1,1-bis-(4'-methoxyphenyl) methyl; silyl such as trimethylsilyl (TMS) and t-butyldimethylsilyl (TBS) and the like. The term "hydroxy protecting group" refers to a protecting group suitable for preventing side reactions of hydroxyl. Representative hydroxy protecting groups include, but are not limited to, alkyl such as methyl, ethyl and t-butyl; acyl such as alkanoyl (e.g., acetyl); arylmethyl such as benzyl (Bn), p-methoxybenzyl (PMB), 9-fluorenylmethyl (Fm) and diphenylmethyl (benzhydryl, DPM); silyl such as trimethylsilyl (TMS) and t-butyldimethylsilyl (TBS) and the like.

The compounds of the present invention can be prepared by various synthetic methods well-known to those skilled in the art, including the embodiments described below, the embodiments combing the embodiments described below with other synthetic methods, and equivalent alternatives known to those skilled in the art. Preferred embodiments include but are not limited to those embodiments of the present invention.

Solvents used in the present invention are commercially available.

The abbreviations used herein are as follows: aq is water; HATU is O-7-azabenzotriazol-1-yl)-N,N,N',N'-tetramethyluronium hexafluorophosphate; EDC is N-(3-dimethylaminopropyl)-N'-ethylcarbodiimide hydrochloride; m-CPBA is 3-chloroperoxybenzoic acid; eq is equivalent; CDI is carbonyl diimidazole; DCM is dichloromethane; PE is petroleum ether; DIAD is diisopropyl azodicarboxylate; DMF is N,N-dimethylformamide; DMSO is dimethyl sulfoxide; EtOAc is ethyl acetate; EtOH is ethanol; MeOH is methanol; CBz is benzyloxycarbonyl (which is used as an amine protecting group); Boc is t-butylcarbonyl (which is used as an amine protecting group); HOAc is acetic acid; NaCNBH$_3$ is sodium cyanoborohydride; r.t. is room temperature; O/N is overnight; THF is tetrahydrofuran; Boc$_2$O is di-tert-butyl dicarbonate; TFA is trifluoroacetic acid; DIPEA is diisopropylethylamine; SOCl$_2$ is thionyl chloride; CS$_2$ is carbon disulfide; TsOH is p-toluenesulfonic acid; NFSI is N-fluoro-N-(phenylsulfonyl) benzenesulfonamide; NCS is 1-chloropyrrolidine-2,5-dione; n-Bu4NF is tetrabutylammonium fluoride; iPrOH is 2-propanol; mp is the melting point; TMSCF3 is (trifluoromethyl) trimethylsilane; TCDI is 1,1'-thiocarbonyldiimidazole; Py is pyridine; HOBt is 1-hydroxybenzotriazole; DIEA is N,N-diisopropylethylamine; MsCl is methylsulfonyl chloride; TosMIC is p-toluenesulfonylmethylisocyanide; TBTU is O-benzotriazole-N,N,N',N'-tetramethyluronium tetrafluoroboric acid; MW is microwave reaction; DAST is diethylaminosulfur trifluoride; DMA-DMA is N,N-dimethylacetamide dimethyl acetal; LAH is aluminum lithium hydride; PhIO is iodosobenzene; DCE is dichloroethane; EDCI is 1-(3-dimethylaminopropyl)-3-ethylcarbodiimide hydrochloride; NMO is N-methyl morpholine oxide.

The compounds are named by human or ChemDraw® software, and the commercially available compounds are described with the catalog names provided by the suppliers.

The compound of the present application can be prepared according to the schemes as follows:

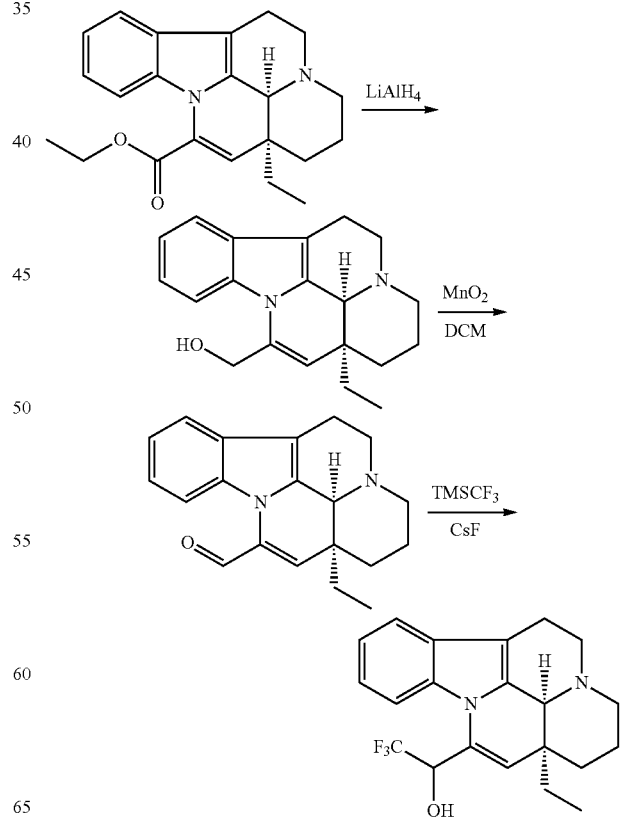

Scheme A

Scheme A1
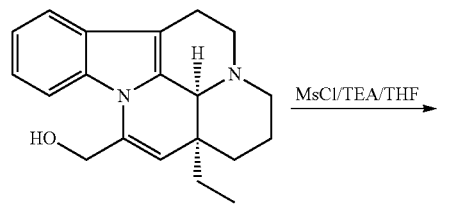
MsCl/TEA/THF
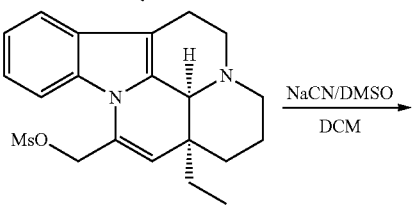
NaCN/DMSO
DCM
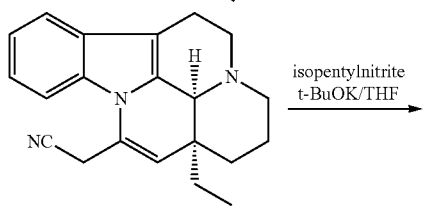
isopentylnitrite
t-BuOK/THF
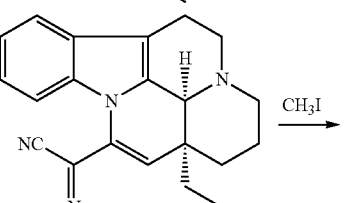
CH₃I
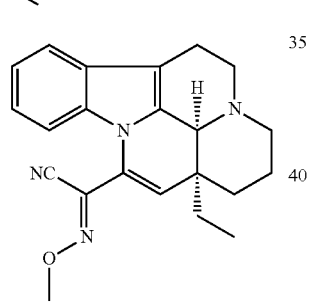
Scheme A2
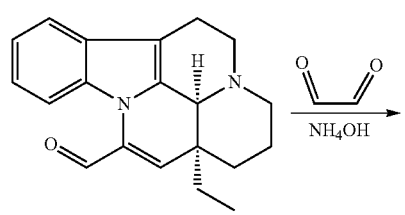
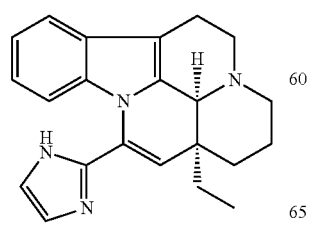
Scheme A3
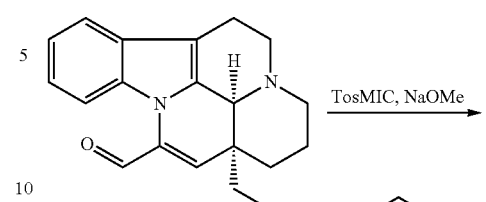
TosMIC, NaOMe
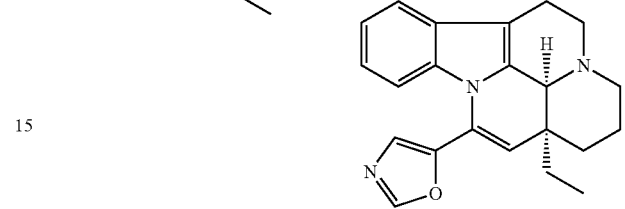
Scheme A4
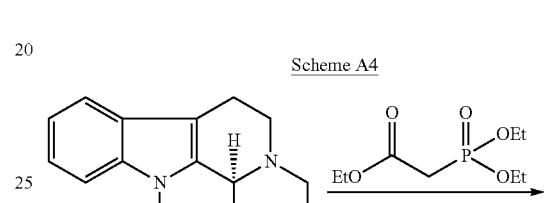
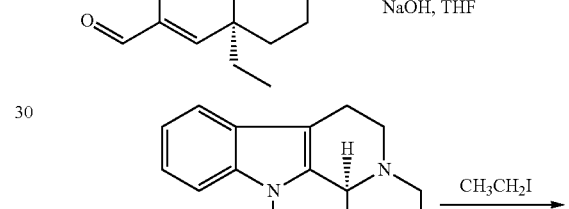
CH₃CH₂I
K₂CO₃, DMF
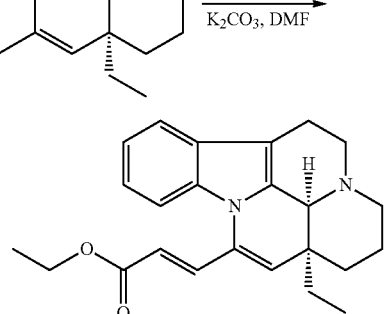
Scheme A5
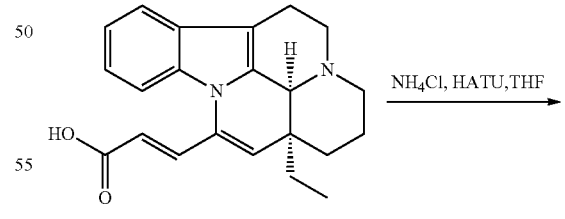
NH₄Cl, HATU, THF
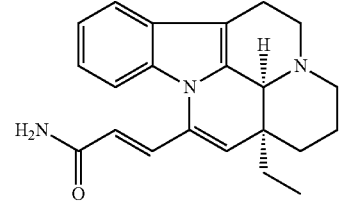

Scheme B
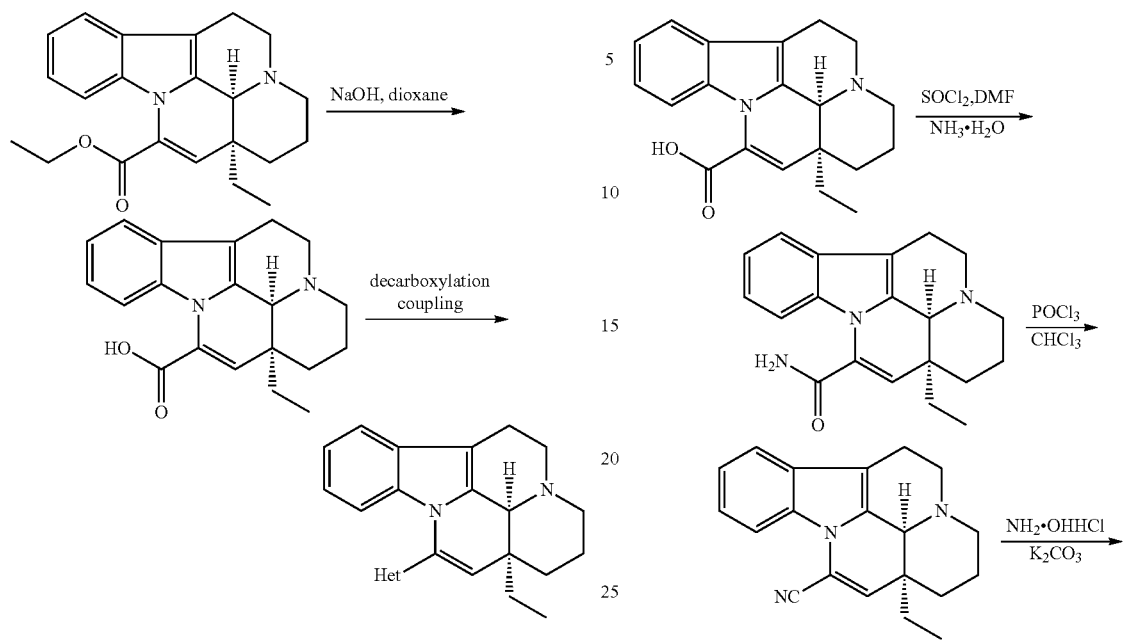
Scheme B2
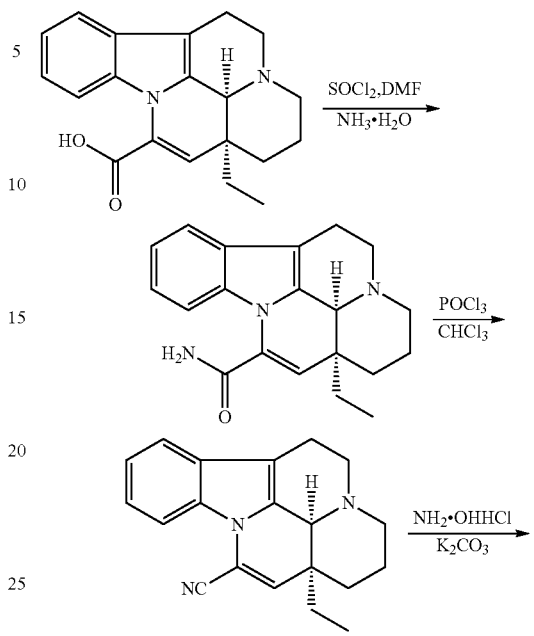
Scheme B1
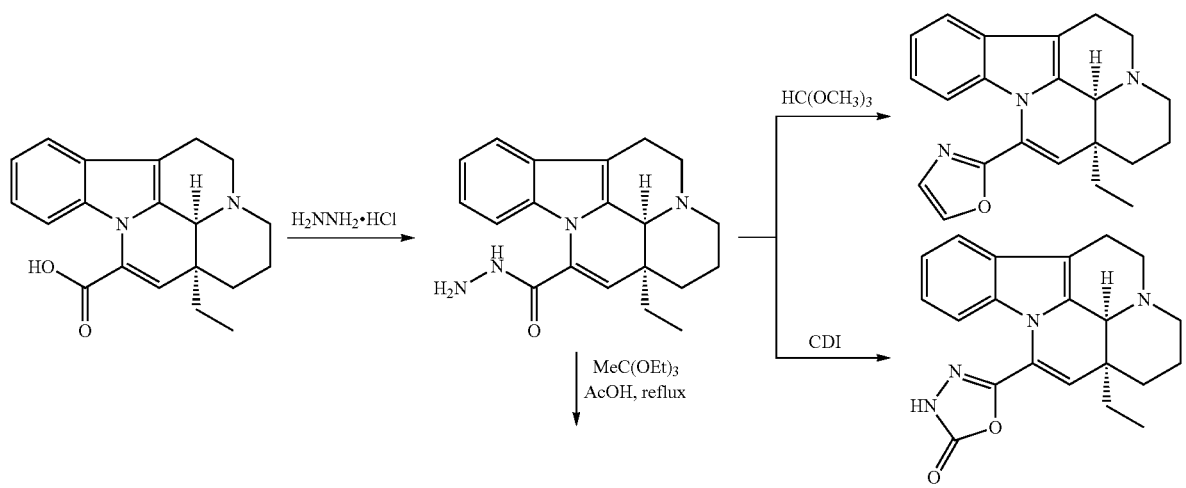
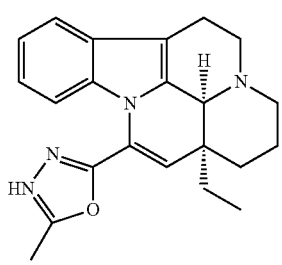

45
-continued
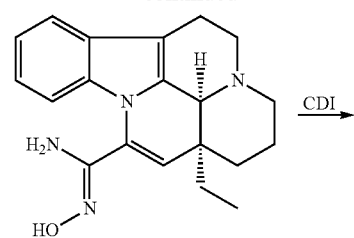
CDI →
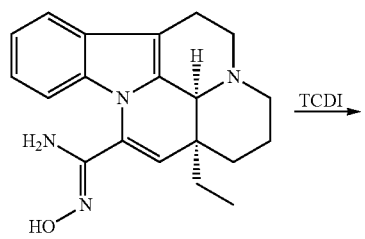
TCDI →
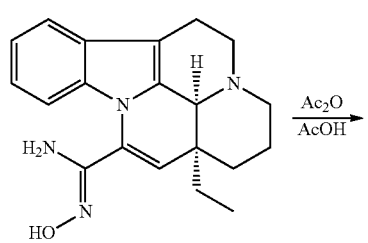
Ac₂O / AcOH →
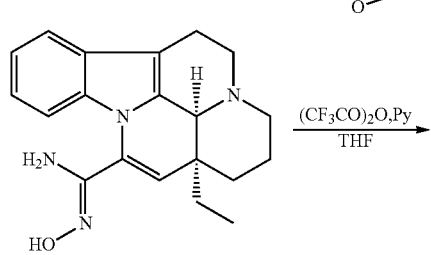
(CF₃CO)₂O, Py / THF →
46
-continued
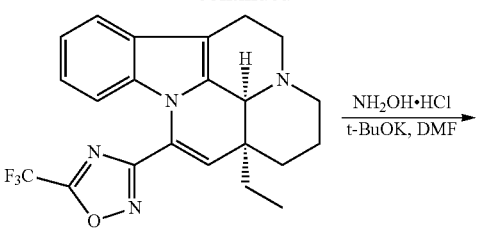
NH₂OH·HCl / t-BuOK, DMF →
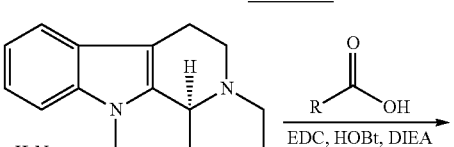
Scheme B3
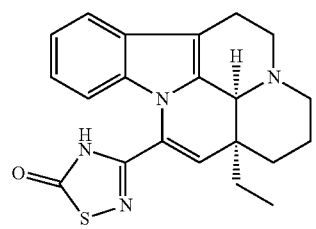
EDC, HOBt, DIEA →
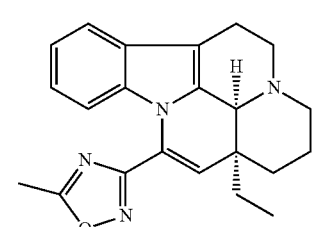
t-BuOK, toluene 110° C. →
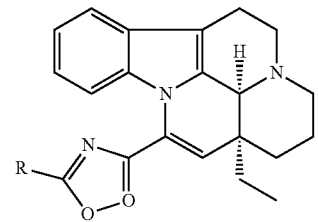
Scheme B7
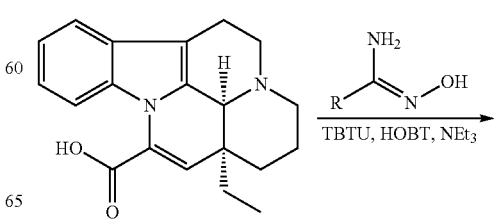
TBTU, HOBT, NEt₃ →

-continued
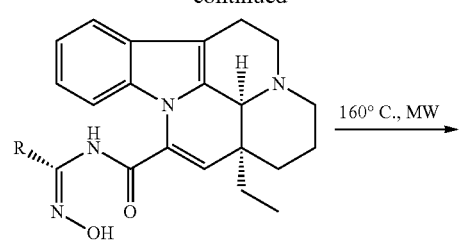
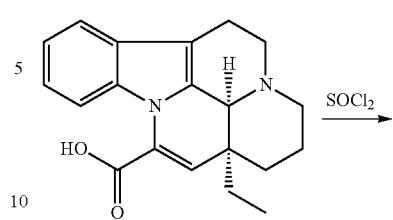
Scheme B6
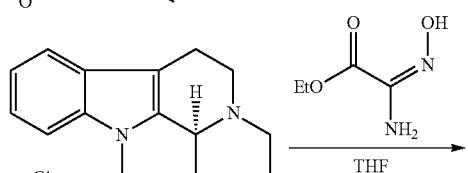
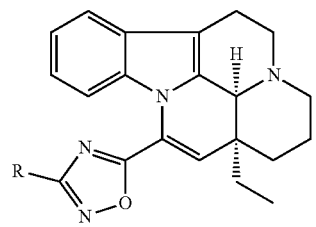
Scheme B5
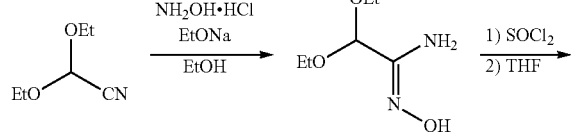
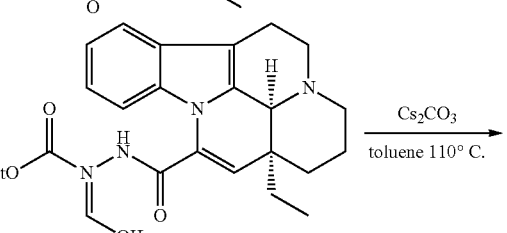
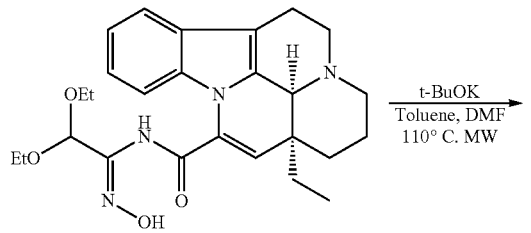
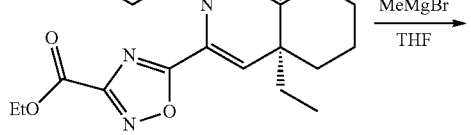
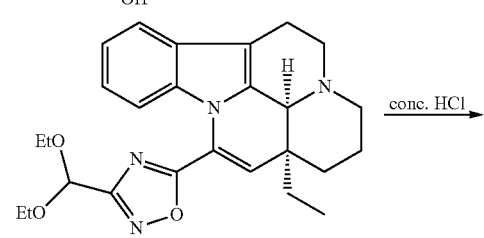
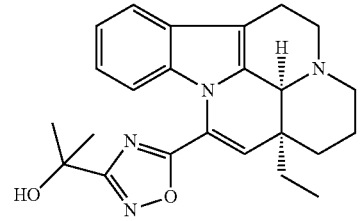
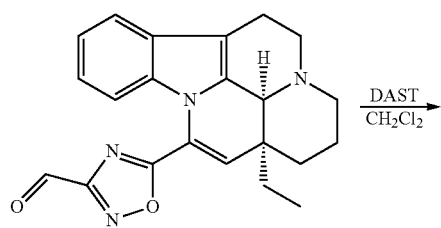
Scheme B7
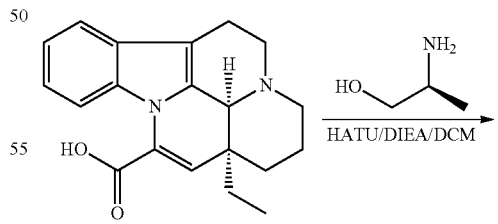
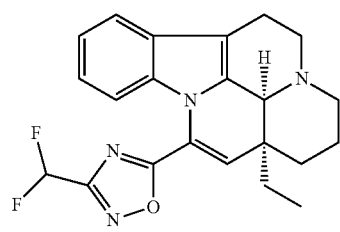

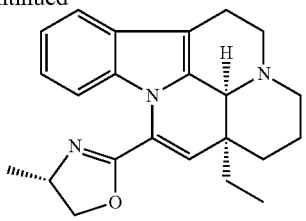
Scheme B8
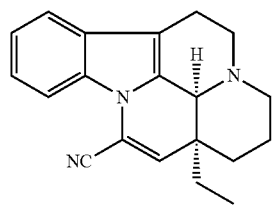
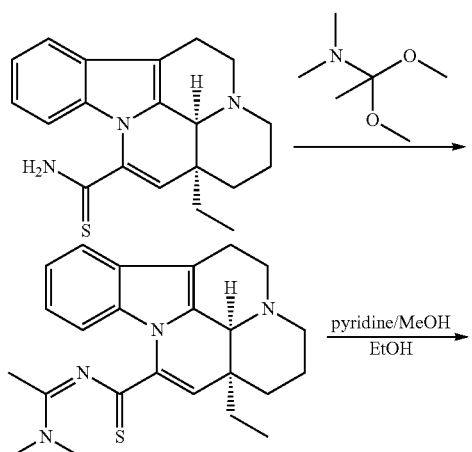
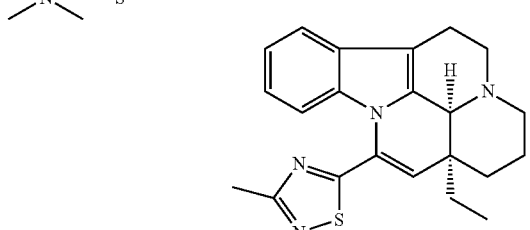
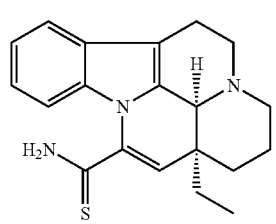
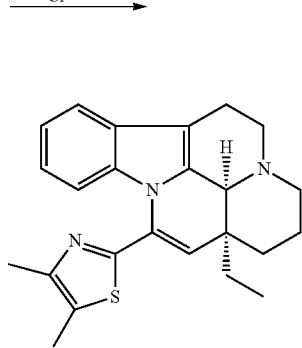
Scheme B9
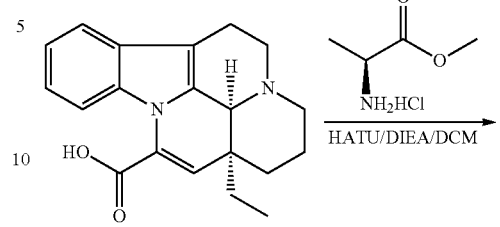
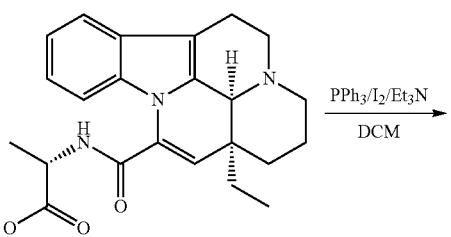
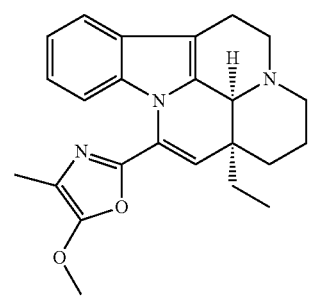
Scheme B10
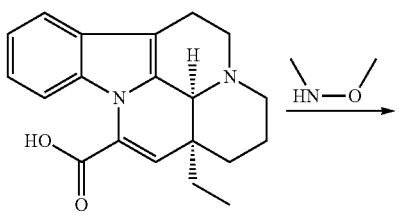
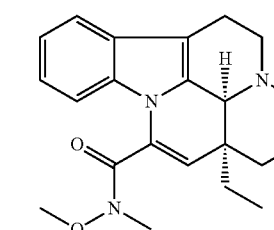
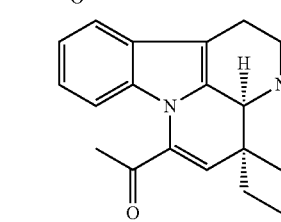

51
-continued
52
-continued
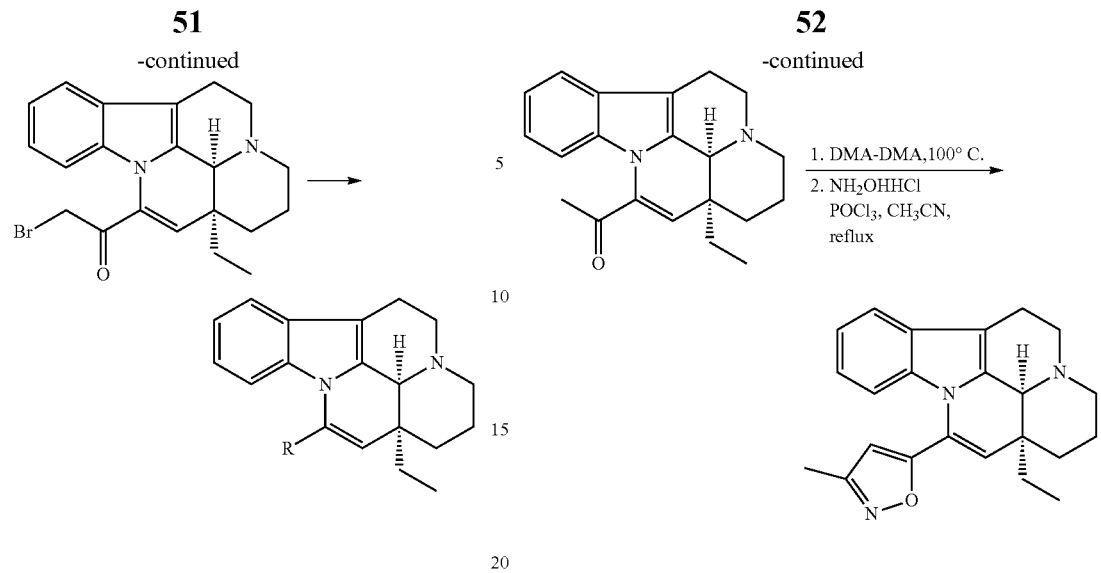
Scheme B11
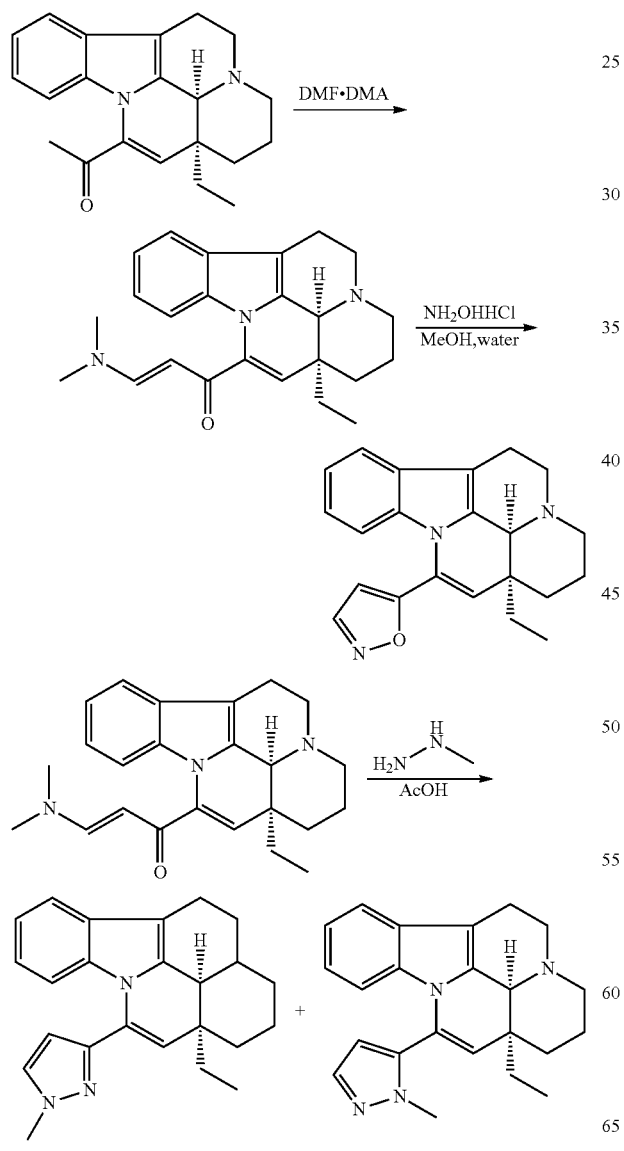
Scheme B12
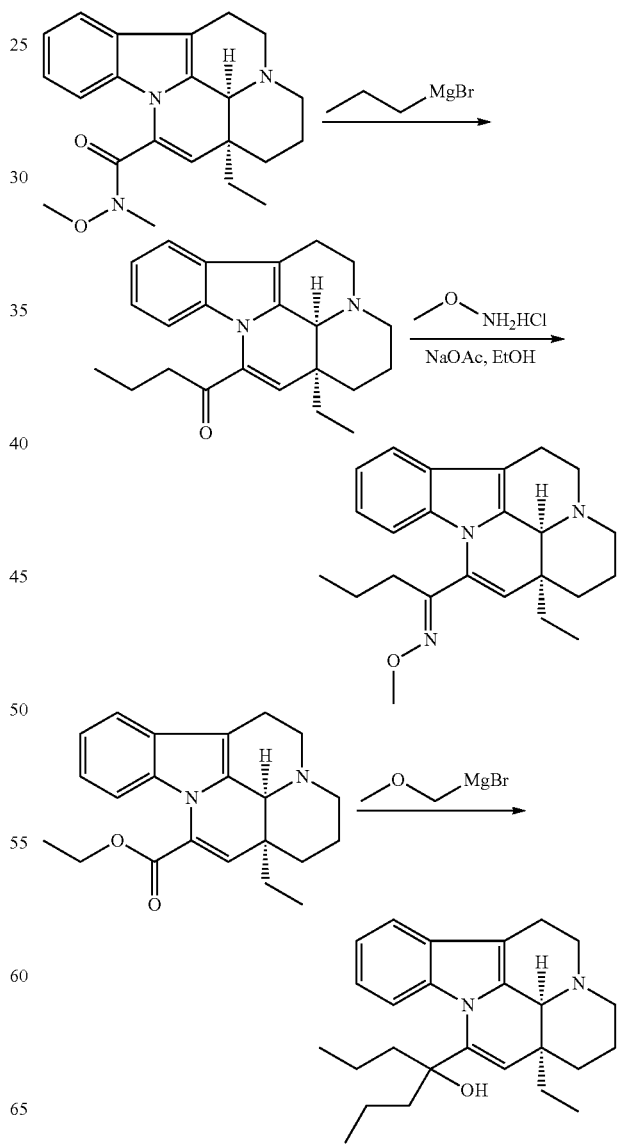

Scheme B13
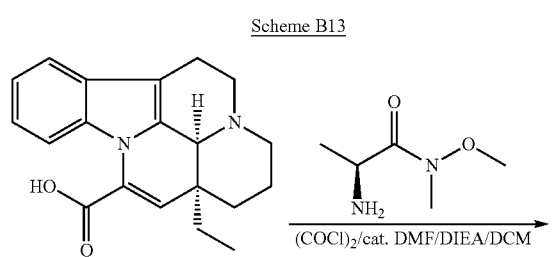
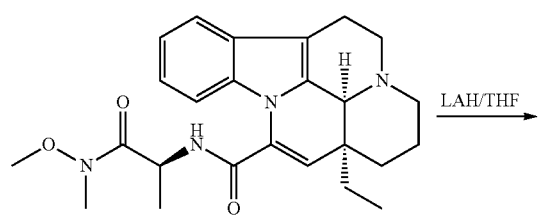
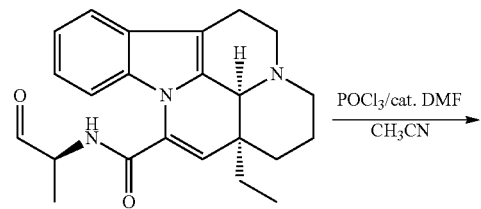
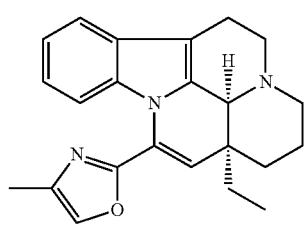
Scheme B14
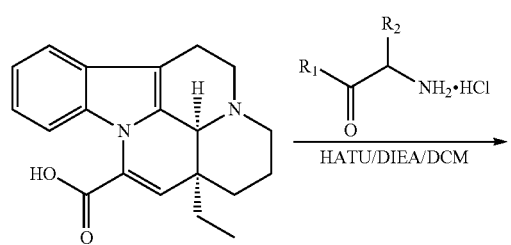
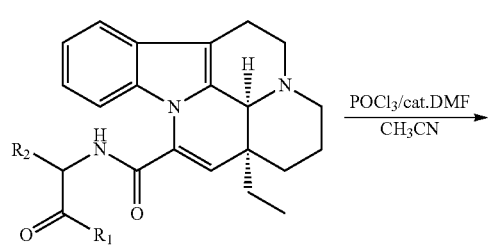
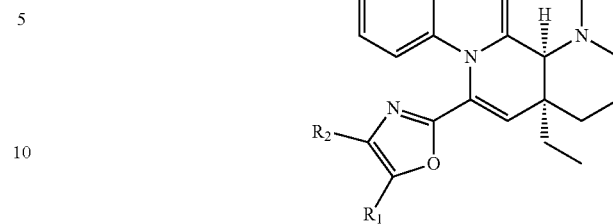
Scheme B15
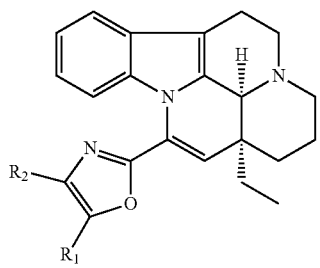
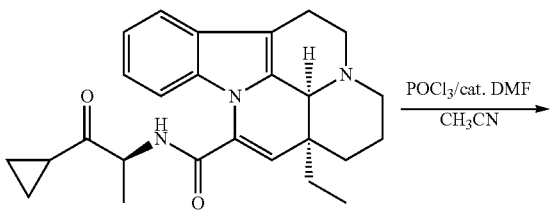
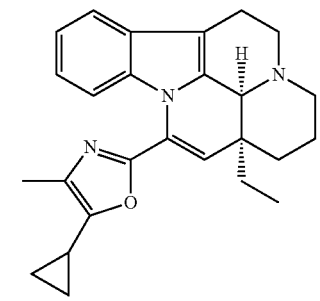

Scheme B16
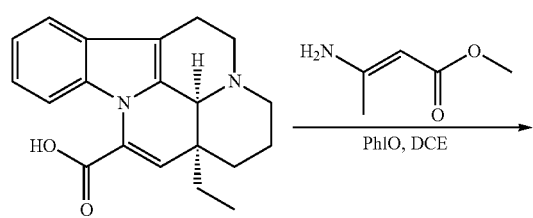
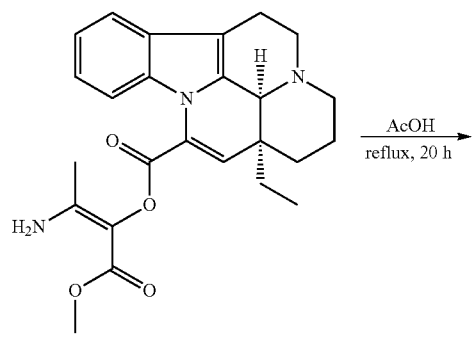
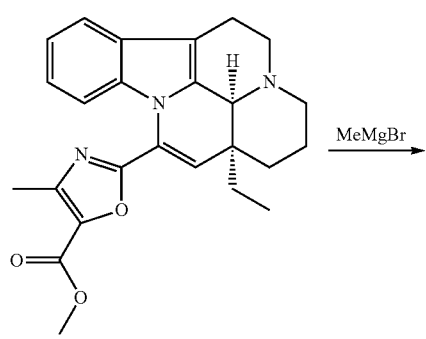
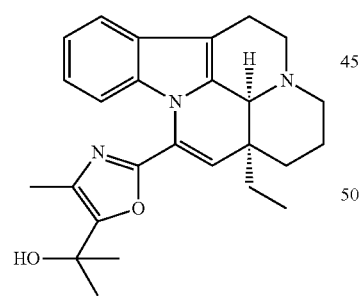
-continued
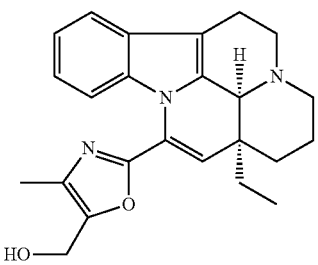
Scheme B17
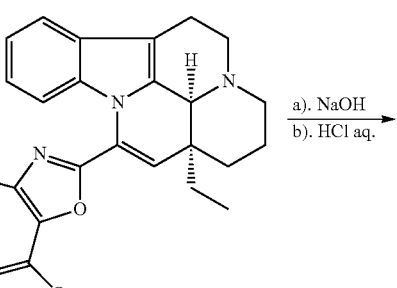
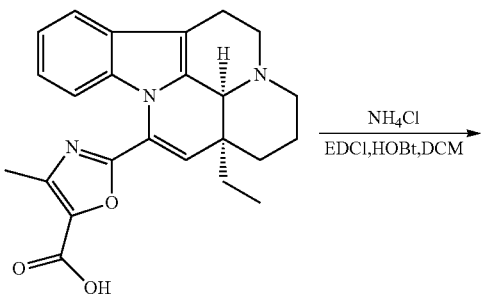
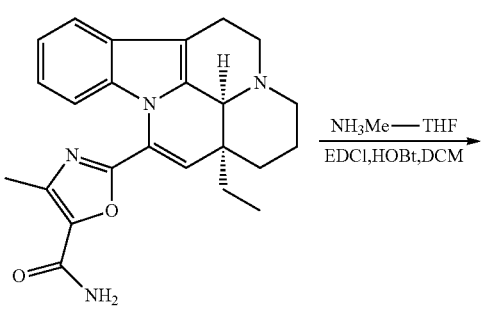
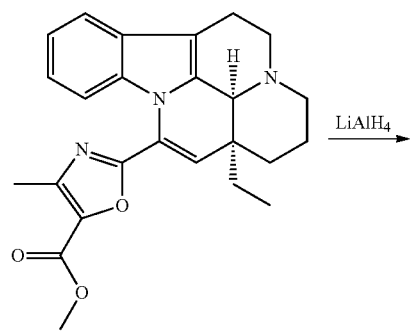
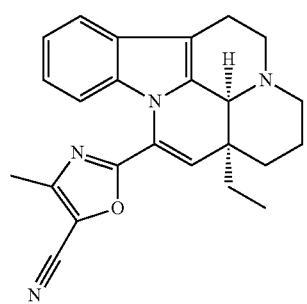

57
-continued
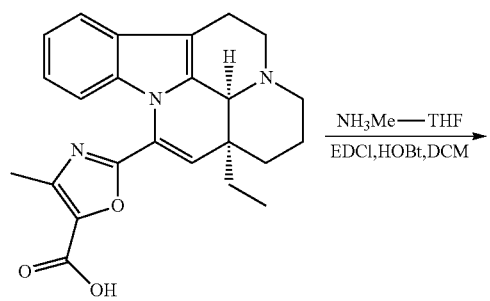
NH3Me—THF
EDCl,HOBt,DCM
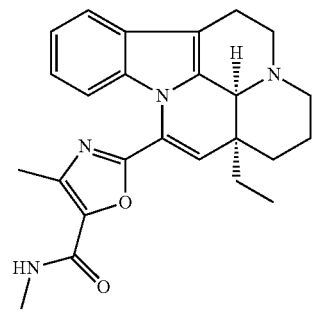
Me2NHHCl
EDCl,HOBt,DCM
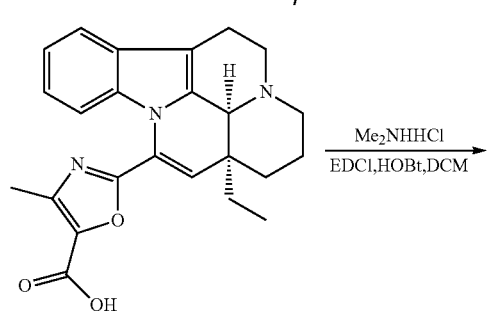
Scheme B18
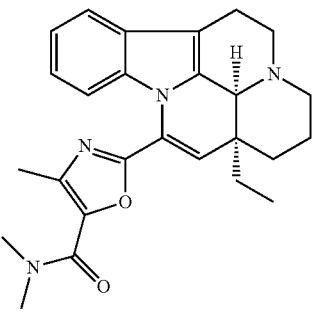
58
-continued
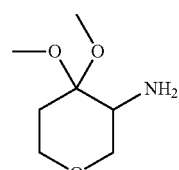
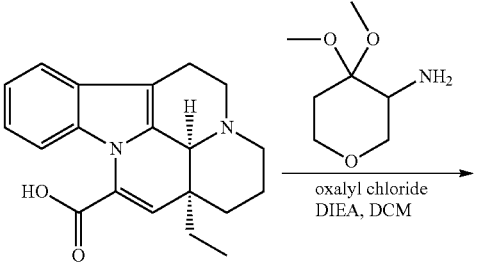
oxalyl chloride
DIEA, DCM
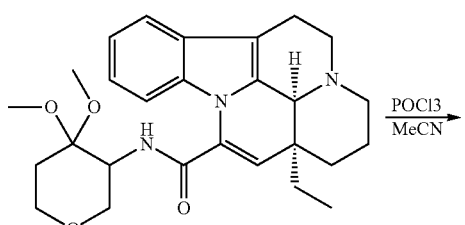
POCl3
MeCN
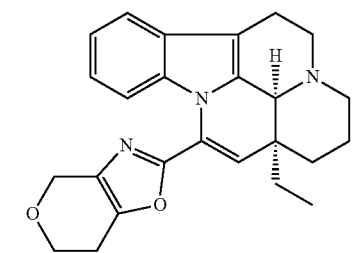
Scheme B19
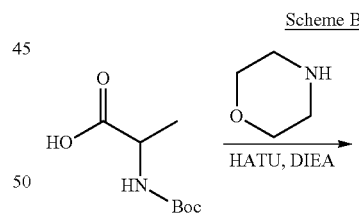
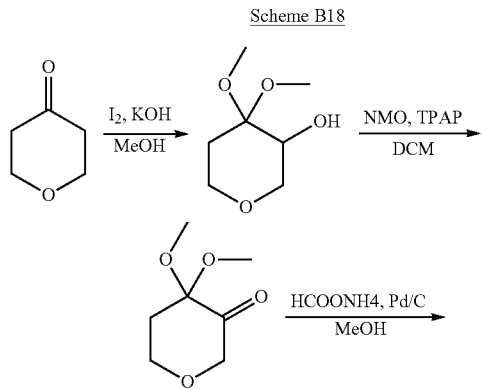
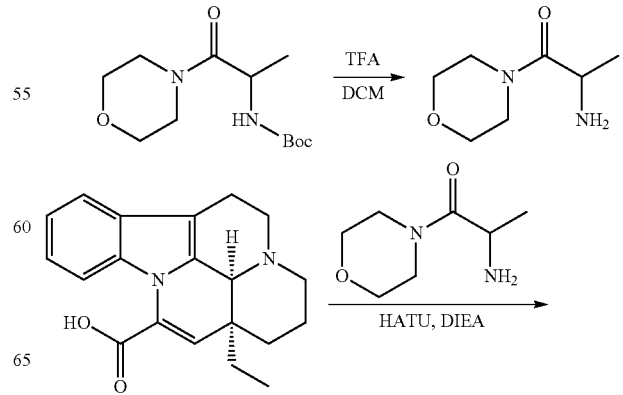
HATU, DIEA

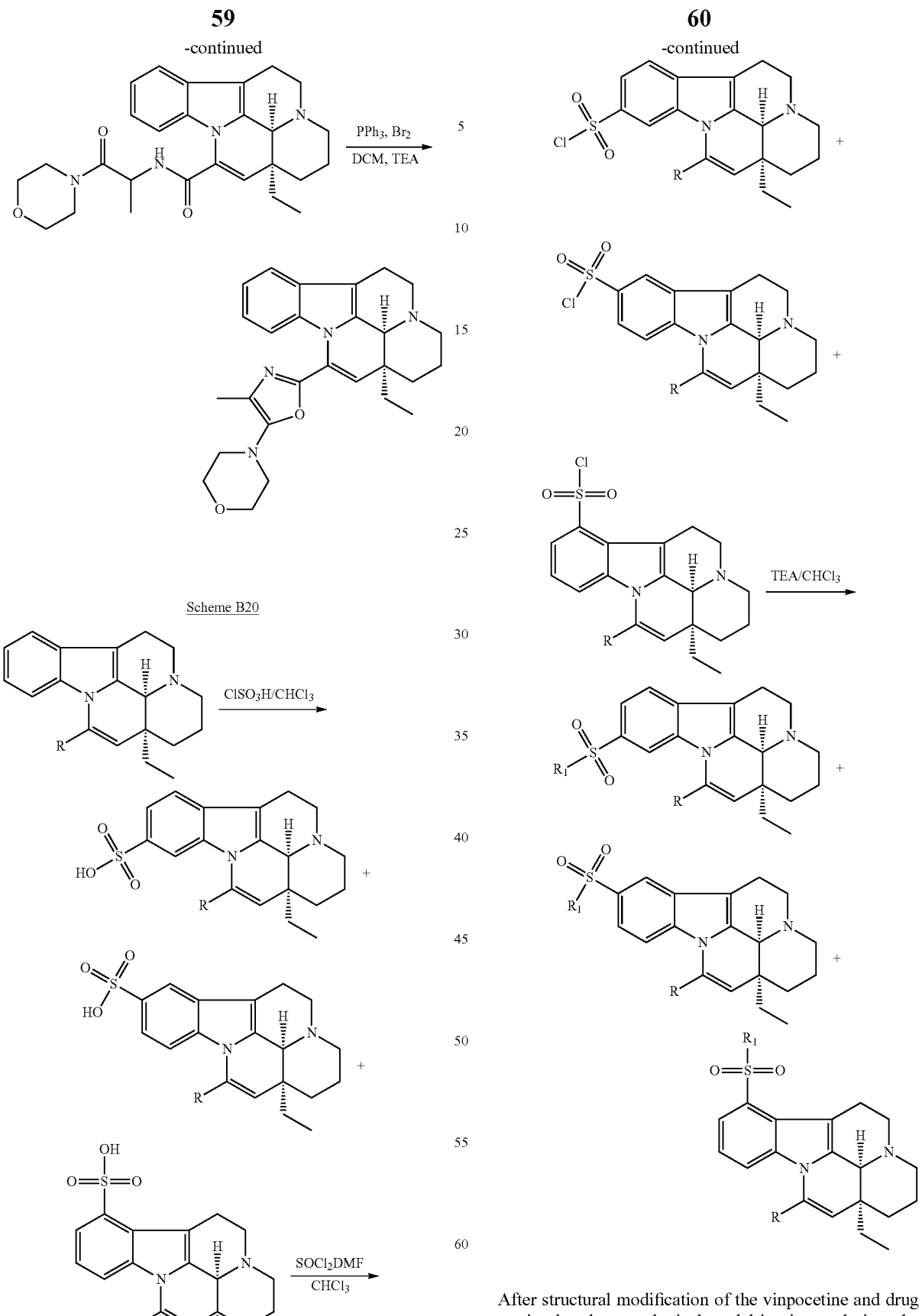
After structural modification of the vinpocetine and drug screening by pharmacological model in vitro and vivo, the present application provides a compound which has a better therapeutic effect in the treatment of cerebral stroke and a higher oral bioavailability than the vinpocetine.

DETAILED DESCRIPTION OF ILLUSTRATED EMBODIMENTS

The present invention will be described in detail in combination with the following preferred embodiments, and it will be appreciated that such embodiments are merely exemplary, the invention is not to be limited to the disclosed embodiments.

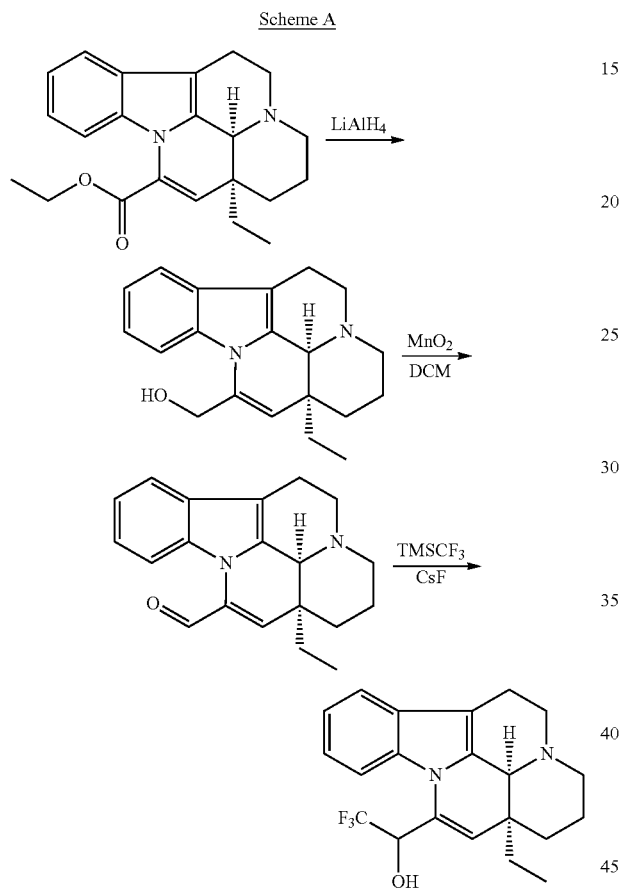

Example 1

1-((4¹S,13aS)-13a-ethyl-2,3,4¹,5,6,13a-hexahydro-1H-indolyl[3,2,1-de]pyridyl[3,2,1-ij][1,5]naphthyridine-12-yl)-2,2,2-trifluoroethanol

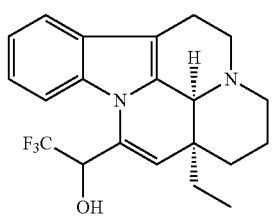

Example 1A ((4¹S,13aS)-13a-ethyl-2,3,4¹,5,6,13a-hexahydro-1H-indolyl[3,2,1-de]pyridyl[3,2,1-ij][1,5]naphthyridine-12-yl) methanol

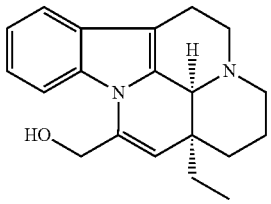

Lithium aluminum hydride (3.2 g, 85.7 mmol) was added in batches to the tetrahydrofuran solution (400 ml) of vinpocetine (10 g, 28.6 gmmol) under 0-5° C., the reaction mixture was stirred for 30 minutes under room temperature and nitrogen atmosphere. After completion, the reaction was quenched with 5 ml water, and 4 ml 2M sodium hydroxide solution and 4 ml water was added to the reaction mixture. The precipitated product was filtered out, water and ethyl acetate was added to extract the concentrated filtrate. The extract was dried and concentrated to obtain the target compound.

¹H NMR (400 MHz, CHLOROFORM-d) δ ppm 0.98 (t, J=7.53 Hz, 3H), 1.08-1.17 (m, 1H), 1.38-1.48 (m, 2H), 1.65-1.82 (m, 2H), 1.86-1.96 (m, 1H), 2.51 (ddd, J=16.00, 4.96, 1.88 Hz, 1H), 2.62-2.76 (m, 2H), 2.98-3.09 (m, 1H), 3.20-3.29 (m, 1H), 3.32-3.39 (m, 1H), 4.16 (br. s., 1H), 4.61 (d, J=13.30 Hz, 1H), 4.83 (d, J=13.30 Hz, 1H), 5.11 (s, 1H), 7.10-7.15 (m, 1H), 7.20 (td, J=7.72, 1.38 Hz, 1H), 7.47 (d, J=7.78 Hz, 1H), 7.67 (d, J=8.53 Hz, 1H).

Example 1B ((4¹S,13aS)-13a-ethyl-2,3,4¹,5,6,13a-hexahydro-1H-indolyl[3,2,1-de]pyridyl[3,2,1-ij][1,5]naphthyridine-12-methanal

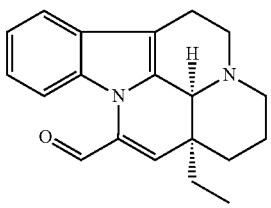

Active manganese dioxide (5.07 g, 58.4 mmol) was added to the dichloromethane solution (20 ml) of ((4¹S,13aS)-13a-ethyl-2,3,4¹,5,6,13a-hexahydro-1H-indolyl[3,2,1-de]pyridyl[3,2,1-ij][1,5]naphthyridine-12-yl) methanol (1.8 g, 5.84 mmol), the reaction mixture was heated and stirred overnight, then filtered, and the filtrate was concentrated. The residue was subjected to column chromatography, eluting with a mixed solution of petroleum ether/ethyl acetate (10/1 by volume) to obtain the target compound (colorless oil, 1.2 g, yield 67.1%).

Example 1C 1-((4¹S,13aS)-13a-ethyl-2,3,4¹,5,6,13a-hexahydro-1H-indolyl[3,2,1-de]pyridyl[3,2,1-ij][1,5]naphthyridine-12-yl-2,2,2,-trifluoroethanol

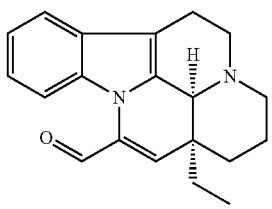

Cesium fluoride (148.73 mg, 0.979 mmol) and (trifluoromethyl) trimethylsilane (139.2 mg, 0.979 mmol) was added to the anhydrous tetrahydrofuran solution (5 ml) of ((4¹S,13aS)-13a-ethyl-2,3,4¹,5,6,13a-hexahydro-1H-indolyl[3,2,1-de]pyridyl[3,2,1-ij][1,5]naphthyridine-12) methanal (200 mg, 0.652 mmol) at 0° C., the reaction mixture was stirred for 1 h at 0° C., then tetrabutylammonium fluoride was added, the mixture was stirred for 1 h under room temperature and then concentrated. The residue was subjected to Preparative High Performance Liquid Chromatography to obtain the target compound (100m g, yield 40.8%).

$^1$H NMR (CD$_3$OD, 400 MHz) δ 7.59 (d, J=8.0 Hz, 1H), 7.43 (d, J=8.0 Hz, 1H), 7.13~7.17 (m, 1H), 7.05~7.09 (m, 1H), 5.54~5.61 (m, 2H), 4.18 (s, 1H), 3.24~3.28 (m, 2H), 2.96~2.98 (m, 1H), 2.53~2.67 (m, 3H), 1.75~1.98 (m, 1H), 1.70~1.74 (m, 2H), 1.44~1.51 (m, 2H), 0.99~1.08 (m, 4H).

LCMS (ESI) m/z: 377 (M+1)

Scheme A1

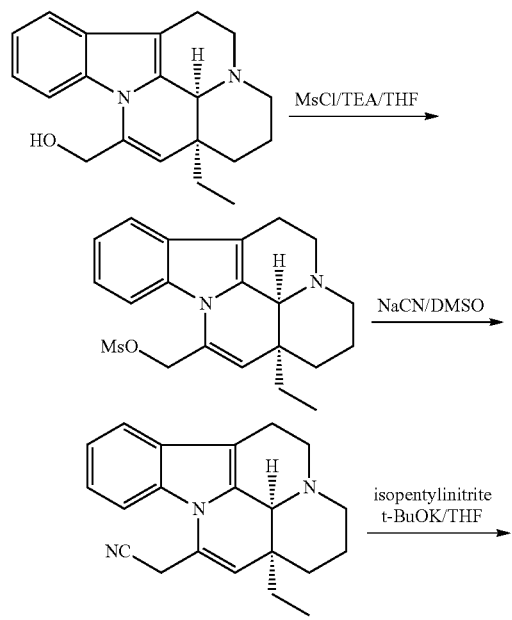

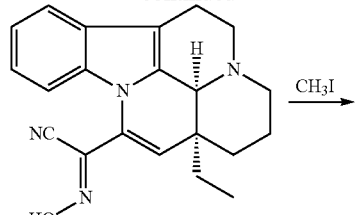

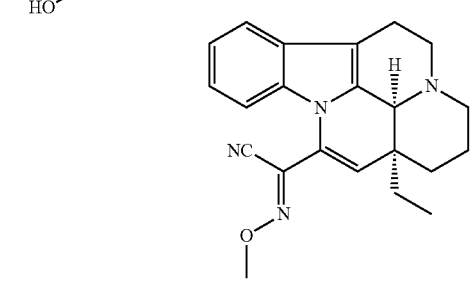

Example 2

(4¹S,13aS,Z)-13a-ethyl-N-methoxyl-2,3,4¹,5,6,13a-hexahydro-1H-indolo[3,2,1-de]pyrido[3,2,1-ij][1,5]naphthyridine-12-carbimidoyl cyanide

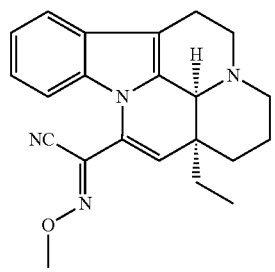

Example 2A

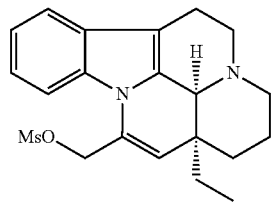

To a solution of ((4¹S,13aS)-13a-ethyl-2,3,4¹,5,6,13a-hexahydro-1H-indolo[3,2,1-de]pyrido[3,2,1-ij][1,5]naphthyridin-12-yl) methyl methanesulfonate (3.8 g, 12.3 mmol) in tetrahydrofuran (80 mL) was added triethylamine (1.9 g, 18.5 mmol) and methanesulfonyl chloride (1.1 mL, 14.8 mmol) at 0-5° C. under an atmosphere of nitrogen, the reaction mixture was heated to room temperature and stirred for 1 hour. After completion, the ammonium chloride solution was added to the reaction mixture. The mixture was extracted with ethyl acetate, the extracts were dried and concentrated to obtain the target compound (yellow solid, 5 g, crude product, for the next step).

Example 2B 2-(($4^1$S,13aS)-13a-ethyl-2,3,$4^1$,5,6,13a-hexahydro-1H-indolo[3,2,1-de]pyrido[3,2,1-ij][1,5]naphthyridin-12-yl) acetonitrile

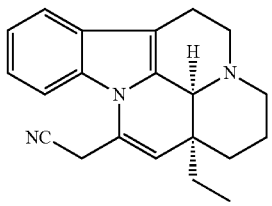

The crude product (5 g, 12.9 mmol) obtained from the previous step was dissolved in dimethylsulfoxide (40 ml), then sodium cyanide (3.2 g, 64.8 mmol) was added and the reaction mixture was stirred overnight at room temperature. After completion, the mixture was poured into 150 ml water, and the precipitated solid was filtered out and dried to obtain the target compound (yellow solid, 3.6 g, yield: 88%).

$^1$H NMR (400 MHz, CHLOROFORM-d) δ ppm 0.94-1.02 (m, 4H), 1.38-1.50 (m, 2H), 1.69-1.80 (m, 2H), 2.03 (dq, J=14.62, 7.51 Hz, 1H), 2.37-2.45 (m, 1H), 2.48-2.62 (m, 3H), 2.88-2.98 (m, 1H), 3.11 (d, J=15.06 Hz, 1H), 3.20-3.36 (m, 2H), 3.98 (s, 1H), 5.62 (d, J=1.76 Hz, 1H), 7.25-7.33 (m, 2H), 7.47-7.52 (m, 1H), 7.65 (d, J=7.53 Hz, 1H).

Example 2C ($4^1$S,13aS,Z)-13a-ethyl-N-methoxyl-2,3,$4^1$,5,6,13a-hexahydro-1H-indolo[3,2,1-de]pyrido[3,2,1-ij][1,5]naphthyridine-12-carbimidoyl cyanide

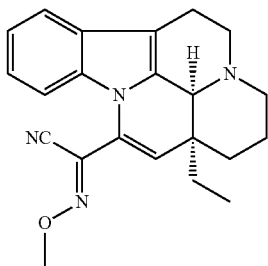

To a solution of 2-(($4^1$S,13aS)-13a-ethyl-2,3,$4^1$,5,6,13a-hexahydro-1H-indolo[3,2,1-de]pyrido[3,2,1-ij][1,5]naphthyridin-12-yl) acetonitrile (300 mg, 0.95 mmol) in tetrahydrofuran (20 mL) was successively added isoamyl nitrite (332 mg, 0.95 mmol) and potassium tert-butoxide (424 mg, 3.8 mmol), and the reaction mixture was stirred at room temperature under an atmosphere of nitrogen for 1 hour. Potassium iodide (538 mg, 3.8 mmol) was added to the reaction mixture, and the mixture was stirred for another 3 hours. After completion, water was added to the reaction mixture and the mixture was extracted with ethyl acetate. The extracts were dried and concentrated. The residue was purified by Preparative High Performance Liquid Chromatography to obtain the target compound (100 mg, yield: 29%).

$^1$H NMR (400 MHz, CHLOROFORM-d) δ ppm 1.07-1.30 (m, 4H), 1.62-1.73 (m, 2H), 2.17-2.35 (m, 3H), 2.90-3.20 (m, 3H), 3.31 (br. s., 1H), 3.58-3.84 (m, 2H), 4.22 (s, 3H), 4.72 (br. s., 1H), 5.75 (s, 1H), 7.20-7.26 (m, 2H), 7.28-7.33 (m, 1H), 7.47-7.56 (m, 1H).

Scheme A2

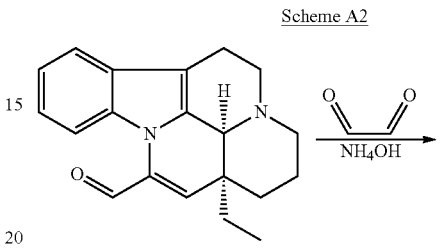

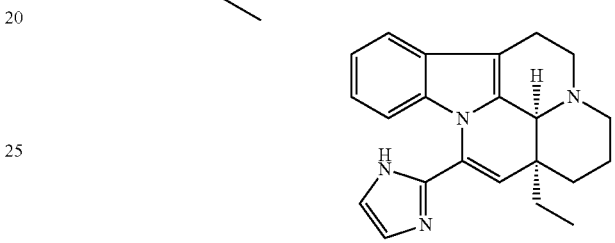

Example 3

($4^1$S,13aS)-13a-ethyl-12-(1H-imidazol-2-yl)-2,3,$4^1$,5,6,13a-hexahydro-1H-indolo[3,2,1-de]pyrido[3,2,1-ij][1,5]naphthyridine

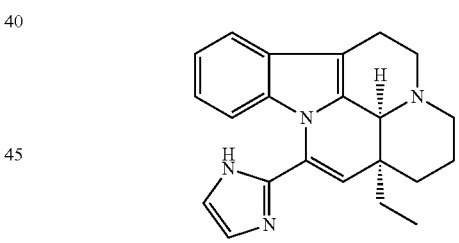

To a solution of ($4^1$S,13aS)-13a-ethyl-2,3,$4^1$,5,6,13a-hexahydro-1H-indolo[3,2,1-de]pyrido[3,2,1-ij][1,5]naphthyridine-12-carbaldehyde (300 mg, 0.97 mmol) in anhydrous ethanol (5 mL) was added glyoxal (568 mg, 0.97 mmol) and aqueous ammonia (343 mg, 9.79 mmol), respectively, and the reaction mixture was heated under reflux for 3 days. The reaction mixture was concentrated and the residue was purified by Preparative High Performance Liquid Chromatography to obtain the target compound (50 mg, yield: 14.8%)

$^1$H NMR (CD3OD, 400 MHz) δ ppm 7.75 (s, 2H), 7.64 (d, J=8.0 Hz, 1H), 7.14-7.24 (m, 2H), 6.11 (d, J=8.0 Hz, 1H), 5.98 (s, 1H), 5.16 (s, 1H), 3.86-3.96 (m, 2H), 3.35-3.38 (m, 2H), 3.16-3.27 (m, 2H), 1.96-2.04 (m, 3H), 1.79-1.87 (m, 2H), 1.38 (m, 1H), 1.12 (t, J=9.8 Hz, 3H).

LCMS (ESI) m/z: 345 (M+1)

Scheme A3

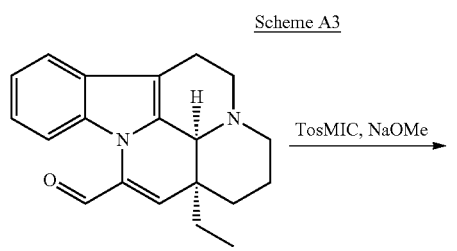

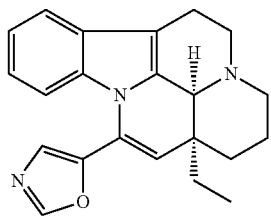

Example 4

5-((4¹S,13aS)-13a-ethyl-2,3,4¹,5,6,13a-hexahydro-1H-indolo[3,2,1-de]pyrido[3,2,1-ij][1,5]naphthyridin-12-yl)oxazole

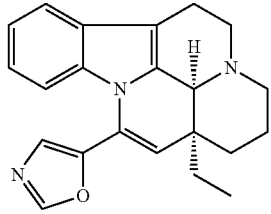

To a solution of (4¹S,13aS)-13a-ethyl-2,3,4¹,5,6,13a-hexahydro-1H-indolo[3,2,1-de]pyrido[3,2,1-ij][1,5]naphthyridine-12-carbaldehyde (500 mg, 1.63 mmol) in methanol (6 mL) was successively added sodium methoxide (450 mg, 8.15 mmol) and (p-tolylsulfonyl)methyl isocyanide (390 mg, 2 mmol) at room temperature, and the reaction mixture was refluxed overnight. After cooling, the mixture was concentrated, and the residue was treated with sodium bicarbonate solution, and then was extracted with ethyl acetate. The organic layer was dried over anhydrous sodium sulfate and filtered. The filtrate was concentrated and the crude product was purified by silica gel chromatography to obtain the target compound (200 mg, yield: 35.6%).

¹H NMR (400 MHz, DMSO) δ ppm 8.58 (s, 1H), 7.59-7.35 (m, 2H), 7.09-6.85 (m, 2H), 6.12 (d, J=8.1 Hz, 1H), 5.52 (s, 1H), 4.10 (q, J=5.1 Hz, 1H), 3.20-3.09 (m, 3H), 2.94 (br. s., 1H), 1.94-1.73 (m, 2H), 1.59 (br. s., 1H), 1.50 (d, J=13.0 Hz, 1H), 1.38 (br. s., 1H), 0.97-0.85 (m, 3H).

LCMS (ESI) m/z: 346 (M+1)

Scheme A4

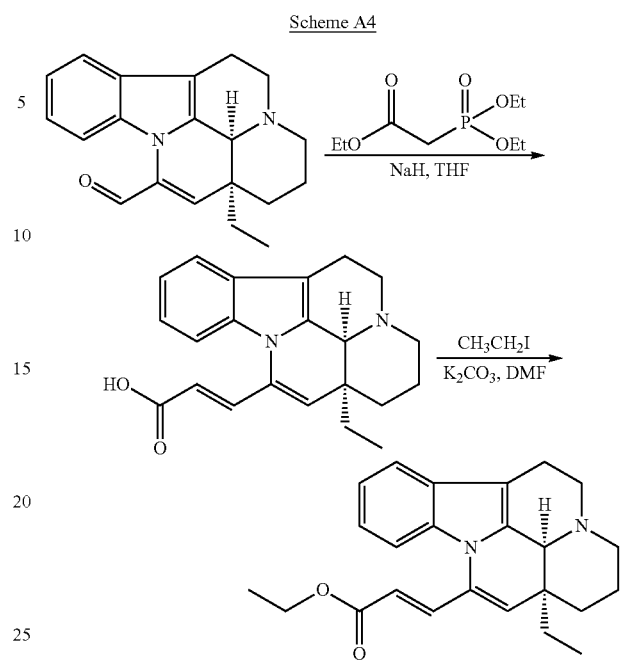

Example 5

(E)-3-((4¹S,13aS)-13a-ethyl-2,3,4¹,5,6,13a-hexahydro-1H-indolo[3,2,1-de]pyrido[3,2,1-ij][1,5]naphthyridin-12-yl)acrylic acid

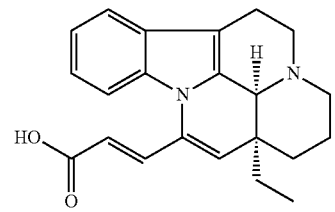

A solution of triethyl phosphonoacetate (293 mg, 1.3 mmol) in 2 mL tetrahydrofuran was cooled to 0° C. with an ice-water bath, then sodium hydride (60%, 80 mg, 2 mmol) was added thereto, then a solution of (4¹S,13aS)-13a-ethyl-2,3,4¹,5,6,13a-hexahydro-1H-indolo[3,2,1-de]pyrido[3,2,1-ij][1,5]naphthyridine-12-carbaldehyde (200 mg, 0.65 mmol) in 2 mL tetrahydrofuran was added thereto after about half an hour, and the reaction mixture was slowly heated to room temperature and stirred overnight. After completion (monitored by TLC), the solvent was distilled off, and the residue was dissolved in 2 mL dimethylsulfoxide. The target compound (17 mg, yield: 7.56%) was separated by Preparative High Performance Liquid Chromatography.

¹H NMR (400 MHz, METHANOL-d₄) δ ppm 7.71-7.60 (m, 1H), 7.52 (t, J=7.9 Hz, 2H), 7.28-7.13 (m, 2H), 6.38 (d, J=15.6 Hz, 1H), 5.51 (s, 1H), 3.73 (d, J=7.0 Hz, 3H), 3.09 (br. s., 6H), 2.17-1.89 (m, 3H), 1.69 (d, J=12.3 Hz, 2H), 1.31-1.16 (m, 2H), 1.10 (t, J=7.3 Hz, 3H).

LCMS (ESI) m/z: 349 (M+1)

Example 6

(E)-ethyl-3-((4¹S,13aS)-13a-ethyl-2,3,4¹,5,6,13a-hexahydro-1H-indolo[3,2,1-de]pyrido[3,2,1-ij][1,5]naphthyridin-12-yl)acrylate

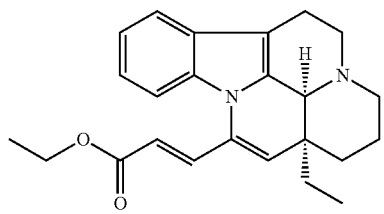

To a solution of (E)-3-((4¹S,13aS)-13a-ethyl-2,3,4¹,5,6,13a-hexahydro-1H-indolo[3,2,1-de]pyrido[3,2,1-ij][1,5]naphthyridin-12-yl)acrylic acid (200 mg, 0.573 mmol) in 5 mL tetrahydrofuran was added potassium carbonate (158 mg, 1.14 mmol) and iodoethane (88 mg, 0.57 mmol), respectively, and the reaction mixture was stirred at room temperature overnight. After completion (monitored by TLC), the solvent was distilled off, and the residue was dissolved in 2 mL dimethylsulfoxide. The target compound was separated by Preparative High Performance Liquid Chromatography.

$^1$H NMR (400 MHz, METHANOL-$d_4$) δ ppm 7.67 (d, J=15.6 Hz, 1H), 7.44-7.24 (m, 2H), 7.15-6.96 (m, 2H), 6.28 (d, J=15.8 Hz, 1H), 5.52 (s, 1H), 4.27 (d, J=7.0 Hz, 2H), 3.85 (br. s., 1H), 3.24-3.11 (m, 1H), 3.08-2.79 (m, 2H), 2.55-2.32 (m, 3H), 1.90-1.67 (m, 2H), 1.67-1.51 (m, 1H), 1.46-1.22 (m, 5H), 0.98 (t, J=7.4 Hz, 3H), 0.90-0.77 (m, 1H).

LCMS (ESI) m/z: 377 (M+1)

Example 7

(E)-3-((4¹S,13aS)-13a-ethyl-2,3,4¹,5,6,13a-hexahydro-1H-indolo[3,2,1-de]pyrido[3,2,1-ij][1,5]naphthyridin-12-yl)acrylamide

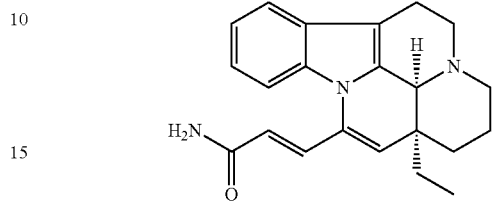

To a mixture of (E)-3-((4¹S,13aS)-13a-ethyl-2,3,4¹,5,6,13a-hexahydro-1H-indolo[3,2,1-de]pyrido[3,2,1-ij][1,5]naphthyridin-12-yl)acrylic acid (200 mg, 0.57 mmol), ammonium chloride (36 mg, 0.688 mmol) and 5 mL tetrahydrofuran was added triethylamine (69 mg, 0.68 mmol) and 2-(7-azobenzotriazole)-N,N,N',N'-tetramethyluronium hexafluophosphate (217 mg, 0.57 mmol), respectively, the reaction mixture was stirred at room temperature for 1 hour, and then the mixture was heated to 60° C. and stirred overnight. After completion (monitored by TLC), the solvent was distilled off, and the residue was dissolved in 2 mL dimethylsulfoxide. The target compound was separated by Preparative High Performance Liquid Chromatography.

$^1$H NMR (400 MHz, MeOD) δ ppm 7.66 (d, J=15.3 Hz, 1H), 7.43 (dd, J=7.9, 12.7 Hz, 2H), 7.25-6.99 (m, 2H), 6.49 (d, J=15.6 Hz, 1H), 5.53 (s, 1H), 4.17 (br. s., 1H), 3.27-3.16 (m, 1H), 3.03 (br. s., 1H), 2.72-2.49 (m, 3H), 2.04-1.64 (m, 3H), 1.57-1.36 (m, 2H), 1.04 (t, J=7.3 Hz, 4H).

LCMS (ESI) m/z: 348 (M+1)

Scheme A5

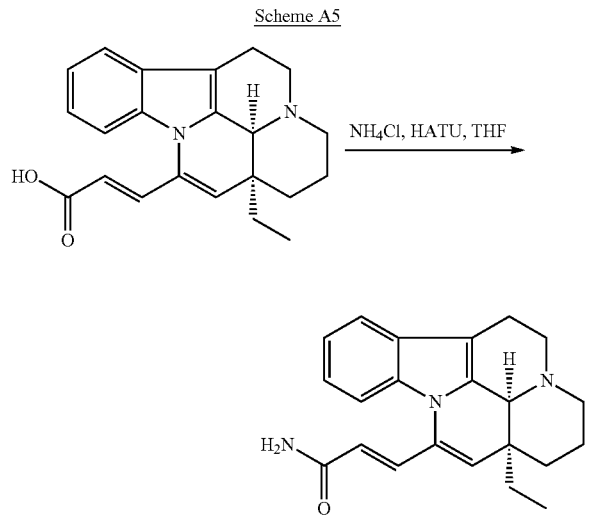

Scheme B

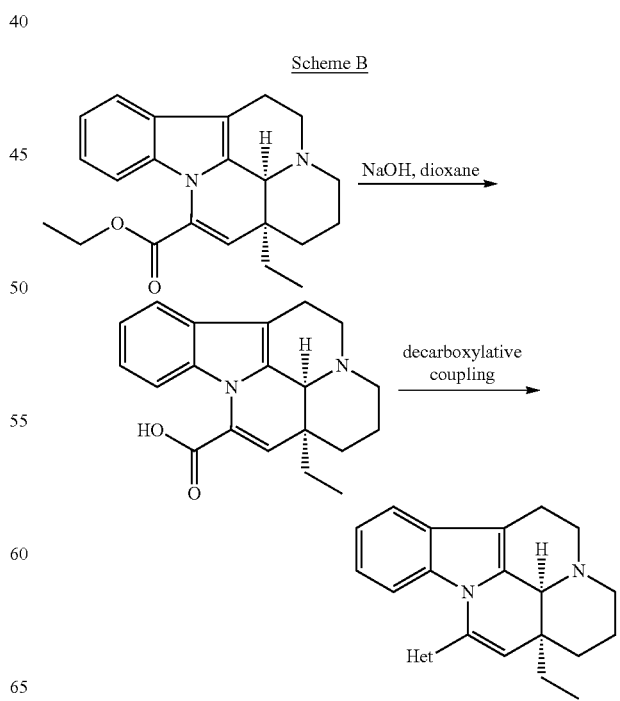

Example 8

(4¹S,13aS)-13a-ethyl-12-(4-methylpyrimidin-2-yl)-2,3,4¹,5,6,13a-hexahydro-1H-indolo[3,2,1-de]pyrido[3,2,1-ij][1,5]naphthyridine

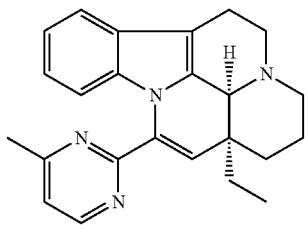

Example 8A (4¹S,13aS)-13a-ethyl-2,3,4¹,5,6,13a-hexahydro-1H-indolo[3,2,1-de]pyrido[3,2,1-ij][1,5]naphthyridine-12-carboxylic acid

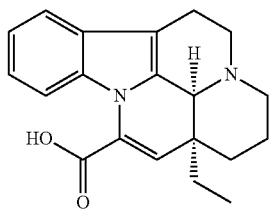

To a mixture of sodium hydroxide (137 mg, 3.43 mmol) and anhydrous dioxane (14 mL) was added vinpocetine (1 g, 2.86 mmol) at 80° C., and the mixture was reacted at such temperature for 2 hours. After vinpocetine was consumed (monitored by TLC), the mixture was concentrated to dry, water was added to dissolve the residue, the pH of the solution obtained was adjusted to 3 with 2M hydrochloric acid. The mixture was extracted with a mixed solution of dichloromethane/isopropanol (10/1 by volume), the extract was dried and concentrated to obtain the target compound (for the next step, 900 mg, yield: 98%).

LCMS (ESI) m/z: 323 (M+1)

Example 8B (4¹S,13aS)-13a-ethyl-12-(4-methylpyrimidin-2-yl)-2,3,4¹,5,6,13a-hexahydro-1H-indolo[3,2,1-de]pyrido[3,2,1-ij][1,5]naphthyridine

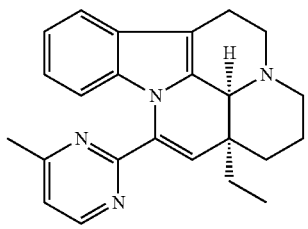

To a microwave tube was added (4¹S,13aS)-13a-ethyl-2,3,4¹,5,6,13a-hexahydro-1H-indolo[3,2,1-de]pyrido[3,2,1-ij][1,5]naphthyridine-12-carboxylic acid (300 mg, 0.93 mmol), 2-chloro-4-methylpyrimidine (180 mg, 1.396 mmol), cesium carbonate (363 mg, 1.117 mmol) and 1,10-phenanthroline (8.4 mg, 0.047 mmol), the mixture was uniformly mixed with N-methylpyrrolidone (3 mL) and then purged three times with nitrogen. Copper(I) iodide (8.9 mg, 0.047 mmol) and palladium (II) acetylacetonate (14 mg, 0.047 mmol) were added, then the tube was sealed. The reaction mixture was heated to 170° C. with microwave and reacted for 30 minutes. The reaction mixture was poured into 20 mL water and filtered, and the filter cake was purified by Preparative High Performance Liquid Chromatography to obtain the target compound (100 mg, yield: 29%).

¹H NMR (400 MHz, METHANOL-d₄) δ ppm 8.77 (d, J=5.3 Hz, 1H), 7.60 (d, J=7.8 Hz, 1H), 7.53 (d, J=5.3 Hz, 1H), 7.15 (t, J=7.5 Hz, 1H), 7.07-7.01 (m, 1H), 6.21 (d, J=8.3 Hz, 1H), 5.90 (s, 1H), 5.15 (s, 1H), 3.99-3.90 (m, 1H), 3.90-3.83 (m, 1H), 3.36 (d, J=3.5 Hz, 1H), 3.31-3.26 (m, 1H), 3.23-3.15 (m, 1H), 2.61 (s, 3H), 2.09-1.91 (m, 3H), 1.90-1.77 (m, 2H), 1.36 (dt, J=3.1, 13.7 Hz, 1H), 1.13 (t, J=7.3 Hz, 3H).

LCMS (ESI) m/z: 371 (M+1)

Example 9

(4¹S,13aS)-13a-ethyl-12-(6-methylpyridazin-3-yl)-2,3,4¹,5,6,13a-hexahydro-1H-indolo[3,2,1-de]pyrido[3,2,1-ij][1,5]naphthyridine

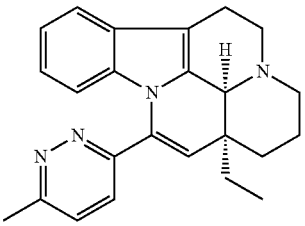

The preparation method of the example was the same as that of Example 8B.

¹H NMR (400 MHz, METHANOL-d₄) δ ppm 8.57-8.51 (m, 1H), 8.50-8.45 (m, 1H), 7.63 (d, J=7.5 Hz, 1H), 7.21-7.15 (m, 1H), 7.13-7.08 (m, 1H), 6.50 (d, J=8.3 Hz, 1H), 6.02 (s, 1H), 5.19 (s, 1H), 3.97-3.82 (m, 2H), 3.38-3.33 (m, 1H), 3.28-3.14 (m, 2H), 3.01 (s, 3H), 2.13-1.95 (m, 3H), 1.91-1.77 (m, 2H), 1.36 (dt, J=3.3, 13.8 Hz, 1H), 1.13 (t, J=7.3 Hz, 3H).

LCMS (ESI) m/z: 371 (M+1)

Example 10

(4¹S,13aS)-13a-ethyl-12-(6-methylpyrazin-2-yl)-2,3,4¹,5,6,13a-hexahydro-1H-indolo[3,2,1-de]pyrido[3,2,1-ij][1,5]naphthyridine

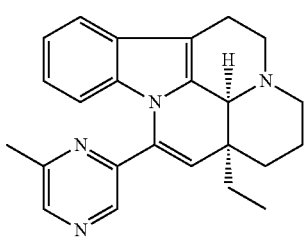

The preparation method of the example was the same as that of Example 8B.

¹H NMR (400 MHz, METHANOL-d₄) δ ppm 8.67 (d, J=11.8 Hz, 2H), 7.61 (d, J=7.8 Hz, 1H), 7.15 (t, J=7.5 Hz, 1H), 7.06-6.97 (m, 1H), 6.13 (d, J=8.3 Hz, 1H), 5.67 (s, 1H), 5.18 (s, 1H), 4.00-3.91 (m, 1H), 3.90-3.84 (m, 1H), 3.38-3.34 (m, 1H), 3.31-3.27 (m, 1H), 3.24-3.16 (m, 1H), 2.60 (s, 3H), 2.08-1.91 (m, 3H), 1.90-1.78 (m, 2H), 1.46-1.36 (m, 1H), 1.14 (t, J=7.4 Hz, 3H).

LCMS (ESI) m/z: 371 (M+1)

Example 11

(4¹S,13aS)-13a-ethyl-12-(pyridin-2-yl)-2,3,4¹,5,6,13a-hexahydro-1H-indolo[3,2,1-de]pyrid o[3,2,1-ij][1,5]naphthyridine

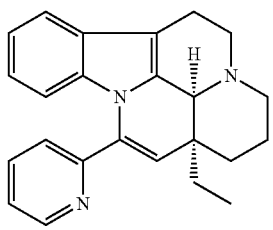

The preparation method of the example was the same as that of Example 8B.

¹H NMR (400 MHz, METHANOL-d₄) δ ppm 8.99 (d, J=5.3 Hz, 1H), 8.79 (t, J=7.7 Hz, 1H), 8.31-8.23 (m, 2H), 7.68 (d, J=7.8 Hz, 1H), 7.23 (t, J=7.5 Hz, 1H), 7.12 (t, J=7.5 Hz, 1H), 6.22 (d, J=8.3 Hz, 1H), 6.07 (s, 1H), 5.23 (br. s., 1H), 4.02-3.93 (m, 1H), 3.92-3.86 (m, 1H), 3.42-3.34 (m, 2H), 3.30-3.19 (m, 2H), 2.14-1.99 (m, 3H), 1.92 (d, J=14.3 Hz, 1H), 1.84 (d, J=14.3 Hz, 1H), 1.40 (dt, J=3.4, 13.9 Hz, 1H), 1.17 (t, J=7.4 Hz, 3H).

LCMS (ESI) m/z: 356 (M+1)

Example 12

(4¹S,13aS)-13a-ethyl-12-(6-methylpyridin-2-yl)-2,3,4¹,5,6,13a-hexahydro-1H-indolo[3,2,1-de]pyrido[3,2,1-ij][1,5]naphthyridine

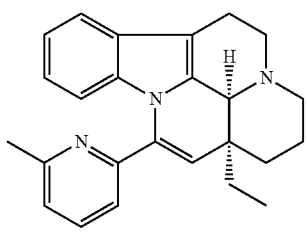

The preparation method of the example was the same as that of Example 8B.

¹H NMR (400 MHz, METHANOL-d₄) δ ppm 8.57 (t, J=8.0 Hz, 1H), 8.10-7.95 (m, 2H), 7.65 (d, J=7.8 Hz, 1H), 7.20 (t, J=7.3 Hz, 1H), 7.13-7.06 (m, 1H), 6.21 (d, J=8.3 Hz, 1H), 6.00 (s, 1H), 5.21 (s, 1H), 4.00-3.91 (m, 1H), 3.90-3.82 (m, 1H), 3.41-3.32 (m, 2H), 3.30-3.24 (m, 1H), 3.24-3.17 (m, 1H), 2.86 (s, 3H), 2.16-1.95 (m, 3H), 1.94-1.77 (m, 2H), 1.40 (dt, J=3.3, 13.9 Hz, 1H), 1.15 (t, J=7.4 Hz, 3H).

LCMS (ESI) m/z: 370 (M+1)

Example 13

(4¹S,13aS)-13a-ethyl-12-(3-methylpyridin-2-yl)-2,3,4¹,5,6,13a-hexahydro-1H-indolo[3,2,1-de]pyrido[3,2,1-ij][1,5]naphthyridine

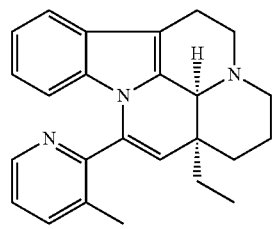

The preparation method of the example was the same as that of Example 8B.

¹H NMR (400 MHz, METHANOL-d₄) δ ppm 8.95 (d, J=5.5 Hz, 1H), 8.62 (d, J=8.0 Hz, 1H), 8.27-8.18 (m, 1H), 7.64 (d, J=7.8 Hz, 1H), 7.22-7.14 (m, 1H), 7.08-6.99 (m, 1H), 6.00 (d, J=8.5 Hz, 0.67H), 5.90-5.82 (m, 1H), 5.73 (d, J=8.3 Hz, 0.33H), 5.38-5.24 (m, 1H), 4.02-3.84 (m, 2H), 3.43-3.32 (m, 2H), 3.30-3.26 (m, 1H), 3.24-3.16 (m, 1H), 2.69 (s, 1H), 2.21 (s, 2H), 2.17-2.08 (m, 1H), 2.07-1.81 (m, 4H), 1.60-1.45 (m, 1H), 1.14 (t, J=7.4 Hz, 3H).

LCMS (ESI) m/z: 370 (M+1)

Example 14

(4¹S,13aS)-12-(5,6-dimethylpyrazin-2-yl)-13a-ethyl-2,3,4¹,5,6,13a-hexahydro-1H-indolo[3,2,1-de]pyrido[3,2,1-ij][1,5]naphthyridine

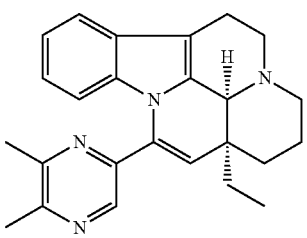

The preparation method of the example was the same as that of Example 8B.

¹H NMR (400 MHz, METHANOL-d₄) δ ppm 8.69 (s, 1H), 7.61 (d, J=7.8 Hz, 1H), 7.19-7.12 (m, 1H), 7.04 (t, J=7.8 Hz, 1H), 6.30 (d, J=8.3 Hz, 1H), 5.75 (s, 1H), 5.17 (br. s., 1H), 3.99-3.83 (m, 2H), 3.40-3.16 (m, 4H), 2.78 (s, 3H), 2.67 (s, 3H), 2.12-1.95 (m, 3H), 1.90-1.79 (m, 2H), 1.39 (t, J=12.5 Hz, 1H), 1.14 (t, J=7.3 Hz, 3H).

LCMS (ESI) m/z: 385 (M+1)

Scheme B1

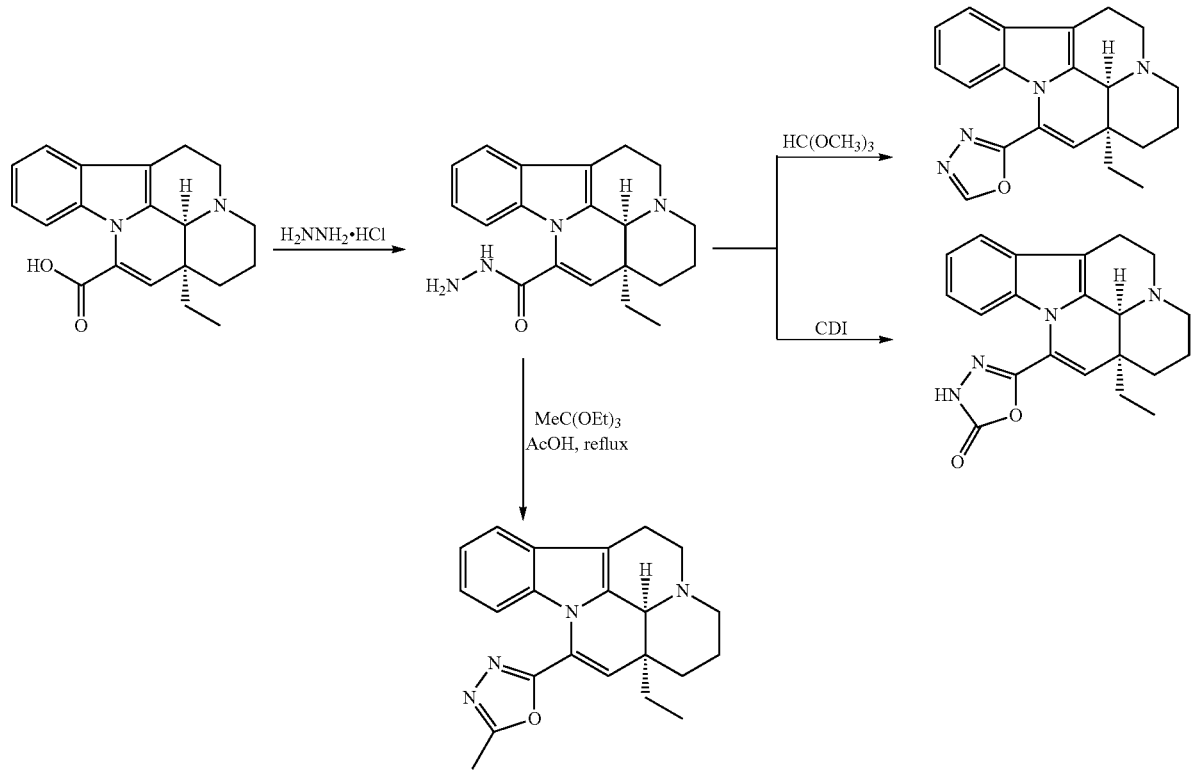

Example 15

2-((4¹S,13aS)-13a-ethyl-2,3,4¹,5,6,13a-hexahydro-1H-indolo[3,2,1-de]pyrido[3,2,1-ij][1,5]naphthyridin-12-yl)-1,3,4-oxadiazole

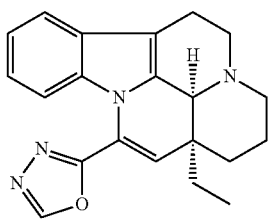

Example 15A (4¹S,13aS)-13a-ethyl-2,3,4¹,5,6,13a-hexahydro-1H-indolo[3,2,1-de]pyrido[3,2,1-ij][1,5]naphthyridine-12-hydrazide

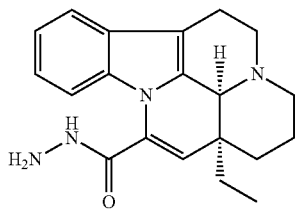

Thionyl chloride (20 mL) was added dropwise to a solution of (4¹S,13aS)-13a-ethyl-2,3,4¹,5,6,13a-hexahydro-1H-indolo[3,2,1-de]pyrido[3,2,1-ij][1,5]naphthyridine-12-carboxylic acid (1.8 g, 5.58 mmol) and DMF (1 mL) in chloroform (15 mL) at 0° C., then the reaction mixture was heated under reflux and maintained for 3 hours. After cooling to room temperature, the reaction mixture was poured into 25% hydrazine hydrate (1.4 g, 27.9 mmol) and stirred for another 2 hours. The mixture was diluted with water and extracted with dichloromethane. The extract was dried over anhydrous sodium sulfate and concentrated to obtain the target compound (yellow solid, 1.7 g, yield: 89%).

Example 15B 2-((4¹S,13aS)-13a-ethyl-2,3,4¹,5,6,13a-hexahydro-1H-indolo[3,2,1-de]pyrido[3,2,1-ij][1,5]naphthyridin-12-yl)-1,3,4-oxadiazole

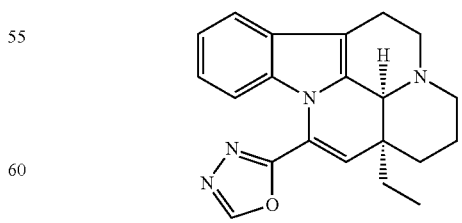

A mixture of (4¹S,13aS)-13a-ethyl-2,3,4¹,5,6,13a-hexahydro-1H-indolo[3,2,1-de]pyrido[3,2,1-ij][1,5]naphthyridine-12-hydrazide (400 mg, 1.2 mmol) and trimethyl orthoformate (5 mL) was heated to 160° C. with microwave and reacted for half an hour. The reaction mixture was concentrated to dry, and the crude product was purified by Preparative High Performance Liquid Chromatography to obtain the target compound (50 mg, yield: 12%).

$^1$H NMR (400 MHz, CDCl$_3$) δ ppm 1.02 (t, J=7.28 Hz, 3H), 1.17 (td, J=13.55, 3.51 Hz, 1H), 1.26 (s, 1H), 1.45 (d, J=13.05 Hz, 1H), 1.60 (d, J=14.05 Hz, 1H), 1.69-1.79 (m, 1H), 1.90-2.01 (m, 2H), 2.54 (d, J=16.31, 3.26 Hz, 1H), 2.63-2.69 (m, 2H), 2.99-3.11 (m, 1H), 3.26-3.41 (m, 2H), 4.25 (s, 1H), 5.99 (s, 1H), 6.52 (d, J=8.53 Hz, 1H), 7.03-7.15 (m, 2H), 7.49 (d, J=7.53 Hz, 1H), 8.57 (s, 1H).

LCMS (ESI) m/z: 346 (M+1)

Example 16

5-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)-1,3,4-oxadiazol-2(3H)-one

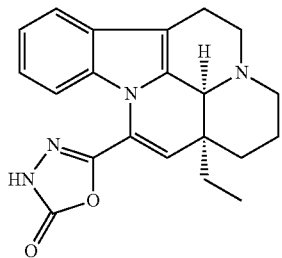

To a solution of (4$^1$S,13aS)-13a-ethyl-2,3,4$^1$,5,6,13a-hexahydro-1H-indolo[3,2,1-de]pyrido[3,2,1-ij][1,5]naphthyridine-12-hydrazide (170 mg, 0.5 mmol) in dioxane (7 ml) was added carbonyl diimidazole (98 mg, 0.6 mmol), and the mixture was heated under reflux for 45 minutes. After the reaction mixture was concentrated, the residue was purified by Preparative High Performance Liquid Chromatography to obtain the target compound (42 mg, yield: 23%).

$^1$H NMR (400 MHz, CDCl$_3$) δ ppm 0.90 (t, J=7.21 Hz, 3H), 1.40 (d, J=13.69 Hz, 1H), 1.50 (d, J=13.69 Hz, 1H), 1.77-1.96 (m, 4H), 2.11 (s, 1H), 2.56 (t, J=11.00 Hz, 1H), 2.68 (s, 1H), 2.76 (d, J=10.27 Hz, 1H), 3.23 (d, J=6.36 Hz, 2H), 4.37 (br. s., 1H), 5.23 (s, 1H), 5.81 (s, 1H), 7.13 (d, J=3.67 Hz, 1H), 7.17-7.22 (m, 1H), 7.31-7.36 (m, 1H).

LCMS (ESI) m/z: 362 (M+1)

Example 17

2-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)-5-methyl-1,3,4-oxadiazole

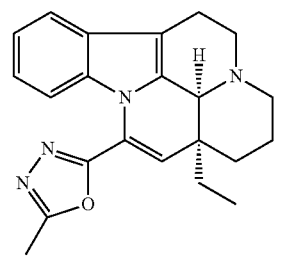

To a 50 mL round bottom flask was added (4$^1$S,13aS)-13a-ethyl-2,3,4$^1$,5,6,13a-hexahydro-1H-indolo[3,2,1-de]pyrido[3,2,1-ij][1,5]naphthyridine-12-hydrazide (500 mg, 1.5 mmol), triethyl orthoacetate (487 mg, 3 mmol) and acetic acid (5 mL), and the reaction mixture was refluxed for 30 min. After completion (monitored by LC-MS), the solvent was distilled off, and the residue was dissolved in 2 mL dimethylsulfoxide. The target compound (200 mg, yield: 31.1%) was separated by Preparative High Performance Liquid Chromatography.

$^1$H NMR (400 MHz, METHANOL-d$_4$) δ ppm 1.12 (t, J=7.28 Hz, 3H), 1.24-1.37 (m, 1H), 1.70-1.85 (m, 2H), 1.89-2.12 (m, 3H), 2.56-2.74 (m, 5H), 3.08-3.29 (m, 3H), 3.84 (d, J=5.27 Hz, 2H), 5.14 (br. s., 1H), 6.08 (s, 1H), 6.78 (d, J=8.78 Hz, 1H), 7.1-7.28 (m, 2H), 7.55-7.68 (m, 1H).

LCMS (ESI) m/z: 363 (M+1)

Scheme B2

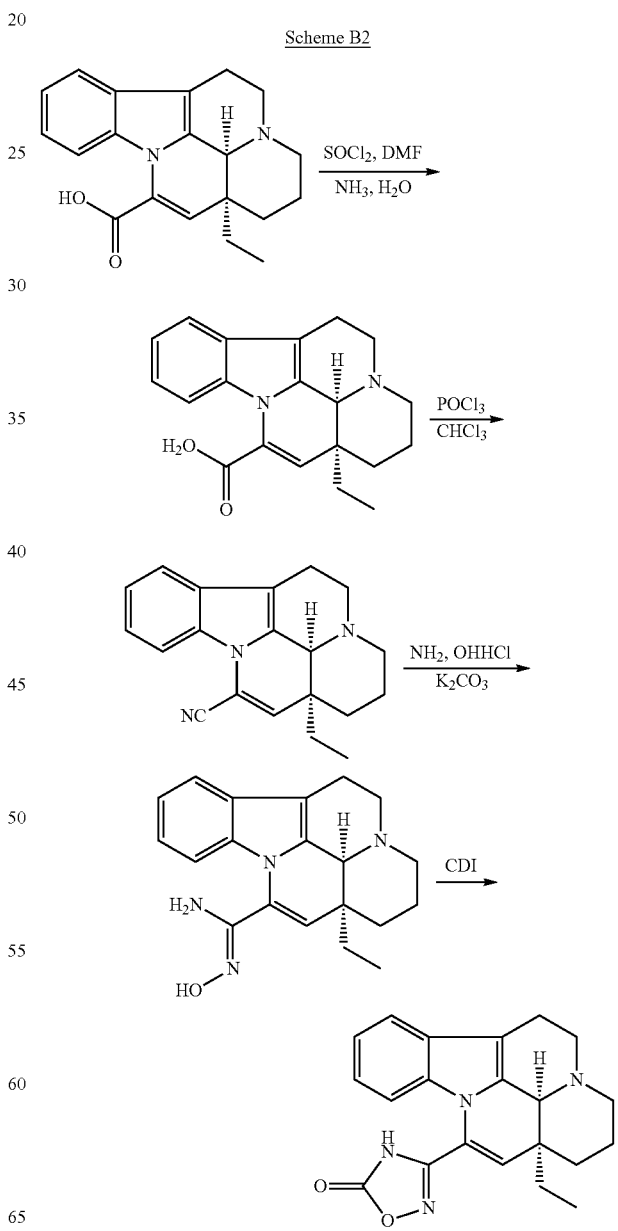

79
-continued

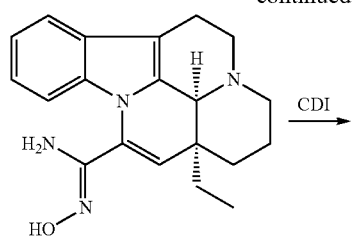

CDI →

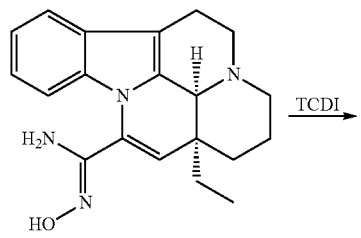

TCDI →

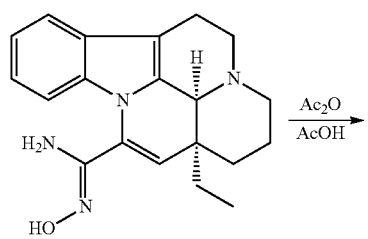

Ac₂O / AcOH →

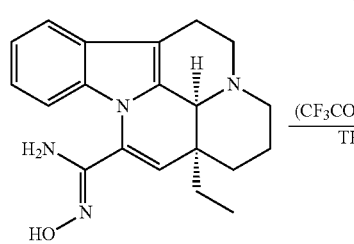

(CF₃CO)₂O, Py / THF →

80
-continued

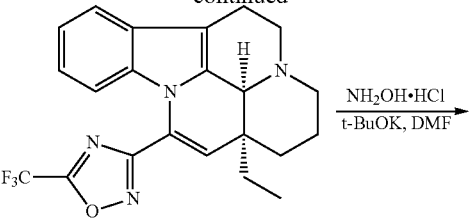

NH₂OH·HCl / t-BuOK, DMF →

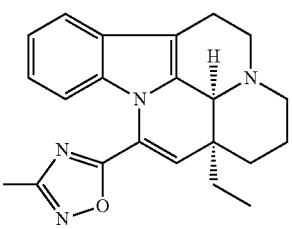

Example 18

3-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazol-5(4H)-one

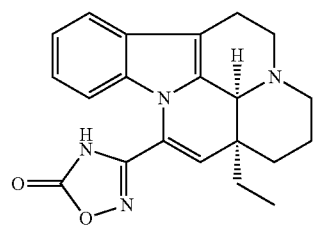

Example 18A (4¹S,13aS)-13a-ethyl-2,3,4¹,5,6,13a-hexahydro-H-indolo[3,2,1-de]pyrido[3,2,1-ij][1,5]naphthyridine-12-carboxamide

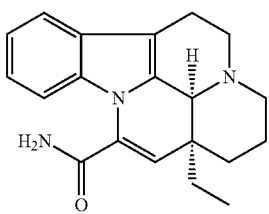

Thionyl chloride (5 mL) was added dropwise to a solution of (4¹S,13aS)-13a-ethyl-2,3,4¹,5,6,13a-hexahydro-1H-indolo[3,2,1-de]pyrido[3,2,1-ij][1,5]naphthyridine-12-carboxylic acid (4 g, 12.4 mmol) and DMF (0.1 mL) in chloroform (40 mL), then the reaction mixture was heated under reflux and maintained for 3 hours. After cooling to room temperature, the reaction mixture was poured into 25% ammonium hydroxide (40 mL) and stirred for 2 hours. The mixture was diluted with water and extracted with dichloromethane. The extract was dried over anhydrous sodium sulfate and concentrated to obtain the target compound (yellow solid, 3.8 g, yield: 95%).

¹H NMR (400 MHz, CDCl₃) δ ppm 7.44 (d, J=6.8 Hz, 1H), 7.36 (d, J=8.0 Hz, 1H), 7.09-7.15 (m, 2H), 5.91-6.10 (m, 2H), 5.84 (s, 1H), 4.14 (s, 1H), 3.32-3.41 (m, 1H), 3.19-3.31 (m, 1H), 2.89-3.09 (m, 1H), 2.58-2.68 (m, 2H), 2.44-2.55 (m, 1H), 1.84-1.96 (m, 3H), 1.65-1.77 (m, 1H), 1.47-1.50 (m, 1H), 1.39-1.42 (m, 1H), 1.01 (t, J=8.0 Hz, 3H).

LCMS (ESI) m/z: 322 (M+1)

Example 18B (4¹S,13aS)-13a-ethyl-2,3,4¹,5,6,13a-hexahydro-1H-indolo[3,2,1-de]pyrido[3,2,1-ij][1,5]naphthyridine-12-carbonitrile

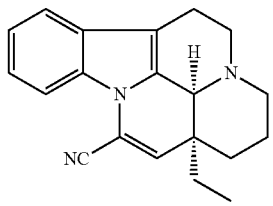

Phosphorus oxychloride was added dropwise to a solution of (4¹S,13aS)-13a-ethyl-2,3,4¹,5,6,13a-hexahydro-1H-indolo[3,2,1-de]pyrido[3,2,1-ij][1,5]naphthyridine-12-carboxamide (3.8 g, 11.8 mmol) in chloroform (50 mL) at 0° C., and the mixture was heated under reflux for 4 hours. After cooling to room temperature, the mixture was poured into ice water, and the pH of the mixture was adjusted to neutral with 40% sodium hydroxide solution. The organic layer was separated, and the remaining aqueous layer was extracted with dichloromethane. The combined organic layers were washed with sodium bicarbonate solution, dried over anhydrous sodium sulfate, filtered and concentrated. The crude product was recrystallized with a mixed solution of isopropanol/water (1/1 by volume) to obtain the target compound (yellow solid, 2.0 g, yield: 56%).

¹H NMR (400 MHz, CDCl₃) δ ppm 7.94 (d, J=8.0 Hz, 1H), 7.40 (d, J=8.0 Hz, 1H), 7.17-7.21 (m, 1H), 7.10-7.13 (m, 1H), 5.86 (s, 1H), 4.16 (s, 1H), 3.27-3.32 (m, 1H), 3.14-3.23 (m, 1H), 2.91-2.98 (m, 1H), 2.61 (d, J=4.0 Hz, 2H), 2.42-2.47 (m, 1H), 1.87-1.99 (m, 1H), 1.70-1.81 (m, 2H), 1.39-1.48 (m, 2H), 1.01-1.09 (m, 1H), 0.95 (t, J=8.0 Hz, 3H).

LCMS (ESI) m/z: 304 (M+1)

Example 18C (4¹S,13aS,Z)-13a-ethyl-N'-hydroxyl-2,3,4¹,5,6,13a-hexahydro-1H-indolo[3,2,1-de]pyrido[3,2,1-ij][1,5]naphthyridine-12-carboxamidine

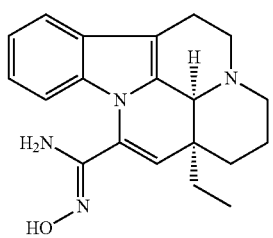

To a solution of (4¹S,13aS)-13a-ethyl-2,3,4¹,5,6,13a-hexahydro-1H-indolo[3,2,1-de]pyrido[3,2,1-ij][1,5]naphthyridine-12-carbonitrile (300 mg, 1 mmol) in methanol (8 mL) was added hydroxylamine hydrochloride (350 mg, 5 mmol) and diisopropylethylamine (323 mg, 2.5 mmol), respectively, the reaction mixture was stirred at room temperature for 2 hours, then hydroxylamine hydrochloride (175 mg, 2.5 mmol) was added, and the reaction mixture was stirred for another 5 hours. Hydroxylamine hydrochloride (175 mg, 2.5 mmol) was added and the reaction mixture was stirred at room temperature for 17 hours. After completion, a small amount of water was added to the mixture, then the mixture was filtered. The solid obtained was washed with ethyl acetate and then dissolved in methanol. The solvent was distilled off to obtain the pure target compound (white solid, 300 mg, yield: 89%).

¹H NMR (400 MHz, MeOD) δ ppm 1.10 (t, J=7.39 Hz, 3H), 1.21-1.33 (m, 2H), 1.34-1.39 (m, 1H), 1.73 (d, J=11.69 Hz, 3H), 1.85-1.92 (m, 2H), 1.98 (dt, J=14.55, 7.28 Hz, 2H), 3.06-3.13 (m, 1H), 3.21-3.26 (m, 2H), 3.34 (s, 1H), 3.79-3.85 (m, 2H), 5.03 (br. s., 1H), 5.49 (s, 1H), 7.13-7.19 (m, 1H), 7.22 (t, J=7.28 Hz, 1H), 7.38 (d, J=8.38 Hz, 1H), 7.54 (d, J=7.72 Hz, 1H).

Example 18D 3-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazol-5(4H)-one

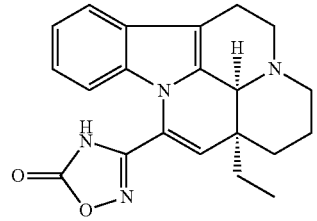

To a solution of (4¹S,13aS, Z)-13a-ethyl-N'-hydroxyl-2,3,4¹,5,6,13a-hexahydro-1H-indolo[3,2,1-de]pyrido[3,2,1-ij][1,5]naphthyridine-12-carboxamidine (200 mg, 0.6 mmol) in dioxane (10 mL) was added carbonyl diimidazole (482 mg, 3.0 mmol), and the reaction mixture was heated under reflux for 45 minutes. After the solvent was distilled off, the residue was purified by Preparative High Performance Liquid Chromatography to obtain the target compound (127 mg, yield: 58%).

¹H NMR (400 MHz, CDCl3) δ ppm 1.00 (s, 3H), 1.26 (d, J=13.55 Hz, 1H), 1.72 (d, J=15.06 Hz, 2H), 1.92 (s, 4H), 3.06 (s, 3H), 3.26 (s, 1H), 3.47 (s, 1H), 3.60 (s, 1H), 4.86 (s, 1H), 5.85 (s, 1H), 7.08 (d, J=7.53 Hz, 1H), 7.16-7.25 (m, 2H), 7.40-7.55 (m, 1H).

LCMS (ESI) m/z: 362 (M+1)

Example 19

3-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-thiadiazol-5(4H)-one

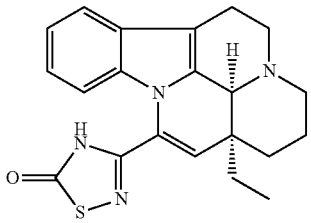

A solution of (4¹S,13aS, Z)-13a-ethyl-N'-hydroxyl-2,3,4¹,5,6,13a-hexahydro-1H-indolo[3,2,1-de]pyrido[3,2,1-ij][1,5]naphthyridine-12-carboxamidine (200 mg, 0.6 mmol) and thiocarbonyldiimidazole in tetrahydrofuran (15 mL) was heated to 60° C. and stirred for 1.5 hours. The reaction mixture was concentrated, and the residue was purified by Preparative High Performance Liquid Chromatography to obtain the target compound (69 mg, yield: 31%).

$^1$H NMR (400 MHz, CDCl$_3$) δ ppm 1.02 (br. s., 3H), 1.14-1.31 (m, 2H), 1.58 (d, J=14.11 Hz, 1H), 1.72 (d, J=13.45 Hz, 1H), 2.03 (br. s., 1H), 2.90 (d, J=11.03 Hz, 2H), 3.14 (br. s., 2H), 3.47 (d, J=2.43 Hz, 1H), 3.56 (br. s., 1H), 4.85 (br. s., 1H), 5.77 (br. s., 1H), 6.81 (br. s., 1H), 7.15 (br. s., 2H), 7.41 (br. s., 1H).

LCMS (ESI) m/z: 378 (M+1)

Example 20

3-((4¹S,13aS)-13a-ethyl-2,3,4¹,5,6,13a-hexahydro-1H-indolo[3,2,1-de]pyrido[3,2,1-ij][1,5]naphthyridin-12-yl)-5-methyl-1,2,4-oxadiazole

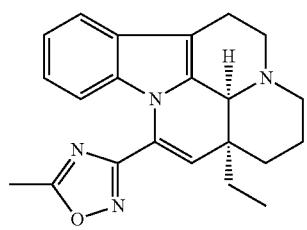

To a 50 mL round bottom flask were added (4¹S,13aS, Z)-13a-ethyl-N'-hydroxyl-2,3,4¹,5,6,13a-hexahydro-1H-indolo[3,2,1-de]pyrido[3,2,1-ij][1,5]naphthyridine-12-carboxamidine (150 mg, 0.45 mmol), acetic anhydride (136.6 mg, 0.134 mmol) and acetic acid (10 mL), respectively, and the reaction mixture was stirred at 110° C. for 1 hour. After the reaction mixture was concentrated, the residue was dissolved in 1 mL N,N-dimethylformamide. The target compound was obtained by Preparative High Performance Liquid Chromatography (17 mg, yield: 10.7%).

$^1$H NMR (400 MHz, METHANOL-d$_4$) δ ppm 7.61-7.55 (m, 1H), 7.20-7.10 (m, 2H), 6.87-6.78 (m, 1H), 5.95 (s, 1H), 5.14 (s, 1H), 3.94-3.76 (m, 2H), 3.29-3.23 (m, 2H), 3.19-3.11 (m, 1H), 2.71 (s, 3H), 2.06-1.99 (m, 1H), 1.99-1.91 (m, 2H), 1.83-1.74 (m, 2H), 1.37-1.29 (m, 2H), 1.11 (t, J=7.4 Hz, 3H).

LCMS (ESI) m/z: 361 (M+1)

Example 21

3-((4¹S,13aS)-13a-ethyl-2,3,4¹,5,6,13a-hexahydro-1H-indolo[3,2,1-de]pyrido[3,2,1-ij][1,5]naphthyridin-12-yl)-5-trifluoromethyl-1,2,4-oxadiazole

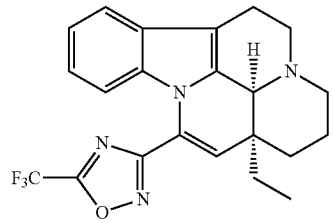

To a solution of (4¹S,13aS, Z)-13a-ethyl-N'-hydroxyl-2,3,4¹,5,6,13a-hexahydro-1H-indolo[3,2,1-de]pyrido[3,2,1-ij][1,5]naphthyridine-12-carboxamidine (700 mg, 2.083 mmol) in tetrahydrofuran (20 mL) was added pyridine (822.92 mg, 10.417 mmol) and trifluoroacetic anhydride (2177.08 mg, 10.417 mmol), and the reaction mixture was stirred at 10° C. for 3 hours. After completion, the solvent was removed under reduced pressure, water was added to the residue, then the mixture obtained was extracted with ethyl acetate. After the extract was concentrated, the crude product was purified by Preparative High Performance Liquid Chromatography to obtain the target compound (400 mg, yield: 46.4%).

$^1$H NMR (400 MHz, Methanol-d4) δ ppm 7.63-7.59 (m, 1H), 7.21-7.19 (m, 2H), 7.01-6.99 (m, 1H), 6.20 (s, 1H), 5.10 (s, 1H), 3.84-3.82 (m, 2H), 3.32-3.16 (m, 4H), 2.08-2.00 (m, 3H), 1.98-1.79 (m, 2H), 1.30-1.15 (m, 1H), 1.13-1.11 (m, 3H).

LCMS (ESI) m/z: 415 (M+1)

Example 22

5-((4¹S,13aS)-13a-ethyl-2,3,4¹,5,6,13a-hexahydro-1H-indolo[3,2,1-de]pyrido[3,2,1-ij][1,5]naphthyridin-12-yl)-3-trifluoromethyl-1,2,4-oxadiazole

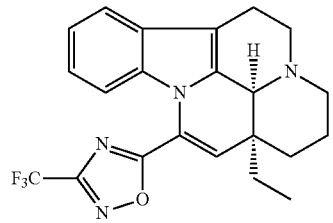

To a solution of 3-((4¹S,13aS)-13a-ethyl-2,3,4¹,5,6,13a-hexahydro-1H-indolo[3,2,1-de]pyrido[3,2,1-ij][1,5]naphthyridin-12-yl)-5-trifluoromethyl-1,2,4-oxadiazole (300 mg, 0.725 mmol) in N,N-dimethylformamide was added hydroxylamine hydrochloride (150 mg, 2.174 mmol) and potassium tert-butoxide (243.93 mg, 2.174 mmol), respectively, and the reaction mixture was stirred at 40° C. for 5 hours. The reaction mixture was filtered, and potassium tert-butoxide (150.62 mg, 1.342 mmol) was added to the filtrate. The mixture obtained was heated to 100° C. and stirred for 1 hour. After cooling to room temperature, the mixture was diluted with water and extracted three times with ethyl acetate. The combined extracts were washed with brine and concentrated. The residue was purified by Preparative High Performance Liquid Chromatography to obtain the target compound (30 mg, yield: 10%).

$^1$H NMR (400 MHz, Methanol-d4) δ ppm 7.65-7.63 (m, 1H), 7.27-7.21 (m, 2H), 6.92-6.90 (m, 1H), 6.51 (s, 1H), 5.16 (s, 1H), 3.94-3.85 (m, 2H), 3.33-3.16 (m, 4H), 2.12-2.03 (m, 3H), 1.99-1.84 (m, 2H), 1.33-1.17 (m, 1H), 1.15-1.14 (m, 3H).

LCMS (ESI) m/z: 415 (M+1)

Scheme B3

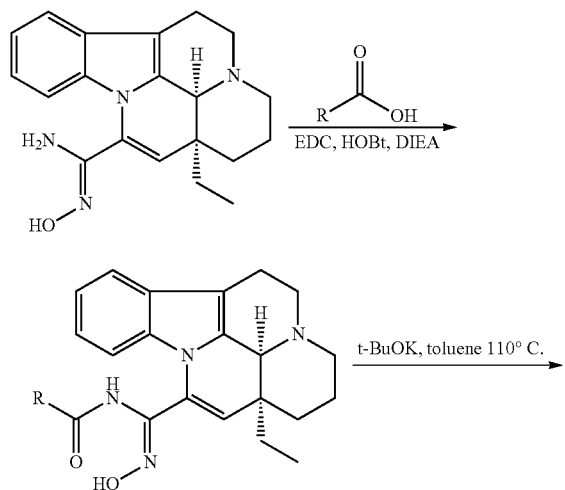

A mixture of diisopropylethylamine (288 mg, 2.23 mmol), tetrahydropyran-4-carboxylic acid (116 mg, 0.89 mmol), 1-(3-dimethylaminopropyl)-3-ethylcarbodiimide hydrochloride (340 mg, 1.78 mmol), 1-hydroxybenzotriazole (120 mg, 0.89 mmol) and N,N-dimethylformamide (4 mL) was stirred at 15° C. for 1 hour, then (4$^1$S,13aS,Z)-13a-ethyl-N'-hydroxyl-2,3,4$^1$,5,6,13a-hexahydro-1H-indolo[3,2,1-de]pyrido[3,2,1-ij][1,5]naphthyridine-12-carboxamidine (250 mg, 0.74 mmol) was added, and the mixture was stirred for another 16 hours. The reaction mixture was extracted with a mixture of dichloromethane/methanol (10/1 by volume), and the extracts were concentrated. The residue was purified by Preparative Thin Layer Chromatography (a mixture of dichloromethane/methanol (10/1 by volume) as a developing solvent) to obtain the intermediate amide (white solid, 205 mg, yield: 62%).

The intermediate amide (205 mg, 0.45 mmol) was dissolved in toluene (15 mL), then potassium tert-butoxide (167 mg, 1.49 mmol) was added. The mixture was heated under reflux and stirred overnight. After cooling to 15° C., the mixture was concentrated. The residue was purified by Preparative High Performance Liquid Chromatography to obtain the target compound (70 mg, yield: 36%).

$^1$H NMR (CDCl$_3$, 400 MHz) δ ppm 12.00 (br. s., 1H), 7.66-8.09 (m, 2H), 7.49 (d, J=7.0 Hz, 1H), 7.17 (q, J=6.9 Hz, 2H), 6.78 (d, J=7.8 Hz, 1H), 5.85-5.98 (m, 1H), 4.95 (br. s., 1H), 4.06 (d, J=11.7 Hz, 2H), 3.74-3.87 (m, 2H), 3.58 (t, J=11.3 Hz, 2H), 3.45 (d, J=11.3 Hz, 1H), 3.26-3.36 (m, 1H), 3.01-3.22 (m, 3H), 1.94-2.15 (m, 7H), 1.63-1.81 (m, 2H), 1.25-1.39 (m, 1H), 1.04 (t, J=7.2 Hz, 3H).

LCMS (ESI) m/z: 431 (M+1)

Example 24

3-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)-5-(pyridin-4-yl)-1,2,4-oxadiazole

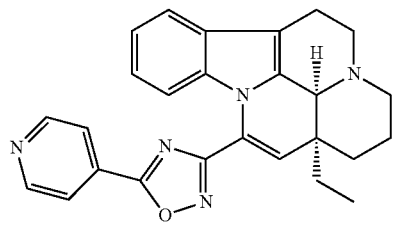

Example 23

3-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)-5-(tetrahydro-2H-pyran-4-yl)-1,2,4-oxadiazole

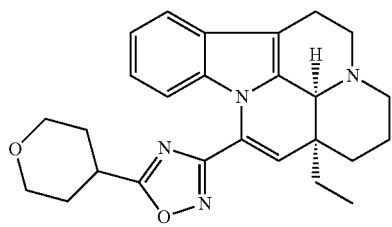

The preparation method of the example was the same as that of Example 23.

$^1$H NMR (CDCl$_3$, 400 MHz) δ ppm 11.54 (br. s., 1H), 9.00 (d, J=5.1 Hz, 2H), 8.35 (d, J=5.5 Hz, 2H), 7.43-7.57 (m, 1H), 7.13-7.18 (m, 2H), 6.83 (d, J=8.2 Hz, 1H), 6.04 (s, 1H), 4.99 (br. s., 1H), 3.71-3.89 (m, 2H), 3.46 (d, J=11.0 Hz, 1H), 3.03-3.21 (m, 3H), 1.90-2.13 (m, 3H), 1.64-1.81 (m, 2H), 1.27-1.40 (m, 1H), 1.02 (t, J=7.0 Hz, 3H).

LCMS (ESI) m/z: 424 (M+1)

Example 25

2-(3-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazol-5-yl)propan-2-ol

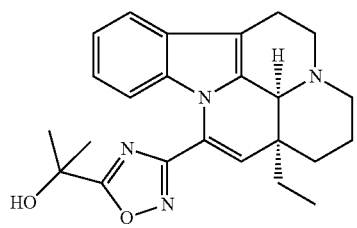

The preparation method of the example was the same as that of Example 23.

¹H NMR (MeOD, 400 MHz) δ ppm 7.46 (d, J=8.0 Hz, 1H), 6.97-7.15 (m, 2H), 6.65 (d, J=8.5 Hz, 1H), 5.87 (s, 1H), 4.33 (br. s., 1H), 3.03-3.15 (m, 1H), 2.53-2.77 (m, 3H), 1.87-2.05 (m, 2H), 1.69-1.83 (m, 7H), 1.49-1.66 (m, 2H), 1.10-1.20 (m, 2H), 1.05 (t, J=7.5 Hz, 3H).

LCMS (ESI) m/z: 405 (M+1)

Example 26

Tert-butyl-4-(3-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazol-5-yl)piperidine-1-carboxylate

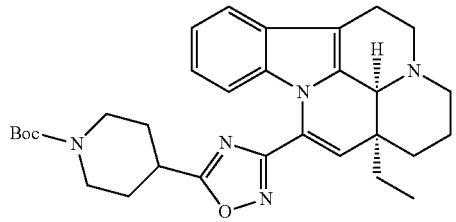

The preparation method of the example was the same as that of Example 23.

¹H NMR (MeOD, 400 MHz) δ ppm 7.46 (d, J=7.5 Hz, 1H), 6.95-7.13 (m, 2H), 6.64 (d, J=8.0 Hz, 1H), 5.85 (s, 1H), 4.32 (br. s., 1H), 4.07-4.14 (m, 2H), 3.35-3.45 (m, 2H), 3.07 (d, J=7.0 Hz, 3H), 2.57-2.75 (m, 3H), 2.15 (d, J=14.1 Hz, 2H), 1.72-2.01 (m, 5H), 1.63 (d, J=13.6 Hz, 1H), 1.01-1.19 (m, 4H).

LCMS (ESI) m/z: 530 (M+1)

Example 27

3-((4¹S,13aS)-13a-ethyl-2,3,4¹,5,6,13a-hexahydro-1H-indolo[3,2,1-de]pyrido[3,2,1-ij][1,5]naphthyridin-12-yl)-5-(4-fluorophenyl)-1,2,4-oxadiazole

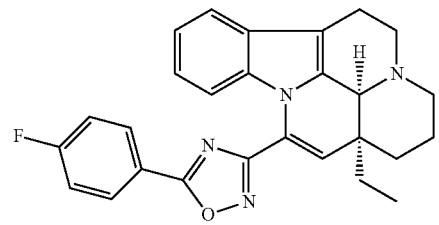

The preparation method of the example was the same as that of Example 23.

¹H NMR (MeOD, 400 MHz) δ ppm 8.24 (dd, J=5.3, 8.8 Hz, 2H), 7.28-7.50 (m, 3H), 6.93-7.11 (m, 2H), 6.76 (d, J=8.2 Hz, 1H), 5.94 (s, 1H), 4.40 (br. s., 1H), 3.39 (d, J=5.5 Hz, 2H), 3.04-3.14 (m, 1H), 2.61-2.79 (m, 3H), 1.89-2.01 (m, 2H), 1.77 (d, J=12.9 Hz, 1H), 1.65 (d, J=13.7 Hz, 1H), 1.51 (d, J=13.3 Hz, 1H), 1.16 (d, J=3.1 Hz, 1H), 1.04 (t, J=7.4 Hz, 3H).

LCMS (ESI) m/z: 441 (M+1)

Example 28

3-((4¹S,13aS)-13a-ethyl-2,3,4¹,5,6,13a-hexahydro-1H-indolo[3,2,1-de]pyrido[3,2,1-ij][1,5]naphthyridin-12-yl)-5-(thiophen-2-yl)-1,2,4-oxadiazole

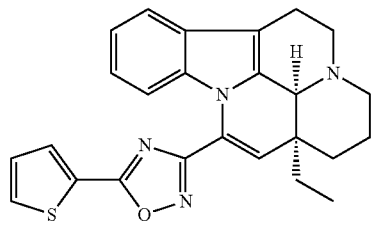

The preparation method of the example was the same as that of Example 23.

¹H NMR (MeOD, 400 MHz,) δ ppm 8.06 (d, J=3.5 Hz, 1H), 7.94 (d, J=5.0 Hz, 1H), 7.47 (d, J=7.5 Hz, 1H), 7.33 (t, J=4.3 Hz, 1H), 6.98-7.11 (m, 2H), 6.80 (d, J=8.0 Hz, 1H), 5.95 (s, 1H), 4.34 (br. s., 1H), 3.03-3.18 (m, 1H), 2.56-2.77 (m, 3H), 1.87-2.08 (m, 2H), 1.78 (d, J=14.1 Hz, 1H), 1.65 (d, J=14.1 Hz, 1H), 1.50 (d, J=13.6 Hz, 1H), 1.11-1.21 (m, 1H), 1.06 (t, J=7.3 Hz, 3H).

LCMS (ESI) m/z: 429 (M+1)

Scheme B4

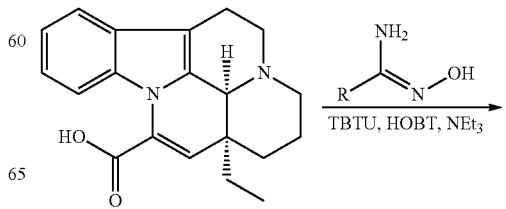

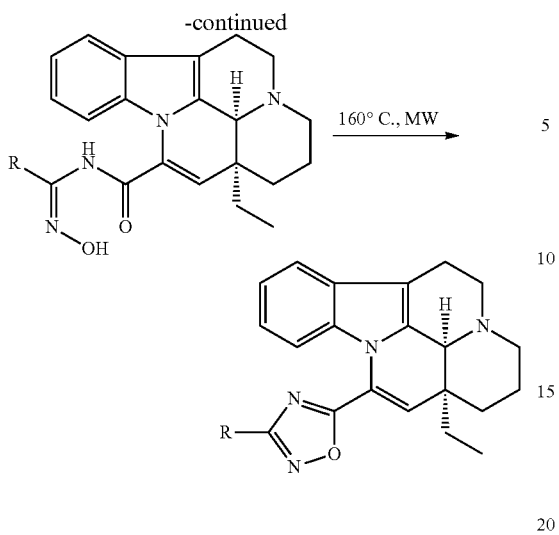

Example 29

5-((4¹S,13aS)-13a-ethyl-2,3,4¹,5,6,13a-hexahydro-1H-indolo[3,2,1-de]pyrido[3,2,1-ij][1,5]naphthyridin-12-yl)-3-methyl-1,2,4-oxadiazole

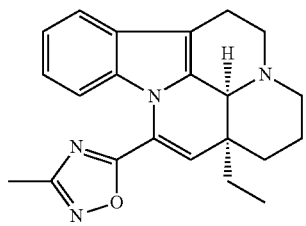

To a solution of (4¹S,13aS)-13a-ethyl-2,3,4¹,5,6,13a-hexahydro-1H-indolo[3,2,1-de]pyrido[3,2,1-ij][1,5]naphthyridine-12-carboxylic acid (14 g, 43.4 mmol), 1-hydroxybenzotriazole (300 mg, 2.17 mmol) and triethylamine (31 mL, 217 mmol) in N,N-dimethylformamide (200 mL) was added O-(benzotriazol-1-yl)-N,N,N',N'-tetramethyluronium tetrafluoroborate (14.6 g, 45.6 mmol) and N-hydroxyacetamidine hydrochloride (5.28 g, 47.8 mmol), respectively, and the reaction mixture was stirred at room temperature overnight. Brine was added to the reaction mixture, then the mixture obtained was filtered, and the filtrate was diluted with water and extracted with dichloromethane. The extract was dried over anhydrous sodium sulfate, and the low boiling components were distilled off. The remaining crude product in N,N-dimethylformamide was directly heated to 160° C. with microwaves and reacted for 50 min. The crude product was purified by Preparative High Performance Liquid Chromatography to obtain the target compound (4.0 g, yield: 25%).

¹H NMR (CDCl₃, 400 MHz) δ ppm 7.46 (d, J=6.8 Hz, 1H), 7.13-7.06 (m, 2H), 6.73 (d, J=8.0 Hz, 1H), 6.08 (s, 1H), 4.23 (s, 1H), 3.38-3.34 (m, 2H), 3.29-3.28 (m, 2H), 2.65-2.63 (m, 2H), 2.55-2.51 (m, 1H), 2.51 (s, 3H), 1.97-1.92 (m, 2H), 1.59-1.55 (m, 2H), 1.45-1.41 (m, 1H), 1.11-1.10 (m, 1H), 1.00 (t, J=7.2 Hz, 3H).

LCMS (ESI) m/z: 361 (M+1)

Example 30

5-((4¹S,13aS)-13a-ethyl-2,3,4¹,5,6,13a-hexahydro-1H-indolo[3,2,1-de]pyrido[3,2,1-ij][1,5]naphthyridin-12-yl)-3-phenyl-1,2,4-oxadiazole

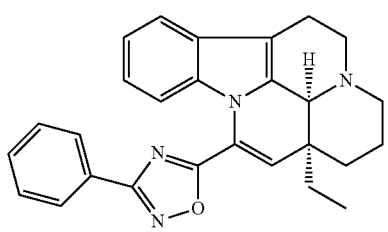

The preparation method of the example was the same as that of Example 29.

¹H NMR (CDCl₃, 400 MHz) δ ppm 8.19-8.13 (m, 2H), 7.55-7.47 (m, 4H), 7.17-7.04 (m, 2H), 6.88 (d, J=7.94 Hz, 1H), 6.19 (s, 1H), 4.26 (br. s., 1H), 3.43-3.25 (m, 2H), 3.13-3.00 (m, 1H), 2.71-2.60 (m, 2H), 2.55 (dd, J=16.21, 2.98 Hz, 1H), 2.06-1.87 (m, 3H), 1.85-1.68 (m, 1H), 1.62 (d, J=13.45 Hz, 1H), 1.52-1.38 (m, 1H), 1.17 (td, J=13.67, 3.53 Hz, 1H), 1.04 (t, J=7.50 Hz, 3H).

LCMS (ESI) m/z: 423 (M+1)

Example 31

5-((4¹S,13aS)-13a-ethyl-2,3,4¹,5,6,13a-hexahydro-1H-indolo[3,2,1-de]pyrido[3,2,1-ij][1,5]naphthyridin-12-yl)-3-(pyridin-4-yl)-1,2,4-oxadiazole

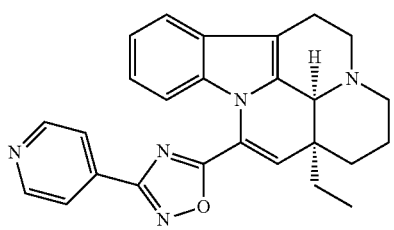

The preparation method of the example was the same as that of Example 29.

¹H NMR (400 MHz, CDCl₃) δ ppm 8.83 (d, J=4.02 Hz, 2H), 8.02 (d, J=6.02 Hz, 2H), 7.54 (d, J=7.53 Hz, 1H), 7.16-7.24 (m, 1H), 6.87 (d, J=7.53 Hz, 1H), 6.26 (s, 1H), 5.30 (s, 1H), 4.69 (br. s., 1H), 3.62 (br. s., 1H), 3.22-3.06 (m, 2H), 2.89 (d, J=11.04 Hz, 2H), 2.03 (td, J=14.68, 6.78 Hz, 2H), 1.75 (d, J=14.05 Hz, 1H), 1.62 (d, J=13.55 Hz, 1H), 1.23-1.32 (m, 2H), 1.09 (t, J=7.28 Hz, 3H).

LCMS (ESI) m/z: 424 (M+1)

Example 32

5-((4S,13aS)-13a-ethyl-2,3,4¹,5,6,13a-hexahydro-1H-indolo[3,2,1-de]pyrido[3,2,1-ij][1,5]naphthyridin-12-yl)-3-(4-fluorophenyl)-1,2,4-oxadiazole

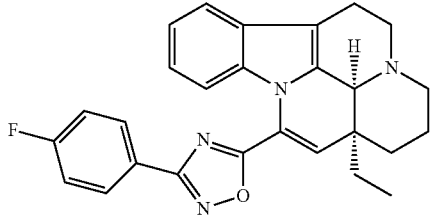

The preparation method of the example was the same as that of Example 29.

¹H NMR (400 MHz, CDCl$_3$) δ ppm 8.16 (d, J=8.71, 5.40 Hz, 2H), 7.50 (d, J=7.50 Hz, 1H), 7.15-7.23 (m, 2H), 7.07-7.15 (m, 2H), 6.87 (d, J=7.94 Hz, 1H), 6.19 (s, 1H), 4.26 (br. s., 1H), 3.36-3.43 (m, 1H), 3.26-3.35 (m, 1H), 3.00-3.12 (m, 1H), 2.67 (d, J=6.39 Hz, 2H), 2.52-2.59 (m, 1H), 1.91-2.03 (m, 2H), 1.71-1.81 (m, 1H), 1.62 (d, J=13.67 Hz, 2H), 1.46 (d, J=13.23 Hz, 1H), 1.10-1.26 (m, 2H), 1.04 (t, J=7.39 Hz, 3H).

LCMS (ESI) m/z: 440 (M+1)

Example 33

3-ethyl-5-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole

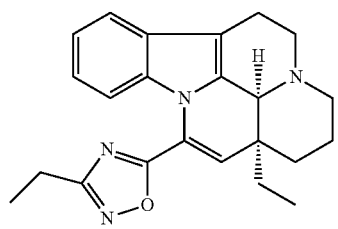

The preparation method of the example was the same as that of Example 29.

¹H NMR (400 MHz, Methanol-d4) δ ppm 7.61-7.59 (d, J=8.0 Hz, 1H), 7.23-7.16 (m, 2H), 6.75-6.73 (d, J=8.0 Hz, 1H), 6.22 (s, 1H), 5.05 (s, 1H), 3.80 (m, 2H), 3.30-3.13 (m, 4H), 2.89-2.85 (m, 2H), 2.09-1.98 (m, 3H), 1.77 (m, 2H), 1.41-1.37 (m, 1H), 1.36-1.25 (m, 1H), 1.14-1.10 (m, 3H).

Example 34

5-((4S,13aS)-13a-ethyl-2,3,4¹,5,6,13a-hexahydro-1H-indolo[3,2,1-de]pyrido[3,2,1-ij][1,5]naphthyridin-12-yl)-3-isopropyl-1,2,4-oxadiazole

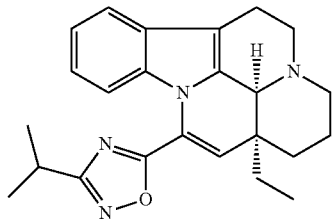

The preparation method of the example was the same as that of Example 29.

¹H NMR (400 MHz, Methanol-d4) δ ppm 7.63-7.61 (d, J=8.0 Hz, 1H), 7.24-7.17 (m, 2H), 6.74-6.72 (d, J=8.0 Hz, 1H), 6.24 (s, 1H), 5.14 (s, 1H), 3.93-3.85 (m, 2H), 3.32-3.20 (m, 5H), 2.07-1.99 (m, 3H), 1.83-1.79 (m, 2H), 1.43-1.40 (m, 6H), 1.32-1.30 (m, 1H), 1.16-1.12 (m, 3H).

Example 35

3-Cyclopropyl-5-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole

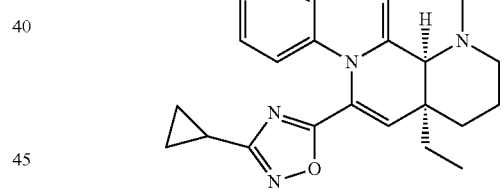

The preparation method of the example was the same as that of Example 29.

¹H NMR (400 MHz, MeOD-d$_4$) δ ppm 7.61 (d, J=6.5 Hz, 1H), 7.26-7.16 (m, 2H), 6.77-6.65 (m, 1H), 6.21 (s, 1H), 5.12 (br. s., 1H), 3.85 (d, J=5.0 Hz, 2H), 3.29-3.12 (m, 3H), 2.30-2.21 (m, 1H), 2.12-1.94 (m, 3H), 1.86-1.73 (m, 2H), 1.58-0.78 (m, 9H).

LCMS (ESI) m/z: 387 (M+1)

Scheme B5

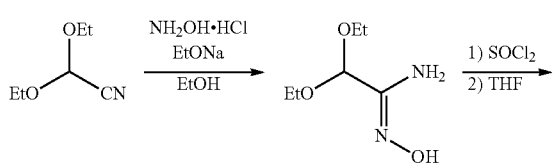

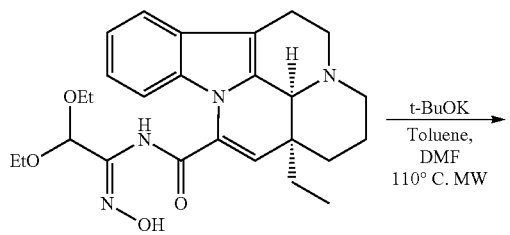

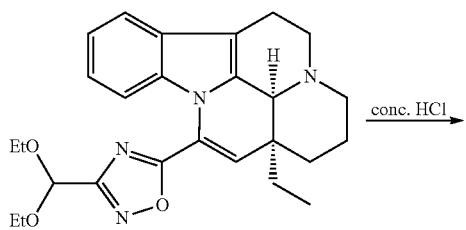

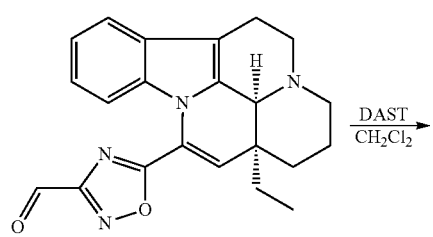

Example 36

3-Difluoromethyl-5-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole

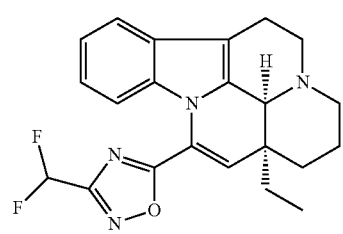

Example 36A 2,2-Diethoxy-N'-hydroxyacetamidine

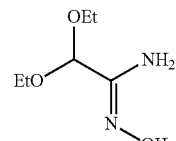

A mixture of hydroxylamine hydrochloride (2.674 g, 38.76 mmol) and sodium methoxide (2.093 g, 38.76 mmol) in methanol (20 mL) was stirred at 0° C. for half an hour, then heated to 25° C. and stirred for half an hour. Diethoxyacetonitrile (1 g, 7.752 mmol) was added, then the mixture was heated to 40° C. and stirred overnight. After the solvent was removed under reduced pressure, the residue was diluted with water and extracted with ethyl acetate (3×20 mL). The extracts were combined, washed with brine, dried over anhydrous sodium sulfate and concentrated to obtain the crude product of the target compound (colorless oil, 900 mg, yield: 71.6%).

Example 36B (4¹S,13aS)-N-(2,2-diethoxy-1-(hydroxyimino)ethyl)-13a-ethyl-2,3,4¹,5,6,13a-hexahydro-1H-indolo[3,2,1-de]pyrido[3,2,1-ij][1,5]naphthyridin-12-carboxamide

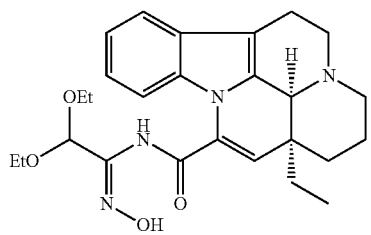

To a solution of 2,2-diethoxy-N'-hydroxyacetamidine (600 mg, 3.529 mmol) in tetrahydrofuran (20 mL) was added (4¹S,13aS)-13a-ethyl-2,3,4¹,5,6,13a-hexahydro-1H-indolo[3,2,1-de]pyrido[3,2,1-ij][1,5]naphthyridin-12-acyl chloride (1 g, 2.941 mmol, prepared by the method of Example 21A, and the excess thionyl chloride was distilled off). After completion, the low boiling-point component was distilled off obtain the crude product of the target compound (yellow solid, 1.6 g, yield: about 100%).

LCMS(ESI) m/z: 467 (M+1)

Example 36C 3-diethoxymethyl-5-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole

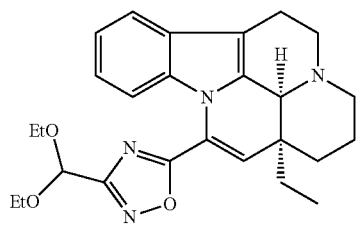

A mixture of (4S,13aS)-N-(2,2-diethoxy-1-(hydroxyimino)ethyl)-13a-ethyl-2,3,4¹,5,6,13a-hexahydro-1H-indolo[3,2,1-de]pyrido[3,2,1-ij][1,5]naphthyridin-12-carboxamide (1.2 g, 2.79 mmol) and potassium tert-butoxide (469 mg, 4.185 mmol) in N, N-dimethylformamide was heated to 110° C. for 2 hours. As the mixture cooled, 20 ml water was added, and the mixture was extracted with ethyl acetate (3×50 mL). The combined extracts were washed with brine and concentrated under vacuum to obtain the crude product of the target compound (yellow solid, 900 mg, yield: 71.9%) LCMS(ESI) m/z: 449 (M+1)

Example 36D 5-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole-3-carbaldehyde

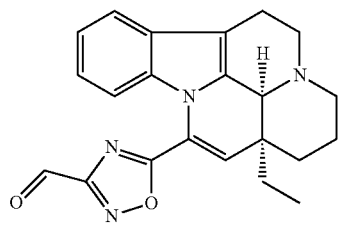

To a mixture of hydrochloride (1.613 g, 44.2 mmol) and water (0.8 g, 44.2 mmol) was added 3-diethoxymethyl-5-((4S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole (200 mg, 0.446 mmol), and the reaction mixture was heated under reflux for 1 hour. After completion (monitored by LC-MS), the mixture was slowly poured into water and extracted with ethyl acetate (3×20 mL). The combined extracts were washed with brine, dried over anhydrous sodium sulfate and concentrated under vacuum to obtain the crude product of the target compound (yellow solid, 100 mg, yield: 59.9%).

LCMS(ESI) m/z: 393 (M+1)

Example 36E 3-difluoromethyl-5-((4S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole

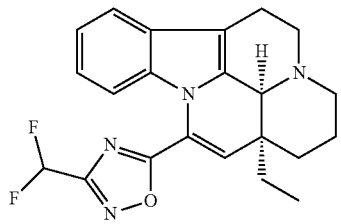

To a solution of 5-((4S,13aS)-13a-ethyl-2,3,4¹,5,6,13a-hexahydro-H-indolo[3,2,1-de]pyrido[3,2,1-ij][1,5]naphthyridin-12-yl)-1,2,4-oxadiazol-3-carbaldehyde (100 mg, 0.267 mmol) in anhydrous dichloromethane (10 mL) was added diethylaminosulphur trifluoride (644.72 mg, 1.070 mmol) at 0° C. under an atmosphere of nitrogen, then the reaction mixture was heated to 15° C. and stirred for 10 hours. The mixture was poured into saturated sodium bicarbonate solution and extracted with dichloromethane (3×15 mL). The combined extracts were washed with brine and concentrated. The crude product was separated by Preparative High Performance Liquid Chromatography to obtain the target compound (15 mg, yield: 14.2%).

¹HNMR (400 MHz, Methanol-d4) δ ppm 7.65-7.63 (m, 1H), 7.25-7.05 (m, 1H), 7.25-7.22 (m, 2H), 6.84-6.82 (m, 1H), 6.44 (s, 1H), 5.20 (s, 1H), 3.97-3.85 (m, 2H), 2.07-1.98 (m, 3H), 1.97-1.85 (m, 2H), 1.36-1.35 (m, 2H), 1.17-1.14 (m, 3H).

LCMS(ESI) m/z: 397 (M+1)

Scheme B6

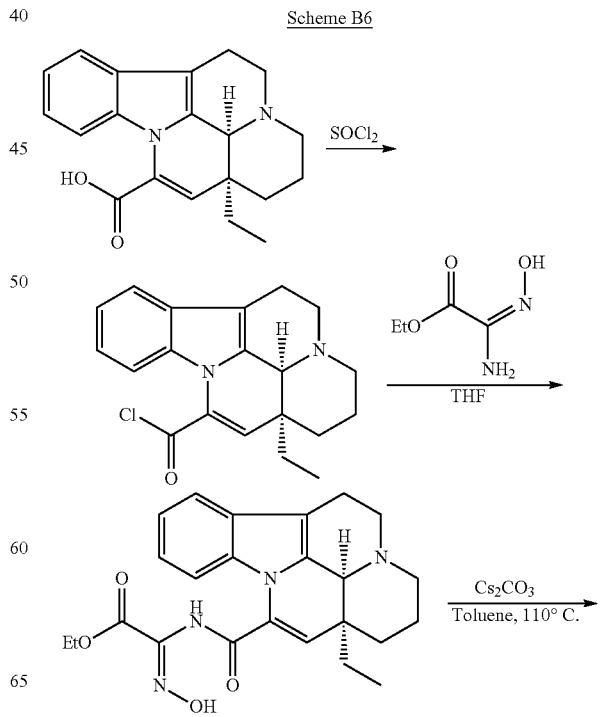

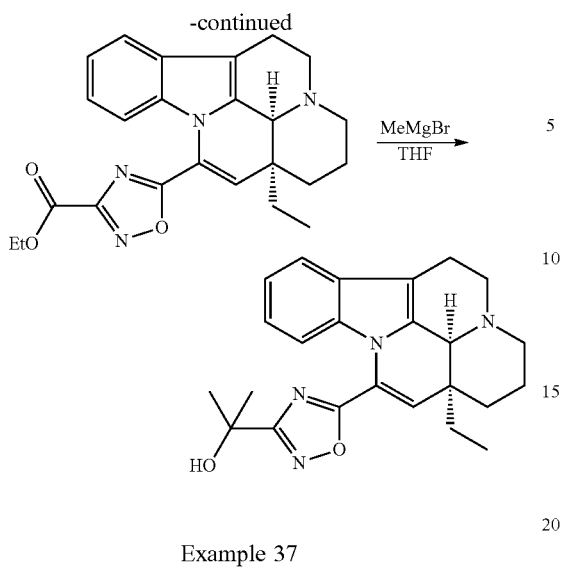

Example 37

2-(5-((4¹S,13aS)-13a-ethyl-2,3,4¹,5,6,13a-hexa-hydro-1H-indolo[3,2,1-de]pyrido[3,2,1-ij][1,5]naph-thyridin-12-yl)-1,2,4-oxadiazol-3-yl)-propan-2-ol

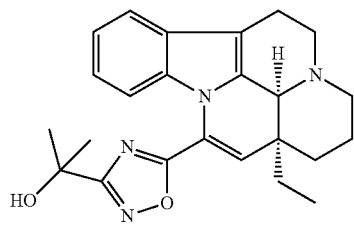

Example 37A

Ethyl-2-(5-((4¹S,13aS)-13a-ethyl-2,3,4¹,5,6,13a-hexahydro-1H-indolo[3,2,1-de]pyrido[3,2,1-ij][1,5]naphthyridin-12-formylamino)-2-(hydroxyimino)acetic acid

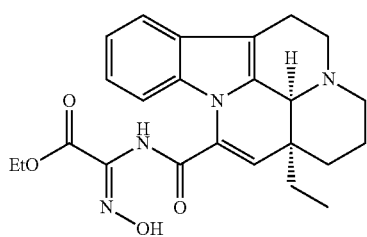

A mixture of (4¹S,13aS)-13a-ethyl-2,3,4¹,5,6,13a-hexahydro-1H-indolo[3,2,1-de]pyrido[3,2,1-ij][1,5]naphthyridin-12-carboxylic acid (2.0 g, 6.20 mmol) and thionyl chloride (10.0 mL) was heated under reflux for 2 hours and concentrated under reduced pressure to obtain the crude product. To the crude product dissolved in dichloromethane (30 mL) was added a solution of ethyl-2-amino-2-(hydroxy-imino) acetic acid (1.0 g, 7.58 mmol) in tetrahydrofuran (30 mL) at 0° C., and the reaction mixture was stirred overnight. After completion, the mixture was concentrated to obtain the target compound (yellow solid, 2.71 g, yield: 100%).

¹HNMR (DMSO-d6, 400 MHz) δ ppm 7.59 (d, J=7.5 Hz, 1H), 7.24-7.14 (m, 3H), 6.51 (s, 1H), 5.05 (br.s., 1H), 4.33 (q, J=7.2 Hz, 2H), 3.25-2.94 (m, 4H), 2.23-2.12 (m, 1H), 1.97-1.82 (m, 2H), 1.76 (td, J=3.3, 6.5 Hz, 3H), 1.63 (d, J=12.3 Hz, 2H), 1.32 (t, J=7.2 Hz, 3H), 1.03 (t, J=7.3 Hz, 3H).

LCMS (ESI) m/z: 437 (M+1)

Example 37B

Ethyl-5-((4¹S,13aS)-13a-ethyl-2,3,4¹,5,6,13a-hexa-hydro-1H-indolo[3,2,1-de]pyrido[3,2,1-ij][1,5]naph-thyridin-12-yl)-1,2,4-oxadiazole-3-carboxylate

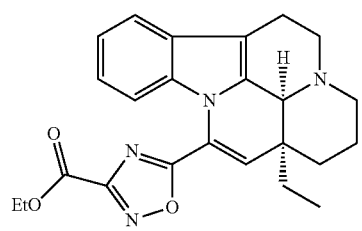

To a solution of ethyl-2-((4¹S,13aS)-13a-ethyl-2,3,4¹,5,6,13a-hexahydro-1H-indolo[3,2,1-de]pyrido[3,2,1-ij][1,5]naphthyridin-12-formylamino)-2-(hydroxyimino)acetic acid (2.71 g, 6.2 mmol) in toluene (250 mL) was added cesium carbonate (4.03 g, 12.4 mmol), and the reaction mixture was stirred at 110° C. for 1 hour. After completion, toluene was concentrated, then water (100 mL) was added to the residue and the mixture was extracted with dichloromethane (3×100 mL). The combined extracts were washed with 200 mL brine, dried over anhydrous sodium sulfate and concentrated. The crude product was separated by Preparative High Performance Liquid Chromatography to obtain the target compound (yellow solid, 400 mg, yield: 15%).

¹HNMR (400 MHz, MeOD) δ ppm 7.51 (d, J=7.0 Hz, 1H), 7.18-7.05 (m, 2H), 6.72 (d, J=8.0 Hz, 1H), 6.32 (s, 1H), 4.53 (q, J=7.0 Hz, 2H), 4.32 (s., 1H), 3.43-3.35 (m, 2H), 3.10 (td, J=7.8, 15.9 Hz, 1H), 2.70-2.58 (m, 3H), 2.10-1.91 (m, 2H), 1.80-1.62 (m, 2H), 1.51 (d, J=13.6 Hz, 1H), 1.46 (t, J=7.3 Hz, 3H), 1.12-1.03 (m, 4H).

LCMS(ESI) m/z: 419 (M+1)

Example 37C 2-(5-((4¹S,13aS)-13a-ethyl-2,3,4¹,5,6,13a-hexa-hydro-1H-indolo[3,2,1-de]pyrido[3,2,1-ij][1,5]naph-thyridin-12-yl)-1,2,4-oxadiazol-3-yl)-propan-2-ol

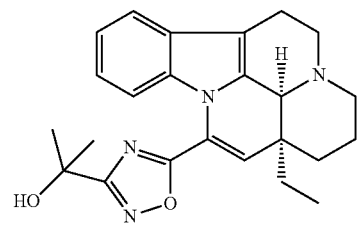

Methylmagnesium bromide (3M, 0.5 mL, 1.5 mmol) was added dropwise to a solution of ethyl-5-((4¹S,13aS)-13a-ethyl-2,3,4¹,5,6,13a-hexahydro-1H-indolo[3,2,1-de]pyrido[3,2,1-ij][1,5]naphthyridin-12-yl)-1,2,4-oxadiazole-3-carboxylate (200 mg, 0.48 mmol) in tetrahydrofuran (5 mL) at 0° C., and the reaction mixture was stirred at 0° C. for 1 hour. After completion, 10 mL water was added to the mixture and the mixture was extracted with dichloromethane (3×20 mL). The combined extracts were washed with brine, dried over anhydrous sodium sulfate and concentrated. The crude product was separated by Preparative High Performance Liquid Chromatography to obtain the target compound (30 mg, yield: 15.4%).

¹HNMR (400 MHz, MeOD) δ ppm 7.50 (d, J=7.5 Hz, 1H), 7.20-7.00 (m, 2H), 6.67 (d, J=8.5 Hz, 1H), 6.1 (s, 1H), 4.34 (s., 1H), 3.36 (s., 1H), 3.08 (d, J=8.0 Hz, 1H), 2.77-2.52 (m, 3H), 2.13-1.87 (m, 2H), 1.85-1.61 (m, 9H), 1.51 (d, J=12.0 Hz, 1H), 1.18-1.10 (m, 1H) 1.07 (t, J=7.5 Hz, 3H).

LCMS(ESI) m/z: 405 (M+1)

Scheme B7

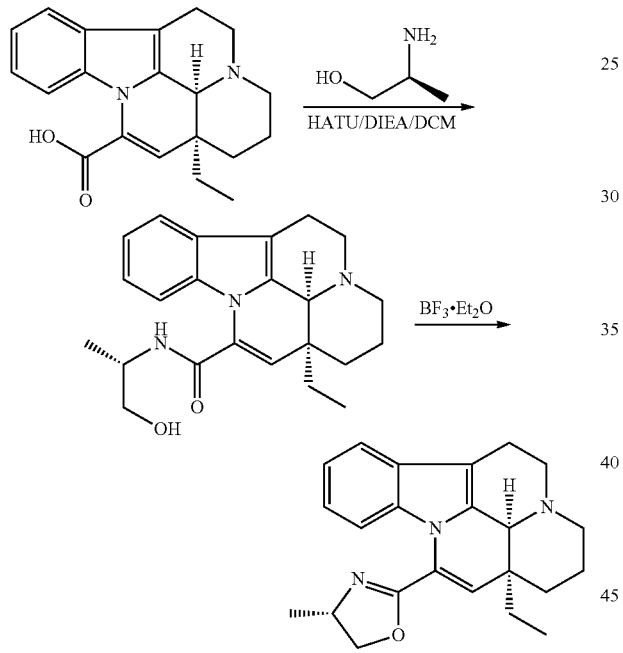

Example 38

(S)-2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyl-4,5-dihydrooxazole

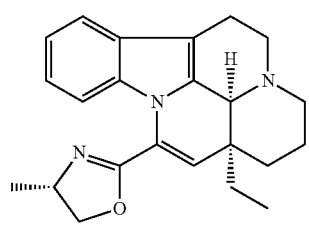

Example 38A (4¹S,13aS)-13a-ethyl-N—((S)-1-hydroxypropan-2-yl)-2,3,4¹,5,6,13a-hexahydro-1H-indolo[3,2,1-de]pyrido[3,2,1-ij][1,5]naphthyridin-12-carboxamide

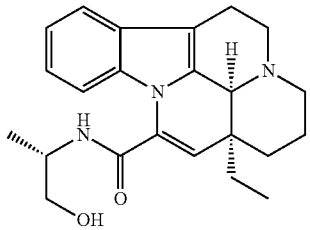

To a solution of (4¹S,13aS)-13a-ethyl-2,3,4¹,5,6,13a-hexahydro-1H-indolo[3,2,1-de]pyrido[,2,1-ij][1,5]naphthyridin-12-carboxylic acid (500 mg, 1.552 mmol) in dichloromethane (7.8 mL) was added O-(7-azabenzotriazole-1-yl)-N,N,N',N'-tetramethyluronium hexafluorophosphate (707.7 mg, 1.862 mmol) and diisopropylethylamine (240.25 mg, 1.862 mmol), the mixture was stirred for 1 hour, then L-aminopropanol (233.01 mg, 3.104 mmol) was added and the reaction mixture was stirred for 4 hours. After dilution with water, the reaction mixture was extracted with dichloromethane. The extracts were washed with water and brine, dried over anhydrous sodium sulfate and concentrated under vacuum. The residue was purified by silica gel column chromatography with dichloromethane/methanol (20/1 by volume) as an eluent to obtain the target compound (570 mg, yield: 96%).

¹HNMR (400 MHz, CHLOROFORM-d) δ ppm 0.94-1.07 (m, 4H), 1.29 (d, J=7.03 Hz, 3H), 1.36-1.57 (m, 3H), 1.65-1.80 (m, 1H), 1.81-2.00 (m, 2H), 2.52 (d, J=14.05 Hz, 1H), 2.58-2.71 (m, 2H), 2.96-3.10 (m, 1H), 3.19-3.30 (m, 1H), 3.31-3.41 (m, 1H), 3.61-3.70 (m, 1H), 3.80 (d, J=10.54 Hz, 1H), 4.18 (br.s., 1H), 4.30 (br.s., 1H), 5.72 (s, 1H), 6.26 (br.s., 1H), 7.08-7.20 (m, 2H), 7.32 (d, J=8.03 Hz, 1H), 7.46 (d, J=7.53 Hz, 1H).

Example 38B (S)-2-((4¹S, 13aS)-13a-ethyl-2,3,4¹,5,6,13a-hexahydro-1H-indolo[3,2,1-de]pyrido[3,2,1-ij][1,5]naphthyridin-12-yl)-4-methyl-4,5-dihydrooxazole

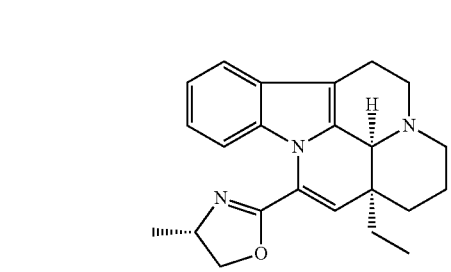

A solution of (4¹S,13aS)-13a-ethyl-N—((S)-1-hydroxypropan-2-yl)-2,3,4¹,5,6,13a-hexahydro-1H-indolo[3,2,1-de]pyrido[3,2,1-ij][1,5]naphthyridin-12-formamide (200 mg, 0.527 mmol) in boron trifluoride diethyl etherate was heated to 120° C. and stirred for 20 hours under an atmosphere of nitrogen. After completion, the reaction mixture was diluted with water, and pH was adjusted to 8 with sodium hydroxide solution. The mixture was extracted with dichloromethane, and the extracts were washed with water and brine, dried over anhydrous sodium sulfate and concentrated under vacuum. The residue was purified by Preparative High Performance Liquid Chromatography to obtain the target compound (white solid, 60 mg, yield: 31%).

¹HNMR (400 MHz, METHANOL-d4) δ ppm 7.42 (d, J=8.03 Hz, 1H), 7.25 (d, J=8.03 Hz, 1H), 7.03-7.16 (m, 2H), 5.87 (s, 1H), 4.54-4.67 (m, 1H), 4.43 (dt, J=9.16, 6.71 Hz, 1H), 4.06-4.21 (m, 2H), 3.12-3.31 (m, 2H), 2.88-3.05 (m, 1H), 2.41-2.63 (m, 3H), 1.77-1.97 (m, 2H), 1.58-1.75 (m, 1H), 1.52 (d, J=13.55 Hz, 1H), 1.38 (d, J=6.53 Hz, 4H), 0.86-1.08 (m, 4H).

Scheme B8

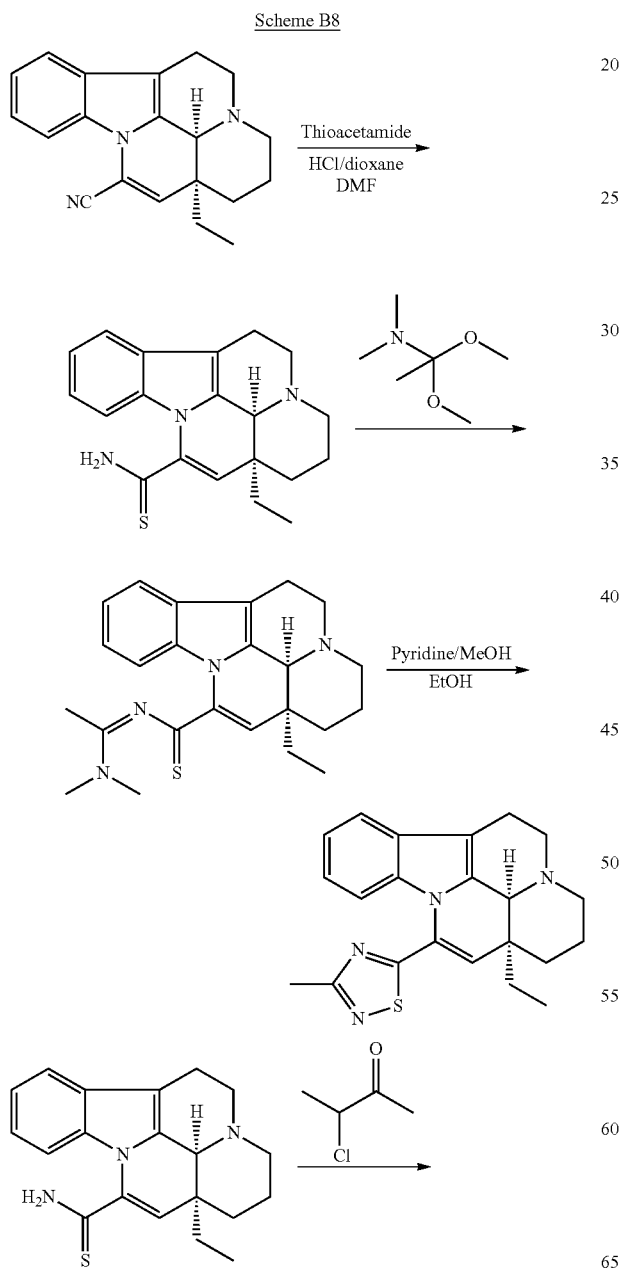

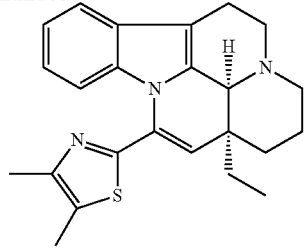

Example 39

5-((4¹S,13aS)-13a-ethyl-2,3,4¹,5,6,13a-hexahydro-1H-indolo[3,2,1-de]pyrido[3,2,1-ij][1,5]naphthyridin-12-yl)-3-methyl-1,2,4-thiadiazole

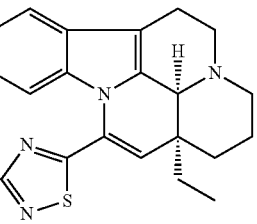

Example 39A (4¹S,13aS)-13a-ethyl-2,3,4¹,5,6,13a-hexahydro-1H-indolo[3,2,1-de]pyrido[3,2,1-ij][1,5]naphthyridin-12-thioamide

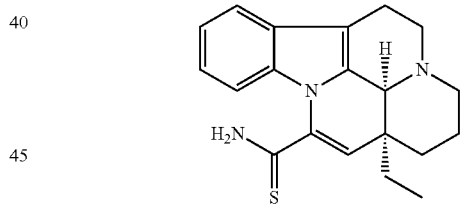

To a solution of (4¹S,13aS)-13a-ethyl-2,3,4¹,5,6,13a-hexahydro-1H-indolo[3,2,1-de]pyrido[3,2,1-ij][1,5]naphthyridin-12-carbonitrile (2 g, 6.6 mmol) in N,N-dimethylformamide (20 mL) was added ethylsulfamide (1.48 g, 19.8 mmol) and 4 mol/L hydrochloric acid in 1,4-dioxane (8 ml, 33 mmol), respectively, and the reaction mixture was stirred at 120° C. overnight. After cooling, the mixture was adjusted to neutral with aqueous sodium bicarbonate and extracted with ethyl acetate. The extracts were dried and concentrated. The residue was purified by silica gel column chromatography with dichloromethane/tetrahydrofuran (20/1 by volume) as an eluent to obtain the target compound (yellow solid, 580 mg, yield: 26%).

¹HNMR (400 MHz, CHLOROFORM-d) δ ppm 0.93-1.05 (m, 4H), 1.35-1.42 (m, 1H), 1.55 (d, J=13.80 Hz, 1H), 1.63-1.76 (m, 1H), 1.88-1.95 (m, 2H), 2.47-2.64 (m, 3H), 2.99-3.08 (m, 1H), 3.20-3.30 (m, 1H), 3.32-3.40 (m, 1H), 4.13 (s, 1H), 6.12 (br.s., 1H), 7.08 (br.s., 1H), 7.12-7.20 (m, 2H), 7.35-7.40 (m, 1H), 7.47-7.51 (m, 1H), 7.90 (br.s., 1H).

Example 39B (4¹S,13 aS)-N-(1-(dimethylamino)ethylidene)-13a-ethyl-2,3,4¹,5,6,13a-hexahydro-1H-indolo[3,2,1-de]pyrido[3,2,1-ij][1,5]naphthyridin-12-thioamide

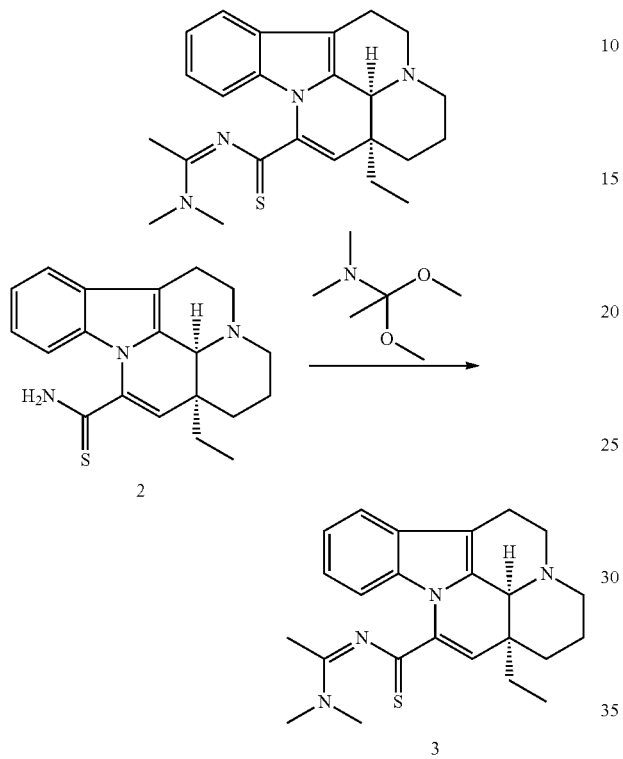

A mixture of (4¹S,13aS)-13a-ethyl-2,3,4¹,5,6,13a-hexahydro-1H-indolo[3,2,1-de]pyrido[3,2,1-ij][1,5]naphthyridin-12-thioamide (560 mg, 1.7 mmol) and N,N-dimethylacetamide dimethyl acetal (3 mL) was stirred at room temperature for 3.5 hours. After evaporation of the solvent, the residue was purified by silica gel column chromatography with dichloromethane/tetrahydrofuran (10/1 by volume) as an eluent to obtain the target compound (orange solid, 800 mg, crude product).

LCMS(ESI) m/z: 407 (M+1)

Example 39C 5-((4¹S,13aS)-13a-ethyl-2,3,4¹,5,6,13a-hexahydro-1H-indolo[3,2,1-de]pyrido[3,2,1-ij][1,5]naphthyridin-12-yl)-3-methyl-1,2,4-thiadiazole

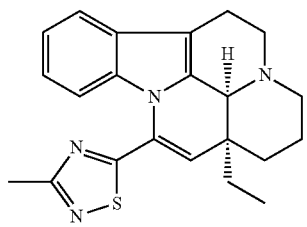

To a solution of (4¹S,13aS)-N-(1-(dimethylamino) ethylidene)-13a-ethyl-2,3,4¹,5,6,13a-hexahydro-1H-indolo[3,2,1-de]pyrido[3,2,1-ij][1,5]naphthyridin-12-thioamide (400 mg, 0.98 mmol) in ethanol/methanol (12 ml/6 mL) was added hydroxylamine-O-sulfonic acid (156 mg, 1.4 mmol) and pyridine (311 mg, 3.9 mmol), and the mixture was stirred at 60° C. overnight. After completion, the mixture was diluted with water and extracted with ethyl acetate. The extracts were dried and concentrated. The residue was purified by Preparative High Performance Liquid Chromatography to obtain the target compound (100 mg, yield: 27%).

¹HNMR (400 MHz, CHLOROFORM-d) δ ppm 1.12 (t, J=7.15 Hz, 3H), 1.29-1.39 (m, 1H), 1.68-1.86 (m, 2H), 2.21-2.35 (m, 3H), 2.79 (s, 3H), 2.98-3.22 (m, 3H), 3.36 (d, J=6.78 Hz, 1H), 3.63-3.87 (m, 2H), 4.80 (br.s., 1H), 5.77 (s, 1H), 6.51 (d, J=8.28 Hz, 1H), 7.09-7.17 (m, 1H), 7.18-7.25 (m, 1H), 7.53 (d, J=7.78 Hz, 1H).

Example 40

2-((4¹S,13aS)-13a-ethyl-2,3,4¹,5,6,13a-hexahydro-1H-indolo[3,2,1-de]pyrido[3,2,1-ij][1,5]naphthyridin-12-yl)-4,5-dimethylthiazole

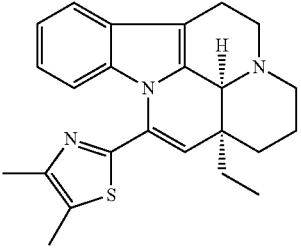

(4¹S,13aS)-ethyl-2,3,4¹,5,6,13a-hexahydro-1H-indolo[3,2,1-de]pyrido[3,2,1-ij][1,5]naphthyridin-12-thioamide (200 mg, 0.59 mmol) and 3-chloro-2-butanone (9.47 g, 88.89 mmol) were packed into a sealed tube and reacted at 130° C. for 20 hours. After cooling to 20° C., 10 mL ethyl acetate and 20 mL water were added and the aqueous layer was extracted with ethyl acetate (2×20 mL). The combined extracts were washed with 10 mL of brine, dried over anhydrous sodium sulfate and concentrated under vacuum. The crude product was purified by Preparative High Performance Liquid Chromatography to obtain the target compound (40 mg, yield: 15.84%).

¹HNMR (400 MHz, METHANOL-d4) δ ppm 7.60 (d, J=7.5 Hz, 1H), 7.20-7.15 (m, 1H), 7.13-7.08 (m, 1H), 6.37 (d, J=8.3 Hz, 1H), 5.80 (s, 1H), 5.16 (br.s., 1H), 3.96-3.80 (m, 2H), 3.33-3.12 (m, 4H), 2.55 (s, 3H), 2.44 (s, 3H), 2.09-1.91 (m, 3H), 1.84-1.73 (m, 2H), 1.38-1.28 (m, 1H), 1.12 (t, J=7.2 Hz, 3H).

LCMS(ESI) m/z: 390 (M+1)

Scheme B9

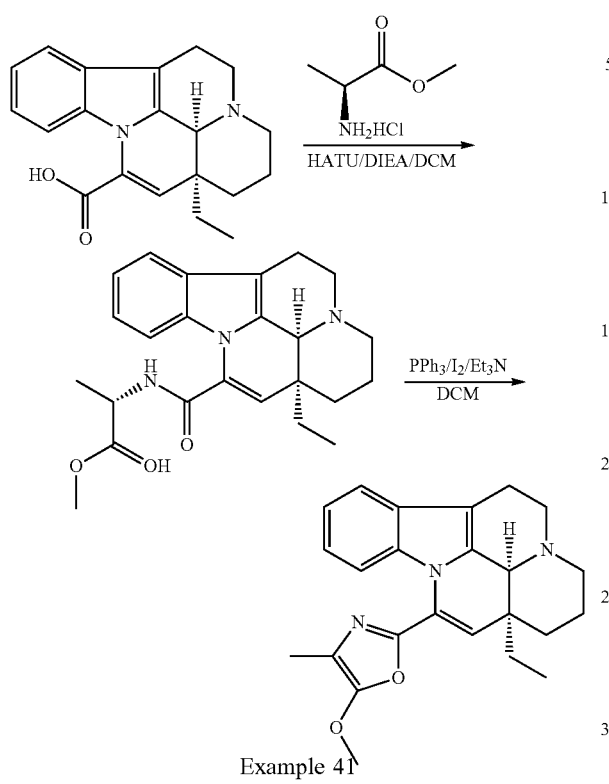

Example 41

2-(($4^1$S,13aS)-13a-ethyl-2,3,$4^1$,5,6,13a-hexahydro-1H-indolo[3,2,1-de]pyrido[3,2,1-ij][1,5]naphthyridin-12-yl)-5-methoxy-4-methyloxazole Example 41A (S)-methyl-2-(($4^1$S,13aS)-13a-ethyl-2,3,$4^1$,5,6,13a-hexahydro-1H-indolo[3,2,1-de]pyrido[3,2,1-ij][1,5]naphthyridin-12-formylamino) propionate ethyl

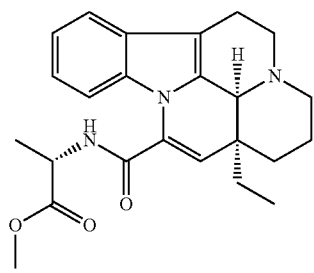

To a solution of ($4^1$S,13aS)-13a-ethyl-2,3,$4^1$,5,6,13a-hexahydro-1H-indolo[3,2,1-de]pyrido[,2,1-ij][1,5]naphthyridin-12-carboxylic acid (500 mg, 1.552 mmol) in dichloromethane (7.7 mL) was added O-(7-azabenzotriazole-1-yl)-N,N,N',N'-tetramethyluronium hexafluorophosphate (707.7 mg, 1.862 mmol) and diisopropylethylamine (600.6 mg, 4.656 mmol), the mixture was stirred for 1 hour, then (S)-alanine methyl ester hydrochloride (431.6 mg, 3.104 mmol) was added and the reaction mixture was stirred for 4 hours. After dilution with water, the reaction mixture was extracted with dichloromethane. The extracts were washed with water and brine, dried over anhydrous sodium sulfate and concentrated under vacuum. The residue was purified by silica gel column chromatography with dichloromethane/methanol (20/1 by volume) as an eluent to obtain the target compound (white solid, 600 mg, yield: 95%).

LCMS(ESI) m/z: 408 (M+1)

Example 41B 2-(($4^1$S,13aS)-13a-ethyl-2,3,$4^1$,5,6,13a-hexahydro-1H-indolo[3,2,1-de]pyrido[3,2,1-ij][1,5]naphthyridin-12-yl)-5-methoxy-4-methyloxazole

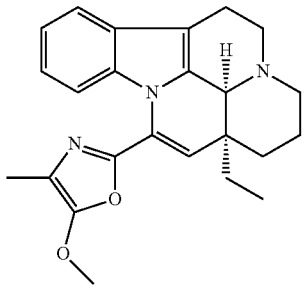

Triethylamine (397.31 mg, 3.93 mmol) was added dropwise to a solution of triphenylphosphine (514.93 mg, 1.96 mmol) and iodine (498.28 mg, 1.96 mmol) in anhydrous dichloromethane (10 mL), the mixture gradually became dark red after stirred for about 10 minutes, a solution of ethyl (S)-methyl-2-((4S,13aS)-13a-ethyl-2,3,$4^1$,5,6,13a-hexahydro-1H-indolo[3,2,1-de]pyrido[3,2,1-ij][1,5]naphthyridin-12-formylamino)propionate (200 mg, 0.49 mmol) in dichloromethane (2.5 ml) was added and the resulting mixture was stirred for 24 hours until the reaction was completed (monitored by thin layer chromatography). The reaction mixture was diluted with dichloromethane, washed with saturated sodium bicarbonate solution, brine, dried over anhydrous sodium sulfate and filtered, and the filtrate was concentrated under vacuum. The residue was purified by silica gel column chromatography with petroleum ether/tetrahydrofuran (5/1 by volume) as an eluent to obtain the target compound (40 mg, yield: 20.9%).

$^1$H NMR (400 MHz, METHANOL-d4) δ ppm 1.13 (t, J=7.03 Hz, 3H) 1.22-1.35 (m, 1H) 1.79 (br.s., 2H) 1.88-2.09 (m, 3H) 2.11-2.16 (s, 3H) 3.10-3.32 (m, 4H) 3.76-4.01 (m, 5H) 5.13 (br.s., 1H) 5.82 (s, 1H) 6.59 (dd, J=5.77, 2.76 Hz, 1H) 7.20 (dd, J=5.52, 2.51 Hz, 2H) 7.60 (d, J=5.02 Hz, 1H).

Scheme B10

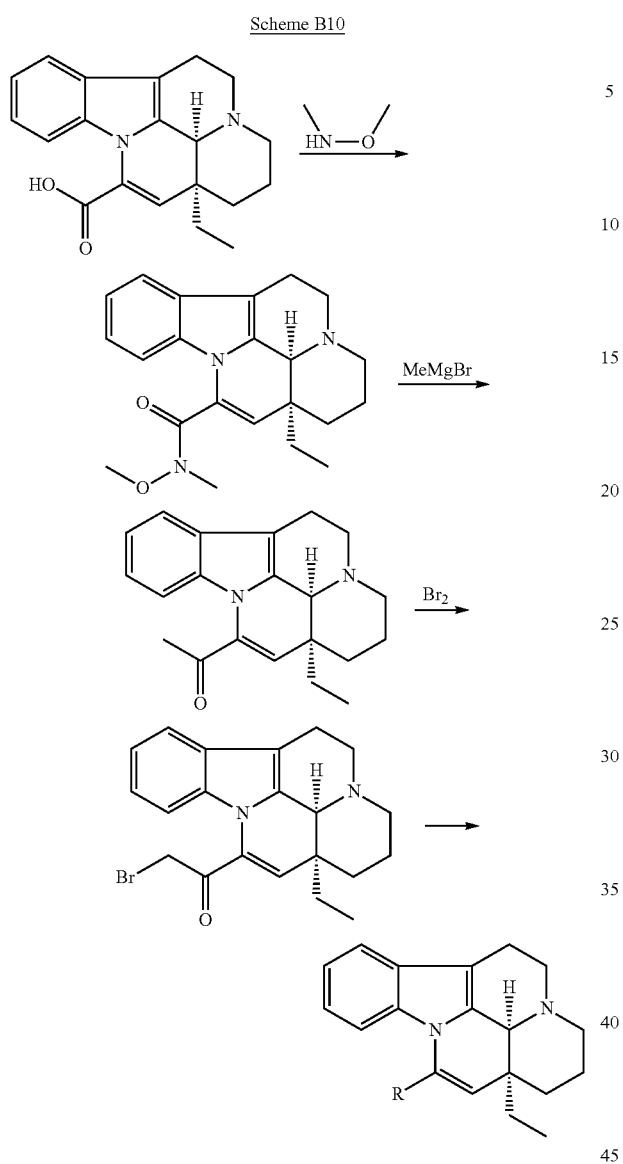

Example 42

(4¹S,13aS)-13a-ethyl-12-(imidazo[1,2-a]pyridin-2-yl)-2,3,4¹,5,6,13a-hexahydro-1H-indolo[3,2,1-de]pyrido[3,2,1-ij][1,5]naphthyridine

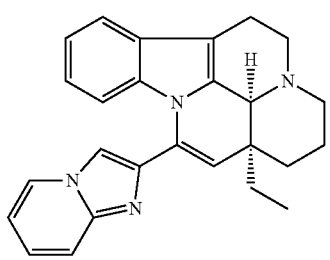

Example 42A (4¹S,13aS)-13a-ethyl-N-methoxy-N-methyl-2,3,4¹,5,6,13a-hexahydro-1H-indolo[3,2,1-de]pyrido[3,2,1-ij][1,5]naphthyridin-12-carboxamide To a solution of (4¹S,13aS)-13a-ethyl-2,3,4¹,5,6,13a-hexahydro-1H-indolo[3,2,1-de]pyrido[,2,1-ij][1,5]naphthyridin-12-carboxylic acid (18 g, 56 mmol) in N,N-dimethylformamide was added N,O-dimethylhydroxylamine hydrochloride (11.3 g, 112 mmol), 0-(7-azabenzotriazole-1-yl)-N,N,N',N'-tetramethyluronium hexafluorophosphate (22 g, 56 mmol) and triethylamine (10.6 g, 112 mmol) at room temperature, and the mixture was stirred overnight. After dilution with water, the reaction mixture was extracted with ethyl acetate. The extracts were dried over anhydrous sodium sulfate, filtered and concentrated to obtain the target compound (solid, 18 g, yield: 90%).

LCMS(ESI) m/z: 366 (M+1)

Example 42B 1-((4¹S,13aS)-13a-ethyl-2,3,4¹,5,6,13a-hexahydro-1H-indolo[3,2,1-de]pyrido[3,2,1-ij][1,5]naphthyridin-12-yl)-ethanone Methylmagnesium bromide (50 mL, 150 mmol) was added dropwise to a solution of (4¹S,13aS)-13a-ethyl-N-methoxy-N-methyl-2,3,4¹,5,6,13a-hexahydro-1H-indolo[3,2,1-de]pyrido[3,2,1-ij][1,5]naphthyridin-12-carboxamide (17 g, 49 mmol) in tetrahydrofuran (170 mL) at 0° C., and the mixture was subsequently stirred at this temperature for 4 hours. The mixture was poured into ammonium chloride solution, extracted with dichloromethane, dried over anhydrous sodium sulfate, filtered and concentrated to obtain the target compound (solid, 11 g, yield: 70.5%).

LCMS(ESI) m/z: 321 (M+1)

Example 42C

2-Bromo-1-((4¹S,13aS)-13a-ethyl-2,3,4¹,5,6,13a-hexahydro-1H-indolo[3,2,1-de]pyrido[3,2,1-ij][1,5]naphthyridin-12-yl)-ethanone

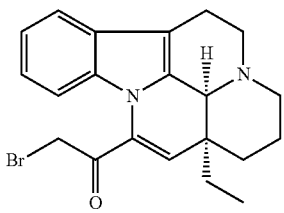

To a solution of 1-((4¹S,13aS)-13a-ethyl-2,3,4¹,5,6,13a-hexahydro-1H-indolo[3,2,1-de]pyrido[3,2,1-ij][1,5]naphthyridin-12-yl)-ethanone (7 g, 21.8 mmol) in dichloromethane was added liquid bromine (3.47 g, 21.8 mmol) portionwise and the mixture was stirred at room temperature for 4 hours. The mixture was poured into water and extracted with dichloromethane. The extracts were dried over anhydrous sodium sulfate, filtered and concentrated to give the crude target compound (5 g, yield: 57.6%), which was used directly in the next step.

Example 42D (4¹S,13aS)-13a-ethyl-12-(imidazo[1,2-a]pyridin-2-yl)-2,3,4¹,5,6,13a-hexahydro-1H-indolo[3,2,1-de]pyrido[3,2,1-ij][1,5]naphthyridine

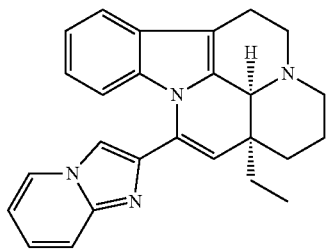

A mixture of 2-bromo-1-((4¹S,13aS)-13a-ethyl-2,3,4¹,5,6,13a-hexahydro-1H-indolo[3,2,1-de]pyrido[3,2,1-ij][1,5]naphthyridin-12-yl)-ethanone (400 mg, 1 mmol) and 2-aminopyridine (92 mg, 1 mmol) in ethanol (3 mL) was heated to 70° C. and reacted for 8 hours. The resulting solid was filtered out, ethyl acetate was added, and the target compound (100 mg, yield: 25.3%) was isolated by Preparative High Performance Liquid Chromatography.

¹HNMR (CD$_3$OD, 400 MHz) δ ppm 8.11 (d, J=6.6 Hz, 1H), 7.69-7.59 (m, 2H), 7.46 (d, J=7.9 Hz, 1H), 7.23 (d, J=7.9 Hz, 1H), 7.04 (t, J=7.5 Hz, 1H), 6.95-6.80 (m, 3H), 6.64 (d, J=8.4 Hz, 1H), 5.60 (s, 1H), 4.31 (br.s., 1H), 3.48-3.27 (m, 2H), 3.15-3.01 (m, 1H), 2.76-2.53 (m, 3H), 2.02-1.86 (m, 2H), 1.60 (d, J=13.7 Hz, 1H), 1.43 (d, J=13.2 Hz, 1H), 1.29-1.15 (m, 1H), 1.01 (t, J=7.5 Hz, 3H).

LCMS(ESI) m/z: 395 (M+1)

Example 43

4-((4¹S,13aS)-13a-ethyl-2,3,4¹,5,6,13a-hexahydro-1H-indolo[3,2,1-de]pyrido[3,2,1-ij][1,5]naphthyridin-12-yl)-thiazole-2-amine

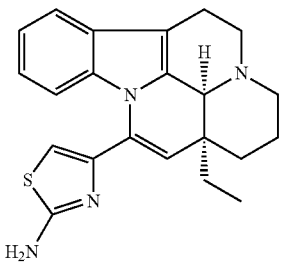

A mixture of 2-bromo-1-((4¹S,13aS)-13a-ethyl-2,3,4¹,5,6,13a-hexahydro-1H-indolo[3,2,1-de]pyrido[3,2,1-ij][1,5]naphthyridin-12-yl)-ethanone (400 mg, 1 mmol) and thiourea (92 mg, 1 mmol) in ethanol (3 mL) was heated to 80° C. and reacted for 2 hours. After cooling, the mixture was poured into water and extracted with dichloromethane. The extracts were concentrated, and then the crude product was purified by Preparative High Performance Liquid Chromatography to obtain the target compound (10 mg, yield: 50%).

¹HNMR (CD$_3$OD, 400 MHz) δ ppm 7.45 (d, J=7.5 Hz, 1H), 7.10-6.96 (m, 2H), 6.70-6.55 (m, 2H), 5.39 (s, 1H), 5.04 (s, 2H), 4.23 (br.s., 1H), 3.42-3.21 (m, 2H), 3.11-2.98 (m, 1H), 2.70-2.45 (m, 3H), 1.96-1.81 (m, 2H), 1.58-1.34 (m, 2H), 1.18-0.90 (m, 3H).

LCMS(ESI) m/z: 377 (M+1)

Example 44

(4¹S,13aS)-13a-ethyl-12(7-(trifluoromethyl)imidazo[1,2-a]pyridin-2-yl)-2,3,4¹,5,6,13a-hexahydro-1H-indolo[3,2,1-de]pyrido[3,2,1-ij][1,5]naphthyridine

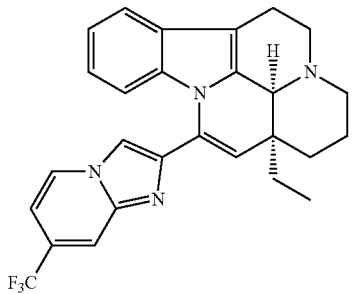

A mixture of 2-bromo-1-((4¹S,13aS)-13a-ethyl-2,3,4¹,5,6,13a-hexahydro-1H-indolo[3,2,1-de]pyrido[3,2,1-ij][1,5]naphthyridin-12-yl)-ethanone (400 mg, 1 mmol) and 2-amino-4-trifluoromethylpyridine (162 mg, 1 mmol) in ethanol (3 mL) was heated under reflux and reacted for 12 hours. Then the mixture was concentrated and the crude product was purified by Preparative High Performance Liquid Chromatography to obtain the target compound (100 mg, yield: 22%).

¹HNMR (CD3OD, 400 MHz) δ ppm 8.24 (d, J=7.0 Hz, 1H), 7.98 (s, 1H), 7.76 (s, 1H), 7.53-7.43 (m, 1H), 7.10-6.99

(m, 2H), 6.93 (t, J=7.8 Hz, 1H), 6.58 (d, J=8.5 Hz, 1H), 5.64 (s, 1H), 4.31 (br.s., 1H), 3.50-3.28 (m, 2H), 3.17-3.00 (m, 1H), 2.79-2.52 (m, 3H), 2.06-1.72 (m, 4H), 1.49-1.35 (m, 1H), 1.30-1.13 (m, 1H), 1.02 (t, J=7.3 Hz, 3H).

LCMS(ESI) m/z: 463 (M+1)

Scheme B11

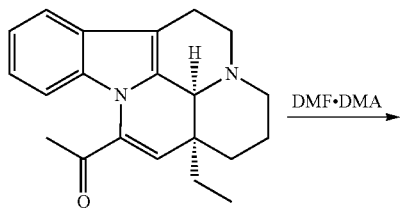

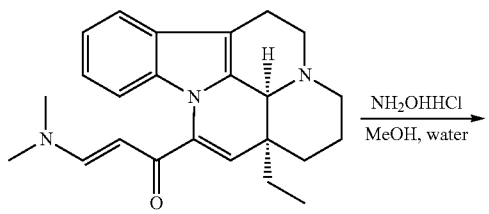

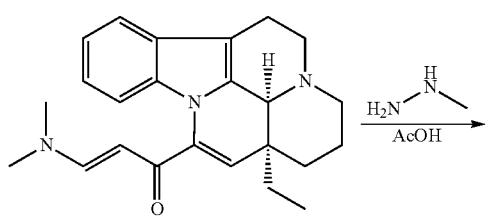

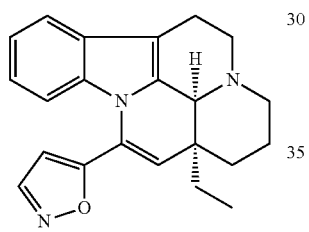

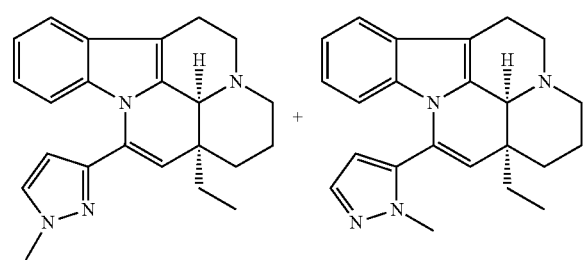

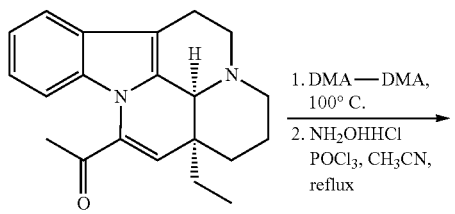

-continued

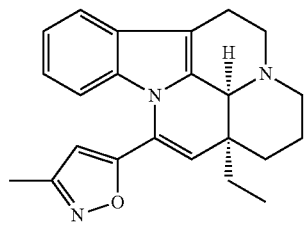

Example 45

5-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)isoxazole

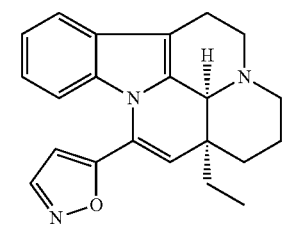

Example 45A (E)-3-(dimethylamino)-1-((4$^1$S,13aS)-13a-ethyl-2,3,4$^1$,5,6,13a-hexahydro-1H-indolo[3,2,1-de]pyrido[3,2,1-ij][1,5]naphthyridin-12-yl) prop-2-en-1-one

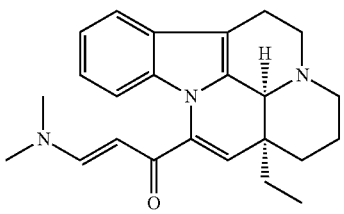

A mixture of 1-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)-ethanone (800 mg, 2.5 mmol) and N,N-dimethylformamide dimethyl acetal (8 ml) was heated under reflux and reacted until the starting material disappeared. The target compound (700 mg, yield: 74.7%) for the next step was obtained by decreasing the temperature and concentrating under reduced pressure.

LCMS(ESI) m/z: 376 (M+1)

Example 45B 5-((4¹S,13aS)-13a-ethyl-2,3,4¹,5,6,13a-hexahydro-1H-indolo[3,2,1-de]pyrido[3,2,1-ij][1,5]naphthyridin-12-yl)isoxazole

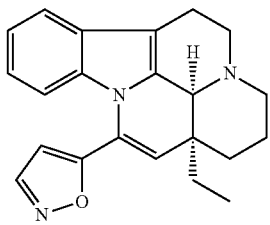

To a solution of (E)-3-(dimethylamino)-1-((4¹S,13aS)-13a-ethyl-2,3,4¹,5,6,13a-hexahydro-1H-indolo[3,2,1-de]pyrido[3,2,1-ij][1,5]naphthyridin-12-yl) prop-2-en-1-one (350 mg, 0.93 mmol) in N,N-dimethylformamide (3 mL) was added hydroxylamine hydrochloride (100 mg, 1.4 mmol), and the reaction mixture was heated to 120° C. by microwaves and reacted for 2 hours. The mixture was concentrated under vacuum and the residue was purified by Preparative High Performance Liquid Chromatography to obtain the target compound (60 mg, yield: 18.7%).

$^1$H NMR (CD$_3$OD, 400 MHz) δ ppm 8.53 (s, 1H), 7.48 (d, J=8.0 Hz, 1H), 7.15-6.96 (m, 3H), 6.67 (d, J=8.5 Hz, 1H), 6.45 (s, 1H), 5.58 (s, 1H), 3.07 (br. s., 1H), 2.70 (br. s., 1H), 2.05-1.84 (m, 2H), 1.48 (br. s., 1H), 1.30-1.12 (m, 2H), 1.02 (t, J=7.3 Hz, 3H).

LCMS (ESI) m/z: 346 (M+1)

Example 46

(4¹S,13aS)-13a-ethyl-12-(1-methyl-1H-pyrazol-3-yl)-2,3,4¹,5,6,13a-hexahydro-1H-indolo[3,2,1-de]pyrido[3,2,1-ij][1,5]naphthyridine, and (4¹S,13aS)-13a-ethyl-12-(1-methyl-1H-pyrazol-5-yl)-2,3,4¹,5,6,13a-hexahydro-1H-indolo[3,2,1-de]pyrido[3,2,1-ij][1,5]naphthyridine

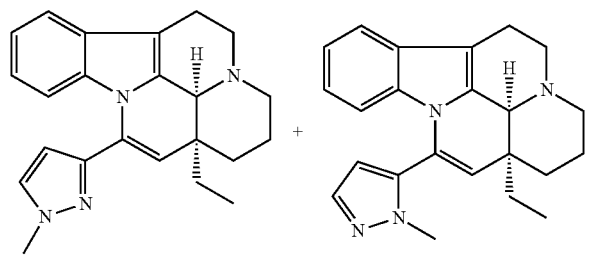

To a solution of (E)-3-(dimethylamino)-1-((4¹S,13aS)-13a-ethyl-2,3,4¹,5,6,13a-hexahydro-1H-indolo[3,2,1-de]pyrido[3,2,1-ij][1,5]naphthyridin-12-yl) prop-2-en-1-one (200 mg, 0.53 mmol) in acetic acid (2 mL) was added methylhydrazine (46 mg, 1 mmol). The mixture was refluxed for 4 hours, then poured into water, extracted with dichloromethane, dried over anhydrous sodium sulfate, filtered and concentrated. The residue was subjected to Supercritical Fluid Chromatography to separate and obtain the two target compounds: (4¹S,13aS)-13a-ethyl-12-(1-methyl-1H-pyrazol-3-yl)-2,3,4¹,5,6,13a-hexahydro-1H-indolo[3,2,1-de]pyrido[3,2,1-ij][1,5]naphthyridine (20 mg, yield: 10.5%) ($^1$H NMR (CD$_3$OD, 400 MHz) δ ppm 7.51-7.41 (m, 2H), 7.10-6.91 (m, 2H), 6.62 (d, J=8.5 Hz, 1H), 6.30 (d, J=2.0 Hz, 1H), 5.38 (s, 1H), 4.00 (s, 3H), 3.53-3.28 (m, 2H), 3.08 (t, J=15.8 Hz, 1H), 2.84-2.55 (m, 3H), 1.95 (br. s., 2H), 1.61 (d, J=13.1 Hz, 5H), 1.45 (d, J=13.1 Hz, 2H), 1.34-1.11 (m, 2H), 1.02 (t, J=7.3 Hz, 3H), LCMS (ESI) m/z: 359 (M+1)), and, (4¹S,13aS)-13a-ethyl-12-(1-methyl-1H-pyrazol-5-yl)-2,3,4¹,5,6,13a-hexahydro-1H-indolo[3,2,1-de]pyrido[3,2,1-ij][1,5]naphthyridine (30 mg, yield: 15.8%) ($^1$H NMR (CD$_3$OD, 400 MHz) δ ppm 7.61 (s, 1H), 7.45 (d, J=7.5 Hz, 1H), 7.11-6.87 (m, 2H), 6.41 (br. s., 1H), 5.89 (d, J=8.5 Hz, 1H), 5.20 (br. s., 1H), 4.37 (br. s., 1H), 3.72-3.27 (m, 5H), 3.14-3.00 (m, 1H), 2.84-2.48 (m, 3H), 2.09-1.93 (m, 1H), 1.86 (dd, J=6.8, 13.8 Hz, 3H), 1.59 (d, J=12.5 Hz, 5H), 1.35-1.15 (m, 3H), 1.02 (t, J=7.3 Hz, 3H), LCMS (ESI) m/z: 359 (M+1)).

Example 47

5-((4¹S,13aS)-13a-ethyl-2,3,4¹,5,6,13a-hexahydro-1H-indolo[3,2,1-de]pyrido[3,2,1-ij][1,5]naphthyridin-12-yl)-3-methylisoxazole

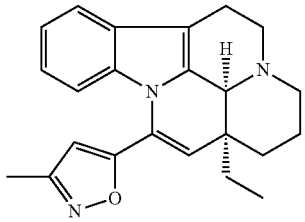

A solution of 1-((4¹S,13aS)-13a-ethyl-2,3,4¹,5,6,13a-hexahydro-1H-indolo[3,2,1-de]pyrido[3,2,1-ij][1,5]naphthyridin-12-yl)-ethanone (80 mg, 0.25 mmol) in 2 mL N,N-dimethylacetamide dimethyl acetal was heated under reflux for 2 hours. The low boiling components were removed under vacuum and the residue was dissolved in 5 mL acetonitrile. Then hydroxylamine hydrochloride (20 mg, 0.3 mmol) and phosphorus oxychloride (100 mg) were added, and the reaction mixture was heated under reflux for 1 hour. After cooling to room temperature, the solution was poured into sodium bicarbonate solution, extracted with dichloromethane, washed with brine, dried over anhydrous sodium sulfate, and the solvent was removed under vacuum. The residue was purified by Preparative High Performance Liquid Chromatography to obtain the target compound.

$^1$H NMR (400 MHz, METHANOL-d$_4$) δ ppm 7.40 (d, J=7.5 Hz, 1H), 7.08-6.91 (m, 2H), 6.52 (s, 1H), 6.39 (d, J=8.3 Hz, 1H), 5.57 (s, 1H), 4.21 (br. s., 1H), 3.38-3.36 (m, 1H), 3.31-3.15 (m, 2H), 3.07-2.91 (m, 1H), 2.65-2.44 (m, 3H), 2.39 (s, 3H), 2.03 (s, 4H), 1.58-1.34 (m, 2H), 1.00 (t, J=7.4 Hz, 4H).

LCMS (ESI) m/z: 360 (M+1)

Scheme B12

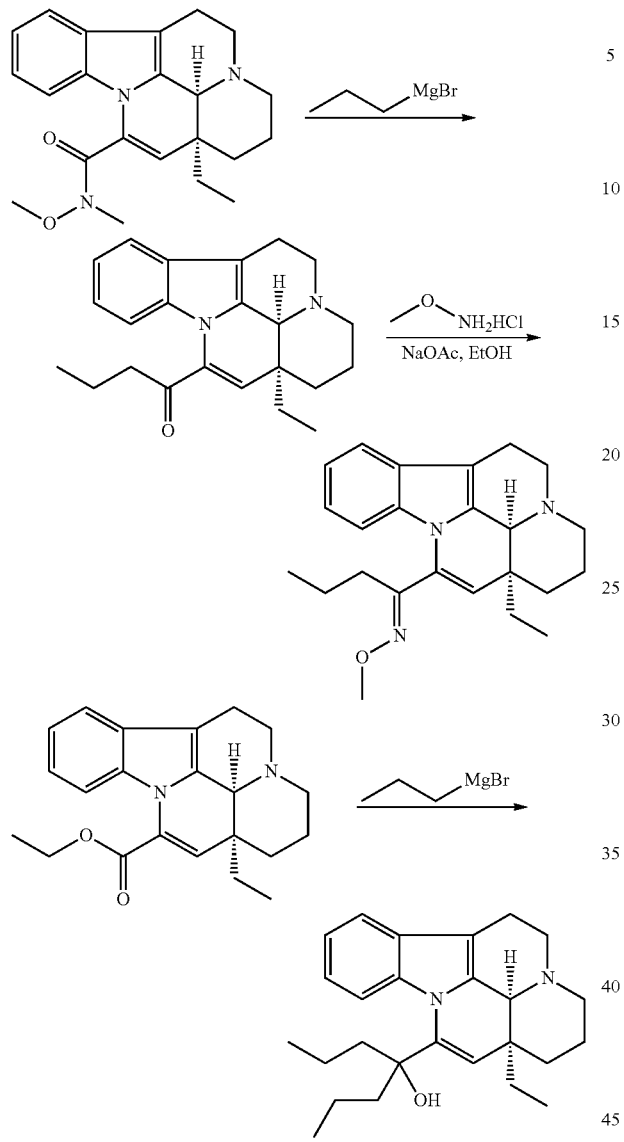

Example 47

1-((4¹S,13aS)-13a-ethyl-2,3,4¹,5,6,13a-hexahydro-1H-indolo[3,2,1-de]pyrido[3,2,1-ij][1,5]naphthyridin-12-yl) butan-1-one-O-methyl oxime

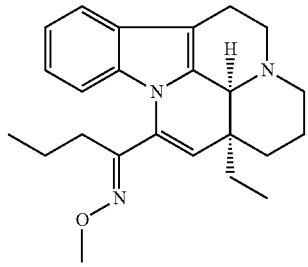

Example 48A 1-((4¹S,13aS)-13a-ethyl-2,3,4¹,5,6,13a-hexahydro-1H-indolo[3,2,1-de]pyrido[3,2,1-ij][1,5]naphthyridin-12-yl)butan-1-one

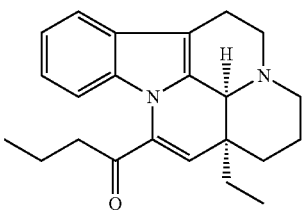

n-propylmagnesium bromide (2M in tetrahydrofuran, 0.825 mL, 1.65 mmol) was slowly added dropwise to a solution of (4¹S,13aS)-13a-ethyl-N-methoxyl-N-methyl-2,3,4¹,5,6,13a-hexahydro-1H-indolo[3,2,1-de]pyrido[3,2,1-ij][1,5]naphthyridin-12-carboxamide (200 mg, 0.55 mmol) in tetrahydrofuran (2 mL) at 0° C. under an atmosphere of nitrogen, then the reaction mixture was stirred for another 4 hours under this condition. Saturated ammonium chloride solution (20 mL) was added to the mixture, and the mixture was extracted with 40 mL ethyl acetate. The extracts were washed with brine, dried over sodium sulfate, filtered and concentrated. The residue was purified by Preparative High Performance Liquid Chromatography to obtain the target compound.

$^1$H NMR (400 MHz, MeOD) δ ppm 7.52-7.61 (m, 1H), 7.16-7.28 (m, 2H), 7.00-7.06 (m, 1H), 6.30 (s, 1H), 3.58-3.77 (m, 2H), 3.23-3.30 (m, 1H), 3.11-3.23 (m, 2H), 2.98-3.08 (m, 1H), 2.84-2.96 (m, 2H), 2.01-2.15 (m, 1H), 1.94 (dt, J=14.68, 7.47 Hz, 2H), 1.70-1.88 (m, 4H), 1.03-1.24 (m, 7H).

LCMS (ESI) m/z: 349 (M+1)

Example 48B 1-((4¹S,13aS)-13a-ethyl-2,3,4¹,5,6,13a-hexahydro-1H-indolo[3,2,1-de]pyrido[3,2,1-ij][1,5]naphthyridin-12-yl)butan-1-one-O-methyl oxime

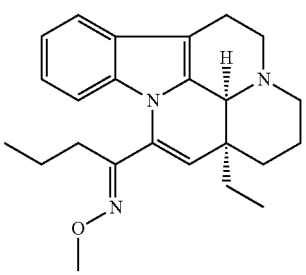

A mixture of 1-((4¹S,13aS)-13a-ethyl-2,3,4¹,5,6,13a-hexahydro-1H-indolo[3,2,1-de]pyrido[3,2,1-ij][1,5]naphthyridin-12-yl)butan-1-one (200 mg, 0.55 mmol), methoxylamine hydrochloride (455 mg, 5.5 mmol), sodium acetate (445 mg, 5.5 mmol) and ethanol (10 mL) was refluxed overnight. The mixture was diluted with water (20 mL) and extracted with 40 mL dichloromethane. The extracts were washed with brine, dried over anhydrous sodium sulfate, filtered and concentrated. The crude product was purified by Preparative High Performance Liquid Chromatography and Supercritical Fluid Chromatography to obtain the target compound.

Supercritical Fluid Chromatography:
"column: Chiralpak AD-H 250×4.6 mm I.D., 5 um; mobile phase: isopropanol (0.05% DEA), $CO_2$ 5%-40%; flow rate: 2.35 mL/min; wavelength: 220 nm"

$^1$H NMR (400 MHz, METHANOL-d4) δ ppm 7.55 (d, J=7.53 Hz, 1H), 7.11-7.24 (m, 3H), 5.28 (s, 1H), 4.01 (s, 3H), 3.64-3.79 (m, 2H), 2.95-3.25 (m, 5H), 2.23 (s, 1H), 1.97-2.12 (m, 2H), 1.77-1.97 (m, 2H), 1.67 (d, J=11.04 Hz, 2H), 1.51 (dt, J=15.18, 7.72 Hz, 2H), 1.42 (s, 3H), 1.17-1.33 (m, 2H), 1.10 (t, J=7.53 Hz, 3H), 0.91 (t, J=7.28 Hz, 3H).

LCMS (ESI) m/z: 378 (M+1)

Example 49

4-(($4^1$S,13aS)-13a-ethyl-2,3,$4^1$,5,6,13a-hexahydro-1H-indolo[3,2,1-de]pyrido[3,2,1-ij][1,5]naphthyridin-12-yl) heptan-4-ol

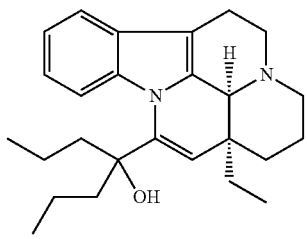

n-propylmagnesium bromide (2M in tetrahydrofuran, 2.14 mL, 4.29 mmol) was slowly added dropwise to a solution of vinpocetine (300 mg, 0.86 mmol) in tetrahydrofuran (2 mL) at 0° C. under an atmosphere of nitrogen, then the mixture was stirred for another 4 hours under such condition. Saturated ammonium chloride solution (20 mL) was added into the mixture, and the mixture was extracted with 40 mL ethyl acetate. The extracts were washed with brine, dried over anhydrous sodium sulfate, filtered and concentrated. The residue was purified by Preparative High Performance Liquid Chromatography to obtain the target compound.

$^1$H NMR (400 MHz, MeOD) δ ppm 8.51-8.63 (m, 1H), 7.34-7.44 (m, 1H), 7.00-7.14 (m, 2H), 5.30 (s, 1H), 4.09 (br. s., 1H), 3.20-3.31 (m, 2H), 2.99-3.13 (m, 1H), 2.52-2.71 (m, 3H), 1.95 (br. s., 4H), 1.43 (br. s., 8H), 0.96-1.14 (m, 8H), 0.72 (t, J=7.28 Hz, 3H).

LCMS (ESI) m/z: 393 (M+1)

Scheme B13

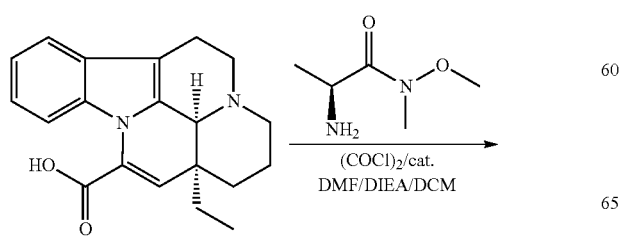

-continued

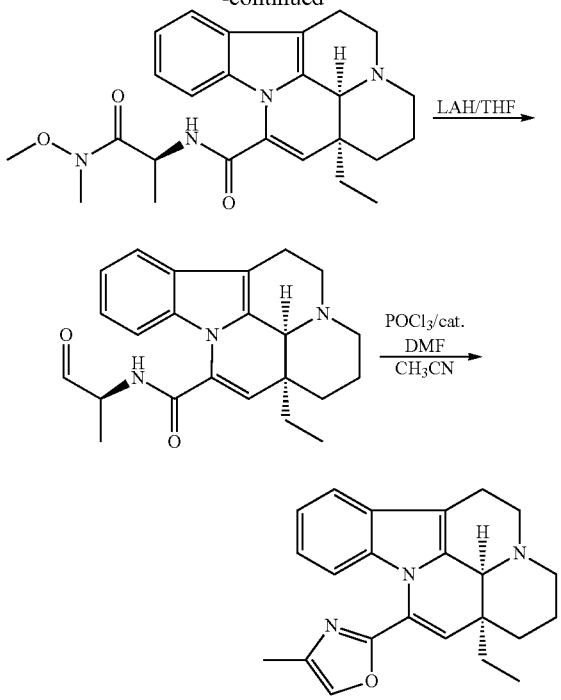

Example 50

2-(($4^1$S,13aS)-13a-ethyl-2,3,$4^1$,5,6,13a-hexahydro-1H-indolo[3,2,1-de]pyrido[3,2,1-ij][1,5]naphthyridin-12-yl)-4-methyloxazole

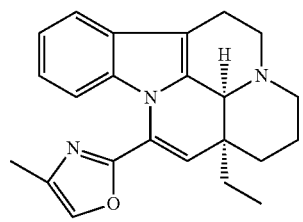

Example 50A ($4^1$S,13aS)-13a-ethyl-N—((S)-1-(methoxyl(methyl)amino)-1-oxopropan-2-yl)-2,3,$4^1$,5,6,13a-hexahydro-1H-indolo[3,2,1-de]pyrido[3,2,1-ij][1,5]naphthyridin-12-carboxamide

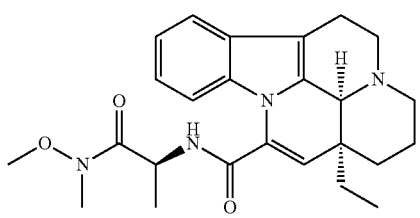

Oxalyl chloride (590.98 mg, 4.656 mmol) was added dropwise to a solution of (4¹S,13aS)-13a-ethyl-2,3,4¹,5,6,13a-hexahydro-1H-indolo[3,2,1-de]pyrido[3,2,1-ij][1,5]naphthyridin-12-carboxylic acid (500 mg, 1.552 mmol) and a catalytic amount of N,N-dimethylformamide (0.075 mL) in anhydrous dichloromethane (7.5 mL) at 0° C. and the reaction mixture was stirred at this temperature for another 1 hour. The solvent was removed under reduced pressure, and the resulting crude product was immediately dissolved in dichloromethane (7.5 mL). Then diisopropylethylamine (600.61 mg, 4.656 mmol) and (S)-2-amino-N-methoxy-N-methylpropanamide (307.5 mg, 2.328 mmol) were added, the reaction mixture was stirred at room temperature for 2 hours. Water was added and the mixture was extracted with dichloromethane. The extracts were washed with water, brine, dried over anhydrous sodium sulfate and the solvent was concentrated under vacuum. The residue was purified by silica gel column chromatography with dichloromethane/methanol (20/1 by volume) as an eluent to obtain the target compound (white solid, 460 mg, yield: 68%).

LCMS (ESI) m/z: 437 (M+1)

Example 50B (4¹S,13aS)-13a-ethyl-N—((S)-1-oxopropan-2-yl)-2,3,4¹,5,6,13a-hexahydro-1H-indolo[3,2,1-de]pyrido[3,2,1-ij][1,5]naphthyridin-12-carboxamide

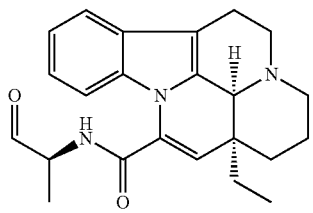

To a solution of (4¹S,13aS)-13a-ethyl-N—((S)-1-(methoxyl(methyl)amino)-1-oxopropan-2-yl)-2,3,4¹,5,6,13a-hexahydro-1H-indolo[3,2,1-de]pyrido[3,2,1-ij][1,5]naphthyridin-12-carboxamide in tetrahydrofuran was added lithium aluminium hydride (32.66 mg, 0.86 mmol) at −78° C. under an atmosphere of nitrogen, then the dry ice-acetone bath was replaced by an ice bath, the reaction temperature was increased to 0° C. After the reaction mixture was stirred for 20 minutes, the reaction temperature was decreased to −78° C. again, then the reaction was rapidly quenched by adding potassium bisulfate solution. After the temperature of the mixture was increased to room temperature, the solid was filtered out, and the filtrate was extracted with ethyl acetate. The combined extracts were washed with brine, dried over anhydrous sodium sulfate, filtered and the solvent was removed to obtain the crude target compound (for the next step, 190 mg, yield: 88%).

LCMS (ESI) m/z: 378 (M+1)

Example 50C 2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole

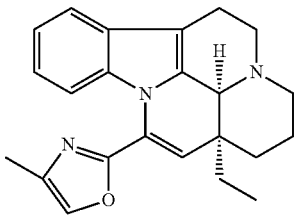

To a solution of (4¹S,13aS)-13a-ethyl-N—((S)-1-oxopropan-2-yl)-2,3,4¹,5,6,13a-hexahydro-1H-indolo[3,2,1-de]pyrido[3,2,1-ij][1,5]naphthyridin-12-carboxamide (190 mg, 0.504 mmol) in anhydrous acetonitrile (5 mL) was added a catalytic amount of N,N-dimethylformamide (0.025 mL) and phosphorus oxychloride (386.59 mg, 2.518 mmol), then the reaction mixture was heated to 90° C. and stirred under an atmosphere of nitrogen for 3 hours. After completion, the reaction solution was poured into a sodium carbonate solution and pH was adjusted to 8, then the mixture was extracted with dichloromethane. The combined extracts were washed with water, brine, dried over anhydrous sodium sulfate, and the solvent was removed under vacuum. The crude product was purified by Preparative High Performance Liquid Chromatography to obtain the target compound (30 mg, yield: 32%).

¹H NMR (400 MHz, METHANOL-d4) δ ppm 1.13 (t, J=6.27 Hz, 3H), 1.24-1.47 (m, 2H), 1.70-1.86 (m, 2H), 1.91-2.14 (m, 3H), 2.30 (s, 3H), 2.72 (s, 2H), 3.11-3.22 (m, 1H), 3.78-3.96 (m, 2H), 5.14 (br. s., 1H), 5.90 (s, 1H), 6.45 (d, J=8.03 Hz, 1H), 7.08-7.24 (m, 2H), 7.60 (d, J=7.03 Hz, 1H), 7.87 (s, 1H).

LCMS (ESI) m/z: 360 (M+1)

Scheme B14

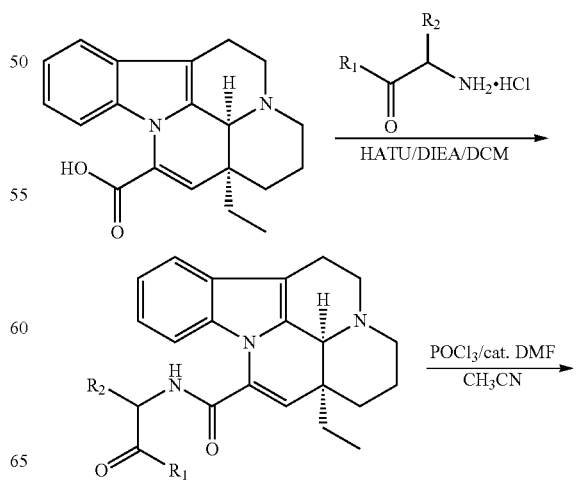

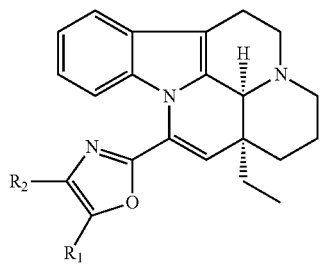

Example 51

2-((4¹S,13aS)-13a-ethyl-2,3,4¹,5,6,13a-hexahydro-1H-indolo[3,2,1-de]pyrido[3,2,1-ij][1,5]naphthyridin-12-yl)-5-methyloxazole

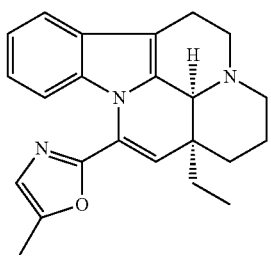

Example 51A (4¹S,13aS)-13a-ethyl-N-(2-oxopropyl)-2,3,4¹,5,6,13a-hexahydro-1H-indolo[3,2,1-de]pyrid o[3,2,1-ij][1,5]naphthyridin-12-carboxamide

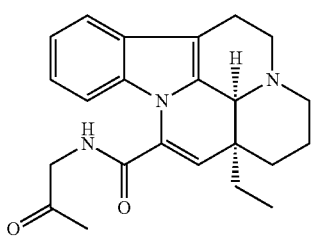

To a solution of (4¹S,13aS)-13a-ethyl-2,3,4¹,5,6,13a-hexahydro-1H-indolo[3,2,1-de]pyrido[3,2,1-ij][1,5]naphthyridin-12-carboxylic acid (200 mg, 0.621 mmol) in dichloromethane (3.1 mL) was added O-(7-azabenzotriazole-1-yl)-N,N,N',N'-tetramethyluronium hexafluorophosphate (283.08 mg, 0.745 mmol) and diisopropylethylamine (240.25 mg, 1.862 mmol) and the mixture was stirred for 1 hour. Then aminopropanone hydrochloride (135.37 mg, 1.242 mmol) was added and the mixture was stirred for another 4 hours. Water was added to the mixture, and the mixture was extracted with dichloromethane. The combined extracts were washed with water, brine and dried over anhydrous sodium sulfate. The organic layer was concentrated under vacuum and the residue was purified by silica gel column chromatography with dichloromethane/methanol (20/1 by volume) as an eluent to obtain the target compound (white solid, 210 mg, yield: 89%).

¹H NMR (400 MHz, CHLOROFORM-d) δ ppm 0.98-1.15 (m, 4H), 1.50-1.55 (m, 1H), 1.59 (d, J=13.55 Hz, 1H), 1.81-2.11 (m, 3H), 2.30 (s, 3H), 2.62-2.93 (m, 3H), 3.00-3.15 (m, 1H), 3.31-3.43 (m, 1H), 3.44-3.56 (m, 1H), 4.27-4.40 (m, 2H), 4.43-4.54 (m, 1H), 5.69-5.75 (m, 1H), 6.78 (br. s., 1H), 7.16 (quin, J=6.71 Hz, 2H), 7.21-7.26 (m, 1H), 7.47 (d, J=7.03 Hz, 1H).

Example 51B 2-((4¹S,13aS)-13a-ethyl-2,3,4¹,5,6,13a-hexahydro-1H-indolo[3,2,1-de]pyrido[3,2,1-ij][1,5]naphthyridin-12-yl)-5-methyloxazole

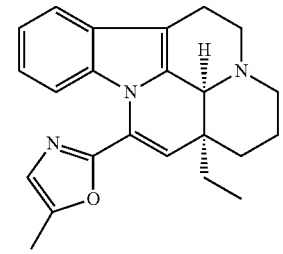

To a solution of (4¹S,13aS)-13a-ethyl-N-(2-oxopropyl)-2,3,4¹,5,6,13a-hexahydro-1H-indolo[3,2,1-de]pyrido[3,2,1-ij][1,5]naphthyridin-12-carboxamide (210 mg, 0.557 mmol) in anhydrous acetonitrile (2.8 mL) was added a catalytic amount of N,N-dimethylformamide (0.028 mL) and phosphorus oxychloride (854.56 mg, 5.567 mmol), then the reaction mixture was heated to 90° C. and stirred under an atmosphere of nitrogen for 3 hours. After completion, the reaction solution was poured into a sodium carbonate solution and the pH was adjusted to 8, then the mixture was extracted with dichloromethane. The combined extracts were washed with water, brine, dried over anhydrous sodium sulfate, and the solvent was removed under vacuum. The crude product was purified by Preparative High Performance Liquid Chromatography to obtain the target compound (50 mg, yield: 25%).

¹H NMR (400 MHz, METHANOL-d4) δ ppm 1.12 (t, J=6.78 Hz, 3H), 1.23-1.36 (m, 1H), 1.79 (t, J=12.55 Hz, 2H), 1.90-2.12 (m, 3H), 2.45 (s, 3H), 3.12 (d, J=16.06 Hz, 1H), 3.25 (d, J=12.05 Hz, 2H), 3.37 (s, 1H), 3.75-4.00 (m, 2H), 5.14 (br. s., 1H), 5.88 (s, 1H), 6.53 (d, J=8.03 Hz, 1H), 7.05-7.26 (m, 3H), 7.60 (d, J=7.03 Hz, 1H).

Example 52

2-((4¹S,13aS)-13a-ethyl-2,3,4¹,5,6,13a-hexahydro-1H-indolo[3,2,1-de]pyrido[3,2,1-ij][1,5]naphthyridin-12-yl)-4,5-dimethyloxazole

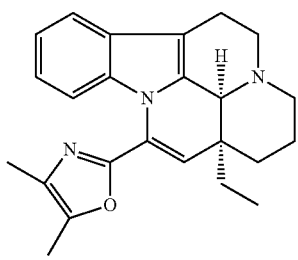

The process of the example was the same as that of Example 51.

$^1$H NMR (400 MHz, CHLOROFORM-d) δ ppm 1.09 (t, J=7.40 Hz, 3H), 1.24 (td, J=13.93, 3.26 Hz, 1H), 1.63 (d, J=14.56 Hz, 1H), 1.73 (d, J=14.05 Hz, 1H), 2.08-2.26 (m, 6H), 2.32 (s, 3H), 2.90-3.07 (m, 2H), 3.08-3.20 (m, 1H), 3.26 (d, J=11.04 Hz, 1H), 3.64 (td, J=12.67, 5.77 Hz, 1H), 3.73-3.84 (m, 1H), 4.73 (br. s., 1H), 5.79 (s, 1H), 6.56-6.64 (m, 1H), 7.11-7.22 (m, 2H), 7.46-7.55 (m, 1H).

Example 53

5-ethyl-2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole

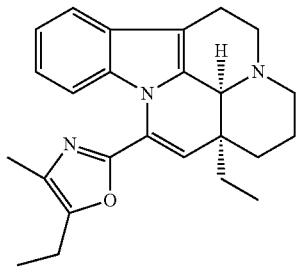

The process of the example was the same as that of Example 51.

$^1$H NMR (400 MHz, CHLOROFORM-d) δ ppm 1.11 (t, J=7.28 Hz, 3H), 1.17-1.34 (m, 4H), 1.60-1.81 (m, 2H), 2.14-2.38 (m, 6H), 2.58-2.78 (m, 2H), 2.91-3.22 (m, 3H), 3.31 (d, J=10.04 Hz, 1H), 3.65 (br. s., 1H), 3.80 (d, J=11.04 Hz, 1H), 4.76 (br. s., 1H), 5.83 (s, 1H), 6.52 (d, J=8.03 Hz, 1H), 7.17 (quin, J=7.03 Hz, 2H), 7.50 (d, J=7.03 Hz, 1H), 13.07 (br. s., 1H).

Example 54

2-((4¹S,13aS)-13a-ethyl-2,3,4¹,5,6,13a-hexahydro-1H-indolo[3,2,1-de]pyrido[3,2,1-ij][1,5]naphthyridin-12-yl)-5-isopropyl-4-methyloxazole

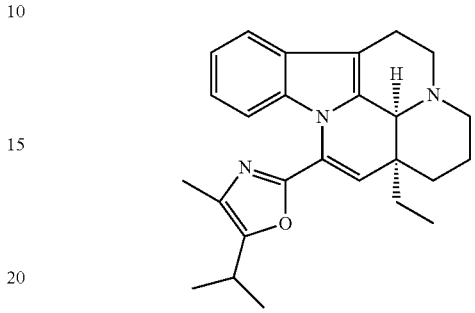

The process of the example was the same as that of Example 51.

$^1$H NMR (400 MHz, CHLOROFORM-d) δ ppm 1.12 (t, J=7.03 Hz, 3H), 1.18-1.35 (m, 7H), 1.66 (d, J=14.05 Hz, 1H), 1.79 (d, J=14.05 Hz, 1H), 2.13-2.38 (m, 6H), 2.94-3.23 (m, 4H), 3.32 (d, J=9.54 Hz, 1H), 3.66 (br. s., 1H), 3.80 (d, J=10.54 Hz, 1H), 4.78 (br. s., 1H), 5.91 (s, 1H), 6.43 (d, J=8.03 Hz, 1H), 7.10-7.24 (m, 2H), 7.51 (d, J=7.53 Hz, 1H).

Example 55

2-((4¹S,13aS)-13a-ethyl-2,3,4¹,5,6,13a-hexahydro-1H-indolo[3,2,1-de]pyrido[3,2,1-ij][1,5]naphthyridin-12-yl)-4,5,6,7-tetrahydrobenzo[d]oxazole

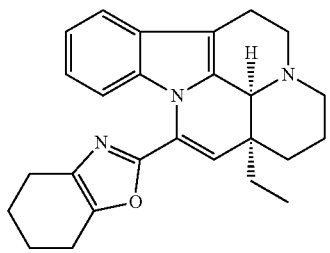

The process of the example was the same as that of Example 51.

$^1$H NMR (400 MHz, CHLOROFORM-d) δ ppm 7.52 (dd, J=6.27, 2.76 Hz, 1H), 7.15-7.25 (m, 2H), 6.65-6.76 (m, 1H), 5.91 (s, 1H), 4.77 (br. s., 1H), 3.81 (d, J=11.29 Hz, 1H), 3.33 (d, J=9.79 Hz, 1H), 3.15 (br. s., 1H), 3.02 (d, J=10.54 Hz, 1H), 2.58-2.77 (m, 4H), 2.17-2.39 (m, 4H), 1.87-2.05 (m, 4H), 1.80 (d, J=14.05 Hz, 1H), 1.68 (d, J=14.31 Hz, 1H), 1.21-1.38 (m, 1H), 1.13 (t, J=7.28 Hz, 3H).

Example 56

4-ethyl-2-((4¹S,13aS)-13a-ethyl-2,3,4¹,5,6,13a-hexahydro-1H-indolo[3,2,1-de]pyrido[3,2,1-ij][1,5]naphthyridin-12-yl)-5-methyloxazole

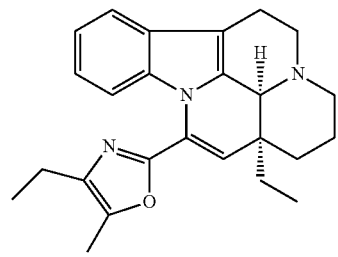

The process of the example was the same as that of Example 51.

$^1$H NMR (400 MHz, METHANOL-$d_4$) δ ppm 1.06-1.17 (m, 3H), 1.28 (t, J=7.53 Hz, 4H), 1.70-1.84 (m, 2H), 1.91-2.15 (m, 4H), 2.38 (s, 3H), 2.54-2.65 (m, 2H), 3.09-3.30 (m, 3H), 3.76-3.96 (m, 2H), 5.12 (br. s., 1H), 5.85 (s, 1H), 6.54 (d, J=7.53 Hz, 1H), 7.16 (quin, J=7.03 Hz, 2H), 7.59 (d, J=7.53 Hz, 1H).

Example 57

2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-isopropyl-5-methyloxazole

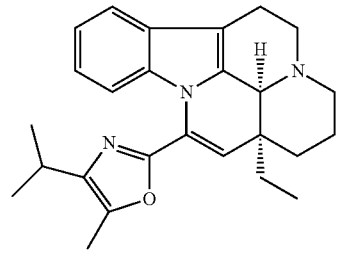

The process of the example was the same as that of Example 51.

$^1$H NMR (400 MHz, METHANOL-$d_4$) δ ppm 1.13 (t, J=7.28 Hz, 3H), 1.29 (dd, J=9.91, 6.90 Hz, 7H), 1.70-1.83 (m, 2H), 1.92-2.14 (m, 3H), 2.38 (s, 3H), 2.96-3.07 (m, 1H), 3.10-3.35 (m, 5H), 3.74-3.96 (m, 2H), 5.12 (br. s., 1H), 5.84 (s, 1H), 6.53 (d, J=7.78 Hz, 1H), 7.09-7.21 (m, 2H), 7.58 (d, J=7.53 Hz, 1H).

Scheme B15

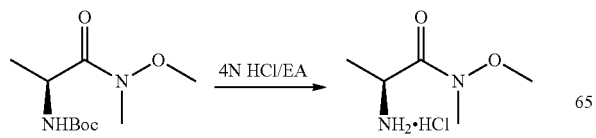

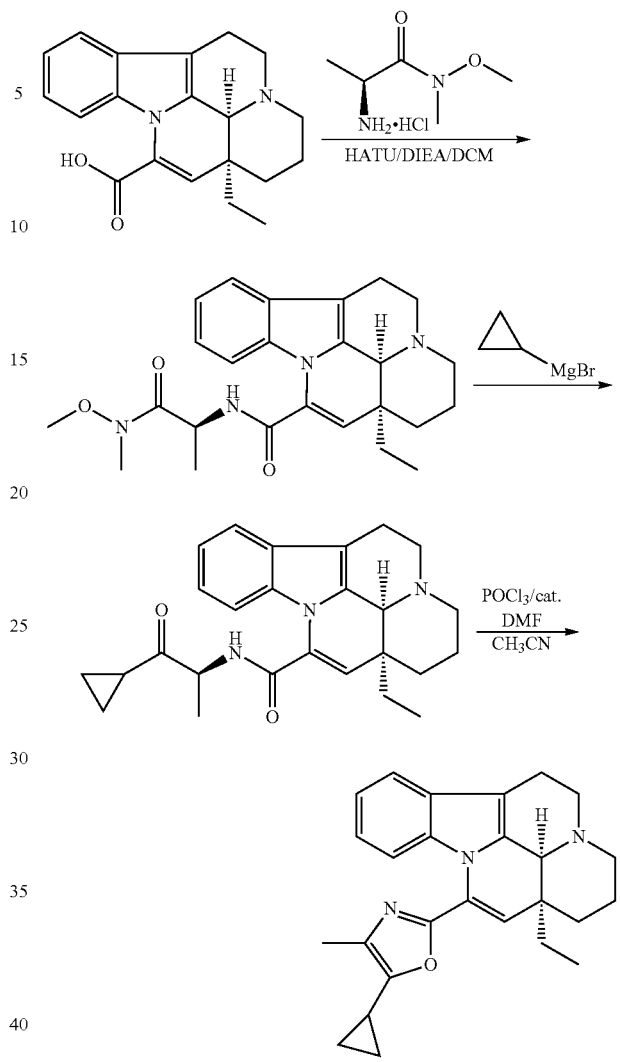

Example 58

5-cyclopropyl-2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole

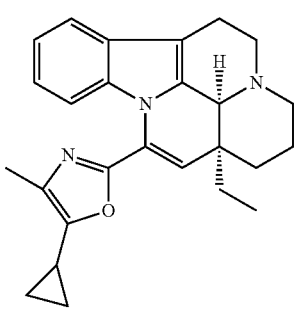

127

Example 58A (S)-2-amino-N-methoxy-N-methylpropanamide hydrochloride

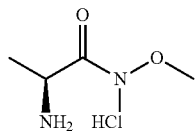

(S)-tert-butyl-(1-(methoxyl(methyl)amino)-1-oxopropyl-2-yl)carbamate (20.0 g, 106.82 mmol) was dissolved in 4M ethyl acetate hydrochloride (100 mL) and the mixture was stirred at 20° C. for 2 hours. The target compound (12.0 g, yield: 90.9%) was obtained by removing the low boiling components.

$^1$H NMR (400 MHz, CHLOROFORM-d) δ ppm 1.54-1.71 (m, 3H), 3.23 (s, 1H), 3.82 (s, 1H), 3.93-4.28 (m, 2H), 4.53 (br. s., 1H), 8.39 (br. s., 3H).

Example 58B (4$^1$S,13aS)-13a-ethyl-N—((S)-1-(methoxyl(methyl)amino)-1-oxopropyl-2-yl)-2,3,4$^1$,5,6,13a-hexahydro-1H-indolo[3,2,1-de]pyrido[3,2,1-ij][1,5]naphthyridin-12-carboxamide

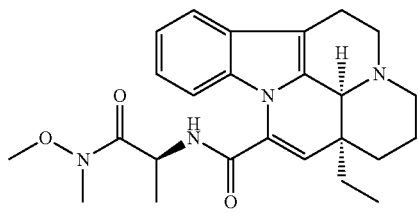

To a solution of (4$^1$S,13aS)-13a-ethyl-2,3,4$^1$,5,6,13a-hexahydro-1H-indolo[3,2,1-de]pyrido[3,2,1-ij][1,5]naphthyridin-12-carboxylic acid (5.0 mg, 15.51 mmol) in dichloromethane (80 mL) was added O-(7-azabenzotriazole-1-yl)-N,N,N',N'-tetramethyluronium hexafluorophosphate (7.08 g, 18.61 mmol) and N,N-diisopropylethylamine (3.01 g, 23.26 mmol) and the mixture was stirred at 20° C. for 1 hour. Then N,N-diisopropylethylamine (4.01 g, 31.02 mmol) and (S)-2-amino-N-methoxy-N-methylpropionamide hydrochloride (2.11 g, 17.06 mmol) were added and the mixture was stirred for another 14 hours. Water was added to the mixture, and the mixture was extracted with dichloromethane (3×10 mL). The combined extracts were washed with water (10 mL), brine (10 mL) and dried over anhydrous sodium sulfate. The solvent was removed under vacuum and the residue was purified by silica gel column chromatography with dichloromethane/methanol (20/1 by volume) as an eluent to obtain the target compound (light yellow gum, 5.5 g, yield: 90.58%).

LCMS (ESI) m/z: 437 (M+1)

128

Example 58C (4$^1$S,13aS)-N—((S)-1-cyclopropyl-1-oxopropyl-2-yl)-13a-ethyl-2,3,4$^1$,5,6,13a-hexahydro-1H-indolo[3,2,1-de]pyrido[3,2,1-ij][1,5]naphthyridin-12-carboxamide

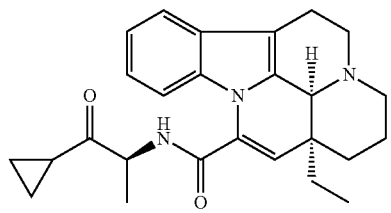

Cyclopropylmagnesium bromide (0.5 M, 307.8 mL, 153.9 mmol) was directly added dropwise to the solid (4$^1$S,13aS)-13a-ethyl-N—((S)-1-(methoxyl(methyl)amino)-1-oxopropyl-2-yl)-2,3,4$^1$,5,6,13a-hexahydro-1H-indolo[3,2,1-de]pyrido[3,2,1-ij][1,5]naphthyridin-12-carboxamide (2.24 g, 5.13 mmol) at 0° C. over a period of more than 60 minutes. After completion, the reaction mixture was heated to 20° C. and stirred for another 18 hours. Then the reaction temperature was decreased to 0° C., and saturated ammonium chloride solution was added, the mixture was extracted with ethyl acetate (3×30 mL). The combined extracts were washed with water (30 mL), brine (30 mL), dried over anhydrous sodium sulfate, and the solvent was removed under vacuum. The residue was purified by silica gel column chromatography with dichloromethane/methanol (20/1 by volume) as an eluant to obtain the target compound (light yellow gum, 1.7 g, yield: 79.37%).

LCMS (ESI) m/z: 418 (M+1)

Example 58D 5-cyclopropyl-2-((4$^1$S,13aS)-13a-ethyl-2,3,4$^1$,5,6,13a-hexahydro-1H-indolo[3,2,1-de]pyrid o[3,2,1-ij][1,5]naphthyridin-12-yl)-4-methyloxazole

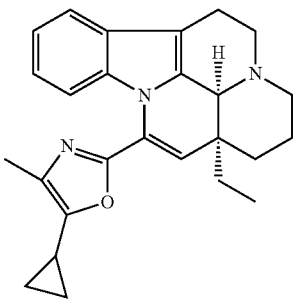

To a solution of (4$^1$S,13aS)-N—((S)-1-cyclopropyl-1-oxopropyl-2-yl)-13a-ethyl-2,3,4$^1$,5,6,13a-hexahydro-1H-indolo[3,2,1-de]pyrido[3,2,1-ij][1,5]naphthyridin-12-carboxamide (200 mg, 0.479 mmol) in anhydrous acetonitrile (2.8 mL) was added a catalytic amount of N,N-dimethylformamide (17.5 mg) and phosphorus oxychloride (367.22 mg, 2.39 mmol), then the reaction mixture was heated to 90° C. and stirred under an atmosphere of nitrogen for 15 hours. After completion, the reaction solution was poured into a sodium carbonate solution and the pH was adjusted to 8, then the mixture was extracted with dichloromethane (3×10 mL). The combined extracts were washed with water (10 mL), brine (10 mL), dried over anhydrous sodium sulfate, and the solvent was removed under vacuum. The residue was purified by silica gel column chromatography with petroleum ether/tetrahydrofuran (5/1 by volume) as an eluent to obtain the target compound (light yellow solid, 100 mg, yield: 52.25%).

$^1$H NMR (400 MHz, CHLOROFORM-d) δ ppm 0.71-0.88 (m, 2H), 0.91-1.03 (m, 2H), 1.12 (t, J=7.28 Hz, 3H), 1.27 (td, J=13.99, 2.89 Hz, 1H), 1.67 (d, J=14.05 Hz, 1H), 1.78 (d, J=14.31 Hz, 1H), 1.86-1.96 (m, 1H), 2.15-2.34 (m, 6H), 2.93-3.25 (m, 3H), 3.32 (d, J=10.29 Hz, 1H), 3.65 (br. s., 1H), 3.81 (d, J=11.29 Hz, 1H), 4.76 (br. s., 1H), 5.82 (s, 1H), 6.45-6.54 (m, 1H), 7.14-7.24 (m, 2H), 7.47-7.56 (m, 1H).

Scheme B16

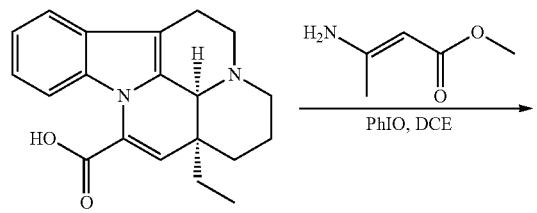

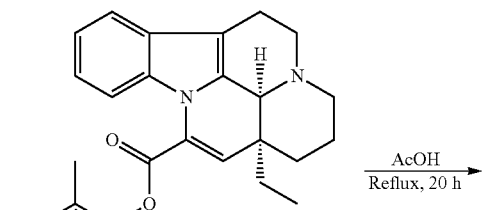

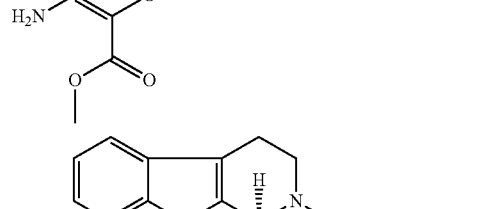

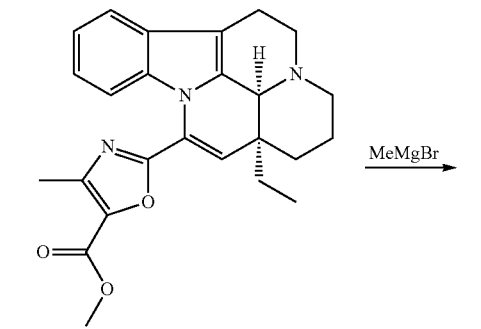

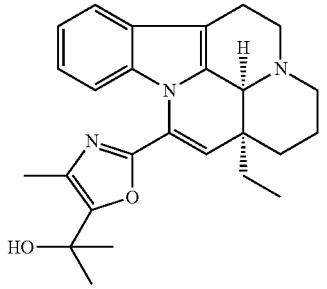

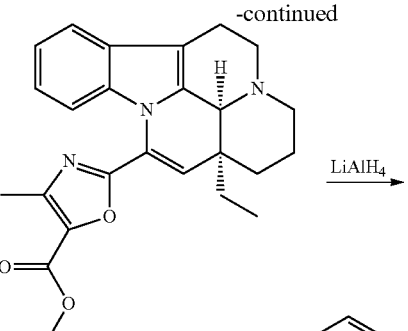

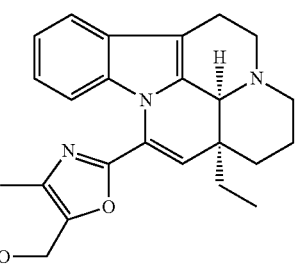

Example 59

2-(2-(($4^1$S,13aS)-13a-ethyl-2,3,$4^1$,5,6,13a-hexahydro-1H-indolo[3,2,1-de]pyrido[3,2,1-ij][1,5]naphthyridin-12-yl)-4-methyloxazol-5-yl)propan-2-ol

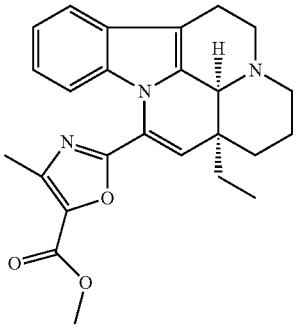

Example 59A ($4^1$S,13aS)-3-amino-1-methoxyl-1-oxobut-2-en-2-yl-13a-ethyl-2,3,$4^1$,5,6,13a-hexahydro-1 H-indolo[3,2,1-de]pyrido[3,2,1-ij][1,5]naphthyridin-12-carbonate

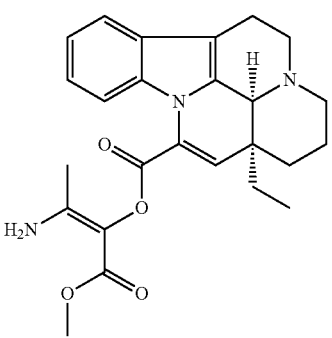

To a mixture of methyl 3-aminocrotonate (1.5 g, 13.03 mmol) and iodosobenzene (3.44 g, 15.63 mmol) in dichloroethane (75 mL) was added (4¹S,13aS)-13a-ethyl-2,3,4¹,5,6,13a-hexahydro-1H-indolo[3,2,1-de]pyrido[3,2,1-ij][1,5]naphthyridin-12-carboxyl acid (5.04 g, 15.63 mmol) at 20° C. and the reaction mixture was stirred at such temperature for 20 hours. The reaction was quenched with saturated sodium bicarbonate solution (150 mL), and the mixture was extracted with dichloromethane (3×100 mL). The combined extracts were dried over anhydrous sodium sulfate. After the solvent was distilled off, the residue was purified by silica gel column chromatography with tetrahydrofuran/petroleum ether (1/10-1/2 by volume) as an eluent to obtain the target compound (white solid, 1.5 g, yield: 26.4%).

¹H NMR (400 MHz, CHLOROFORM-d) δ ppm 7.49-7.44 (m, 1H), 7.40-7.34 (m, 1H), 7.18-7.09 (m, 2H), 6.39 (br. s., 1H), 4.21 (br. s., 1H), 3.85-3.68 (m, 3H), 3.40-3.33 (m, 1H), 3.32-3.21 (m, 1H), 3.10-2.98 (m, 1H), 2.68-2.61 (m, 2H), 2.52 (dd, J=2.9, 16.2 Hz, 1H), 2.02 (br. s., 3H), 1.87-1.72 (m, 2H), 1.52 (br. s., 1H), 1.47-1.40 (m, 1H), 1.12-0.98 (m, 5H).

Example 59B

Methyl-2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carbonate

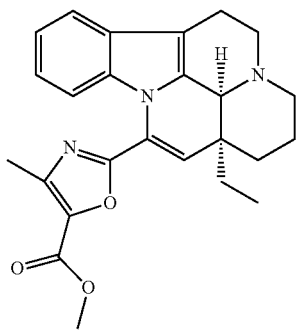

(4¹S,13aS)-3-amino-1-methoxyl-1-oxobut-2-en-2-yl-13a-ethyl-2,3,4¹,5,6,13a-hexahydro-1H-indolo[3,2,1-de]pyrido[3,2,1-ij][1,5]naphthyridin-12-carbonate (1.5 g, 3.44 mmol) was added to acetic acid (20 mL), the mixture was heated to 120° C. and stirred for 20 hours. The solvent was distilled off, dichloromethane (50 mL) and water (30 mL) were added to the residue, and the separated aqueous layer was extracted with dichloromethane (2×50 mL). The combined organic phases were washed with 30 mL of brine, dried over sodium sulfate, filtered and the filtrate was concentrated. The crude product was purified by silica gel column chromatography with tetrahydrofuran/petroleum ether (0-2/5 by volume) as an eluent to obtain the target compound (580 mg, yield: 40.38%).

¹H NMR (400 MHz, METHANOL-d₄) δ ppm 7.61 (dd, J=2.0, 6.5 Hz, 1H), 7.25-7.13 (m, 2H), 6.79-6.67 (m, 1H), 6.12 (s, 1H), 5.13 (s, 1H), 3.97-3.79 (m, 5H), 3.37-3.34 (m, 0.5H), 3.32-3.13 (m, 3.5H), 2.56 (s, 3H), 2.08-1.91 (m, 3H), 1.87-1.74 (m, 2H), 1.35-1.24 (m, 1H), 1.13 (t, J=7.3 Hz, 3H).

LCMS (ESI) m/z: 418 (M+1)

Example 60

2-(2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazol-5-yl)propan-2-ol

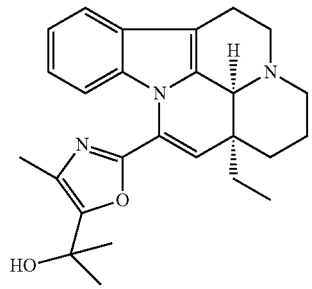

To a solution of methyl-2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazol-5-carbonate (100 mg, 0.24 mmol) in anhydrous tetrahydrofuran (2 mL) was added methylmagnesium bromide (3M, 0.4 mL, 1.2 mmol) at −70° C. under an atmosphere of nitrogen, and the reaction mixture was stirred at −70 to 20° C. for 16 hours. The reaction was quenched with 2 mL saturated ammonium chloride solution at −78 to 0° C., and the mixture was extracted with ethyl acetate (3×10 mL). The combined extracts were washed with brine (10 mL), dried over anhydrous sodium sulfate, filtered and the filtrate was concentrated. The residue was purified by Preparative High Performance Liquid Chromatography to obtain the target compound (52.0 mg, yield: 52.0%).

¹H NMR (400 MHz, METHANOL-d₄) δ ppm 7.59 (d, J=7.3 Hz, 1H), 7.24-7.08 (m, 2H), 6.42 (d, J=7.8 Hz, 1H), 5.86 (s, 1H), 5.14 (br. s., 1H), 3.96-3.77 (m, 2H), 3.38-3.07 (m, 4H), 2.40 (s, 3H), 2.09-1.91 (m, 3H), 1.86-1.72 (m, 2H), 1.53 (d, J=14.1 Hz, 6H), 1.35-1.25 (m, 1H), 1.12 (t, J=7.0 Hz, 3H).

LCMS (ESI) m/z: 418 (M+1)

Example 61

(2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazol-5-yl)methanol

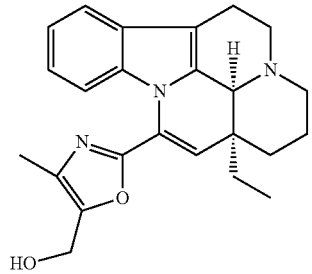

To a solution of methyl-2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carbonate (100 mg, 0.24 mmol) in anhydrous dichloromethane (8 mL) was added dibutyl aluminium hydride (1 M, 0.527 mL, 0.527 mmol) at −70° C., and the reaction mixture was stirred at −70 to 15° C. for 2 hours. The reaction was quenched by slow addition of saturated ammonium chloride (5 mL) at −78 to 0° C. and the mixture was extracted with ethyl acetate (3×30 mL). The combined extracts were washed with brine (20 mL), dried over sodium sulfate, filtered and the filtrate was concentrated. The crude product was purified by Preparative High Performance Liquid Chromatography to obtain the target compound (50.0 mg, yield: 53.6%).

$^1$H NMR (400 MHz, METHANOL-$d_4$) δ ppm 7.60 (d, J=7.5 Hz, 1H), 7.24-7.12 (m, 2H), 6.60 (d, J=7.8 Hz, 1H), 5.93 (s, 1H), 5.14 (br. s., 1H), 4.64 (s, 2H), 3.99-3.74 (m, 2H), 3.36-3.09 (m, 4H), 2.31 (s, 3H), 2.10-1.91 (m, 3H), 1.86-1.73 (m, 2H), 1.35-1.24 (m, 1H), 1.13 (t, J=7.0 Hz, 3H).

LCMS (ESI) m/z: 390 (M+1)

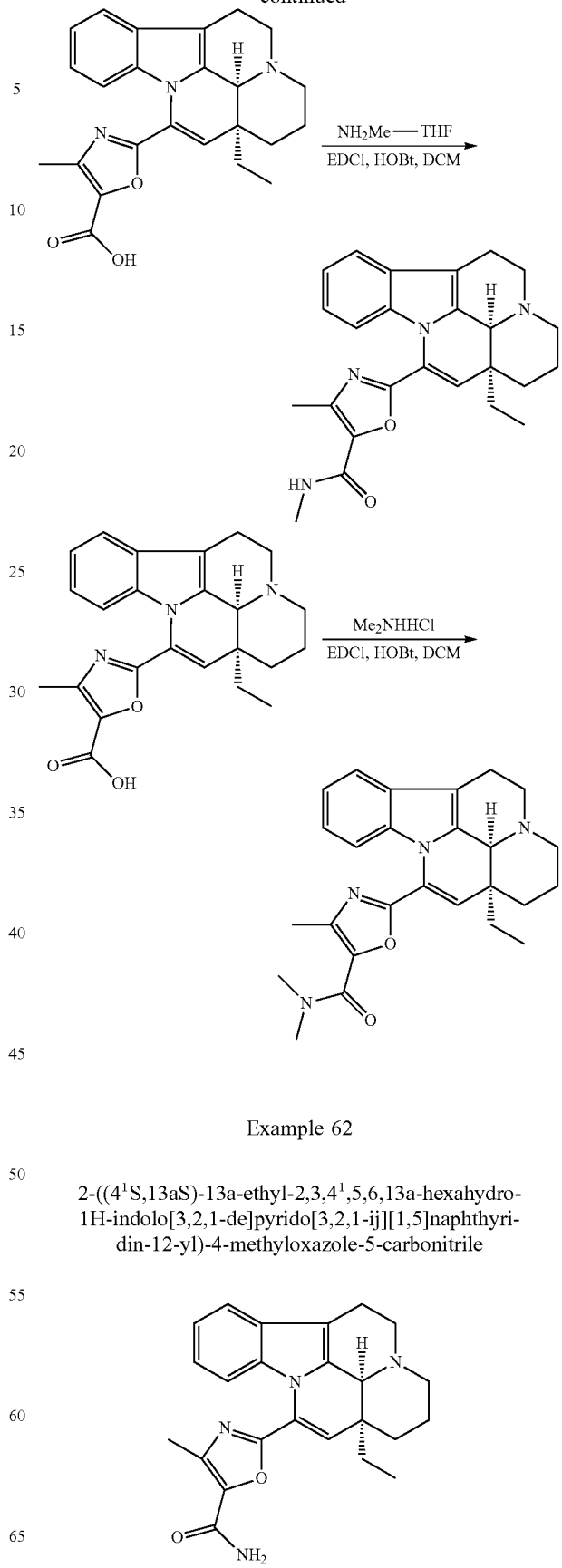

Example 62

2-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)-4-methyloxazole-5-carbonitrile

Example 62A 2-((4 is, 3aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carboxylic acid

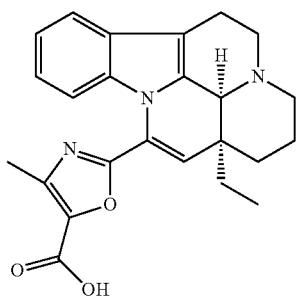

A solution of sodium hydroxide (330.0 mg, 8.25 mmol) in water (10 mL) was added dropwise to a solution of methyl-2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazol-5-carbonate (1.80 g, 4.31 mmol) in methanol (10 mL) under stirring, and the mixture was stirred for about 16 hours. After completion, the low boiling components were distilled off and the residue was washed with ethyl acetate (3×30 ml). The aqueous phase was acidified with 6M hydrochloric acid. After being filtered, the precipitated solid (filter cake) was washed with water (3×20 mL), dissolved in methanol (20 mL), dried over anhydrous sodium sulfate, filtered and concentrated to obtain the target compound (1.20 g, yield: 69.01%).

LCMS (ESI) m/z: 404 (M+1)

Example 62B 2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carboxamide

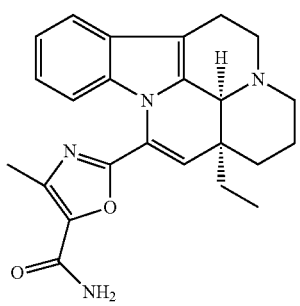

To a solution of 2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazol-5-carboxylic acid (100 mg, 0.248 mmol), 1-hydroxybenzotriazole (50 mg, 0.372 mmol) and 1-(3-dimethyllaminopropyl)-3-ethyl-carbodiimide hydrochloride (71 mg, 0.372 mmol) in N,N-dimethylformamide (5 mL) was added triethylamine (75 mg, 0.744 mmol) and ammonium chloride (40 mg, 0.744 mmol), respectively, and the reaction mixture was stirred for about 16 hours. After completion, the mixture was poured into water (with a volume of 5 times) and extracted with ethyl acetate (5×30 mL). The combined extracts were dried over anhydrous sodium sulfate, filtered and concentrated. The crude product was purified by Preparative High Performance Liquid Chromatography to obtain the target compound (white solid, 50 mg, yield: 50.12%).

¹H NMR (400 MHz, METHANOL-$d_4$) δ ppm 7.72-7.55 (m, 1H), 7.31-7.13 (m, 2H), 6.83-6.59 (m, 1H), 6.18 (s, 1H), 5.14 (br. s., 1H), 3.99-3.76 (m, 2H), 3.30-3.09 (m, 3H), 2.56 (s, 3H), 2.19-1.93 (m, 3H), 1.88-1.65 (m, 2H), 1.43-1.25 (m, 1H), 1.16 (t, J=7.3 Hz, 3H).

LCMS (ESI) m/z: 403 (M+1)

Example 63

2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carbonitrile

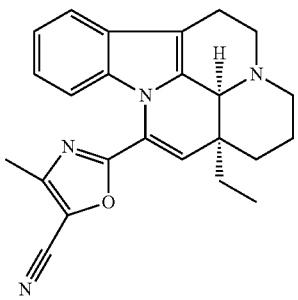

To a solution of 2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carboxamide (150 mg) in chloroform (10 mL) was added phosphorus oxychloride (571 mg, 3.73 mmol) under stirring, the reaction mixture was heated to 50° C. and stirred for 6 hours. After cooling, the mixture was carefully poured into water (10 mL), the pH was adjusted to 7-8 with saturated sodium bicarbonate solution, and the mixture was extracted with dichloromethane (3×20 mL). The combined extracts were concentrated and the residue was purified by Preparative High Performance Liquid Chromatography to obtain the target compound (80 mg, yield: 55.83%).

¹H NMR (400 MHz, METHANOL-$d_4$) δ ppm 7.63 (dd, J=2.5, 6.3 Hz, 1H), 7.32-7.18 (m, 2H), 6.90-6.70 (m, 1H), 6.19 (s, 1H), 5.15 (br. s., 1H), 4.07-3.78 (m, 2H), 3.32-3.13 (m, 4H), 2.47 (s, 3H), 2.13-1.92 (m, 3H), 1.88-1.71 (m, 2H), 1.40-1.24 (m, 1H), 1.14 (t, J=7.3 Hz, 3H).

LCMS (ESI) m/z: 385 (M+1)

Example 64

2-((4¹S,13aS)-13a-ethyl-2,3,4¹,5,6,13a-hexahydro-1H-indolo[3,2,1-de]pyrido[3,2,1-ij][1,5]naphthyridin-12-yl)-N,4-dimethyloxazole-5-carboxamide

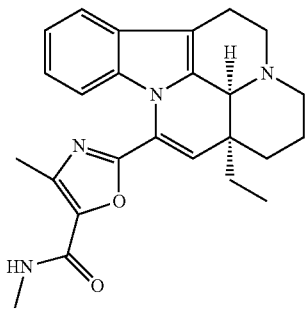

To a solution of 2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carboxylic acid (100 mg, 0.248 mmol), 1-hydroxylbenzotriazole (50 mg, 0.37 mmol) and 1-(3-dimethyllaminopropyl)-3-ethyl-carbodiimide hydrochloride (72 mg, 0.376 mmol) in N,N-dimethylformamide (5 mL) was added triethylamine (75 mg, 0.744 mmol) and a solution of methylamine in tetrahydrofuran (1 M, 0.74 mL, 0.74 mmol), respectively, and the reaction mixture was stirred for about 16 hours. After completion, the mixture was poured into water with a volume of 5 times and extracted with ethyl acetate (5×30 mL). The combined extracts were dried over anhydrous sodium sulfate, filtered and concentrated. The crude product was purified by Preparative High Performance Liquid Chromatography to obtain the target compound (20 mg, yield: 19.37%).

¹H NMR (400 MHz, METHANOL-d₄) δ ppm 7.78-7.54 (m, 1H), 7.30-7.16 (m, 2H), 6.87-6.65 (m, 1H), 6.16 (s, 1H), 5.15 (br. s., 1H), 4.08-3.77 (m, 2H), 3.31-3.23 (m, 2H), 3.21 (d, J=5.0 Hz, 1H), 2.87 (s, 3H), 2.57 (s, 3H), 2.01 (dd, J=7.5, 10.0 Hz, 3H), 1.82 (br. s., 2H), 1.32 (br. s., 1H), 1.16 (t, J=7.5 Hz, 3H).

LCMS (ESI) m/z: 417 (M+1)

Example 65

2-((4¹S,13aS)-13a-ethyl-2,3,4¹,5,6,13a-hexahydro-1H-indolo[3,2,1-de]pyrido[3,2,1-ij][1,5]naphthyridin-12-yl)-N,N,4-trimethyloxazole-5-carboxamide

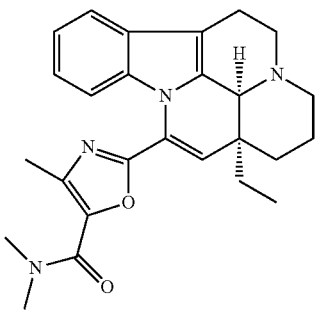

To a solution of 2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazole-5-carboxylic acid (100 mg, 0.248 mmol), 1-hydroxylbenzotriazole (50 mg, 0.37 mmol) and 1-(3-dimethyllaminopropyl)-3-ethyl-carbodiimide hydrochloride (72 mg, 0.376 mmol) in N,N-dimethylformamide (5 mL) was added triethylamine (75 mg, 0.744 mmol) and dimethylamine hydrochloride (60 ml, 0.744 mmol), respectively, and the reaction mixture was stirred for about 16 hours. After completion, the mixture was poured into water with a volume of 5 times and extracted with ethyl acetate (5×30 mL). The combined extracts were dried over anhydrous sodium sulfate, filtered and concentrated. The crude product was purified by Preparative High Performance Liquid Chromatography to obtain the target compound (50 mg, yield: 46.86%).

¹H NMR (400 MHz, METHANOL-d₄) δ ppm 7.75-7.55 (m, 1H), 7.32-7.10 (m, 2H), 6.76-6.51 (m, 1H), 6.07 (s, 1H), 5.18 (br. s., 1H), 4.03-3.76 (m, 2H), 3.30-3.16 (m, 2H), 3.16-2.96 (m, 6H), 2.48 (s, 3H), 2.15-1.90 (m, 3H), 1.82 (br. s., 2H), 1.32 (br. s., 1H), 1.15 (t, J=7.3 Hz, 3H).

LCMS (ESI) m/z: 431 (M+1)

Scheme B18

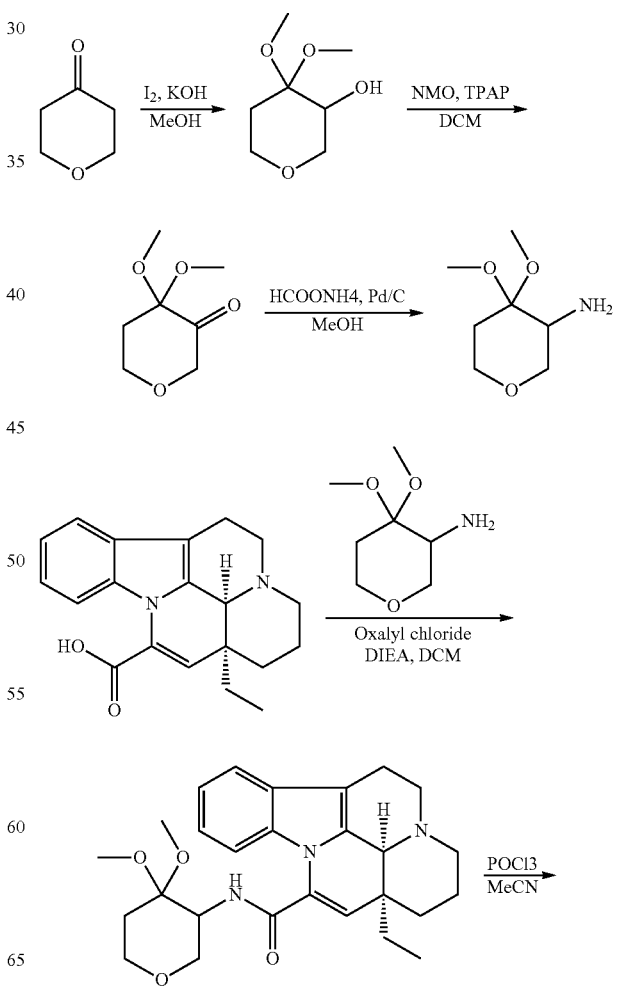

-continued

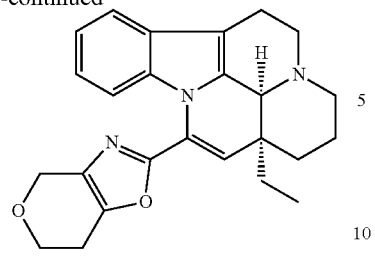

Example 66

2-((4¹S,13aS)-13a-ethyl-2,3,4¹,5,6,13a-hexahydro-1H-indolo[3,2,1-de]pyrido[3,2,1-ij][1,5]naphthyridin-12-yl)-6,7-dihydro-4H-pyrano[3,4-d]oxazole

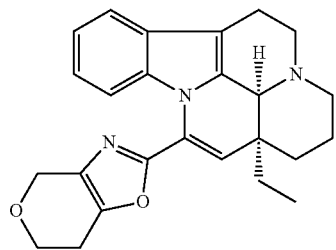

Example 66A 4,4-dimethoxytetrahydro-2H-pyran-3-ol

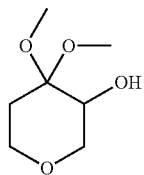

To a solution of potassium hydroxide (15.82 g, 240 mmol) in 210 mL of methanol was added tetrahydropyran-4-one (10 g, 99.88 mmol) at 0-5° C. After about 5-10 minutes, a solution of iodine (27.89 g, 109.87 mmol) dissolved in 185 ml methanol was added dropwise over a period of more than 1.5 hours, then the mixture was gradually heated to room temperature. The mixture was concentrated, 50 mL toluene was added and the mixture was filtered. The filtrate was distilled off and the residue was purified by silica gel column chromatography with petroleum ether/ethyl acetate (1/1 by volume) as an eluent to obtain the target compound (yellow liquid, 10.0 g, yield: 61.73%)

$^1$H NMR (400 MHz, CDCl3-d) δ ppm 4.13 (q, J=7.03 Hz, 1H), 3.77-3.90 (m, 2H), 3.65-3.74 (m, 2H), 3.50 (td, J=11.67, 2.51 Hz, 1H), 3.27 (d, J=7.28 Hz, 6H), 2.31 (br. s., 1H), 2.05 (s, 1H), 1.95 (ddd, J=14.31, 11.80, 4.77 Hz, 1H), 1.71-1.83 (m, 2H), 1.27 (t, J=7.03 Hz, 1H).

Example 66B 4,4-dimethoxy-dihydro-2H-pyran-3(4H)-one

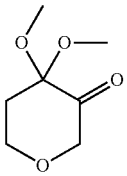

To a solution of 4,4-dimethoxytetrahydro-2H-pyran-3-ol (2.0 g, 12.33 mmol) in dichloromethane (30 mL) was added 4 Å molecular sieve (5.0 g, 12.33 mmol), N-methyl morpholine-N-oxide (3.64 g, 31.08 mmol) and tetrapropyl perruthenate (200 mg, 0.569 mmol), and the reaction mixture was stirred for about 30 minutes. After filtration, the filtrate was concentrated, and the residue was purified by silica gel column chromatography with petroleum ether/ethyl acetate (10/1 by volume) as an eluent to obtain the target compound (yellow liquid, 1.2 g, yield: 60.76%).

$^1$H NMR (400 MHz, CDCl3-d) δ ppm 4.05 (s, 2H), 3.90-3.98 (m, 2H), 3.66-3.72 (m, 1H), 3.19-3.27 (m, 6H), 2.27 (s, 1H), 2.16-2.23 (m, 2H).

Example 66C 4,4-dimethoxy-tetrahydro-2H-pyran-3-amine

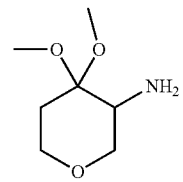

To a solution of 4,4-dimethoxy-dihydro-2H-pyran-3(4H)-one (1.2 g, 7.49 mmol) in methanol (30 mL) was added palladium on carbon (50 mg) and formamide (4.72 g, 74.9 mmol) at 20° C. under an atmosphere of nitrogen, respectively, and the mixture was stirred at 20° C. overnight. The reaction mixture was filtered and the filtrate was concentrated to obtain the crude target compound (for the next step, 800 mg).

Example 66D (4¹S,13aS)-N-(4,4-dimethoxy-tetrahydro-2H-pyran-3-yl)-13a-ethyl-2,3,4¹,5,6,13a-hexahydro-1H-indolo[3,2,1-de]pyrido[3,2,1-ij][1,5]naphthyridin-12-carboxamide

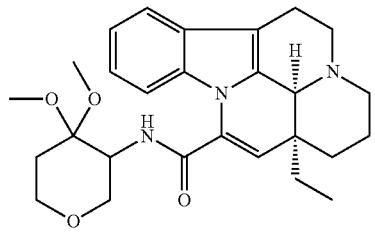

To a solution of (4¹S,13aS)-13a-ethyl-2,3,4¹,5,6,13a-hexahydro-1H-indolo[3,2,1-de]pyrido[3,2,1-ij][1,5]naphthyridin-12-carboxylic acid (300 mg, 0.93 mmol) in dichloromethane (20 mL) was added two drops of N,N- dimethylformamide at 0° C., then oxalyl chloride (236.22 mg, 1.86 mmol) was slowly added dropwise thereto, and the reaction mixture was stirred at 0° C. under an atmosphere of nitrogen for 1 hour. After the mixture was concentrated under vacuum, the residue was dissolved in dichloromethane (20 mL), and then diisopropylethylamine (240.52 mg, 1.86 mmol) and 4,4-dimethoxy-tetrahydro-2H-pyran-3-amine (100 mg, 0.62 mmol) were added thereto at 0° C. The mixture was stirred at room temperature for 1 hour, then water (50 mL) and dichloromethane (50 mL) were added thereto. The dichloromethane layer was washed with water (2×50 mL), brine (50 mL), dried over anhydrous sodium sulfate and filtered. The filtrate was concentrated to get a crude product, which was further purified by silica gel column chromatography with dichloromethane/tetrahydrofuran (2/1 by volume) as an eluent to obtain the target compound (colorless oil, 220 mg, yield: 76.17%).

LCMS (ESI) m/z: 420 (M+1)

Example 66E 2-((4¹S,13aS)-13a-ethyl-2,3,4¹,5,6,13a-hexahydro-1H-indolo[3,2,1-de]pyrido[3,2,1-ij][1,5]naphthyridin-12-yl)-6,7-dihydro-4H-pyrano[3,4-d]oxazole

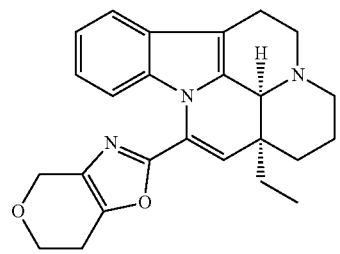

To a solution of (4¹S,13aS)-N-(4,4-dimethoxy-tetrahydro-2H-pyran-3-yl)-13a-ethyl-2,3,4¹,5,6,13a-hexahydro-1H-indolo[3,2,1-de]pyrido[3,2,1-ij][1,5]naphthyridin-12-carboxamide (120 mg, 0.258 mmol) in acetonitrile (10 mL) was added two drops of N,N-dimethylformamide under an atmosphere of nitrogen, then phosphorus oxychloride (350 mg, 2.28 mmol) was slowly added thereto, and the reaction mixture was heated to 80-90° C. and stirred for 4 hours. The reaction mixture was concentrated and the residue was purified by Preparative High Performance Liquid Chromatography to obtain the target compound (40 mg, yield: 35%).

¹H NMR (400 MHz, MeOD-d₄) δ ppm 7.57-7.64 (m, 1H), 7.13-7.24 (m, 2H), 6.57-6.64 (m, 1H), 5.93 (s, 1H), 5.16 (s, 1H), 4.69 (s, 2H), 3.99-4.17 (m, 2H), 3.79-3.99 (m, 2H), 3.13-3.30 (m, 3H), 2.90 (t, J=5.27 Hz, 2H), 1.89-2.11 (m, 3H), 1.74-1.89 (m, 2H), 1.32 (td, J=14.12, 3.89 Hz, 1H), 1.14 (t, J=7.40 Hz, 3H).

LCMS (ESI) m/z: 402 (M+1)

Scheme B19

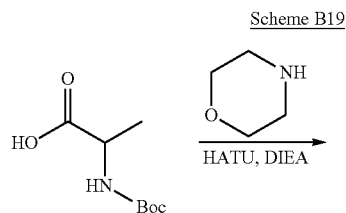

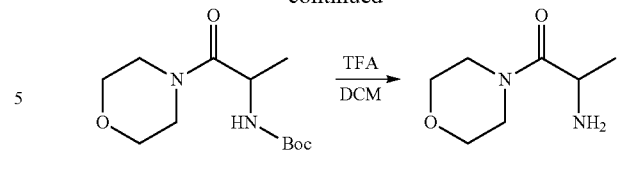

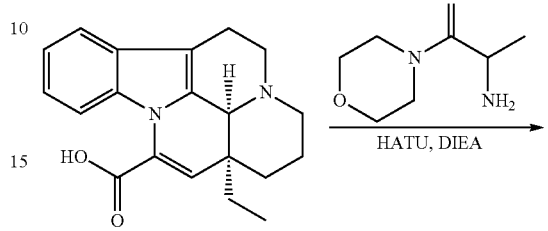

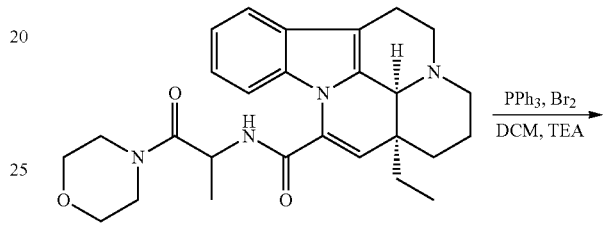

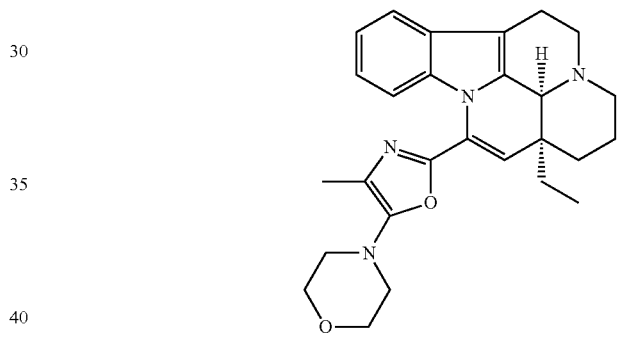

Example 67

4-(2-((4¹S,13aS)-13a-ethyl-2,3,4¹,5,6,13a-hexahydro-1H-indolo[3,2,1-de]pyrido[3,2,1-ij][1,5]naphthyridin-12-yl)-4-methyloxazol-5-yl)morpholine

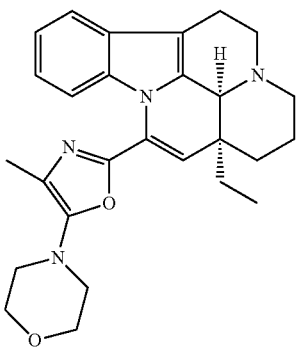

Example 67A

Tert-butyl-(1-morpholinyl-1-oxopropan-2-yl)-carbamate

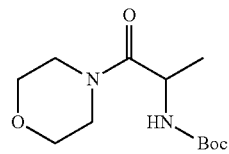

To a solution of 2-(tert-butoxycarbonylamino)-propionic acid (2.0 g, 10.57 mmol) and morpholine (1.11 g, 12.68 mmol) in dichloromethane (30 mL) was added only one time O-(7-azabenzotriazole-1-yl)-N,N,N',N'-tetramethyluronium hexafluoro-phosphate (4.82 g, 12.68 mmol) under an atmosphere of nitrogen, then diisopropylethylamine (3.01 g, 23.25 mmol) was added and the reaction mixture was stirred at room temperature for 15 hour. 20 mL water was added to the mixture, and the aqueous phase was extracted with ethyl acetate (3×50 mL). The combined organic phase was washed with saturated brine (20 mL), dried over anhydrous sodium sulfate, filtered, and the filtrate was concentrated under vacuum. The residue was purified by silica gel column chromatography with tetrahydrofuran/petroleum ether (0-1/2 by volume) as an eluent to obtain the target compound (colorless oil, 2.5 g, yield: 91.56%).

$^1$H NMR (400 MHz, DMSO-d$_6$) δ ppm 6.97 (d, J=7.8 Hz, 1H), 4.40 (quin, J=7.2 Hz, 1H), 3.54 (d, J=4.3 Hz, 4H), 3.45 (td, J=4.6, 13.4 Hz, 4H), 1.36 (s, 9H), 1.12 (d, J=6.8 Hz, 3H).

Example 67B 2-amino-1-morpholinyl-propyl-1-one

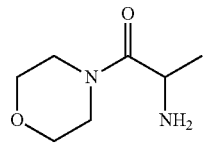

To a solution of tert-butyl-(1-morpholinyl-1-oxopropan-2-yl)-carbamate (900 mg, 3.48 mmol) in dichloromethane (15 mL) was added trifluoroacetic acid (5 mL) under an atmosphere of nitrogen and the mixture was reacted at 15° C. for 2 hours. The mixture was concentrated at 40° C. under reduced pressure. The residue was diluted with 20 mL sodium bicarbonate solution and the aqueous phase was extracted with dichloromethane (3×30 mL). The combined organic phases were washed with saturated brine (20 mL), dried over anhydrous sodium sulfate, filtered and concentrated under vacuum to obtain the target compound (light yellow liquid, 400 mg, yield: 72.66%).

$^1$H NMR (400 MHz, DMSO-d$_6$) δ ppm 3.75 (q, J=6.6 Hz, 1H), 3.60-3.52 (m, 1H), 3.50-3.40 (m, 4H), 1.07 (d, J=6.8 Hz, 3H).

Example 67C (4$^1$S,13aS)-13a-ethyl-N-(1-morpholinyl-1-oxopropyl-2-yl)-2,3,4$^1$,5,6,13a-hexahydro-1H-indolo[3,2,1-de]pyrido[3,2,1-ij][1,5]naphthyridin-12-carboxamide

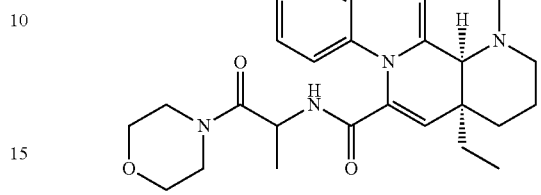

To a solution of (4$^1$S,13aS)-13a-ethyl-2,3,4$^1$,5,6,13a-hexahydro-1H-indolo[3,2,1-de]pyrido[3,2,1-ij][1,5]naphthyridin-12-caboxylic acid (800 mg, 2.48 mmol) and 2-amino-1-morpholinyl-propyl-1-one (400.18 mg, 2.53 mmol) in dichloromethane (20 mL) was added O-(7-azabenzotriazole-1-yl)-N,N,N',N'-tetramethyluronium hexafluoro-phosphate (1.13 g, 2.98 mmol) and triethylamine (552.09 mg, 5.46 mmol) under an atmosphere of nitrogen, respectively, and the reaction mixture was stirred at 20° C. for 15 hour. 20 mL water was added to the mixture, and the aqueous phase was extracted with ethyl acetate (3×50 mL). The combined organic phase was washed with saturated brine (20 mL), dried over anhydrous sodium sulfate, filtered, and the filtrate was concentrated under vacuum. The residue was purified by silica gel column chromatography with tetrahydrofuran/petroleum ether (1/5-4/5 by volume) as an eluent to obtain the target compound (yellow solid, 350 mg, yield: 30.51%).

$^1$H NMR (400 MHz, CHLOROFORM-d) δ ppm 7.49-7.43 (m, 1H), 7.24-7.18 (m, 1H), 7.15-7.08 (m, 2H), 7.05 (d, J=7.3 Hz, 1H), 5.69 (s, 1H), 5.11 (quin, J=6.9 Hz, 1H), 4.15 (s, 1H), 3.82-3.52 (m, 8H), 3.39-3.31 (m, 1H), 3.30-3.20 (m, 1H), 3.08-2.96 (m, 1H), 2.66-2.60 (m, 2H), 2.51 (dd, J=2.9, 16.2 Hz, 1H), 1.97-1.81 (m, 3H), 1.78-1.63 (m, 1H), 1.55-1.45 (m, 4H), 1.39 (br. s., 1H), 1.07-0.95 (m, 4H).

Example 67D 4-(2-((4$^1$S,13aS)-13a-ethyl-2,3,4$^1$,5,6,13a-hexahydro-1H-indolo[3,2,1-de]pyrido[3,2,1-ij][1,5]naphthyridin-12-yl)-4-methyloxazol-5-yl)morpholine

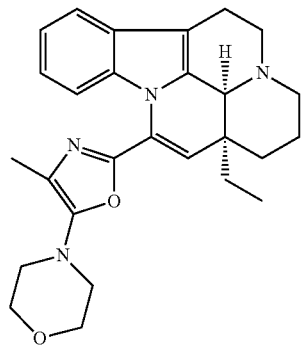

A solution of liquid bromine (128.52 mg, 0.804 mmol) in dichloromethane (2 mL) was added dropwise to a solution of triphenylphosphine (210.93 mg, 0.804 mmol) in dichloromethane (10 mL), the mixture was stirred for 30 minutes, triethylamine (203.44 mg, 2.01 mmol) and a solution of (4¹S,13aS)-13a-ethyl-N-(1-morpholinyl-1-oxopropyl-2-yl)-2,3,4¹,5,6,13a-hexahydro-1H-indolo[3,2,1-de]pyrido[3,2,1-ij][1,5]naphthyridin-12-carboxamide (310 mg, 0.67 mmol) in dichloromethane (8 mL) were added, respectively, and the reaction mixture was refluxed under an atmosphere of nitrogen for 30 minutes and maintained at 20° C. for more than 12 hours. The mixture was diluted with petroleum ether (50 mL) and the precipitated triethylamine hydrobromide was filtered off. The filtrate was evaporated to dryness under reduced pressure and the residue was purified by basic High Performance Liquid Chromatography to obtain the target compound (100 mg, yield: 33.57%).

$^1$H NMR (400 MHz, METHANOL-$d_4$) δ ppm 7.45 (d, J=7.0 Hz, 1H), 7.11-6.98 (m, 2H), 6.34 (d, J=7.8 Hz, 1H), 5.72 (s, 1H), 4.28 (s, 1H), 3.78-3.70 (m, 4H), 3.37-3.24 (m, 1H), 3.11-2.98 (m, 5H), 2.68-2.53 (m, 3H), 2.21 (s, 3H), 2.04-1.82 (m, 2H), 1.79-1.66 (m, 1H), 1.60 (d, J=13.8 Hz, 1H), 1.50-1.40 (m, 1H), 1.12-0.99 (m, 4H).

LCMS (ESI) m/z: 445 (M+1)

Scheme B20

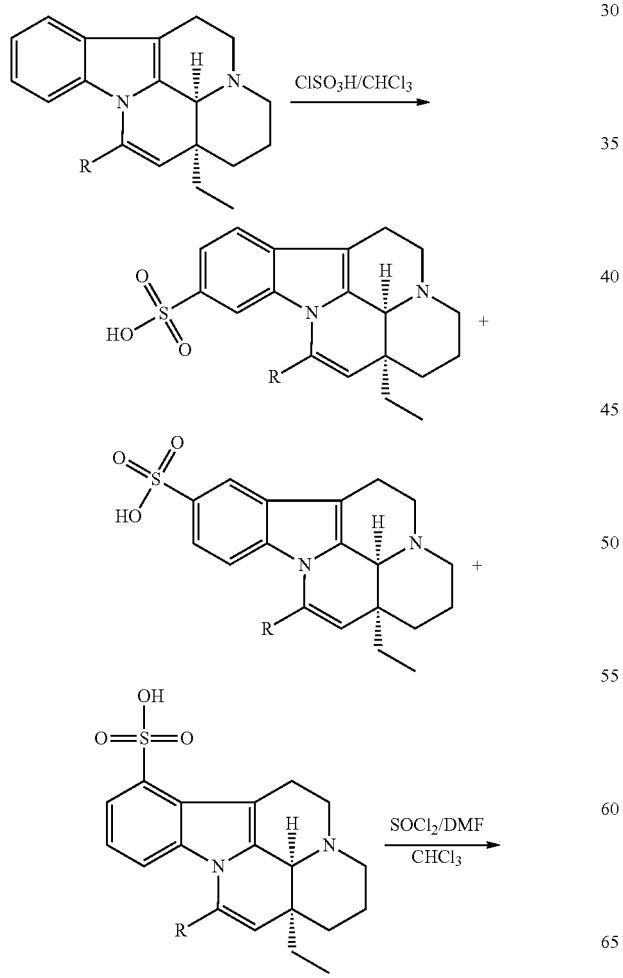

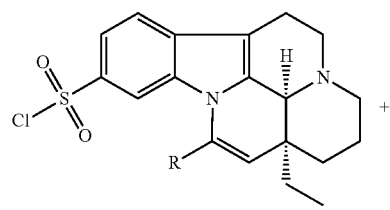

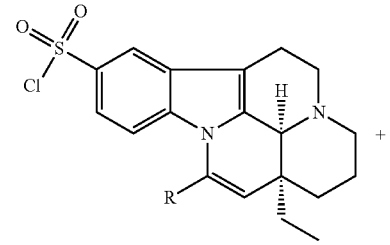

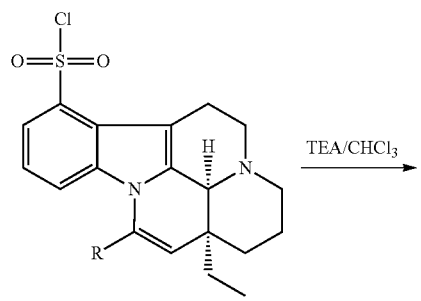

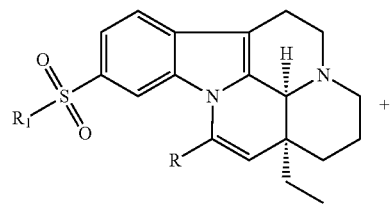

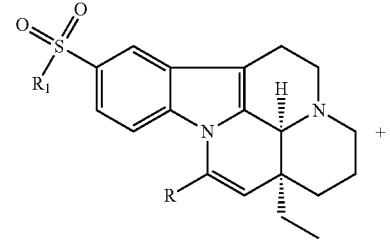

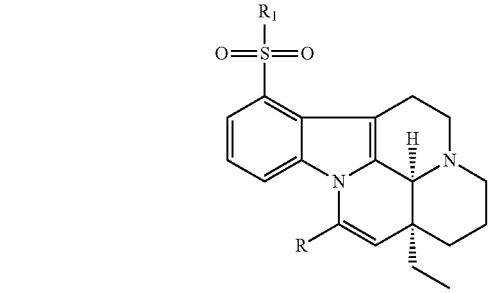

Example 68

(4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-9-sulfonamide

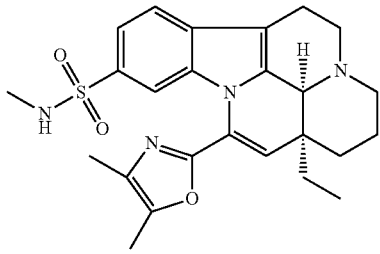

Example 68A (4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-9-sulfonic acid

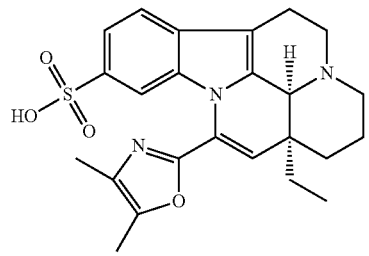

Chlorosulfonic acid (2.0 g, 17.21 mmol) was added dropwise to a solution of 2-((4¹S,13aS)-13a-ethyl-2,3,4¹,5,6,13a-hexahydro-1H-indolo[3,2,1-de]pyrido[3,2,1-ij][1,5]naphthyridin-12-yl)-4,5-dimethyloxazole (1.5 g, 4.02 mmol) in chloroform (40 mL) at 0-5° C. over a period of 10-15 minutes, and the reaction mixture was stirred at 20° C. for 0.5 hour, and 30 mL chloroform was added thereto. The mixture was poured into ice water, the pH was adjusted to 8 with triethylamine. The mixture was extracted with 50 mL dichloromethane, and the organic phase was washed with water (50 mL), dried over anhydrous sodium sulfate and concentrated. The residue was purified by Preparative High Performance Liquid Chromatography to obtain (4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-8-sulfonic acid (yellow solid, 600 mg, yield: 32.91%) and (4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-7-sulfonic acid (210 mg, yield: 11.52%).

$^1$H NMR (400 MHz, DMSO-d$_6$) δ ppm 0.97 (t, J=7.28 Hz, 3H), 1.06-1.14 (m, 1H), 1.57-1.83 (m, 4H), 1.87-1.98 (m, 1H), 2.13 (s, 3H), 2.30 (s, 3H), 2.95-3.11 (m, 3H), 3.21 (d, J=11.29 Hz, 1H), 3.68-3.88 (m, 2H), 5.17 (br. s., 1H), 5.81 (s, 1H), 7.02 (s, 1H), 7.41-7.46 (m, 1H), 7.48-7.51 (m, 1H), 10.49 (br. s., 1H).

(4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-8-sulfonic acid

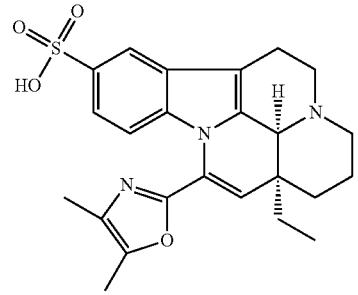

$^1$H NMR (400 MHz, DMSO-d$_6$) δ ppm 0.97 (t, J=7.03 Hz, 3H), 1.06-1.21 (m, 1H), 1.54-1.83 (m, 4H), 1.88-1.98 (m, 1H), 2.13 (s, 3H), 2.30 (s, 3H), 3.11 (br. s., 3H), 3.22 (d, J=11.54 Hz, 1H), 3.72-3.86 (m, 2H), 5.17 (br. s., 1H), 5.80 (s, 1H), 6.47 (d, J=8.78 Hz, 1H), 7.39 (d, J=8.78 Hz, 1H), 7.82 (s, 1H), 10.47 (br. s., 1H).

(4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-7-sulfonic acid

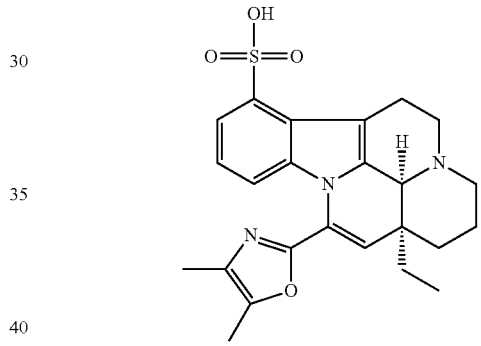

$^1$H NMR (400 MHz, DMSO-d$_6$) δ ppm 0.98 (t, J=7.28 Hz, 3H), 1.11-1.21 (m, 1H), 1.58-1.85 (m, 4H), 1.92 (dq, J=14.37, 7.26 Hz, 1H), 2.13 (s, 3H), 2.28 (s, 3H), 2.93-3.04 (m, 1H), 3.25 (d, J=11.54 Hz, 1H), 3.37-3.50 (m, 1H), 3.69 (br. s., 3H), 5.17 (br. s., 1H), 5.79 (s, 1H), 6.34 (d, J=8.53 Hz, 1H), 7.02 (t, J=7.91 Hz, 1H), 7.48 (d, J=7.28 Hz, 1H), 10.31 (d, J=7.53 Hz, 1H).

Example 68B (4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-9-sulfonyl-chloride

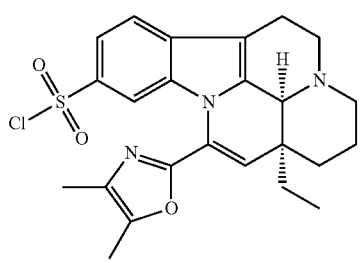

To a solution of (4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-9-sulfonic acid (300 mg, 0.66 mmol) in chloroform (10 mL) was added thionyl chloride (236 mg, 1.98 mmol) and N,N-dimethylformamide (95 mg, 1.3 mmol), and the reaction mixture was heated to 55° C. and stirred for 2 hours. After the low boiling components were concentrated to dry, the resulting yellow oil was directly used for the next step.

Example 68C (4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-9-sulfonamide

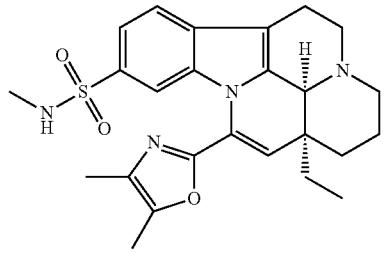

To a solution of (4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-9-sulfonylchloride (100 mg, 0.212 mmol) in chloroform was respectively added triethylamine (60 mg, 0.632 mmol) and a solution of methylamine in tetrahydrofuran (1 M, 0.426 mL, 0.426 mmol), and the reaction mixture was stirred at 20° C. for 1 hour. Dichloromethane (30 mL) and water (20 mL) was added to the mixture, and the separated organic lay was dried over anhydrous sodium sulfate and concentrated. The residue was purified by Preparative High Performance Liquid Chromatography to obtain the target compound.

¹H NMR (400 MHz, METHANOL-d4) δ ppm 1.15 (t, J=7.40 Hz, 3H), 1.28-1.38 (m, 1H), 1.77-1.88 (m, 2H), 1.94-2.13 (m, 3H), 2.23 (s, 3H), 2.39 (s, 3H), 2.48 (s, 3H), 3.19-3.30 (m, 2H), 3.38 (br. s., 2H), 3.83-3.99 (m, 2H), 5.22 (br. s., 1H), 6.04 (s, 1H), 7.29 (s, 1H), 7.64 (d, J=8.28 Hz, 1H), 7.80 (d, J=8.28 Hz, 1H).

Example 69

(4¹S,13aS)-12-(4,5-dimethyloxazol-2-yl)-13a-ethyl-N,N-dimethyl-2,3,4¹,5,6,13a-hexahydro-1H-indolo[3,2,1-de]pyrido[3,2,1-ij][1,5]naphthyridin-9-sulfonamide

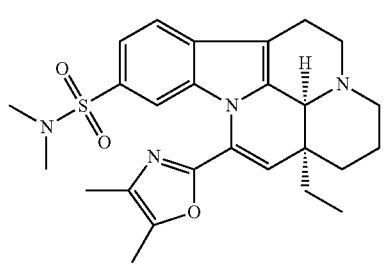

The process of the example was the same as that of Example 68C.

¹H NMR (400 MHz, METHANOL-d4) δ ppm 1.15 (t, J=7.40 Hz, 3H), 1.34 (td, J=14.18, 4.02 Hz, 1H), 1.77-1.88 (m, 2H), 1.94-2.13 (m, 3H), 2.20 (s, 3H), 2.39 (s, 3H), 2.65 (s, 6H), 3.19-3.31 (m, 2H), 3.33-3.41 (m, 2H), 3.85-4.00 (m, 2H), 5.24 (s, 1H), 6.04 (s, 1H), 7.20 (s, 1H), 7.58 (dd, J=8.28, 1.25 Hz, 1H), 7.83 (d, J=8.28 Hz, 1H).

Example 70

(4¹S,13aS)-12-(4,5-dimethyloxazol-2-yl)-13a-ethyl-N-(3-methoxylpropyl)-2,3,4¹,5,6,13a-hexahydro-1H-indolo[3,2,1-de]pyrido[3,2,1-ij][1,5]naphthyridin-9-sulfonamide

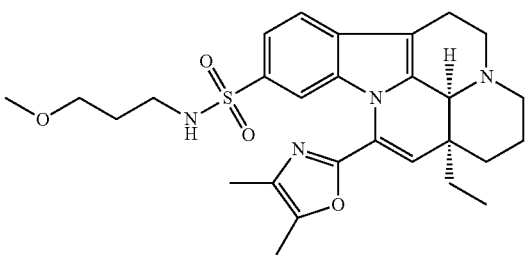

The process of the example was the same as that of Example 68C.

¹H NMR (400 MHz, METHANOL-d4) δ ppm 1.15 (t, J=7.28 Hz, 3H), 1.28-1.37 (m, 1H), 1.65 (quin, J=6.46 Hz, 2H), 1.76-1.87 (m, 2H), 1.96-2.15 (m, 3H), 2.24 (s, 3H), 2.40 (s, 3H), 2.77-2.94 (m, 2H), 3.18-3.32 (m, 6H), 3.34-3.40 (m, 3H), 3.84-3.99 (m, 2H), 5.22 (s, 1H), 6.04 (s, 1H), 7.29 (s, 1H), 7.65 (dd, J=8.28, 1.25 Hz, 1H), 7.79 (d, J=8.53 Hz, 1H).

Example 71

(4¹S,13aS)-12-(4,5-dimethyloxazol-2-yl)-13a-ethyl-N,N-dimethyl-2,3,4¹,5,6,13a-hexahydro-1H-indolo[3,2,1-de]pyrido[3,2,1-ij][1,5]naphthyridin-8-sulfonamide

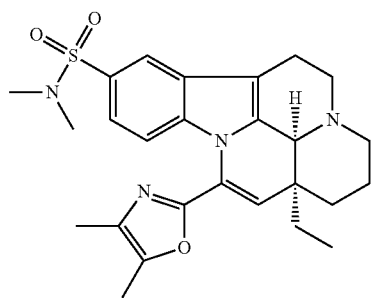

The process of the example was the same as that of Examples 68B, 68C.

¹H NMR (400 MHz, METHANOL-d4) δ ppm 1.14 (t, J=7.28 Hz, 3H), 1.26-1.38 (m, 1H), 1.76-1.87 (m, 2H), 1.95-2.15 (m, 3H), 2.23 (s, 3H), 2.39 (s, 3H), 2.68 (s, 6H), 3.22-3.30 (m, 2H), 3.33-3.43 (m, 2H), 3.84-4.00 (m, 2H), 5.22 (s, 1H), 6.04 (s, 1H), 6.87 (d, J=8.78 Hz, 1H), 7.57 (dd, J=8.91, 1.38 Hz, 1H), 8.06 (d, J=1.00 Hz, 1H).

Example 72

(4¹S,13aS)-12-(4,5-dimethyloxazol-2-yl)-13a-ethyl-N-(3-methoxylpropyl)-2,3,4¹,5,6,13a-hexahydro-1H-indolo[3,2,1-de]pyrido[3,2,1-ij][1,5]naphthyridin-9-sulfonamide

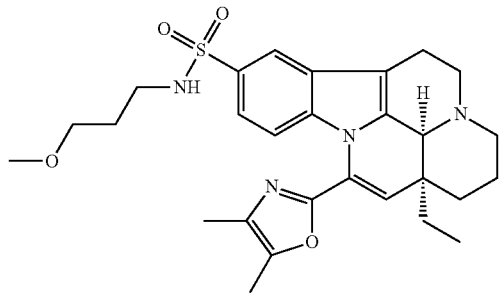

The process of the example was the same as that of Examples 68B, 68C.

¹H NMR (400 MHz, METHANOL-d4) δ ppm 1.14 (t, J=7.28 Hz, 3H), 1.27-1.37 (m, 1H), 1.70 (quin, J=6.40 Hz, 2H), 1.75-1.87 (m, 2H), 1.94-2.13 (m, 3H), 2.22 (s, 3H), 2.38 (s, 3H), 2.90 (t, J=6.90 Hz, 2H), 3.20-3.32 (m, 6H), 3.39 (t, J=6.02 Hz, 3H), 3.84-4.01 (m, 2H), 5.20 (br. s., 1H), 6.02 (s, 1H), 6.82 (d, J=9.03 Hz, 1H), 7.64 (dd, J=8.78, 1.25 Hz, 1H), 8.14 (s, 1H).

Example 73

(4¹S,13aS)-12-(4,5-dimethyloxazol-2-yl)-13a-ethyl-N-methyl-2,3,4¹,5,6,13a-hexahydro-1H-indolo[3,2,1-de]pyrido[3,2,1-ij][1,5]naphthyridin-7-sulfonamide

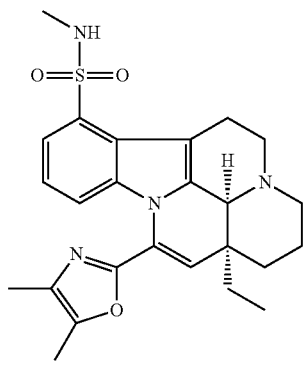

The process of the example was the same as that of Examples 68B, 68C.

¹H NMR (400 MHz, METHANOL-d4) δ ppm 1.14 (t, J=7.28 Hz, 3H), 1.31 (td, J=14.05, 3.51 Hz, 1H), 1.75-1.87 (m, 2H), 1.93-2.12 (m, 3H), 2.22 (s, 3H), 2.37 (s, 3H), 2.68-2.74 (m, 3H), 3.20-3.30 (m, 1H), 3.34-3.40 (m, 1H), 3.52-3.69 (m, 2H), 3.80-3.91 (m, 2H), 5.22 (s, 1H), 6.04 (s, 1H), 6.81 (d, J=8.28 Hz, 1H), 7.29 (t, J=8.03 Hz, 1H), 7.68 (d, J=7.53 Hz, 1H).

Example 74

(4¹S,13aS)-12-(4,5-dimethyloxazol-2-yl)-13a-ethyl-N,N-dimethyl-2,3,4¹,5,6,13a-hexahydro-1H-indolo[3,2,1-de]pyrido[3,2,1-ij][1,5]naphthyridin-7-sulfonamide

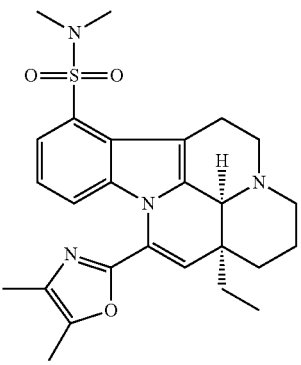

The process of the example was the same as that of Examples 68B, 68C.

¹H NMR (400 MHz, METHANOL-d4) δ ppm 1.14 (t, J=7.28 Hz, 3H), 1.31 (td, J=13.99, 3.64 Hz, 1H), 1.76-1.86 (m, 2H), 1.95-2.11 (m, 3H), 2.23 (s, 3H), 2.37 (s, 3H), 2.92 (s, 6H), 3.19-3.29 (m, 1H), 3.34-3.40 (m, 1H), 3.49-3.61 (m, 2H), 3.81-3.92 (m, 2H), 5.22 (s, 1H), 6.07 (s, 1H), 6.87 (d, J=8.53 Hz, 1H), 7.31 (t, J=8.16 Hz, 1H), 7.64 (d, J=7.53 Hz, 1H).

Example 75

(4¹S,13aS)-12-(4,5-dimethyloxazol-2-yl)-13a-ethyl-N-(3-methoxylpropyl)-2,3,4¹,5,6,13a-hexahydro-1H-indolo[3,2,1-de]pyrido[3,2,1-ij][1,5]naphthyridin-7-sulfonamide

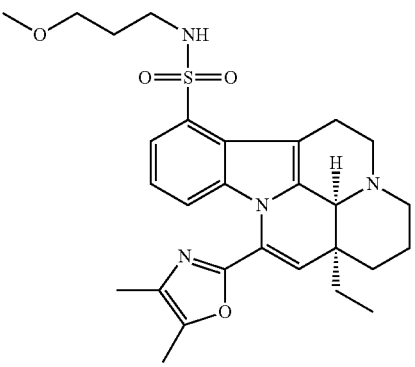

The process of the example was the same as that of Examples 68B, 68C.

¹H NMR (400 MHz, METHANOL-d4) δ ppm 1.14 (t, J=7.28 Hz, 3H), 1.31 (td, J=13.93, 3.76 Hz, 1H), 1.73-1.87 (m, 4H), 1.93-2.09 (m, 3H), 2.22 (s, 3H), 2.36 (s, 3H), 3.11-3.17 (m, 2H), 3.22-3.31 (m, 4H), 3.36 (br. s., 1H), 3.41 (t, J=6.02 Hz, 2H), 3.54-3.70 (m, 2H), 3.79-3.93 (m, 2H), 5.23 (br. s., 1H), 6.04 (s, 1H), 6.80 (d, J=8.28 Hz, 1H), 7.29 (t, J=8.03 Hz, 1H), 7.70 (d, J=7.53 Hz, 1H).

Example 76

(4¹S,13aS)-13a-ethyl-N-methyl-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-9-sulfonamide

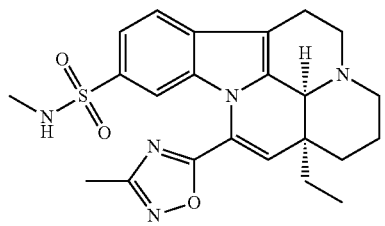

The process of the example was the same as that of Examples 68A, 68B, 68C.

¹H NMR (400 MHz, CD₃OD) Oδ ppm 8.10 (s, 1H), 7.62 (dd, J=1.1, 8.9 Hz, 1H), 7.04 (d, J=9.0 Hz, 1H), 6.41 (s, 1H), 5.23 (br. s., 1H), 4.06-3.78 (m, 2H), 3.32-3.16 (m, 3H), 2.60-2.42 (m, 7H), 2.22-1.93 (m, 3H), 1.87-1.70 (m, 2H), 1.42-1.25 (m, 1H), 1.15 (t, J=7.3 Hz, 3H).

LCMS (ESI) m/z: 444 (M+1)

Example 77

(4¹S,13aS)-13a-ethyl-N,N-dimethyl-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-9-sulfonamide

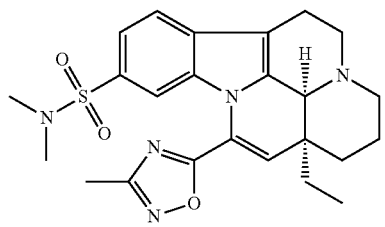

The process of the example was the same as that of Examples 68A, 68B, 68C.

¹H NMR (400 MHz, CD₃OD) δ ppm 8.07 (d, J=1.3 Hz, 1H), 7.60 (dd, J=1.5, 9.0 Hz, 1H), 7.11 (d, J=9.0 Hz, 1H), 6.44 (s, 1H), 5.25 (br. s., 1H), 4.07-3.82 (m, 2H), 3.29-3.16 (m, 2H), 2.78-2.65 (m, 7H), 2.54 (s, 3H), 2.21-1.96 (m, 3H), 1.91-1.75 (m, 2H), 1.43-1.30 (m, 3H), 1.16 (t, J=7.3 Hz, 3H).

LCMS (ESI) m/z: 468 (M+1)

Example 78

(4¹S,13aS)-13a-ethyl-N-(3-methoxylpropyl)-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-9-sulfonamide

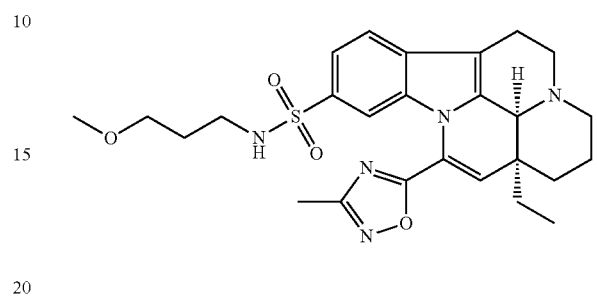

The process of the example was the same as that of Examples 68A, 68B, 68C.

¹H NMR (400 MHz, CD₃OD) δ ppm 8.12 (d, J=1.0 Hz, 1H), 7.65 (dd, J=1.5, 8.8 Hz, 1H), 7.05 (d, J=9.0 Hz, 1H), 6.42 (s, 1H), 5.23 (br. s., 1H), 4.04-3.82 (m, 2H), 3.41-3.35 (m, 3H), 3.29-3.19 (m, 5H), 2.90 (t, J=6.9 Hz, 2H), 2.53 (s, 3H), 2.23-1.98 (m, 3H), 1.90-1.77 (m, 2H), 1.69 (quin, J=6.5 Hz, 2H), 1.40-1.26 (m, 2H), 1.15 (t, J=7.3 Hz, 3H).

LCMS (ESI) m/z: 502 (M+1)

Example 79

(4¹S,13aS)-13a-ethyl-N-methyl-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-8-sulfonamide

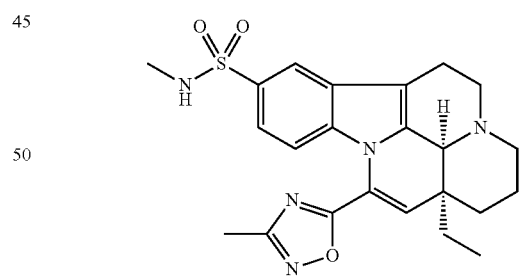

The process of the example was the same as that of Examples 68A, 68B, 68C.

¹H NMR (400 MHz, CD₃OD) δ ppm 7.80 (d, J=8.3 Hz, 1H), 7.67 (d, J=8.3 Hz, 1H), 7.51 (s, 1H), 6.45 (s, 1H), 5.25 (s, 1H), 4.08-3.81 (m, 2H), 3.31-3.17 (m, 3H), 2.63-2.44 (m, 7H), 2.20-1.96 (m, 3H), 1.92-1.73 (m, 2H), 1.47-1.28 (m, 2H), 1.16 (t, J=7.3 Hz, 3H).

LCMS (ESI) m/z: 444 (M+1)

Example 80

(4¹S,13aS)-13a-ethyl-N,N-dimethyl-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-8-sulfonamide

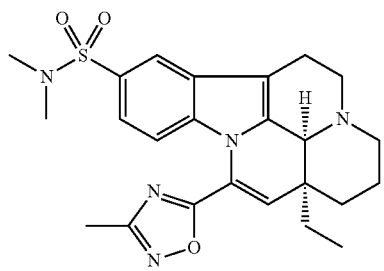

The process of the example was the same as that of Examples 68A, 68B, 68C.

¹H NMR (400 MHz, CD$_3$OD) δ ppm 7.86 (d, J=8.3 Hz, 1H), 7.63 (d, J=8.3 Hz, 1H), 7.44 (s, 1H), 6.48 (s, 1H), 5.26 (br. s., 1H), 4.01-3.86 (m, 2H), 3.32-3.21 (m, 4H), 2.67 (s, 6H), 2.51 (s, 3H), 2.17-1.92 (m, 3H), 1.91-1.78 (m, 2H), 1.44-1.32 (m, 1H), 1.16 (t, J=7.3 Hz, 3H).

Example 81

(4¹S,13aS)-13a-ethyl-N-(3-methoxylpropyl)-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-8-sulfonamide

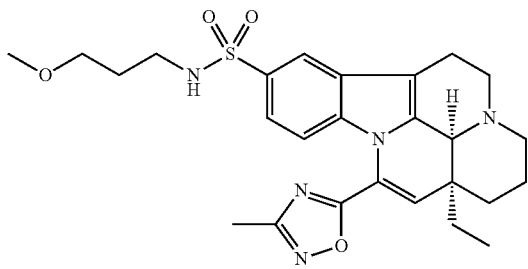

The process of the example was the same as that of Examples 68A, 68B, 68C.

¹H NMR (400 MHz, CD$_3$OD) δ ppm 7.80 (d, J=8.5 Hz, 1H), 7.69 (dd, J=1.0, 8.5 Hz, 1H), 7.52 (s, 1H), 6.44 (s, 1H), 5.25 (s, 1H), 4.02-3.84 (m, 2H), 3.37 (t, J=6.0 Hz, 3H), 3.32-3.19 (m, 6H), 2.99-2.79 (m, 2H), 2.53 (s, 3H), 2.16-1.94 (m, 3H), 1.90-1.77 (m, 2H), 1.67 (quin, J=6.5 Hz, 2H), 1.42-1.29 (m, 1H), 1.16 (t, J=7.3 Hz, 3H).

LCMS (ESI) m/z: 502 (M+1)

Example 82

(4¹S,13aS)-13a-ethyl-N-methyl-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-7-sulfonamide

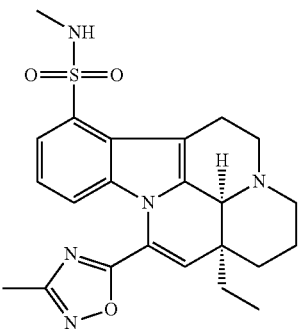

The process of the example was the same as that of Examples 68A, 68B, 68C.

¹H NMR (400 MHz, CD$_3$OD) δ ppm 7.71 (d, J=7.5 Hz, 1H), 7.32 (t, J=8.2 Hz, 1H), 7.06 (d, J=8.5 Hz, 1H), 6.43 (s, 1H), 5.24 (s, 1H), 3.93-3.79 (m, 2H), 3.71-3.49 (m, 2H), 3.33-3.24 (m, 2H), 2.72 (s, 3H), 2.52 (s, 3H), 2.14-1.94 (m, 3H), 1.90-1.76 (m, 2H), 1.34 (dt, J=3.8, 14.1 Hz, 1H), 1.15 (t, J=7.3 Hz, 3H).

LCMS (ESI) m/z: 444 (M+1)

Example 83

(4¹S,13aS)-13a-ethyl-N,N-dimethyl-12-(3-methyl-1,2,4-oxadiazol-5-yl)-2,3,4¹,5,6,13a-hexahydro-1H-indolo[3,2,1-de]pyrido[3,2,1-ij][1,5]naphthyridin-7-sulfonamide

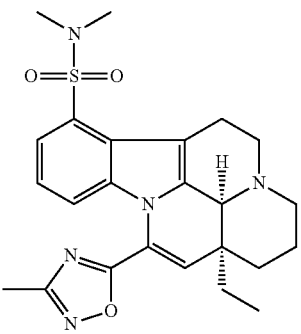

The process of the example was the same as that of Examples 68A, 68B, 68C.

¹H NMR (400 MHz, CD$_3$OD) δ ppm 7.66 (d, J=7.8 Hz, 1H), 7.34 (t, J=8.2 Hz, 1H), 7.10 (d, J=8.5 Hz, 1H), 6.45 (s, 1H), 5.24 (s, 1H), 3.93-3.80 (m, 2H), 3.64-3.47 (m, 2H), 3.43-3.35 (m, 1H), 3.30-3.19 (m, 2H), 2.93 (s, 6H), 2.72 (s, 1H), 2.52 (s, 3H), 2.16-1.94 (m, 3H), 1.90-1.77 (m, 2H), 1.40-1.28 (m, 3H), 1.15 (t, J=7.3 Hz, 3H).

LCMS (ESI) m/z: 468 (M+1)

Example 84

(4¹S,13aS)-13a-ethyl-N-(3-methoxylpropyl)-12-(3-methyl-1,2,4-oxadiazol-5-yl)-2,3,4,5,6,13a-hexahydro-1H-indolo[3,2,1-de]pyrido[3,2,1-ij][1,5]naphthyridin-7-sulfonamide

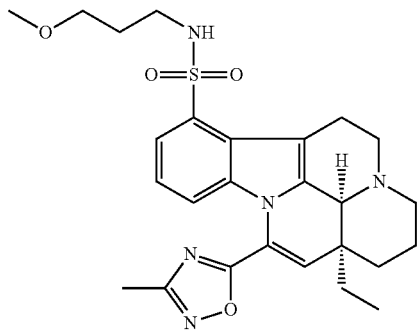

The process of the example was the same as that of Examples 68A, 68B, 68C.

¹H NMR (400 MHz, CD$_3$OD) δ ppm 7.72 (d, J=7.8 Hz, 1H), 7.32 (t, J=8.2 Hz, 1H), 7.06 (d, J=8.5 Hz, 1H), 6.44 (s, 1H), 5.26 (s, 1H), 3.97-3.81 (m, 2H), 3.72-3.51 (m, 3H), 3.45-3.36 (m, 4H), 3.30-3.24 (m, 4H), 3.16 (t, J=6.8 Hz, 2H), 3.06 (t, J=6.9 Hz, 1H), 2.52 (s, 3H), 2.13-1.74 (m, 8H), 1.41-1.27 (m, 1H), 1.15 (t, J=7.4 Hz, 3H).

LCMS (ESI) m/z: 502 (M+1)

Test 1: In Vitro Detection of Phosphodiesterase (PDE)

Experimental Principle:

the enzyme activity of PDE1A was determined by detecting the production of AMP/GMP by fluorescence polarization immunoassay, wherein AlexaFluor 633 labeled AMP/GMP was used to replace AMP/GMP to bind with the antibody.

Experiment Reagent:

Reaction buffer: 10 mM Tris-HCl, pH 7.5, 5 mM magnesium chloride, 0.01% Brij 35, 1 mM DTT and 1% DMSO;

Enzyme substrate: 1M cAMP or cGMP (Ca²⁺-calmodulin acts as a cofactor of PDE1A)

Detection reagent: Transcreener® AMP2/GMP2 antibody; AMP2/GMP2 AlexaFluor 633 tracer.

Experimental Procedure and Method:

1. Human-derived enzyme (commercially available from SignalChem) to be tested and substrate were diluted with freshly prepared reaction buffer;

2. The enzyme solution (with a concentration of 3 pM) was added to the holes of the microplates;

3. A series of solutions of the compounds in 100% DMSO (with the desired concentrations) were added to the holes containing the enzyme solution by Echo550, and then the microplates were incubated for 10 minutes at room temperature;

4. The substrate solution was added to the holes containing the enzyme and compounds to start the reaction;

5. The microplates were incubated for 1 hour under room temperature and vibration;

6. The detection mixture (tracer and antibody in stop buffer) was added to stop the enzyme reaction, and the microplates were incubated for 90 minutes under vibration;

7. The equipment EnVision (PerkinElmer), Cy5 FP Ex FP 620, Em S-pol 688/P-pol 688, FP mirror D658fp/D688 was used to detect the reaction mixture, and Ex/Em 620/688 was used to detect the fluorescence polarization.

Data Analysis:

In the Excel table, the enzyme activity corresponding to the FP signal was found on the AMP/GMP standard curve by reference to the DMSO negative control, and then was converted to product concentration (nM). GraphPad Prism was used to analyze and calculate the IC$_{50}$ values.

The experimental result was shown in Table 1.

TABLE 1

| IC$_{50}$s for PDE1 | |
|---|---|
| Test samples (target compounds) | PDE1 |
| Example 1 | D |
| Example 2 | B |
| Example 3 | D |
| Example 4 | C |
| Example 5 | D |
| Example 6 | B |
| Example 7 | C |
| Example 8 | C |
| Example 9 | B |
| Example 10 | B |
| Example 11 | C |
| Example 12 | B |
| Example 13 | C |
| Example 14 | B |
| Example 15 | D |
| Example 16 | B |
| Example 17 | B |
| Example 18 | D |
| Example 19 | D |
| Example 20 | B |
| Example 21 | D |
| Example 22 | C |
| Example 23 | B |
| Example 24 | C |
| Example 25 | B |
| Example 26 | D |
| Example 27 | D |
| Example 28 | D |
| Example 29 | B |
| Example 30 | D |
| Example 31 | B |
| Example 32 | D |
| Example 33 | B |
| Example 34 | B |
| Example 35 | B |
| Example 36 | C |
| Example 37 | B |
| Example 38 | C |
| Example 39 | B |
| Example 40 | B |
| Example 41 | A |
| Example 42 | B |
| Example 43 | C |
| Example 44 | C |
| Example 45 | C |
| Example 46 | C |
| Example 47 | B |
| Example 48 | B |
| Example 49 | D |
| Example 50 | B |
| Example 51 | B |
| Example 52 | A |
| Example 53 | A |
| Example 54 | B |
| Example 55 | A |
| Example 56 | A |
| Example 57 | A |
| Example 58 | A |
| Example 59 | A |
| Example 60 | B |
| Example 61 | A |
| Example 62 | B |
| Example 63 | A |

TABLE 1-continued

IC$_{50}$s for PDE1

| Test samples (target compounds) | PDE1 |
|---|---|
| Example 64 | A |
| Example 65 | A |
| Example 66 | A |
| Example 67 | A |
| Example 68 | A |
| Example 69 | B |
| Example 70 | A |
| Example 71 | B |
| Example 72 | C |
| Example 73 | B |
| Example 74 | B |
| Example 75 | C |
| Example 76 | B |
| Example 77 | C |
| Example 78 | C |
| Example 79 | B |
| Example 80 | C |

TABLE 1-continued

IC$_{50}$s for PDE1

| Test samples (target compounds) | PDE1 |
|---|---|
| Example 81 | C |
| Example 82 | C |
| Example 83 | C |
| Example 84 | D |

Note:
A ≤1 uM;
1 uM < B ≤ 20 uM;
20 uM < C ≤ 100 uM;
D >100 uM

Test 2: Comparison of Pharmacokinetics in Beagle Dogs

In this study, male Beagle dogs were given the compounds of the examples and vinpocetine (as a control compound) by intravenous injection or oral administration, respectively, then the drug concentration in plasma at different time points was determined by the LC/MS/MS method, so as to investigate the pharmacokinetic characteristics of the two test drugs in Beagle dogs.

Eight healthy adult Beagle dogs with a weight of 7.0 to 10.83 kg (purchased from Beijing Marshall Biotechnology Co., Ltd.) were selected. The formulation for intravenous injection group was DMSO: PEG400: water=5:20:75. A solvent was added to the test compound which had been accurately weighed, after vortex oscillation and ultrasound, a clear solution with a final concentration of 1.0 mg/mL was obtained. The solution was filtered with a filter membrane of 0.22 μm and stored at room temperature for use. The formulation for oral administration group was PEG 400: Tween 80: H$_2$O=40:10:50. A solvent was added to the test compound which had been accurately weighed, after vortex oscillation and ultrasound, a clear solution with a final concentration of 1.5 mg/mL was obtained. The formulations for both the intravenous injection and the oral administration were formulated on the day of administration. The intravenous dose was 1.0 mg/kg, and the oral dose was 3.0 mg/kg. The whole blood for each test compound was respectively taken at 0.083 (for intravenous injection only), 0.25, 0.5, 1, 2, 4, 6, 8 and 24 hours after administration. The whole blood was centrifuged (3000 g, 15 min, 4° C.) to obtain the plasma. The drug concentration in each plasma sample was determined by LC/MS/MS method. The data about drug concentration in plasma was processed by WinNonlin™ Version 6.3 (Pharsight, Mountain View, Calif.) software, using a non-compartmental model, and the pharmacokinetic parameters were calculated by using the linear-logarithmic trapezoidal method.

TABLE 2

Pharmacokinetic parameters of the target compound of Example 29 and vinpocetine in Beagle dogs

| | Pharmacokinetic parameters in beagel dogs ||||||| |
|---|---|---|---|---|---|---|---|
| | Intravenous Injection (1 mg/kg) ||| Oral Administration (3 mg/kg) |||| |
| | Plasma clearance (mL/min/kg) | Half-life period (h) | area under the concentration-time curve (0-inf, nM · h) | Peak concentration (nM) | Time to Peak (h) | area under the concentration-time curve (0-inf, nM · h) | Bioavailability |
| Vinpocetine | 80.5 | 6.03 | 588 | 142 | 0.5 | 216 | 12.3 |
| Example 29 | 11.97 | 9.42 | 4040 | 1299 | 1.0 | 4545 | 37.5 |

As shown in Table 2, the compound of Example 29 had a plasma clearance about 85% lower than that of vinpocetine, had a half-life 56% longer than that of vinpocetine, and had an oral bioavailability 3.1 times that of vinpocetine. In non-rodent Beagle dogs, the pharmacokinetics parameters of Example 29 were significantly superior to vinpocetine.

Test 3: Inhibition Effect on Pentylenetetrazole-Kindling Model of Epilepsy in Cynomolgus Monkey In this test, six male cynomolgus monkeys were selected, and each monkey was intragastrically administrated by nasal feeding. Besides pentylenetetrazole which was administrated by subcutaneous injection, the compound of Example 29 and carbamazepine were consecutively administered for 8 days, respectively. The monkeys were respectively given a solvent prior to the first administration, and were injected subcutaneously with pentylenetetrazole immediately after the last administration. The administration interval between two tests was about 10 days. Pentylenetetrazine was administered once to induce epilepsy prior to the first administration of the compound of Example 29. The dosage was calculated according to the latest weight of the animal, and the date of first administration was designated as Day 1.

Surgical procedure: the animals were fed adaptively for at least one week in feeding facilities, and then they were anesthetized during preoperative preparation according to the company standards. The main operation procedures were as follows: cutting the head skin, fully exposing the skull, stripping the periosteum, and cleaning the skull surface with a dry absorbent cotton; drilling 2 holes on the skull of the cynomolgus monkey with cranial drill, implanting a brain electrode, and fixing it with dental cement; then burying two myoelectric electrodes into the neck muscles of the cynomolgus monkey, and burying eye-electric electrodes into the bilateral eye muscles, fixing the implant body in the abdominal muscle layer. Postoperative care was performed according to the company standards.

The raw data was collected by Ponemah of DSI system, and analyzed and revised by Neuronscore.

The data was shown by mean±standard error (Mean±SEM), statistical analysis was performed by t-test and ANOVA. P<0.05 indicated a significant difference, P<0.01 indicated a very significant difference, P<0.001 indicated an extremely significant difference.

The characteristics of electroencephalic response and electroencephalic energy for pentylenetetrazole-kindling epilepsy were observed and analyzed, and then a comparison was made between Example 29 and carbamazepine in terms of the latency for the onset of epilepsy seizure, and the times and lasting time of clonic convulsions and tonic convulsions in cynomolgus monkey pentylenetetrazole-kindling model, so as to compare the pharmacodynamic inhibitory effect of Example 29 and carbamazepine on cynomolgus monkey pentylenetetrazole-kindling model.

After the cynomolgus monkeys were injected subcutaneously with 40 mg/kg pentylenetetole on the back and were induced epilepsy-like behaviors, the electroencephalic response, electromyogrphic response and locomotor activity were detected by DSI wireless remote sensing signal recording system. The cynomolgus monkeys injected with pentylenetetrazole showed characteristic epilepsy-like electroencephalic response and electromyogrphic response. The behaviors were divided into paroxysmal activity, clonic convulsion and tonic convulsions according to the status of epilepsy.

The changes of electroencephalic energy within 4-24 Hz were statistically analyzed when cynomolgus monkeys suffered epileptic seizure within 24 hours after injection of pentylenetetrazole. The results showed that the electroencephalic energy within 4-24 Hz was significantly enhanced when pentylenetetrazole-kindling epilepsy occurred.

After injection of pentylenetetrazole, the latency for the onset of epilepsy seizure was calculated, so as to compare the effect of Example 29 and carbamazepine on the the latency for the onset of epilepsy seizure in pentylenetetrazole-kindling model. The results showed that Example 29 and carbamazepine significantly prolonged the latency for the onset of epilepsy seizure. After continuous administration of 8 days, the latency for the onset of epilepsy seizure in pentylenetetrazole-kindling model was 24.86±3.97 minutes for the Vehicle group, 45.20±9.11 minutes for the carbamazepine group, 64.10±13.21 minutes for Example 29 group, respectively. There was a significant difference (P<0.05) for both the Example 29 group and the carbamazepine group compared with the solvent control group. The carbamazepine group prolonged 20.34 min than the Vehicle group, a relative increase of 81%; Example 29 prolonged 39.24 min than the Vehicle group, a relative increase of 160%; Example 29 prolonged 18.9 min than the camazepine group, a relative increase of 42%.

Thus, both Example 29 and carbamazepine given the same dosage (10 mg/kg) showed a significant effect on prolonging the latency for the onset of epilepsy seizure, and the effect of Example 29 on prolonging the latency for the onset of epilepsy seizure was significantly superior to (about 42%) that of carmazepine.

Furthermore, both Example 29 and carbamazepine significantly reduced the times of clonic convulsion and tonic convulsion within 24 hours after administration of pentylenetetrazol. The times of clonic convulsion and tonic convulsion were 107.50±15.60 for the Vehicle group, 39.20±14.92 for the carbamazepine group and 25.7±7.07 for the Example 29 group, respectively. There was a very significant difference (P<0.01) for both Example 29 group and carbamazepine group compared with Vehicle control group. The carbamazepine group reduced by about 68 times on average compared with the Vehicle Group, a relative reduction of 63%; the Example 29 group reduced by about 82 times on average compared with the Vehicle Group, a relative reduction of 76%; the Example 29 reduced by about 14 times compared with the carbamazepine group, a relative reduction of 36%.

Thus, both Example 29 and carbamazepine given the same dosage (10 mg/kg) significantly reduced the times of clonic convulsion and tonic convulsion, and the effect of Example 29 on reducing the times of seizures was significantly superior to (about 36%) that of carmazepine.

Finally, the effect of Example 29 and carbamazepine on the lasting time of clonic convulsions and tonic convulsions were detected. The results showed that both Example 29 and carbamazepine significantly shortened the lasting time of clonic convulsions and tonic convulsions in pentylenetetrazole-kindled cynomolgus monkeys. The lasting time of clonic convulsions and tonic convulsions was 11.68±3.15 min for the Vehicle group, 4.71±2.35 min for the carbamazepine group and 2.61±0.99 min for the Example 29 group, respectively. There was significant difference (P<0.05) for both Example 29 group and carbamazepine group compared with Vehicle control group. The carbamazepine group shortened 6.97 min on average compared with the Vehicle Group, a relative reduction of 60%; the Example 29 shortened 9.07 min on average compared with the Vehicle group, a relative reduction of 78%; the Example 29 shortened about 2.1 min compared with the carbamazepine group, a relative reduction of 45%.

Thus, both Example 29 and carbamazepine given the same dosage (10 mg/kg) significantly shortened the lasting time of clonic convulsions and tonic convulsions, and the effect of Example 29 on shortening the lasting time of clonic convulsions and tonic convulsions was significantly superior to (about 45%) that of carmazepine.

In conclusion, the results showed that all of the six male cynomolgus monkeys injected subcutaneously with pentylenetetrazole showed epileptiform pattern, convulsion and myotonic discharge; and the compound of Example 29 and carbamazepine not only significantly prolonged the latency for the onset of epilepsy seizure in pentylenetetrazole-kindling cynomolgus monkeys, but also significantly reduced the times and lasting time of clonic convulsion and tonic convulsion within 24 hours after administration of pentylenetetrazol. The data indicated that Example 29 was superior to carbamazepine in terms of all the three main outcome measurements of anti-epileptic effects.

What is claimed is:

1. A compound of formula (I), or a pharmaceutically acceptable salt or a tautomer thereof,

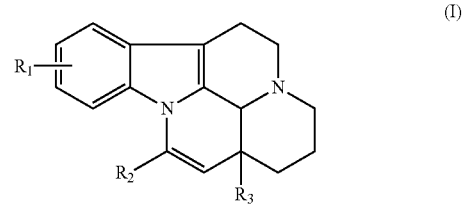

(I)

wherein:
R₁ and R₃ are separately and independently selected from H; or
R₁ and R₃ are separately and independently selected from the group, optionally substituted by R$_{01}$, consisting of S(=O)₂NH₂ or C$_{1-4}$ alkyl;
R₂ is selected from

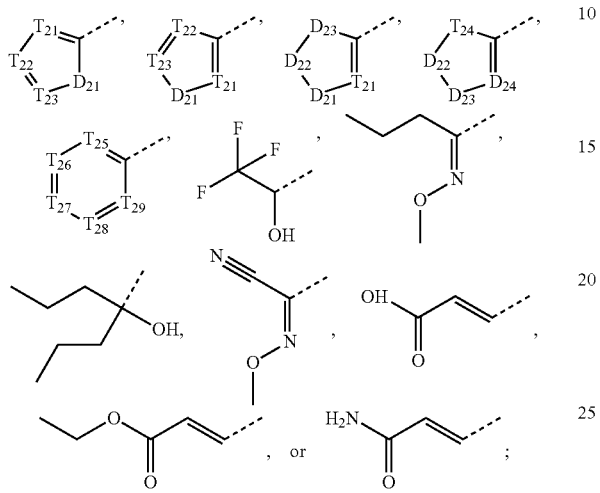

wherein:
from zero to two of T$_{21-23}$ is N, and the rest is C(R$_t$);
D$_{21}$ is selected from—C(R$_{d1}$)(R$_{d2}$)—, —C(=O)N(R$_{d3}$)—, —N(R$_{d4}$)—, —C(=NR$_{d5}$)—, —S(=O)₂N(R$_{d6}$)—, —S(=O)N(R$_{d7}$)—, —O—, —S—, —C(=O)O—, —C(=O)-, —C(=S)-, —S(=O)—, —S(=O)₂— or —N(R$_{d8}$)C(=O)N(R$_{d9}$)—;
T$_{24}$ is selected from N or C(R$_t$);
D$_{22-24}$ are separately and independently selected from —C(R$_{d1}$)(R$_{d2}$)—, —C(=O)N(R$_{d3}$)—, —N(R$_{d4}$)—, —C(=NR$_{d5}$)—, —S(=O)₂N(R$_{d6}$)—, —S(=O)N(R$_{d7}$)—, —O—, —S—, —C(=O)O—, —C(=O)—, —C(=S)—, —S(=O)—, —S(=O)₂— or —N(R$_{d8}$)C(=O)N(R$_{d9}$)—;
from zero to two of T$_{25-29}$ is N, and the rest is C(R$_t$);
optionally, any two of R$_t$ and R$_{d1-d9}$ are bonded to a common atom or group together to form one or two 3- to 8-membered rings;
R$_t$, R$_{d1}$ and R$_{d2}$ are separately and independently selected from H, F, Cl, Br, I, CN, OH, SH, NH₂, CHO, COOH, C(=O)NH₂, S(=O)NH₂, or S(=O)₂NH₂; or
R$_t$, R$_{d1}$ and R$_{d2}$ are separately and independently selected from the group, optionally substituted by R$_{01}$, consisting of C$_{1-10}$ alkyl, C$_{1-10}$ alkyl heteroalkyl, C$_{3-10}$ cyclic hydrocarbyl, or C$_{3-10}$ heterocyclic hydrocarbyl, C$_{1-10}$ alkyl substituted by C$_{3-10}$ cyclohydrocarbyl or C$_{3-10}$ heterocyclohydrocarbyl, C$_{1-10}$ heteroalkyl substituted by C$_{3-10}$ cyclohydrocarbyl or C$_{3-10}$ heterocyclohydrocarbyl, C$_{1-10}$ alkenyl, and C$_{1-10}$ heteroalkenyl;
R$_{01}$ is selected from F, Cl, Br, I, CN, OH, SH, NH₂, CHO, COOH, C(=O)NH₂, S(=O)NH₂, S(=O)₂NH₂ or R$_{02}$;
R$_{02}$ is selected from C$_{1-10}$ alkyl, C$_{1-10}$ heteroalkyl, C$_{3-10}$ cycloalkyl, C$_{3-10}$ heterocyclic alkyl, aminoacyl, or a 5- to 12-membered unsaturated heterocyclic group;
"hetero-" represents a hetero atom or a hetero atom-containing group, which is selected from the group consisting of —C(=O)N(R$_{d3}$)—, —N(R$_{d4}$)—, —C(=NR$_{d5}$)—, —S(=O)₂N(R$_{d6}$)-, —S(=O)N(R$_{d7}$)—, —O—, —S—, =O, =S, —C(=O)O—, —C(=O)—, —C(=S)—, —S(=O)—, —S(=O)₂— and —N(R$_{d8}$)C(=O)N(R$_{d9}$)—;
R$_{d3-d9}$ are separately and independently selected from H, NH₂, or R$_{02}$;
R$_{02}$ is optionally substituted by R$_{001}$;
R$_{001}$ is selected from F, Cl, Br, I, CN, OH, N(CH₃)₂, NH(CH₃), NH₂, CHO, COOH, C(=O)NH₂, S(=O)NH₂, S(=O)₂NH₂, trifluoromethyl, aminomethyl, hydroxymethyl, methyl, methoxy, formyl, methoxycarbonyl, methanesulfonyl, or methylsulfinyl;
the number of R$_{01}$, R$_{001}$, the hetero atom or the hetero atom-containing group are separately and independently selected from 0, 1, 2, 3, or 4.

2. The compound, or the pharmaceutically acceptable salt or the tautomer thereof according to claim 1, wherein:
R₁ and R₃ are separately and independently selected from the group consisting of H,

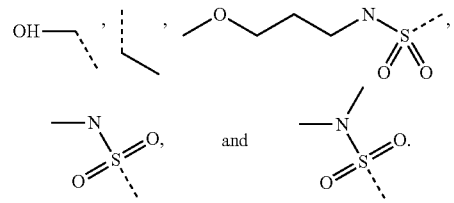

3. The compound, or the pharmaceutically acceptable salt or the tautomer thereof according to claim 1, wherein R₂ is separately and independently selected from

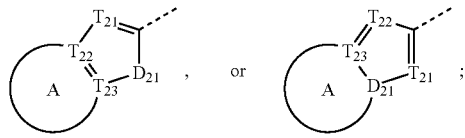

wherein
A represents 6-membered saturated or unsaturated carbocycle or heterocycle, each optionally substituted by 0, 1, 2 or 3 R$_t$.

4. The compound, or the pharmaceutically acceptable salt or the tautomer thereof according to claim 3, wherein R₂ is separately and independently selected from

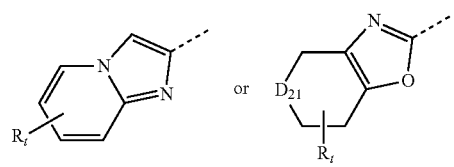

5. The compound, or the pharmaceutically acceptable salt or the tautomer thereof according to claim 1, wherein
R$_t$ and R$_{d1-d9}$ are separately and independently selected from H, NH₂, or CN; or C$_{1-6}$ alkyl, C$_{1-6}$ heteroalkyl, C$_{3-6}$ cycloalkyl, C$_{3-6}$ heterocyclic alkyl, a 5- or 6-membered unsaturated heterocyclic group, or aminoacyl, each optionally substituted by R$_{001}$;
R$_t$ and R$_{d1-d2}$ are separately and independently selected from F, Cl, Br, or I;

$R_t$ and $R_{d1-d9}$ are preferably separately and independently selected from $C_{1-6}$ alkylamino, N,N-di($C_{1-3}$ alkyl)amino, $C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{3-6}$ cycloalkyl, $C_{3-6}$ cycloalkylamino, $C_{3-6}$ heterocyclic alkylamino, $C_{3-6}$ cycloalkoxy, $C_{3-6}$ cycloalkyl acyl, $C_{3-6}$ cyclic alkoxycarbonyl, $C_{3-6}$ cycloalkylsulfonyl, $C_{3-6}$ cycloalkylsulfinyl, aminoacyl, or 5- to 6-membered unsaturated heterocyclyl, each optionally substituted by $R_{001}$;

$R_t$ and $R_{d1-d9}$ are more preferably separately and independently selected from 5- to 6-membered aryl or 5- to 6-membered heteroaryl, each optionally substituted by $R_{001}$;

$R_t$ and $R_{d1-d9}$ are more preferably separately and independently selected from phenyl, pyridyl or thienyl, each optionally substituted by $R_{001}$.

6. The compound, or the pharmaceutically acceptable salt or the tautomer thereof according to claim 5, wherein the hetero atom or the hetero atom-containing group is selected from O, N, S, —C(=O)O—, or

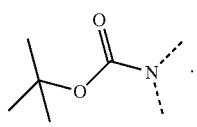

7. The compound, or the pharmaceutically acceptable salt or the tautomer thereof according to claim 6, wherein $R_t$ and $R_{d1-d9}$ are separately and independently selected from H, F, Cl, Br, I, $NH_2$, $CH_3$, CN,

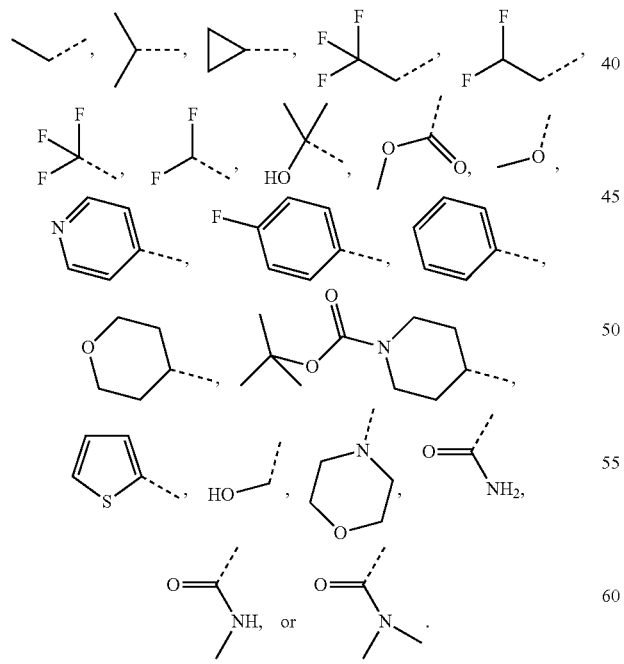

8. The compound, or the pharmaceutically acceptable salt or the tautomer thereof according to claim 7, wherein $R_{1-3}$ are separately and independently selected from:

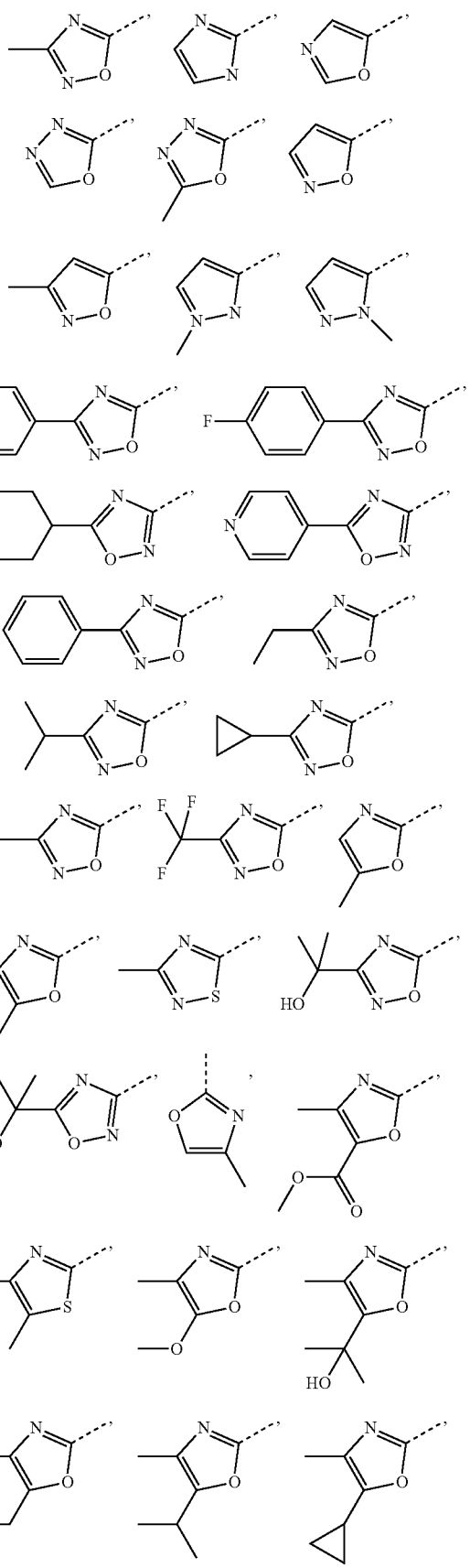

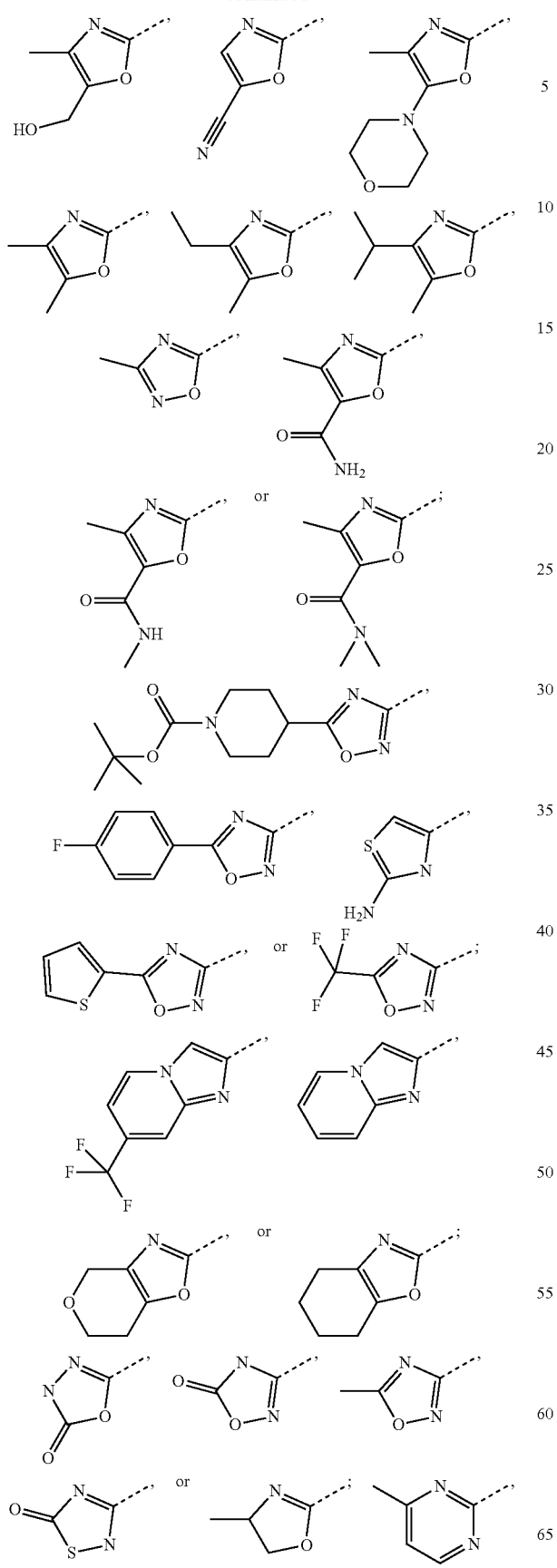
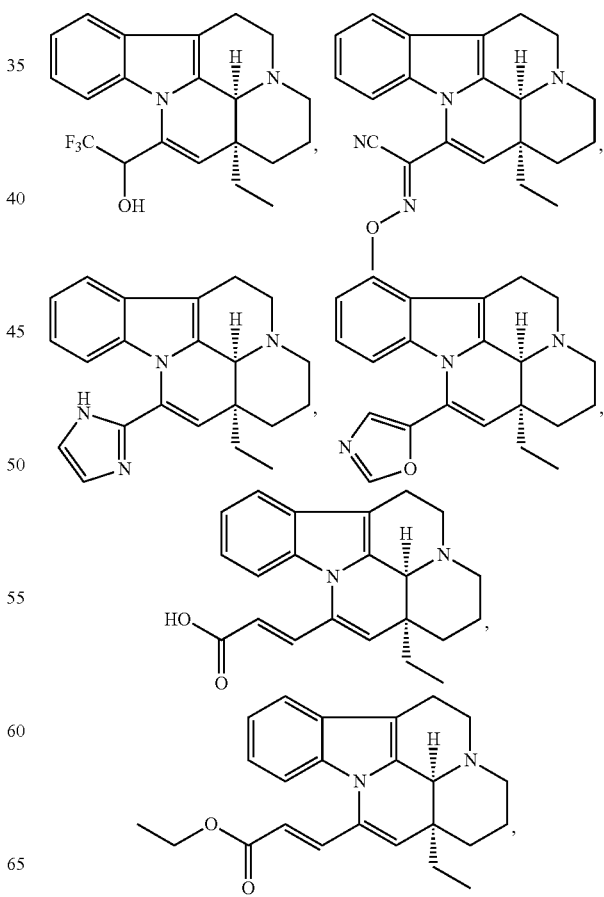
9. The compound, or the pharmaceutically acceptable salt or the tautomers thereof according to claim 1 selected from:

169
-continued
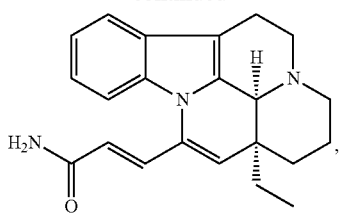
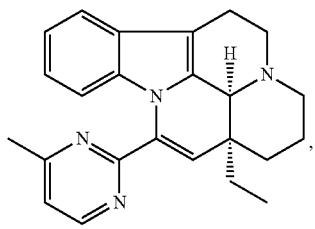
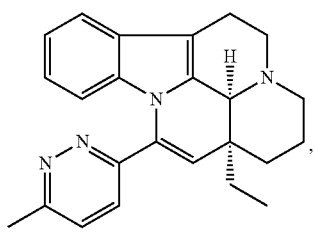
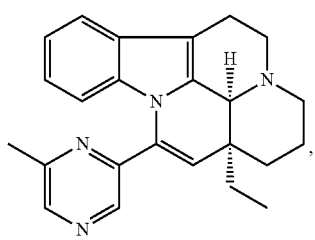
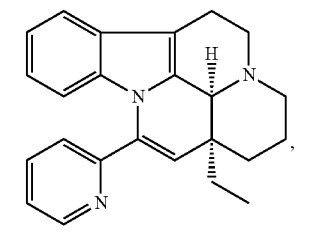
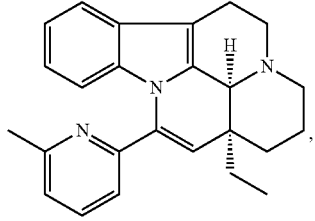
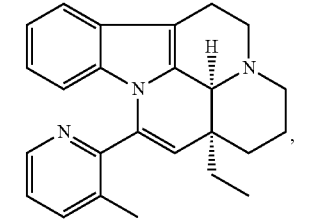
170
-continued
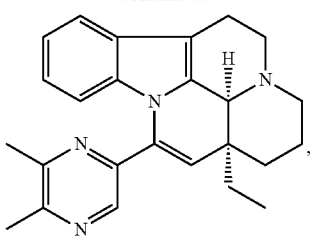
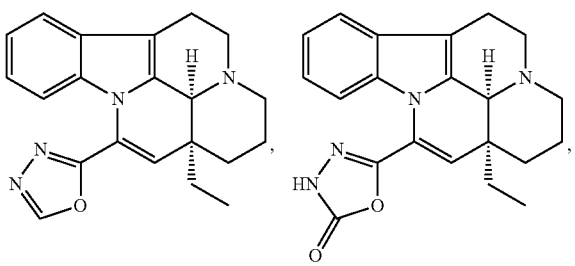
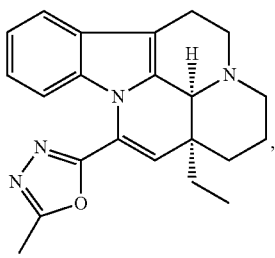
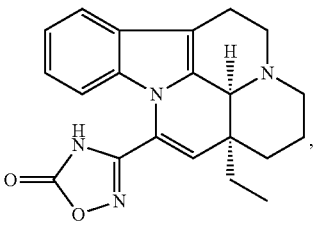
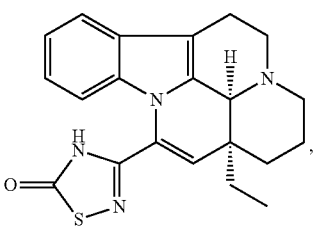
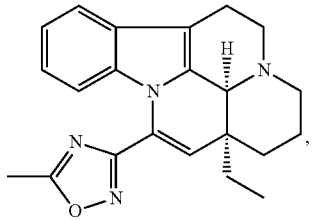
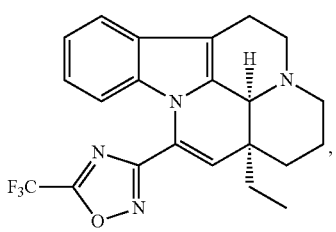

171
-continued
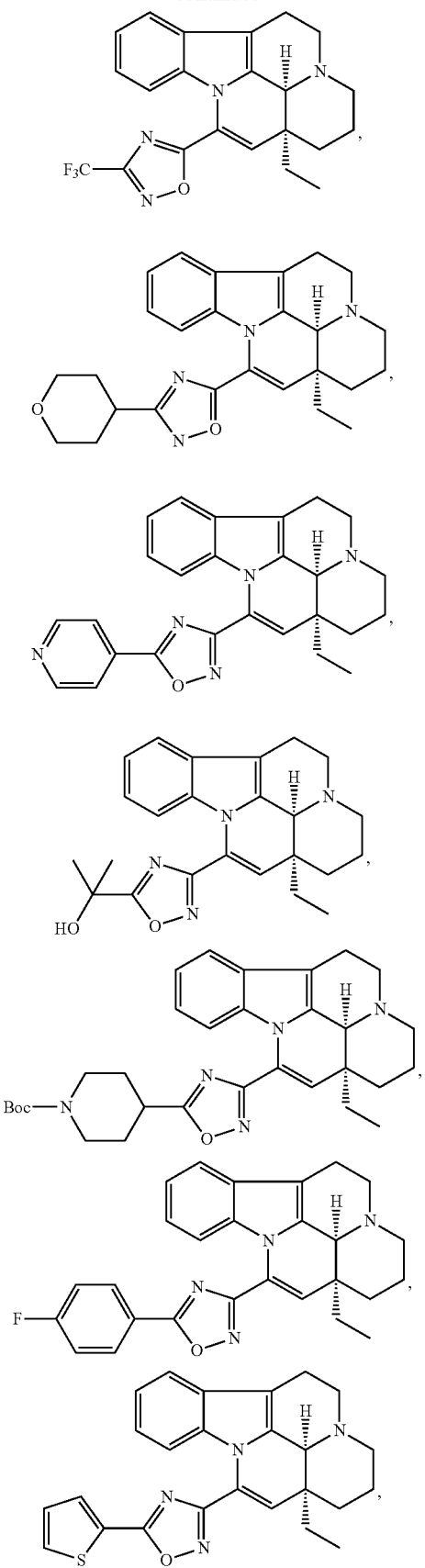
172
-continued
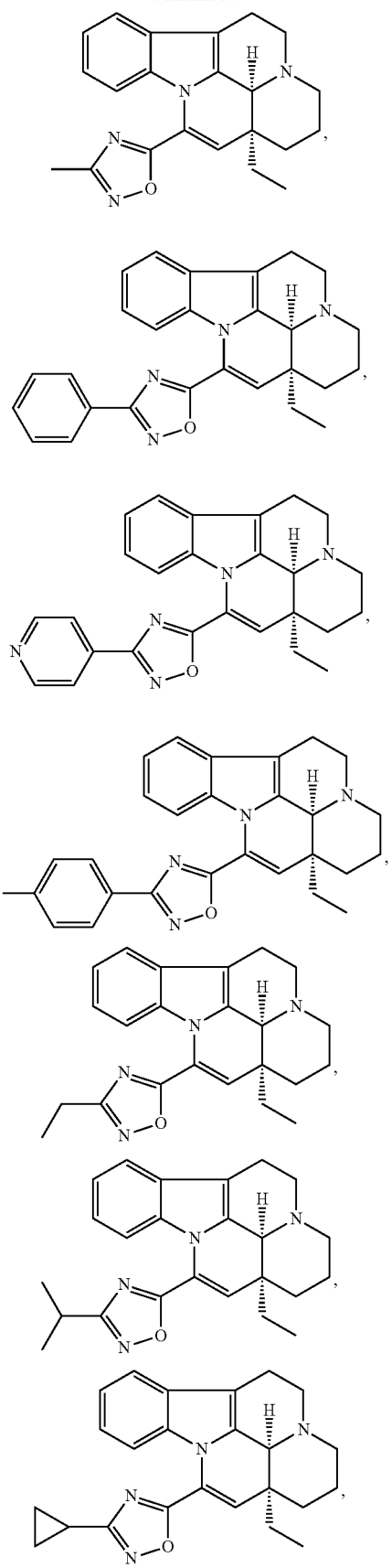

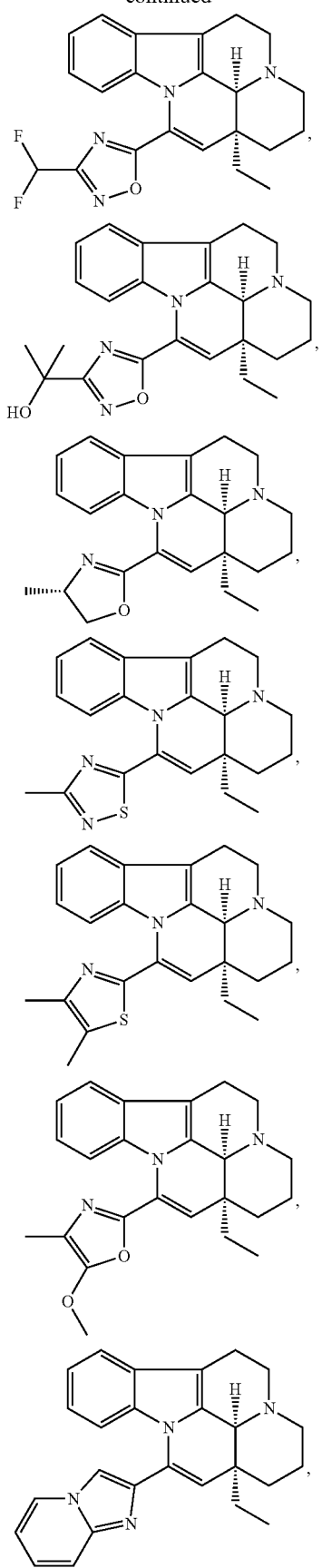
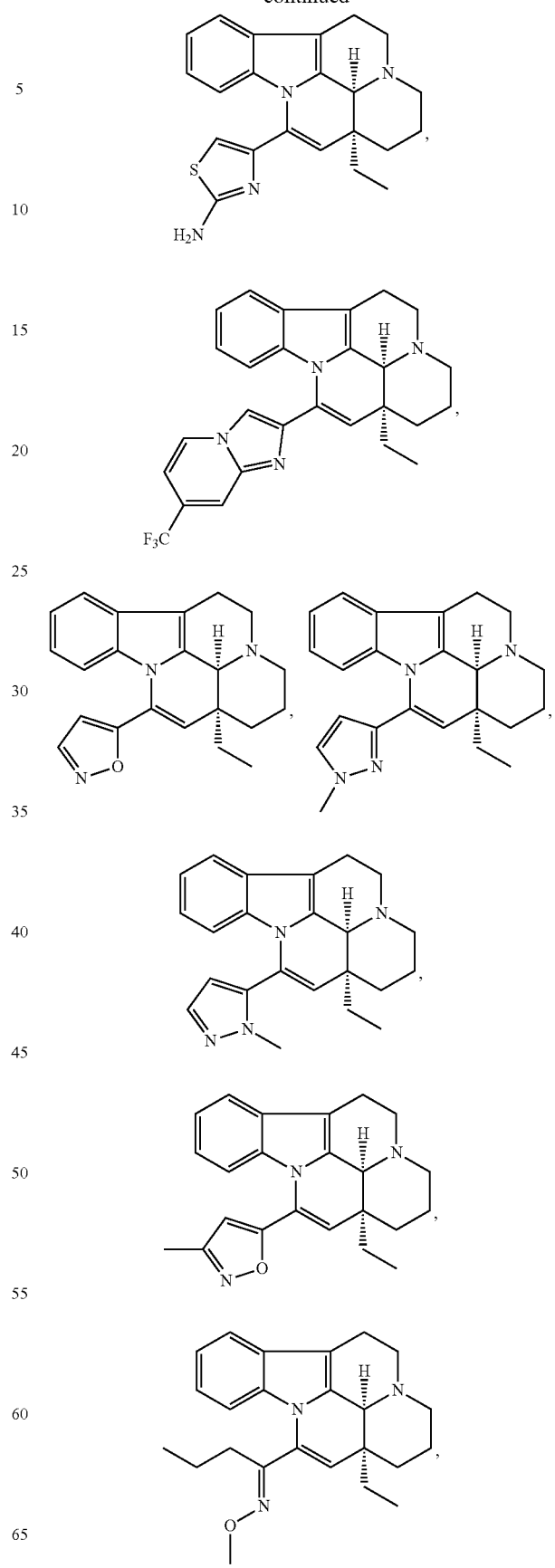

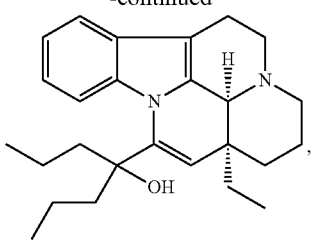,
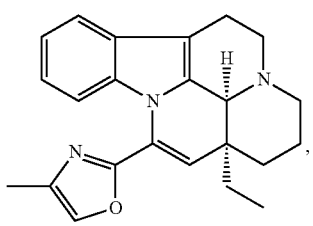,
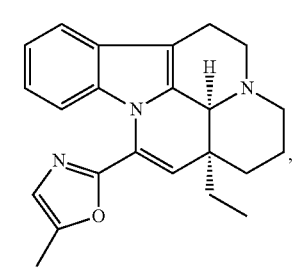,
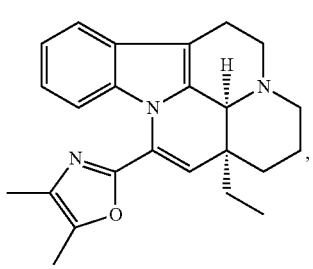,
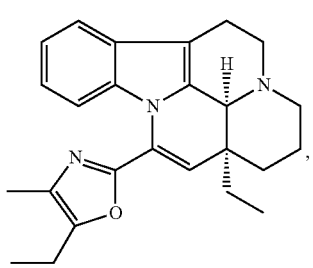,
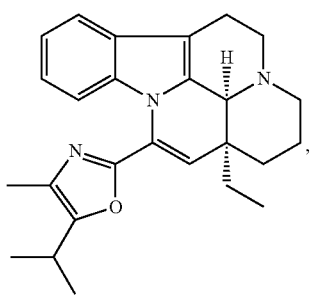,
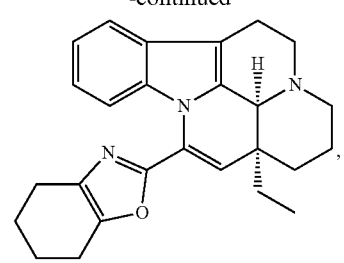,
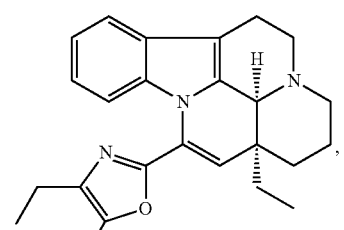,
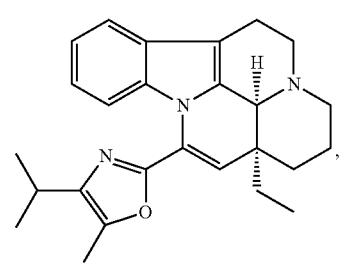,
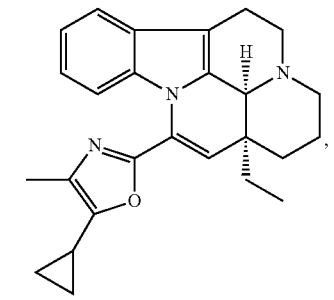,
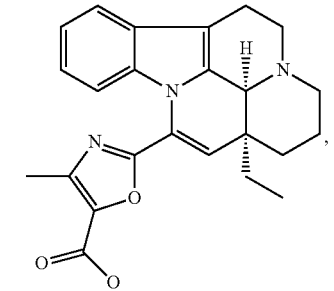,
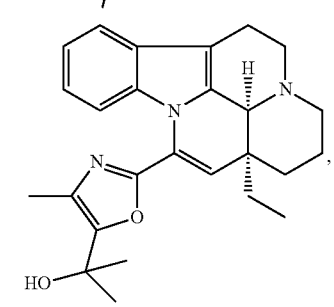,

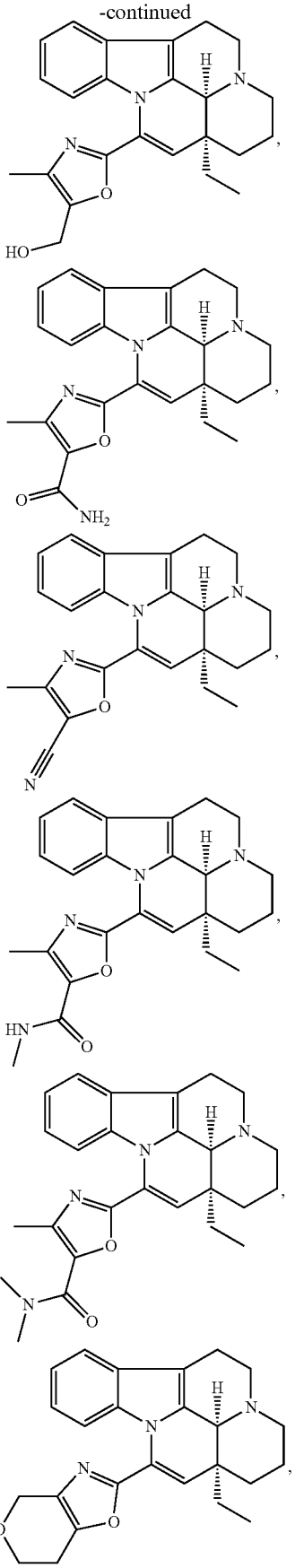
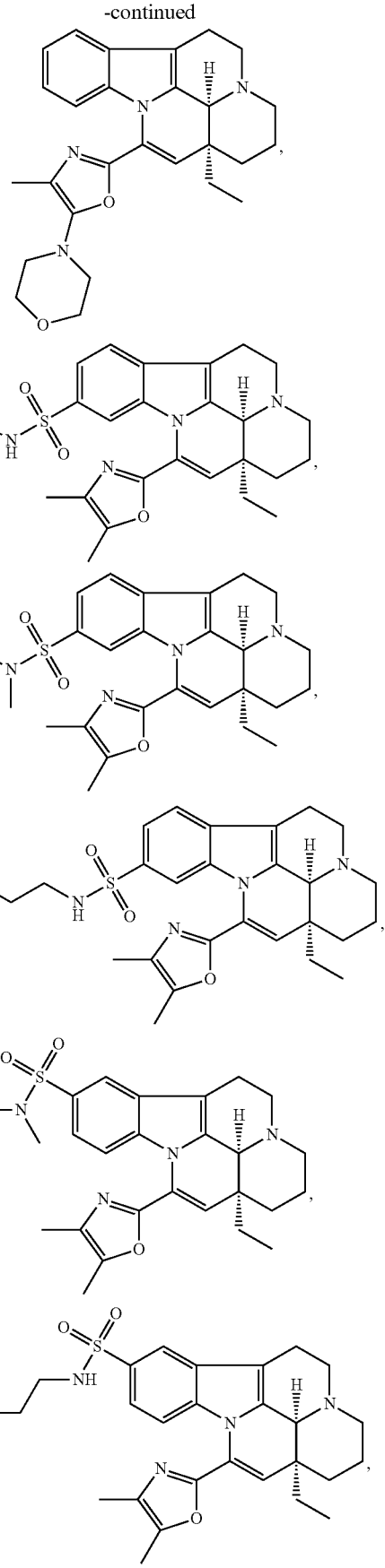

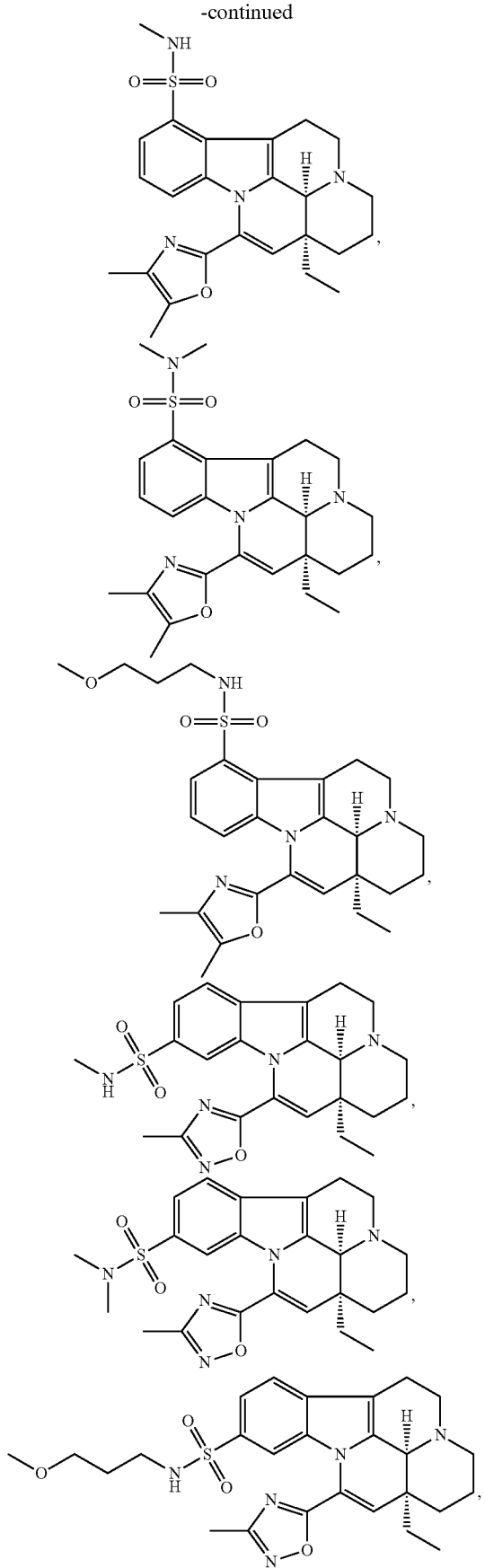
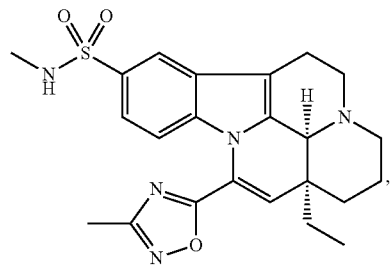

-continued

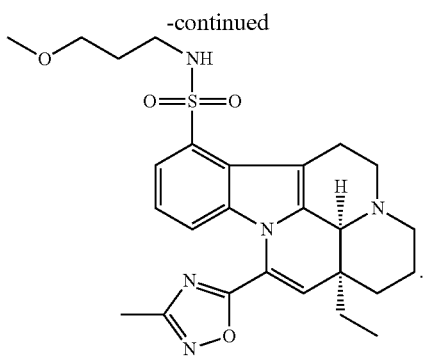

10. A method of treating cerebral apoplexy or epilepsy in a subject, comprising administering to the subject a therapeutically effective amount of the compound, or the pharmaceutically acceptable salt or the tautomer thereof according to claim 1.

11. A method of treating cerebral apoplexy or epilepsy in a subject, comprising administering to the subject a therapeutically effective amount of the compound, or the pharmaceutically acceptable salt or tautomer thereof according to claim 2.

12. A method of treating cerebral apoplexy or epilepsy in a subject, comprising administering to the subject a therapeutically effective amount of the compound, or the pharmaceutically acceptable salt or the tautomer thereof according to claim 3.

13. A method of treating cerebral apoplexy or epilepsy in a subject, comprising administering to the subject a therapeutically effective amount of the compound, or the pharmaceutically acceptable salt or the tautomer thereof according to claim 4.

14. A method of treating cerebral apoplexy or epilepsy in a subject, comprising administering to the subject a therapeutically effective amount of the compound, or the pharmaceutically acceptable salt or the tautomer thereof according to claim 5.

15. A method of treating cerebral apoplexy or epilepsy in a subject, comprising administering to the subject a therapeutically effective amount of the compound, or the pharmaceutically acceptable salt or the tautomer thereof according to claim 6.

16. A method of treating cerebral apoplexy or epilepsy in a subject, comprising administering to the subject a therapeutically effective amount of the compound, or the pharmaceutically acceptable salt or the tautomer thereof according to claim 7.

17. A method of treating cerebral apoplexy or epilepsy in a subject, comprising administering to the subject a therapeutically effective amount of the compound, or the pharmaceutically acceptable salt or the tautomer thereof according to claim 8.

18. A method of treating cerebral apoplexy or epilepsy in a subject, comprising administering to the subject a therapeutically effective amount of the compound, or the pharmaceutically acceptable salt or the tautomer thereof according to claim 9.

* * * * *